United States Patent

Hill et al.

Patent Number: 6,028,035
Date of Patent: Feb. 22, 2000

[54] SUBSTITUTED 4-BENZOYLPYRAZOLES

[75] Inventors: Regina Luise Hill, Speyer; Uwe Kardorff, Mannheim; Michael Rack, Heidelberg; Norbert Götz, Worms; Ernst Baumann, Dudenhofen; Wolfgang von Deyn, Neustadt; Stefan Engel, Idstein; Guido Mayer, Neustadt; Martina Otten, Ludwigshafen; Joachim Rheinheimer, Ludwigshafen; Matthias Witschel, Ludwigshafen; Ulf Misslitz, Neustadt; Helmut Walter, Obrigheim; Karl-Otto Westphalen, Speyer, all of Germany

[73] Assignee: BASF Aktiengesellschaft, Ludwigshafen, Germany

[21] Appl. No.: 09/331,671

[22] PCT Filed: Dec. 19, 1997

[86] PCT No.: PCT/EP97/07210

§ 371 Date: Jun. 23, 1999

§ 102(e) Date: Jun. 23, 1999

[87] PCT Pub. No.: WO98/29392

PCT Pub. Date: Jul. 9, 1998

[30] Foreign Application Priority Data

Jan. 3, 1997 [DE] Germany ............... 197 00 096

[51] Int. Cl.[7] .................... A01N 43/56; C07D 231/20
[52] U.S. Cl. ............... 504/282; 548/365.7; 548/369.4
[58] Field of Search .................. 548/369.4; 504/282

[56] References Cited

U.S. PATENT DOCUMENTS

| 4,063,925 | 12/1977 | Konotsune et al. |
| 4,146,726 | 3/1979 | Konotsune et al. |
| 4,261,729 | 4/1981 | Konotsune et al. |
| 4,414,392 | 11/1983 | Konotsune et al. |
| 4,508,910 | 4/1985 | Konotsune et al. |
| 4,643,757 | 2/1987 | Baba et al. |
| 4,687,858 | 8/1987 | Konotsune et al. |

FOREIGN PATENT DOCUMENTS

| 203 428 | 12/1986 | European Pat. Off. |
| 282 944 | 9/1988 | European Pat. Off. |
| 344 775 | 12/1989 | European Pat. Off. |
| 2 122 188 | 1/1984 | United Kingdom |

OTHER PUBLICATIONS

Tanaka er al, *Chemical Abstracts*, vol. 129:302,634, 1998.

*Primary Examiner*—Robert W. Ramsuer
*Attorney, Agent, or Firm*—Keil & Weinkauf

[57] ABSTRACT

The invention relates to 4-benzoylpyrazoles of the formula I

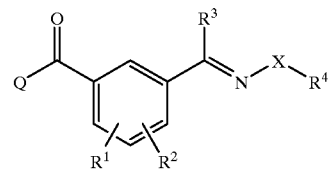

and their agriculturally useful salts thereof, processes and intermediates; compositions thereof; and use thereof for controlling undesireable plants.

7 Claims, No Drawings

SUBSTITUTED 4-BENZOYLPYRAZOLES

This application is a 371 of PCT/EP97/07210 Dec. 19, 1997.

The present invention relates to substituted 4-benzoylpyrazoles of the formula I

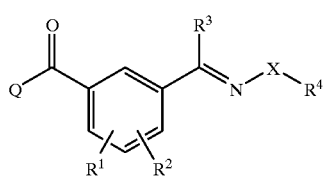

where the variables have the following meanings:

$R^1$, $R^2$ are hydrogen, nitro, halogen, cyano, thiocyanato, $C_1-C_6$-alkyl, $C_1-C_6$-haloalkyl, $C_1-C_6$-alkoxy-$C_1-C_6$-alkyl, $C_2-C_6$-alkenyl, $C_2-C_6$-alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;

$R^3$ is hydrogen, cyano, $C_1-C_6$-alkyl, $C_1-C_6$-haloalkyl, —$OR^7$, —$SR^7$ or —$NR^7R^{10}$;

$R^4$ is hydrogen, $C_1-C_6$-alkyl, $C_3-C_6$-cycloalkyl, $C_3-C_6$-alkenyl, $C_4-C_6$-cycloalkenyl, $C_3-C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1-C_4$-alkyliminooxy, $C_1-C_4$-alkoxyamino, $C_1-C_4$-alkylcarbonyl, $C_1-C_4$-alkoxy-$C_2-C_6$-alkoxycarbonyl, $C_1-C_4$-alkylsulfonyl, heterocyclyl, heterocyclyloxy, phenyl, benzyl, hetaryl, phenoxy, benzyloxy and hetaryloxy, it being possible for the eight last-mentioned radicals, in turn, to be substituted;

X is oxygen or $NR^8$;

n is 0, 1 or 2;

$R^5$ is hydrogen, $C_1-C_6$-alkyl, $C_1-C_6$-haloalkyl, $C_1-C_6$-alkoxy-$C_2-C_6$-alkyl, $C_3-C_6$-alkenyl or $C_3-C_6$-alkynyl;

$R^6$ is $C_1-C_6$-alkyl or $C_1-C_6$-haloalkyl;

$R^7$ is $C_1-C_6$-alkyl, $C_1-C_6$-haloalkyl, $C_1-C_6$-alkoxy-$C_2-C_6$-alkyl, $C_3-C_6$-alkenyl or $C_3-C_6$-alkynyl;

$R^8$ is hydrogen or $C_1-C_6$-alkyl;

$R^9$ is $C_1-C_6$-alkyl, $C_3-C_6$-alkenyl, $C_3-C_6$-alkynyl, phenyl or benzyl;

$R^{10}$ is $C_1-C_6$-alkyl, $C_1-C_6$-haloalkyl, $C_3-C_6$-alkenyl or $C_3-C_6$-alkynyl;

Q is a pyrazole of the formula II

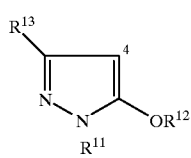

which is linked in the 4-position and where $R^{11}$ is $C_1-C_6$-alkyl, $C_1-C_6$-haloalkyl, phenyl or phenyl which is partially or fully halogenated and/or has attached to it one to three of the following radicals: nitro, cyano, $C_1-C_4$-alkyl, $C_1-C_4$-haloalkyl, $C_1-C_4$-alkoxy, $C_1-C_4$-haloalkoxy;

$R^{12}$ is hydrogen, $C_1-C_6$-alkyl, $C_1-C_6$-haloalkyl, $C_1-C_6$-alkylcarbonyl, $C_1-C_6$-haloalkylcarbonyl, $C_1-C_6$-alkoxycarbonyl, $C_1-C_6$-alkylsulfonyl, $C_1-C_6$-haloalkylsulfonyl, phenylcarbonyl, phenylcarbonylmethyl, phenoxycarbonyl or phenylsulfonyl, the four last-mentioned substituents being unsubstituted or the phenyl ring being in each case partially or fully halogenated and/or having attached to it one to three of the following radicals: nitro, cyano, $C_1-C_4$-alkyl, $C_1-C_4$-haloalkyl, $C_1-C_4$-alkoxy, $C_1-C_4$-haloalkoxy;

$R^{13}$ is hydrogen, $C_1-C_6$-alkyl or $C_1-C_6$-haloalkyl;

and agriculturally useful salts thereof.

Moreover, the invention relates to processes and intermediates for the preparation of compounds of the formula I, to compositions which comprise the latter, and to the use of the compounds of the formula I and of the compositions comprising them for controlling weeds.

4-Benzoylpyrazoles are disclosed in the literature, for example in EP-A 282 944.

However, the herbicidal properties of the prior-art compounds and the crop plant tolerances are only partly satisfactory. It was an object of the present invention to find novel, in particular herbicidally active, compounds with improved properties.

This object is achieved by the 4-benzoylpyrazoles of the formula I and by their herbicidal activity.

Furthermore, there have been found herbicidal compositions which comprise the compounds I and which have a very good herbicidal activity. In addition, there have been found processes for the preparation of these compositions and methods of controlling undesirable vegetation using the compounds I.

The present invention also relates to stereoisomers of the compounds of the formula I. These include pure stereoisomers and mixtures of these.

The compounds of the formula I contain a carbon-nitrogen double bond and therefore exist in the form of E isomers or Z isomers or E/Z isomer mixtures. Furthermore, the compounds of the formula I may contain further carbon or carbon-nitrogen double bonds. The invention relates both to the pure geometric isomers and to mixtures of these.

Depending on the substitution pattern, the compounds of the formula I may contain one or more chiral centers, in which case they exist in the form of enantiomers or diastereomer mixtures.

The invention relates both to the pure enantiomers or diastereomers and to the mixtures of these.

The compounds of the formula I may also be present in the form of their agriculturally useful salts, the type of salt generally being of no importance. In general, suitable salts are salts of those cations, or the acid addition salts of those acids, whose cations, or anions, respectively, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium where, if desired, one to four hydrogen atoms may be replaced by $C_1-C_4$-alkyl or hydroxy-$C_1-C_4$-alkyl and/or a phenyl or benzyl, preferably diisopropylammonium, tetramethylammonium, tetrabutylammonium, trimethylbenzylammonium, moreover phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Special mention must be made of the compounds of the formula I according to the invention where $R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, it being possible for the eight last-mentioned radicals, in turn, to be partially or fully halogenated and/or to have attached to them one to three radicals from the following group:

nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl.

The organic moieties mentioned for the substituents $R^1$–$R^{13}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylsulfonyl, haloalkylsulfonyl, alkylcarbonyl, haloalkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably have attached to them one to five identical or different halogen atoms, the meaning halogen being in each case fluorine, chlorine, bromine or iodine.

Examples of other meanings are:

$C_2$–$C_4$-alkyl: ethyl, propyl, 1-methylethyl, butyl, 1-methylpropyl, 2-methylpropyl and 1,1-dimethylethyl;

$C_1$–$C_4$-alkyl, and the alkyl moieties of $C_1$–$C_4$-alkylcarbonyl: $C_2$–$C_4$-alkyl as mentioned above and also methyl;

$C_2$–$C_6$-alkyl and the alkyl moieties of $C_1$–$C_6$-alkoxy-$C_2$–$C_6$-alkyl: $C_2$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_6$-alkyl and the alkyl moieties of $C_1$–$C_6$-alkoxy-$C_1$–$C_6$-alkyl and $C_1$alkyl $C_6$-alkylcarbonyl: $C_2$alkyl $C_6$-alkyl as mentioned above, and also methyl;

$C_1$–$C_4$-haloalkyl: a $C_1$alkyl $C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$alkyl $C_6$-haloalkyl and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties of $C_1$–$C_4$-alkoxyamino, $C_1$–$C_4$-alkoxy-$C_2$alkyl $C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$alkyl $C_6$-alkoxy and the alkoxy moieties of $C_1$–$C_6$-alkoxy-$C_1$–$C_6$-alkyl, $C_1$–$C_6$-alkoxy-$C_2$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylsulfonyl ($C_1$–$C_4$-alkyl-$S(=O)_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(choromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-mnethylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1yl, 3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl:

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and also the heterocyclyl radicals in heterocyclyloxy: three- to seven-membered saturated or partially unsaturated mono- or polycyclic heterocycles which contain one to three hetero atoms selected from a group consisting of oxygen, nitrogen and sulfur, such as oxiranyl, oxetan-3-yl, thietan-3-yl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3- dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroitidazol-2-yl, 2,3-dihydroitidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dioxan-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dithiolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and also the hetaryl radicals in hetaryloxy: aromatic mono- or polycyclic radicals which, besides carbon ring members, may additionally contain one to four nitrogen atoms or one to three nitrogen atoms and one oxygen or one sulfur atom or one oxygen or one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzofuzed derivatives.

All phenyl, hetaryl and heterocyclyl rings are preferably unsubstituted or have attached to them one to three halogen atoms and/or one or two radicals selected from the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;
especially preferably nitro, halogen, eg. fluorine, chlorine or bromine, $C_1$–$C_6$-haloalkyl, —$OR^5$ or —$SO_2R^7$, eg. methylsulfonyl, ethylsulfonyl or difluoromethylsulfonyl; particularly preferably nitro, fluorine, chlorine, bromine, trifluoromethyl, methoxy, ethoxy, methylsulfonyl, ethylsulfonyl or difluoromethylsulfonyl;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;
especially preferably hydrogen, nitro, halogen, eg. fluorine, chlorine or bromine, $C_1$–$C_6$-alkyl, eg. methyl or ethyl, $C_1$–$C_6$-haloalkyl, —$OR^5$ or —$SO_2R^7$, eg. methylsulfonyl, ethylsulfonyl or difluoromethylsulfonyl;
particularly preferably nitro, fluorine, chlorine, bromine, methyl, ethyl, trifluoromethyl, methoxy, ethoxy, methylsulfonyl, ethylsulfonyl or difluoromethylsulfonyl;

$R^3$ is hydrogen, cyano, $C_1$–$C_6$-alkyl, $C_1$–$C_6$-haloalkyl or —$OR^7$;

$R^4$ is hydrogen, $C_1$–$C_6$-alkyl, $C_3$–$C_6$-cycloalkyl, $C_3$–$C_6$-alkenyl or $C_3$–$C_6$-alkynyl, it being possible for the 4 last-mentioned substituents to be partially or fully halogenated and/or to have attached to them one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, benzyl, hetaryl, phenoxy, benzyloxy or hetaryloxy, it being possible for the eight last-mentioned radicals, in turn, to be partially or fully halogenated and/or to contain one to three radicals selected from the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;
particularly preferably $C_1$–$C_6$-alkyl, $C_3$–$C_6$-cycloalkyl, $C_3$–$C_6$-alkenyl or $C_3$–$C_6$-alkynyl, it being possible for the 4 last-mentioned substituents to be partially or fully halogenated and/or to have attached to them one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, benzyl, hetaryl, phenoxy, benzyloxy or hetaryloxy, it being possible for the eight last-mentioned radicals, in turn, to be partially or fully halogenated and/or to contain one to three radicals selected from the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

X is oxygen or NH;

n is 0 or 2;

$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
especially preferably methyl, ethyl, trifluoromethyl, difluoromethyl, methoxyethyl, allyl or propargyl;

$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
especially preferably methyl, ethyl, trifluoromethyl, difluoromethyl, methoxyethyl, allyl or propargyl;

$R^8$ is hydrogen or $C_1$–$C_6$-alkyl;

$R^{10}$ is $C_1$–$C_6$-alkyl, $C_1$–$C_6$-haloalkyl, $C_3$–$C_6$-alkenyl or $C_3$–$C_6$-alkynyl;

$R^{11}$ is $C_1$–$C_6$-alkyl or $C_1$–$C_6$-haloalkyl; especially preferably methyl, ethyl, propyl, isopropyl, butyl or isobutyl;

$R^{12}$ is hydrogen, $C_1$–$C_6$-alkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonylmethyl, or phenylsulfonyl, it being possible for the phenyl ring of the two last-mentioned substituents to be partially or fully halogenated and/or to have attached to it one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{13}$ is hydrogen, $C_1$–$C_6$-alkyl or $C_1$–$C_6$-haloalkyl; especially preferably hydrogen, methyl, ethyl or trifluoromethyl.

Particularly preferred are compounds of the formula Ia (=I where $R^1$ is bonded in the 4-position of the phenyl ring and $R^2$ in the 2-position of the phenyl ring).

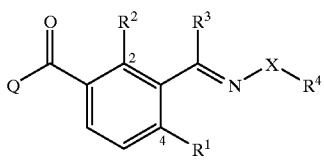

Ia

Extraordinarily preferred are the compounds of the formula Ia where the variables $R^1$ to $R^3$, Q and X have the abovementioned meanings and $R^4$ is hydrogen, $C_1$–$C_6$-alkyl, $C_3$–$C_6$-cycloalkyl, $C_3$–$C_6$-alkenyl or $C_3$–$C_6$-alkynyl, it being possible for the 4 last-mentioned substituents to be partially or fully halogenated and/or to have attached to them one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, benzyl, hetaryl, phenoxy, benzyloxy or hetaryloxy, it being possible for the eight last-mentioned radicals, in turn, to be partially or fully halogenated and/or to have attached to them one to three radicals selected from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl.

Particularly extraordinarily preferred are the compounds Ia1 (=I where $R^1$=Cl, $R^{11}$=$CH_3$ and $R^{12}$ and $R^{13}$=H, where $R^1$ is bonded in the 4-position of the phenyl ring and $R^2$ in the 2-position of the phenyl ring), in particular the compounds of Table 1.

TABLE 1

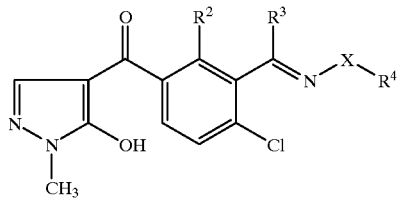

Ia1

| No. | $R^2$ | $R^3$ | $R^4$ | X |
|---|---|---|---|---|
| Ia1.001 | Cl | H | $CH_3$ | O |
| Ia1.002 | Cl | H | $C_2H_5$ | O |
| Ia1.003 | Cl | H | $CH_2$—C≡CH | O |
| Ia1.004 | Cl | $CH_3$ | $CH_3$ | O |
| Ia1.005 | Cl | $CH_3$ | $C_2H_5$ | O |
| Ia1.006 | Cl | $CH_3$ | $CH_2$—C≡CH | O |

TABLE 1-continued

Ia1

| No. | $R^2$ | $R^3$ | $R^4$ | X |
|---|---|---|---|---|
| Ia1.007 | Cl | $C_2H_5$ | $CH_3$ | O |
| Ia1.008 | Cl | $C_2H_5$ | $C_2H_5$ | O |
| Ia1.009 | Cl | $C_2H_5$ | $CH_2$—C≡CH | O |
| Ia1.010 | Cl | $OCH_3$ | $CH_3$ | O |
| Ia1.011 | Cl | $OCH_3$ | $C_2H_5$ | O |
| Ia1.012 | Cl | $OCH_3$ | $CH_2$—C≡CH | O |
| Ia1.013 | Cl | $OC_2H_5$ | $CH_3$ | O |
| Ia1.014 | Cl | $OC_2H_5$ | $C_2H_5$ | O |
| Ia1.015 | Cl | $OC_2H_5$ | $CH_2$—C≡CH | O |
| Ia1.016 | Cl | H | $CH_3$ | NH |
| Ia1.017 | Cl | H | $C_2H_5$ | NH |
| Ia1.018 | Cl | H | $CH_2$—C≡CH | NH |
| Ia1.019 | Cl | $CH_3$ | $CH_3$ | NH |
| Ia1.020 | Cl | $CH_3$ | $C_2H_5$ | NH |
| Ia1.021 | Cl | $CH_3$ | $CH_2$—C≡CH | NH |
| Ia1.022 | Cl | $C_2H_5$ | $CH_3$ | NH |
| Ia1.023 | Cl | $C_2H_5$ | $C_2H_5$ | NH |
| Ia1.024 | Cl | $C_2H_5$ | $CH_2$—C≡CH | NH |
| Ia1.025 | Cl | $OCH_3$ | $CH_3$ | NH |
| Ia1.026 | Cl | $OCH_3$ | $C_2H_5$ | NH |
| Ia1.027 | Cl | $OCH_3$ | $CH_2$—C≡CH | NH |
| Ia1.028 | Cl | $OC_2H_5$ | $CH_3$ | NH |
| Ia1.029 | Cl | $OC_2H_5$ | $C_2H_5$ | NH |
| Ia1.030 | Cl | $OC_2H_5$ | $CH_2$—C≡CH | NH |
| Ia1.031 | $CH_3$ | H | $CH_3$ | O |
| Ia1.032 | $CH_3$ | H | $C_2H_5$ | O |
| Ia1.033 | $CH_3$ | H | $CH_2$—C≡CH | O |
| Ia1.034 | $CH_3$ | $CH_3$ | $CH_3$ | O |
| Ia1.035 | $CH_3$ | $CH_3$ | $C_2H_5$ | O |
| Ia1.036 | $CH_3$ | $CH_3$ | $CH_2$—C≡CH | O |
| Ia1.037 | $CH_3$ | $C_2H_5$ | $CH_3$ | O |
| Ia1.038 | $CH_3$ | $C_2H_5$ | $C_2H_5$ | O |
| Ia1.039 | $CH_3$ | $C_2H_5$ | $CH_2$—C≡CH | O |
| Ia1.040 | $CH_3$ | $OCH_3$ | $CH_3$ | O |
| Ia1.041 | $CH_3$ | $OCH_3$ | $C_2H_5$ | O |
| Ia1.042 | $CH_3$ | $OCH_3$ | $CH_2$—C≡CH | O |
| Ia1.043 | $CH_3$ | $OC_2H_5$ | $CH_3$ | O |
| Ia1.044 | $CH_3$ | $OC_2H_5$ | $C_2H_5$ | O |
| Ia1.045 | $CH_3$ | $OC_2H_5$ | $CH_2$—C≡CH | O |
| Ia1.046 | $CH_3$ | H | $CH_3$ | NH |
| Ia1.047 | $CH_3$ | H | $C_2H_5$ | NH |
| Ia1.048 | $CH_3$ | H | $CH_2$—C≡CH | NH |
| Ia1.049 | $CH_3$ | $CH_3$ | $CH_3$ | NH |
| Ia1.050 | $CH_3$ | $CH_3$ | $C_2H_5$ | NH |
| Ia1.051 | $CH_3$ | $CH_3$ | $CH_2$—C≡CH | NH |
| Ia1.052 | $CH_3$ | $C_2H_5$ | $CH_3$ | NH |
| Ia1.053 | $CH_3$ | $C_2H_5$ | $C_2H_5$ | NH |
| Ia1.054 | $CH_3$ | $C_2H_5$ | $CH_2$—C≡CH | NH |
| Ia1.055 | $CH_3$ | $OCH_3$ | $CH_3$ | NH |
| Ia1.056 | $CH_3$ | $OCH_3$ | $C_2H_5$ | NH |
| Ia1.057 | $CH_3$ | $OCH_3$ | $CH_2$—C≡CH | NH |
| Ia1.058 | $CH_3$ | $OC_2H_5$ | $CH_3$ | NH |
| Ia1.059 | $CH_3$ | $OC_2H_5$ | $C_2H_5$ | NH |
| Ia1.060 | $CH_3$ | $OC_2H_5$ | $CH_2$—C≡CH | NH |
| Ia1.061 | $OCH_3$ | H | $CH_3$ | O |
| Ia1.062 | $OCH_3$ | H | $C_2H_5$ | O |
| Ia1.063 | $OCH_3$ | H | $CH_2$—C≡CH | O |
| Ia1.064 | $OCH_3$ | $CH_3$ | $CH_3$ | O |
| Ia1.065 | $OCH_3$ | $CH_3$ | $C_2H_5$ | O |
| Ia1.066 | $OCH_3$ | $CH_3$ | $CH_2$—C≡CH | O |
| Ia1.067 | $OCH_3$ | $C_2H_5$ | $CH_3$ | O |
| Ia1.068 | $OCH_3$ | $C_2H_5$ | $C_2H_5$ | O |
| Ia1.069 | $OCH_3$ | $C_2H_5$ | $CH_2$—C≡CH | O |
| Ia1.070 | $OCH_3$ | $OCH_3$ | $CH_3$ | O |
| Ia1.071 | $OCH_3$ | $OCH_3$ | $C_2H_5$ | O |

TABLE 1-continued

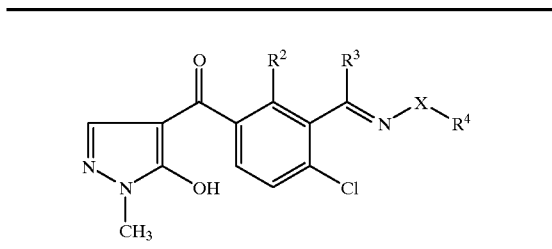

| No. | R² | R³ | R⁴ | X |
|---|---|---|---|---|
| Ia1.072 | OCH₃ | OCH₃ | CH₂—C≡CH | O |
| Ia1.073 | OCH₃ | OC₂H₅ | CH₃ | O |
| Ia1.074 | OCH₃ | OC₂H₅ | C₂H₅ | O |
| Ia1.075 | OCH₃ | OC₂H₅ | CH₂—C≡CH | O |
| Ia1.076 | OCH₃ | H | CH₃ | NH |
| Ia1.077 | OCH₃ | H | C₂H₅ | NH |
| Ia1.078 | OCH₃ | H | CH₂—C≡CH | NH |
| Ia1.079 | OCH₃ | CH₃ | CH₃ | NH |
| Ia1.080 | OCH₃ | CH₃ | C₂H₅ | NH |
| Ia1.081 | OCH₃ | CH₃ | CH₂—C≡CH | NH |
| Ia1.082 | OCH₃ | C₂H₅ | CH₃ | NH |
| Ia1.083 | OCH₃ | C₂H₅ | C₂H₅ | NH |
| Ia1.084 | OCH₃ | C₂H₅ | CH₂—C≡CH | NH |
| Ia1.085 | OCH₃ | OCH₃ | CH₃ | NH |
| Ia1.086 | OCH₃ | OCH₃ | C₂H₅ | NH |
| Ia1.087 | OCH₃ | OCH₃ | CH₂—C≡CH | NH |
| Ia1.088 | OCH₃ | OC₂H₅ | CH₃ | NH |
| Ia1.089 | OCH₃ | OC₂H₅ | C₂H₅ | NH |
| Ia1.090 | OCH₃ | OC₂H₅ | CH₂—C≡CH | NH |
| Ia1.091 | CF₃ | H | CH₃ | O |
| Ia1.092 | CF₃ | H | C₂H₅ | O |
| Ia1.093 | CF₃ | H | CH₂—C≡CH | O |
| Ia1.094 | CF₃ | CH₃ | CH₃ | O |
| Ia1.095 | CF₃ | CH₃ | C₂H₅ | O |
| Ia1.096 | CF₃ | CH₃ | CH₂—C≡CH | O |
| Ia1.097 | CF₃ | C₂H₅ | CH₃ | O |
| Ia1.098 | CF₃ | C₂H₅ | C₂H₅ | O |
| Ia1.099 | CF₃ | C₂H₅ | CH₂—C≡CH | O |
| Ia1.100 | CF₃ | OCH₃ | CH₃ | O |
| Ia1.101 | CF₃ | OCH₃ | C₂H₅ | O |
| Ia1.102 | CF₃ | OCH₃ | CH₂—C≡CH | O |
| Ia1.103 | CF₃ | OC₂H₅ | CH₃ | O |
| Ia1.104 | CF₃ | OC₂H₅ | C₂H₅ | O |
| Ia1.105 | CF₃ | OC₂H₅ | CH₂—C≡CH | O |
| Ia1.106 | CF₃ | H | CH₃ | NH |
| Ia1.107 | CF₃ | H | C₂H₅ | NH |
| Ia1.108 | CF₃ | H | CH₂—C≡CH | NH |
| Ia1.109 | CF₃ | CH₃ | CH₃ | NH |
| Ia1.110 | CF₃ | CH₃ | C₂H₅ | NH |
| Ia1.111 | CF₃ | CH₃ | CH₂—C≡CH | NH |
| Ia1.112 | CF₃ | C₂H₅ | CH₃ | NH |
| Ia1.113 | CF₃ | C₂H₅ | C₂H₅ | NH |
| Ia1.114 | CF₃ | C₂H₅ | CH₂—C≡CH | NH |
| Ia1.115 | CF₃ | OCH₃ | CH₃ | NH |
| Ia1.116 | CF₃ | OCH₃ | C₂H₅ | NH |
| Ia1.117 | CF₃ | OCH₃ | CH₂—C≡CH | NH |
| Ia1.118 | CF₃ | OC₂H₅ | CH₃ | NH |
| Ia1.119 | CF₃ | OC₂H₅ | C₂H₅ | NH |
| Ia1.120 | CF₃ | OC₂H₅ | CH₂—C≡CH | NH |
| Ia1.121 | SO₂CH₃ | H | CH₃ | O |
| Ia1.122 | SO₂CH₃ | H | C₂H₅ | O |
| Ia1.123 | SO₂CH₃ | H | CH₂—C≡CH | O |
| Ia1.124 | SO₂CH₃ | CH₃ | CH₃ | O |
| Ia1.125 | SO₂CH₃ | CH₃ | C₂H₅ | O |
| Ia1.126 | SO₂CH₃ | CH₃ | CH₂—C≡CH | O |
| Ia1.127 | SO₂CH₃ | C₂H₅ | CH₃ | O |
| Ia1.128 | SO₂CH₃ | C₂H₅ | C₂H₅ | O |
| Ia1.129 | SO₂CH₃ | C₂H₅ | CH₂—C≡CH | O |
| Ia1.130 | SO₂CH₃ | OCH₃ | CH₃ | O |
| Ia1.131 | SO₂CH₃ | OCH₃ | C₂H₅ | O |
| Ia1.132 | SO₂CH₃ | OCH₃ | CH₂—C≡CH | O |
| Ia1.133 | SO₂CH₃ | OC₂H₅ | CH₃ | O |
| Ia1.134 | SO₂CH₃ | OC₂H₅ | C₂H₅ | O |
| Ia1.135 | SO₂CH₃ | OC₂H₅ | CH₂—C≡CH | O |
| Ia1.136 | SO₂CH₃ | H | CH₃ | NH |
| Ia1.137 | SO₂CH₃ | H | C₂H₅ | NH |
| Ia1.138 | SO₂CH₃ | H | CH₂—C≡CH | NH |
| Ia1.139 | SO₂CH₃ | CH₃ | CH₃ | NH |
| Ia1.140 | SO₂CH₃ | CH₃ | C₂H₅ | NH |
| Ia1.141 | SO₂CH₃ | CH₃ | CH₂—C≡CH | NH |
| Ia1.142 | SO₂CH₃ | C₂H₅ | CH₃ | NH |
| Ia1.143 | SO₂CH₃ | C₂H₅ | C₂H₅ | NH |
| Ia1.144 | SO₂CH₃ | C₂H₅ | CH₂—C≡CH | NH |
| Ia1.145 | SO₂CH₃ | OCH₃ | CH₃ | NH |
| Ia1.146 | SO₂CH₃ | OCH₃ | C₂H₅ | NH |
| Ia1.147 | SO₂CH₃ | OCH₃ | CH₂—C≡CH | NH |
| Ia1.148 | SO₂CH₃ | OC₂H₅ | CH₃ | NH |
| Ia1.149 | SO₂CH₃ | OC₂H₅ | C₂H₅ | NH |
| Ia1.150 | SO₂CH₃ | OC₂H₅ | CH₂—C≡CH | NH |
| Ia1.151 | NO₂ | H | CH₃ | O |
| Ia1.152 | NO₂ | H | C₂H₅ | O |
| Ia1.153 | NO₂ | H | CH₂—C≡CH | O |
| Ia1.154 | NO₂ | CH₃ | CH₃ | O |
| Ia1.155 | NO₂ | CH₃ | C₂H₅ | O |
| Ia1.156 | NO₂ | CH₃ | CH₂—C≡CH | O |
| Ia1.157 | NO₂ | C₂H₅ | CH₃ | O |
| Ia1.158 | NO₂ | C₂H₅ | C₂H₅ | O |
| Ia1.159 | NO₂ | C₂H₅ | CH₂—C≡CH | O |
| Ia1.160 | NO₂ | OCH₃ | CH₃ | O |
| Ia1.161 | NO₂ | OCH₃ | C₂H₅ | O |
| Ia1.162 | NO₂ | OCH₃ | CH₂—C≡CH | O |
| Ia1.163 | NO₂ | OC₂H₅ | CH₃ | O |
| Ia1.164 | NO₂ | OC₂H₅ | C₂H₅ | O |
| Ia1.165 | NO₂ | OC₂H₅ | CH₂—C≡CH | O |
| Ia1.166 | NO₂ | H | CH₃ | NH |
| Ia1.167 | NO₂ | H | C₂H₅ | NH |
| Ia1.168 | NO₂ | H | CH₂—C≡CH | NH |
| Ia1.169 | NO₂ | CH₃ | CH₃ | NH |
| Ia1.170 | NO₂ | CH₃ | C₂H₅ | NH |
| Ia1.171 | NO₂ | CH₃ | CH₂—C≡CH | NH |
| Ia1.172 | NO₂ | C₂H₅ | CH₃ | NH |
| Ia1.173 | NO₂ | C₂H₅ | C₂H₅ | NH |
| Ia1.174 | NO₂ | C₂H₅ | CH₂—C≡CH | NH |
| Ia1.175 | NO₂ | OCH₃ | CH₃ | NH |
| Ia1.176 | NO₂ | OCH₃ | C₂H₅ | NH |
| Ia1.177 | NO₂ | OCH₃ | CH₂—C≡CH | NH |
| Ia1.178 | NO₂ | OC₂H₅ | CH₃ | NH |
| Ia1.179 | NO₂ | OC₂H₅ | C₂H₅ | NH |
| Ia1.180 | NO₂ | OC₂H₅ | CH₂—C≡CH | NH |

In addition, the following 4-benzoyl-pyrazoles of the formula I are particularly extraordinarily preferred:

the compounds Ia2, in particular the compounds Ia2.001–Ia2.180, which differ from the corresponding compounds Ia1.001–Ia1.180 by the fact that $R^{11}$ is ethyl:

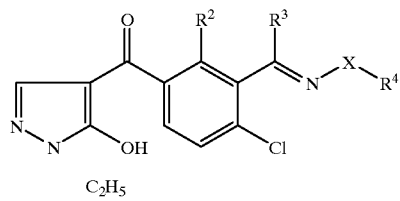

Ia2 the compounds Ia3, in particular the compounds Ia3.001–Ia3.180, which differ from the corresponding compounds Ia1.001–Ia1.180 by the fact that $R^{11}$ is n-propyl:

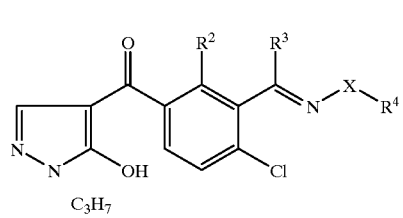

Ia3 the compounds Ia4, in particular the compounds Ia4.001–Ia4.180, which differ from the corresponding compounds Ia1.001–Ia1.180 by the fact that $R^{11}$ is n-butyl:

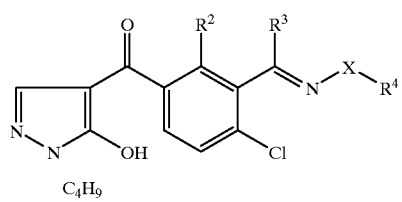

Ia4 the compounds Ia5, in particular the compounds Ia5.001–Ia5.180, which differ from the corresponding compounds Ia1.001–Ia1.180 by the fact that $R^{11}$ is iso-butyl:

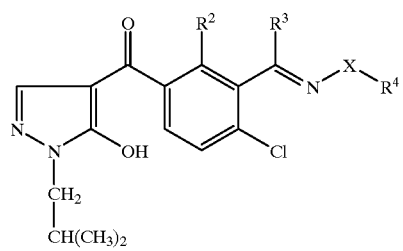

Ia5 the compounds Ia6, in particular the compounds Ia6.001–Ia6.180, which differ from the corresponding compounds Ia1.001–Ia1.180 by the fact that $R^{12}$ is methyl:

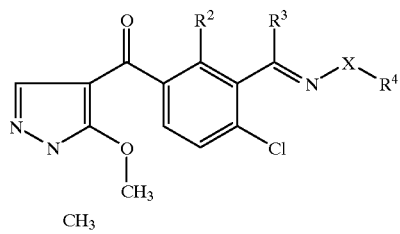

Ia6 the compounds Ia7, in particular the compounds Ia7.001–Ia7.180, which differ from the corresponding compounds Ia1.001–Ia1.180 by the fact that $R^{11}$ is ethyl and $R^{12}$ is methyl:

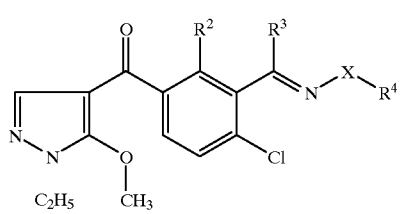

Ia7 the compounds Ia8, in particular the compounds Ia8.001–Ia8.180, which differ from the corresponding compounds Ia1.001–Ia1.180 by the fact that $R^{11}$ is n-propyl and $R^{12}$ is methyl:

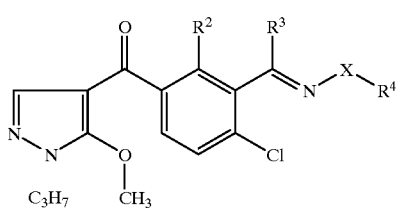

Ia8 the compounds Ia9, in particular the compounds Ia9.001–Ia9.180, which differ from the corresponding compounds Ia1.001–Ia1.180 by the fact that $R^{11}$ is n-butyl and $R^{12}$ is methyl:

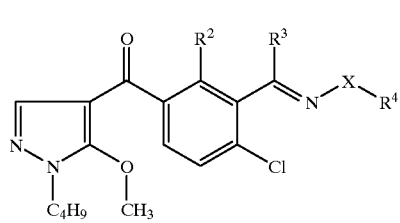

Ia9 the compounds Ia10, in particular the compounds Ia10.001–Ia10.180, which differ from the corresponding compounds Ia1.001–Ia1.180 by the fact that $R^{11}$ is iso-butyl and $R^{12}$ is methyl:

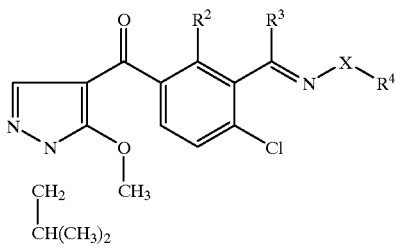

Ia10 the compounds Ia11, in particular the compounds Ia11.001–Ia11.180, which differ from the corresponding compounds Ia1.001–Ia1.180 by the fact that $R^{12}$ is ethyl:

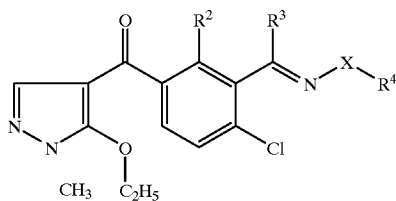

Ia11 the compounds Ia12, in particular the compounds Ia12.001–Ia12.180, which differ from the corresponding compounds Ia1.001–Ia1.180 by the fact that $R^{11}$ and $R^{12}$ are ethyl:

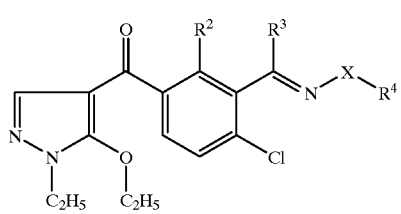

Ia12 the compounds Ia13, in particular the compounds Ia13.001–Ia13.180, which differ from the corresponding compounds Ia1.001–Ia1.180 by the fact that $R^{11}$ is propyl and $R^{12}$ is ethyl:

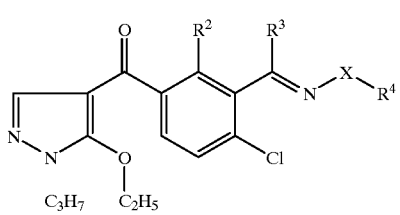

Ia13 the compounds Ia14, in particular the compounds Ia14.001–Ia14.180, which differ from the corresponding compounds Ia1.001–Ia1.180 by the fact that $R^{11}$ is n-butyl and $R^{12}$ is ethyl:

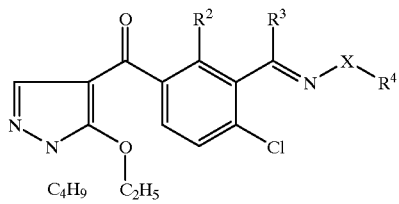

Ia14 the compounds Ia15, in particular the compounds Ia15.001–Ia15.180, which differ from the corresponding compounds Ia1.001–Ia1.180 by the fact that $R^{11}$ is iso-butyl and $R^{12}$ is ethyl:

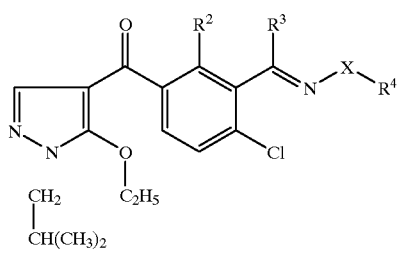

Ia15 the compounds Ia16, in particular the compounds Ia16.001–Ia16.180, which differ from the corresponding compounds Ia1.001–Ia1.180 by the fact that $R^{12}$ is n-propyl:

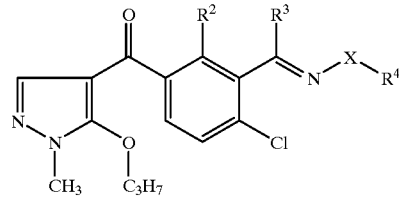

Ia16 the compounds Ia17, in particular the compounds Ia17.001–Ia17.180, which differ from the corresponding compounds Ia1.001–Ia1.180 by the fact that $R^{11}$ is ethyl and $R^{12}$ is n-propyl:

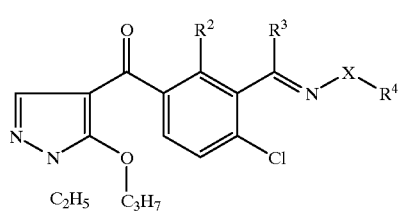

Ia17 the compounds Ia18, in particular the compounds Ia18.001–Ia18.180, which differ from the corresponding compounds Ia1.001–Ia1.180 by the fact that $R^{11}$ and $R^{12}$ are n-propyl:

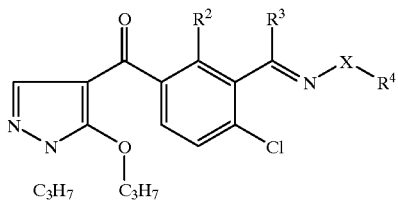

Ia18 the compounds Ia19, in particular the compounds Ia19.001–Ia19.180, which differ from the corresponding compounds Ia1.001–Ia1.180 by the fact that $R^{11}$ is n-butyl and $R^{12}$ is n-propyl:

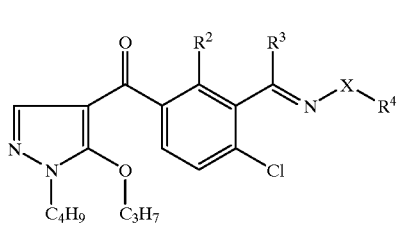

Ia19 the compounds Ia20, in particular the compounds Ia20.001–Ia20.180, which differ from the corresponding compounds Ia1.001–Ia1.180 by the fact that $R^{11}$ is iso-butyl and $R^{12}$ is n-propyl:

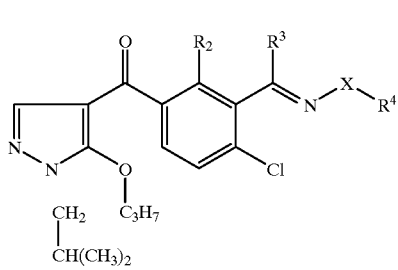

Ia20 the compounds Ia21, in particular the compounds Ia21.001–Ia21.180, which differ from the corresponding compounds Ia1.001–Ia1.180 by the fact that $R^{12}$ is iso-propyl:

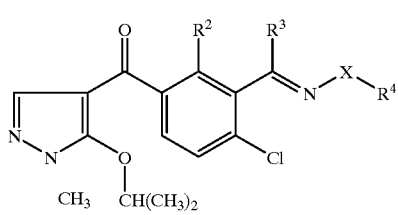

Ia21 the compounds Ia22, in particular the compounds Ia22.001–Ia22.180, which differ from the corresponding compounds Ia1.001–Ia1.180 by the fact that $R^{11}$ is ethyl and $R^{12}$ is iso-propyl:

Ia22 the compounds Ia23, in particular the compounds Ia23.001–Ia23.180, which differ from the corresponding compounds Ia1.001–Ia1.180 by the fact that $R^{11}$ is n-propyl and $R^{12}$ is iso-propyl:

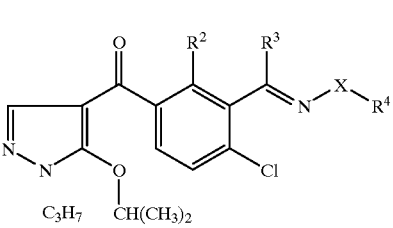

Ia23 the compounds Ia24, in particular the compounds Ia24.001–Ia24.180, which differ from the corresponding compounds Ia1.001–Ia1.180 by the fact that $R^{11}$ is n-butyl and $R^{12}$ is iso-propyl:

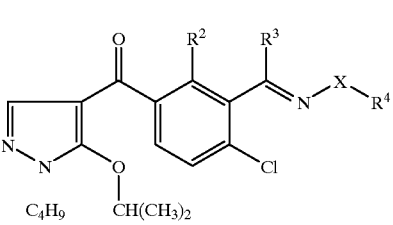

Ia24 the compounds Ia25, in particular the compounds Ia25.001–Ia25.180, which differ from the corresponding compounds Ia1.001–Ia1.180 by the fact that $R^{11}$ is iso-butyl and $R^{12}$ is iso-propyl:

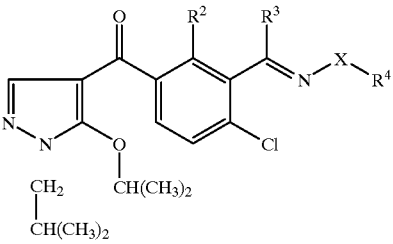

Ia25 the compounds Ia26, in particular the compounds Ia26.001–Ia26.180, which differ from the corresponding compounds Ia1.001–Ia1.180 by the fact that $R^{12}$ is n-butyl:

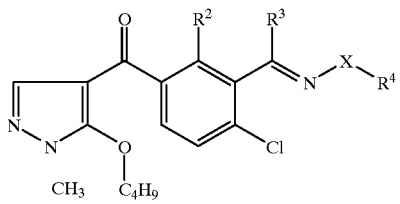
Ia26 the compounds Ia27, in particular the compounds Ia27.001–Ia27.180, which differ from the corresponding compounds Ia1.001–Ia1.180 by the fact that $R^{11}$ is ethyl and $R^{12}$ is n-butyl:

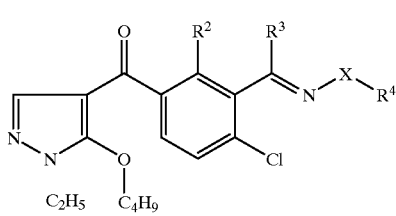
Ia27 the compounds Ia28, in particular the compounds Ia28.001–Ia28.180, which differ from the corresponding compounds Ia1.001–Ia1.180 by the fact that $R^{11}$ is n-propyl and $R^{12}$ is n-butyl:

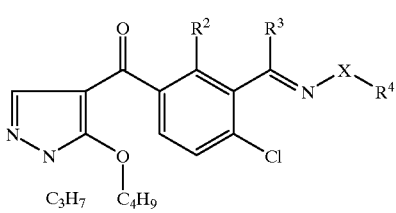
Ia28 the compounds Ia29, in particular the compounds Ia29.001–Ia29.180, which differ from the corresponding compounds Ia1.001–Ia1.180 by the fact that $R^{11}$ and $R^{12}$ are n-butyl:

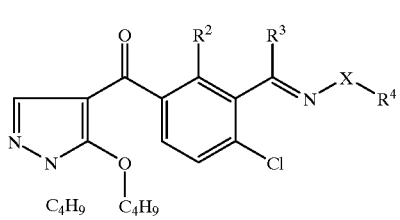
Ia29 the compounds Ia30, in particular the compounds Ia30.001–Ia30.180, which differ from the corresponding compounds Ia1.001–Ia1.180 by the fact that $R^{11}$ is iso-butyl and $R^{12}$ is n-butyl:

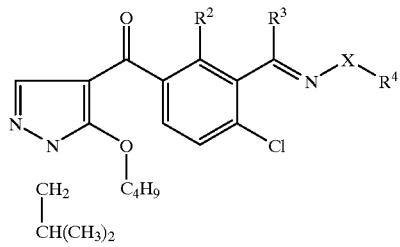
Ia30 the compounds Ia31, in particular the compounds Ia31.001–Ia31.180, which differ from the corresponding compounds Ia1.001–Ia1.180 by the fact that $R^{12}$ is sec-butyl:

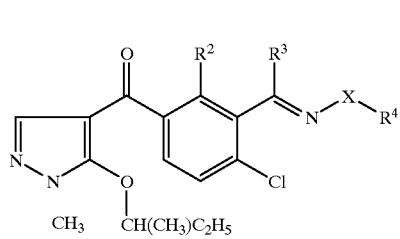
Ia31 the compounds Ia32, in particular the compounds Ia32.001–Ia32.180, which differ from the corresponding compounds Ia1.001–Ia1.180 by the fact that $R^{11}$ is ethyl and $R^{12}$ is sec-butyl:

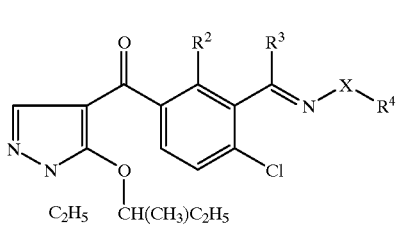
Ia32 the compounds Ia33, in particular the compounds Ia33.001–Ia33.180, which differ from the corresponding compounds Ia1.001–Ia1.180 by the fact that $R^{11}$ is n-propyl and $R^{12}$ is sec-butyl:

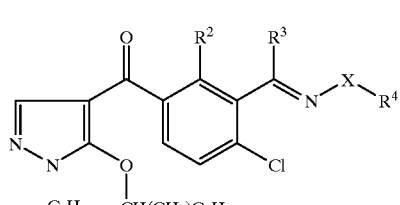
Ia33 the compounds Ia34, in particular the compounds Ia34.001–Ia34.180, which differ from the corresponding compounds Ia1.001–Ia1.180 by the fact that $R^{11}$ is n-butyl and $R^{12}$ is sec-butyl:

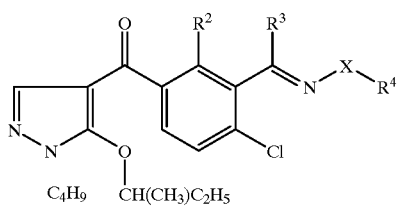

Ia34 the compounds Ia35, in particular the compounds Ia35.001–Ia35.180, which differ from the corresponding compounds Ia1.001–Ia1.180 by the fact that $R^{11}$ is iso-butyl and $R^{12}$ is sec-butyl:

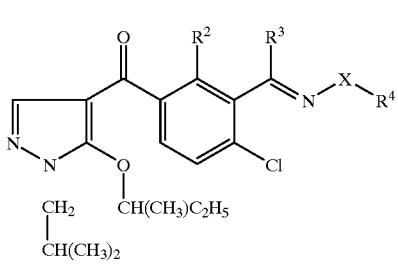

Ia35 the compounds Ia36, in particular the compounds Ia36.001–Ia36.180, which differ from the corresponding compounds Ia1.001–Ia1.180 by the fact that $R^{12}$ is iso-butyl:

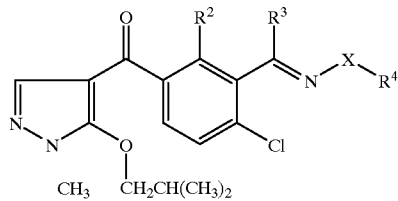

Ia36 the compounds Ia37, in particular the compounds Ia37.001–Ia37.180, which differ from the corresponding compounds Ia1.001–Ia1.180 by the fact that $R^{12}$ is [sic] ethyl and $R^{13}$ is iso-butyl:

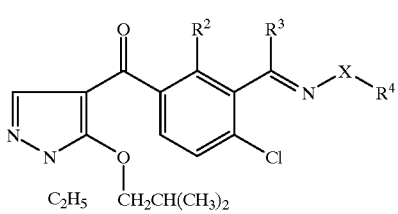

Ia37 the compounds Ia38, in particular the compounds Ia38.001–Ia38.180, which differ from the corresponding compounds Ia1.001–Ia1.180 by the fact that $R^{11}$ is n-propyl and $R^{12}$ is iso-butyl:

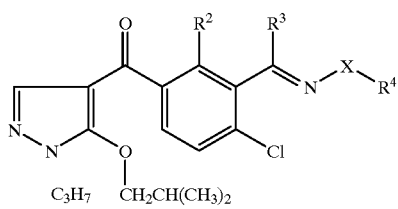

Ia38 the compounds Ia39, in particular the compounds Ia39.001–Ia39.180, which differ from the corresponding compounds Ia1.001–Ia1.180 by the fact that $R^{11}$ is n-butyl and $R^{12}$ is iso-butyl:

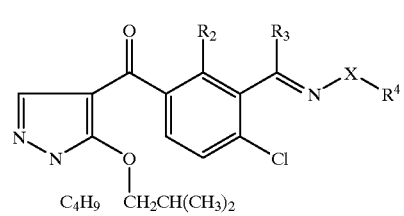

Ia39 the compounds Ia40, in particular the compounds Ia40.001–Ia40.180, which differ from the corresponding compounds Ia1.001–Ia1.180 by the fact that $R^{11}$ and $R^{12}$ are iso-butyl:

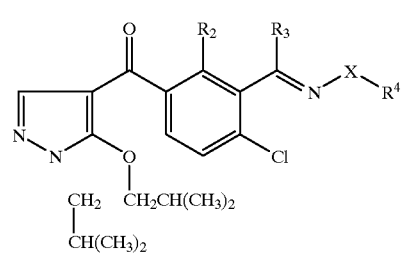

Ia40 the compounds Ia41, in particular the compounds Ia41.001–Ia41.180, which differ from the corresponding compounds Ia1.001–Ia1.180 by the fact that $R^{12}$ is methylcarbonyl:

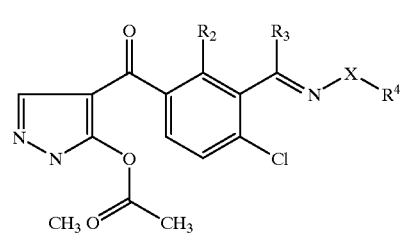

Ia41 the compounds Ia42, in particular the compounds Ia42.001–Ia42.180, which differ from the corresponding compounds Ia1.001–Ia1.180 by the fact that $R^{11}$ is ethyl and $R^{12}$ is methylcarbonyl:

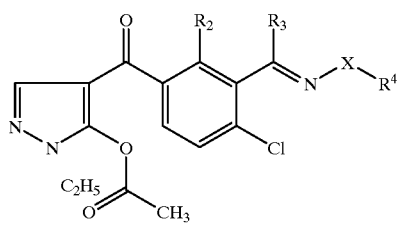

Ia42 the compounds Ia43, in particular the compounds Ia43.001–Ia43.180, which differ from the corresponding compounds Ia1.001–Ia1.180 by the fact that $R^{11}$ is propyl and $R^{12}$ is methylcarbonyl:

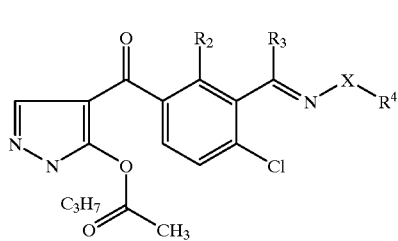

Ia43 the compounds Ia44, in particular the compounds Ia44.001–Ia44.180, which differ from the corresponding compounds Ia1.001–Ia1.180 by the fact that $R^{11}$ is n-butyl and $R^{12}$ is methylcarbonyl:

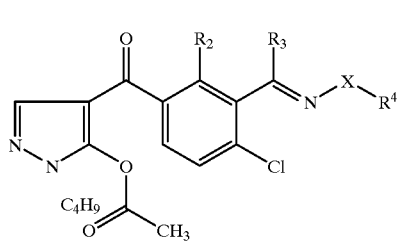

Ia44 the compounds Ia45, in particular the compounds Ia45.001–Ia45.180, which differ from the corresponding compounds Ia1.001–Ia1.180 by the fact that $R^{11}$ is iso-butyl and $R^{12}$ is methylcarbonyl:

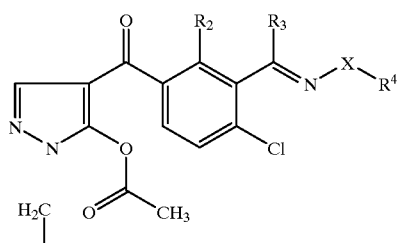

Ia45 the compounds Ia46, in particular the compounds Ia46.001–Ia46.180, which differ from the corresponding compounds Ia1.001–Ia1.180 by the fact that $R^{12}$ is ethylcarbonyl:

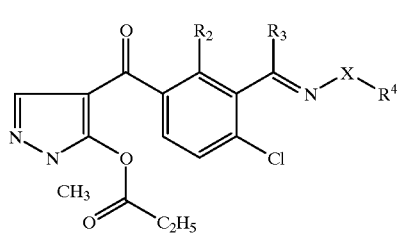

Ia46 the compounds Ia47, in particular the compounds Ia47.001–Ia47.180, which differ from the corresponding compounds Ia1.001–Ia1.180 by the fact that $R^{11}$ is ethyl and $R^{12}$ is ethylcarbonyl:

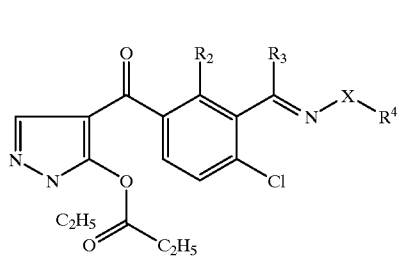

Ia47 the compounds Ia48, in particular the compounds Ia48.001–Ia48.180, which differ from the corresponding compounds Ia1.001–Ia1.180 by the fact that $R^{11}$ is propyl and $R^{12}$ is ethylcarbonyl:

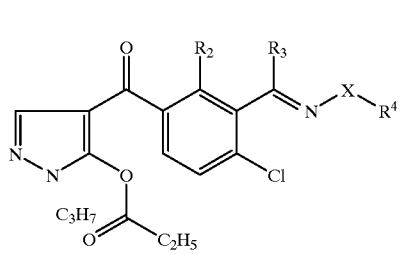

Ia48 the compounds Ia49, in particular the compounds Ia49.001–Ia49.180, which differ from the corresponding compounds Ia1.001–Ia1.180 by the fact that $R^{11}$ is n-butyl and $R^{12}$ is ethylcarbonyl:

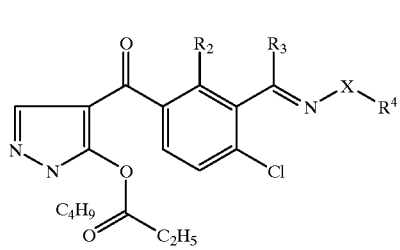

Ia49 the compounds Ia50, in particular the compounds Ia50.001–Ia50.180, which differ from the corresponding compounds Ia1.001–Ia1.180 by the fact that $R^{11}$ is iso-butyl and $R^{12}$ is ethylcarbonyl:

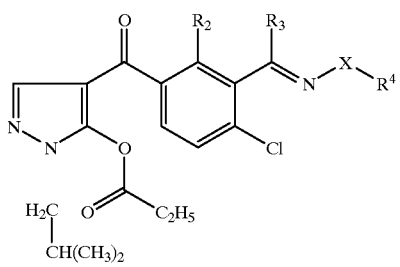

Ia50 the compounds Ia51, in particular the compounds Ia51.001–Ia51.180, which differ from the corresponding compounds Ia1.001–Ia1.180 by the fact that $R^{12}$ is n-propylcarbonyl:

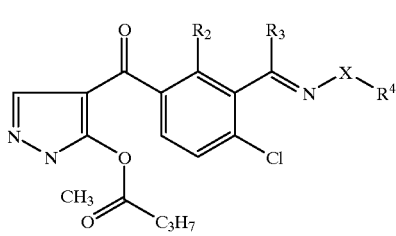

Ia51 the compounds Ia52, in particular the compounds Ia52.001–Ia52.180, which differ from the corresponding compounds Ia1.001–Ia1.180 by the fact that $R^{11}$ is ethyl and $R^{12}$ is n-propylcarbonyl:

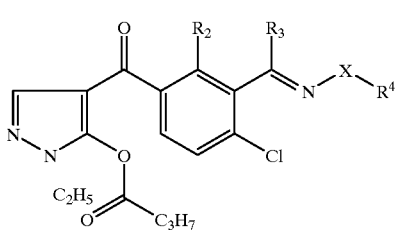

Ia52 the compounds Ia53, in particular the compounds Ia53.001–Ia53.180, which differ from the corresponding compounds Ia1.001–Ia1.180 by the fact that $R^{11}$ is propyl and $R^{12}$ is n-propylcarbonyl:

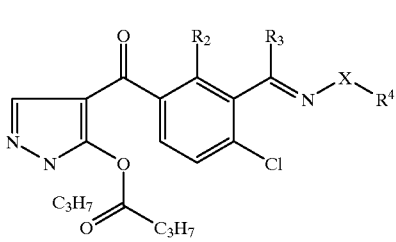

Ia53 the compounds Ia54, in particular the compounds Ia54.001–Ia54.180, which differ from the corresponding compounds Ia1.001–Ia1.180 by the fact that $R^{11}$ is n-butyl and $R^{12}$ is n-propylcarbonyl:

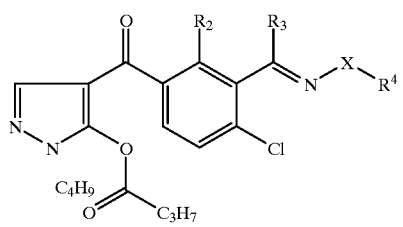

Ia54 the compounds Ia55, in particular the compounds Ia55.001–Ia55.180, which differ from the corresponding compounds Ia1.001–Ia1.180 by the fact that $R^{11}$ is iso-butyl and $R^{12}$ is n-propylcarbonyl:

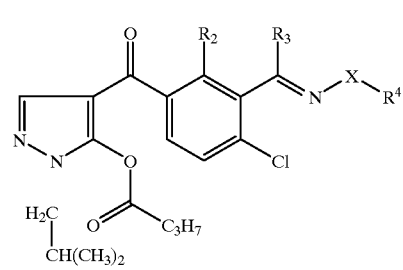

Ia55 the compounds Ia56, in particular the compounds Ia56.001–Ia56.180, which differ from the corresponding compounds Ia1.001–Ia1.180 by the fact that $R^{12}$ is trifluoromethylcarbonyl:

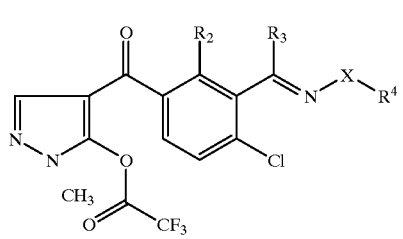

Ia56 the compounds Ia57, in particular the compounds Ia57.001–Ia57.180, which differ from the corresponding compounds Ia1.001–Ia1.180 by the fact that $R^{11}$ is ethyl and $R^{12}$ is trifluoromethylcarbonyl:

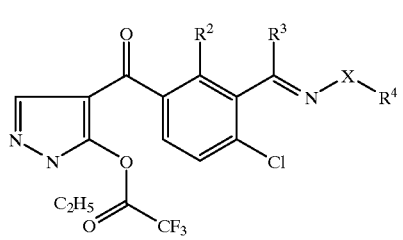

Ia57 the compounds Ia58, in particular the compounds Ia58.001–Ia58.180, which differ from the corresponding compounds Ia1.001–Ia1.180 by the fact that $R^{11}$ is n-propyl and $R^{12}$ is trifluoromethylcarbonyl:

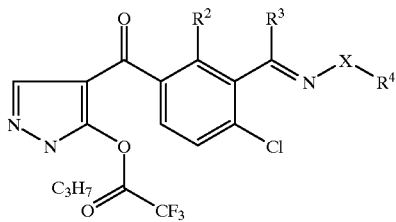

Ia58

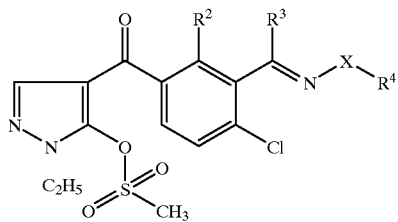

Ia62 the compounds Ia59, in particular the compounds Ia59.001–Ia59.180, which differ from the corresponding compounds Ia1.001–Ia1.180 by the fact that $R^{11}$ is n-butyl and $R^{12}$ is trifluoromethylcarbonyl:

the compounds Ia63, in particular the compounds Ia63.001–Ia63.180, which differ from the corresponding compounds Ia1.001–Ia1.180 by the fact that $R^{11}$ is n-propyl and $R^{12}$ is methylsulfonyl:

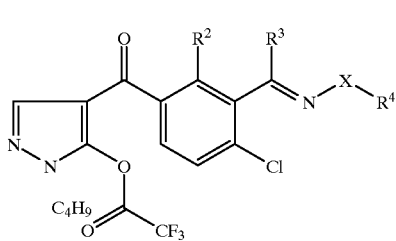

Ia59

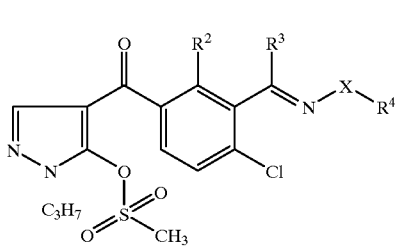

Ia63 the compounds Ia60, in particular the compounds Ia60.001–Ia60.180, which differ from the corresponding compounds Ia1.001–Ia1.180 by the fact that $R^{11}$ is iso-butyl and $R^{12}$ is trifluoromethylcarbonyl:

the compounds Ia64, in particular the compounds Ia64.001–Ia64.180, which differ from the corresponding compounds Ia1.001–Ia1.180 by the fact that $R^{11}$ is n-butyl and $R^{12}$ is methylsulfonyl:

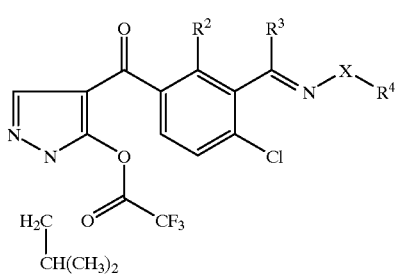

Ia60

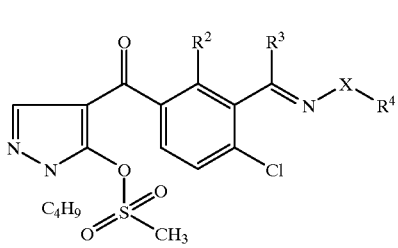

Ia64 the compounds Ia61, in particular the compounds Ia61.001–Ia61.180, which differ from the corresponding compounds Ia1.001–Ia1.180 by the fact that $R^{12}$ is methylsulfonyl:

the compounds Ia65, in particular the compounds Ia65.001–Ia65.180, which differ from the corresponding compounds Ia1.001–Ia1.180 by the fact that $R^{11}$ is iso-butyl and $R^{12}$ is methylsulfonyl:

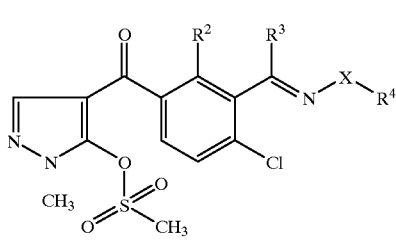

Ia61

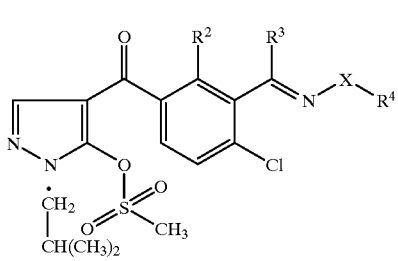

Ia65 the compounds Ia62, in particular the compounds Ia62.001–Ia62.180, which differ from the corresponding compounds Ia1.001–Ia1.180 by the fact that $R^{11}$ is ethyl and $R^{12}$ is methylsulfonyl:

the compounds Ia66, in particular the compounds Ia66.001–Ia66.180, which differ from the corresponding compounds Ia1.001–Ia1.180 by the fact that $R^{12}$ is ethylsulfonyl:

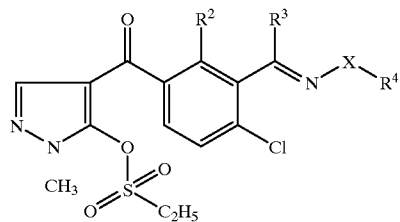

Ia66 the compounds Ia67, in particular the compounds Ia67.001–Ia67.180, which differ from the corresponding compounds Ia1.001–Ia1.180 by the fact that $R^{11}$ is ethyl and $R^{12}$ is ethylsulfonyl:

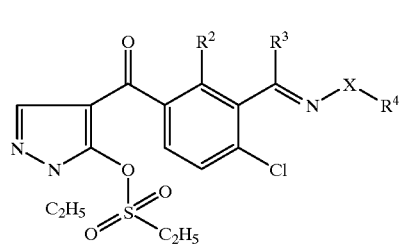

Ia67 the compounds Ia68, in particular the compounds Ia68.001–Ia68.180, which differ from the corresponding compounds Ia1.001–Ia1.180 by the fact that $R^{11}$ is propyl and $R^{12}$ is ethylsulfonyl:

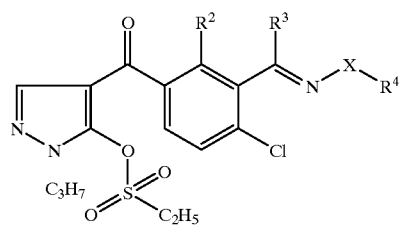

Ia68 the compounds Ia69, in particular the compounds Ia69.001–Ia69.180, which differ from the corresponding compounds Ia1.001–Ia1.180 by the fact that $R^{11}$ is n-butyl and $R^{12}$ is ethylsulfonyl:

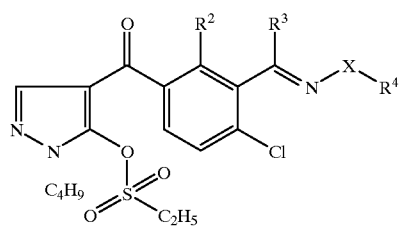

Ia69 the compounds Ia70, in particular the compounds Ia70.001–Ia70.180, which differ from the corresponding compounds Ia1.001–Ia1.180 by the fact that $R^{11}$ is iso-butyl and $R^{12}$ is ethylsulfonyl:

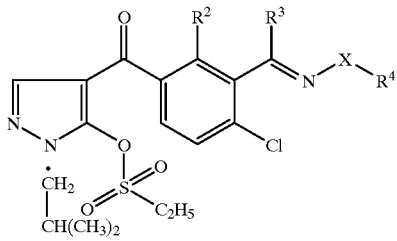

Ia70 the compounds Ia71, in particular the compounds Ia71.001–Ia71.180, which differ from the corresponding compounds Ia1.001–Ia1.180 by the fact that $R^{12}$ is n-propylsulfonyl:

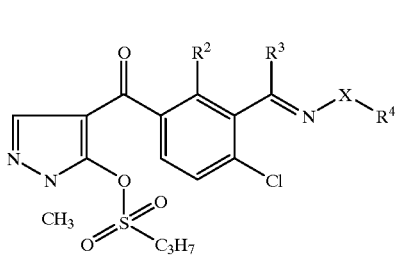

Ia71 the compounds Ia72, in particular the compounds Ia72.001–Ia72.180, which differ from the corresponding compounds Ia1.001–Ia1.180 by the fact that $R^{11}$ is ethyl and $R^{12}$ is n-propylsulfonyl:

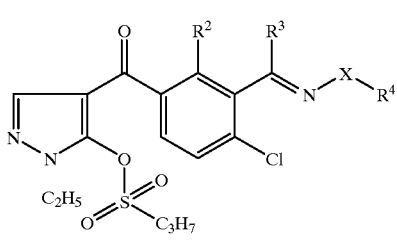

Ia72 the compounds Ia73, in particular the compounds Ia73.001–Ia73.180, which differ from the corresponding compounds Ia1.001–Ia1.180 by the fact that $R^{11}$ is n-propyl and $R^{12}$ is n-propylsulfonyl:

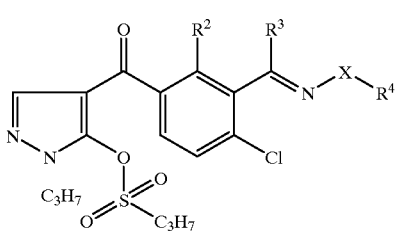

Ia73 the compounds Ia74, in particular the compounds Ia74.001–Ia74.180, which differ from the corresponding compounds Ia1.001–Ia1.180 by the fact that $R^{11}$ is n-butyl and $R^{12}$ is n-propylsulfonyl:

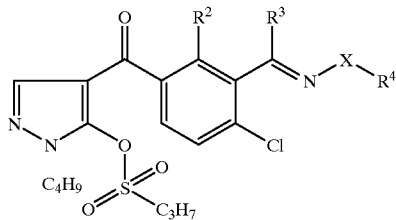

Ia74 the compounds Ia75, in particular the compounds Ia75.001–Ia75.180, which differ from the corresponding compounds Ia1.001–Ia1.180 by the fact that $R^{11}$ is iso-butyl and $R^{12}$ is n-propylsulfonyl:

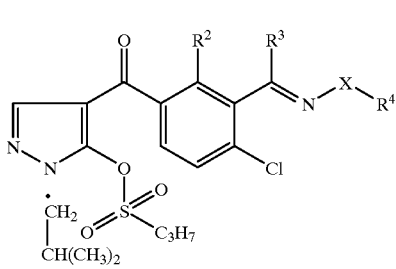

Ia75 the compounds Ia76, in particular the compounds Ia76.001–Ia76.180, which differ from the corresponding compounds Ia1.001–Ia1.180 by the fact that $R^{12}$ is iso-propylsulfonyl:

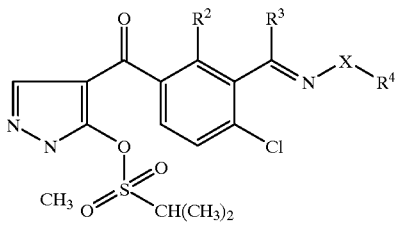

Ia76 the compounds Ia77, in particular the compounds Ia77.001–Ia77.180, which differ from the corresponding compounds Ia1.001–Ia1.180 by the fact that $R^{11}$ is ethyl and $R^{12}$ is iso-propylsulfonyl:

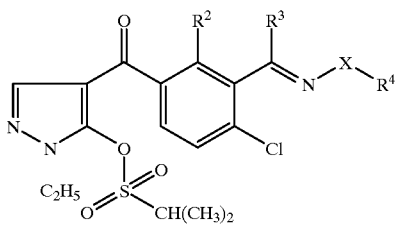

Ia77 the compounds Ia78, in particular the compounds Ia78.001–Ia78.180, which differ from the corresponding compounds Ia1.001–Ia1.180 by the fact that $R^{11}$ is propyl and $R^{12}$ is iso-propylsulfonyl:

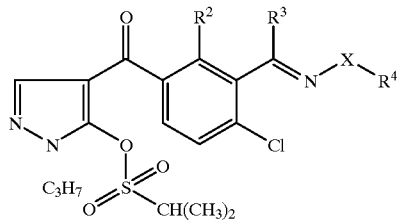

Ia78 the compounds Ia79, in particular the compounds Ia79.001–Ia79.180, which differ from the corresponding compounds Ia1.001–Ia1.180 by the fact that $R^{11}$ is n-butyl and $R^{12}$ is iso-propylsulfonyl:

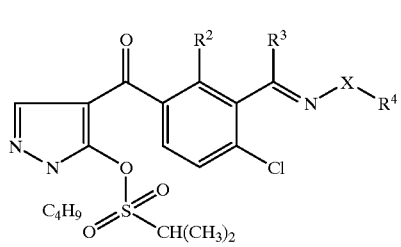

Ia79 the compounds Ia80, in particular the compounds Ia80.001–Ia80.180, which differ from the corresponding compounds Ia1.001–Ia1.180 by the fact that $R^{11}$ is iso-butyl and $R^{12}$ is iso-propylsulfonyl:

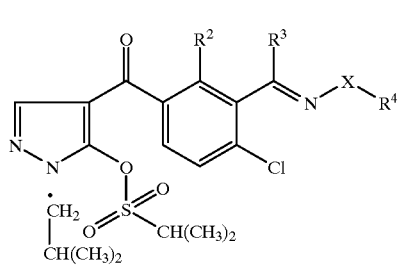

Ia80 the compounds Ia81, in particular the compounds Ia81.001–Ia81.180, which differ from the corresponding compounds Ia1.001–Ia1.180 by the fact that $R^{12}$ is n-butylsulfonyl:

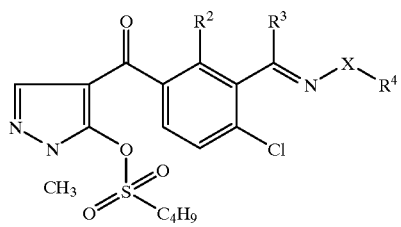

Ia81 the compounds Ia82, in particular the compounds Ia82.001–Ia82.180, which differ from the corresponding compounds Ia1.001–Ia1.180 by the fact that $R^{11}$ is ethyl and $R^{12}$ is n-butylsulfonyl:

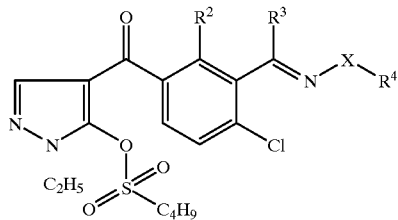

Ia82 the compounds Ia83, in particular the compounds Ia83.001–Ia83.180, which differ from the corresponding compounds Ia1.001–Ia1.180 by the fact that $R^{11}$ is n-propyl and $R^{12}$ is n-butylsulfonyl:

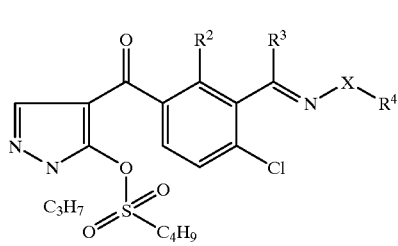

Ia83 the compounds Ia84, in particular the compounds Ia84.001–Ia84.180, which differ from the corresponding compounds Ia1.001–Ia1.180 by the fact that $R^{11}$ is n-butyl and $R^{12}$ is n-butylsulfonyl:

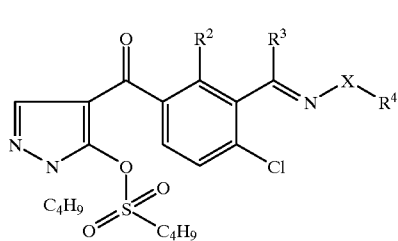

Ia84 the compounds Ia85, in particular the compounds Ia85.001–Ia85.180, which differ from the corresponding compounds Ia1.001–Ia1.180 by the fact that $R^{11}$ is iso-butyl and $R^{12}$ is n-butylsulfonyl:

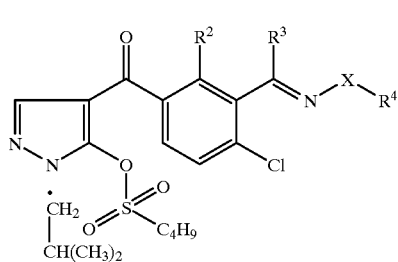

Ia85 the compounds Ia86, in particular the compounds Ia86.001–Ia86.180, which differ from the corresponding compounds Ia1.001–Ia1.180 by the fact that $R^{12}$ is iso-butylsulfonyl:

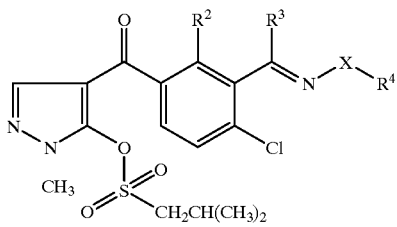

Ia86 the compounds Ia87, in particular the compounds Ia87.001–Ia87.180, which differ from the corresponding compounds Ia1.001–Ia1.180 by the fact that $R^{11}$ is ethyl and $R^{12}$ is iso-butylsulfonyl:

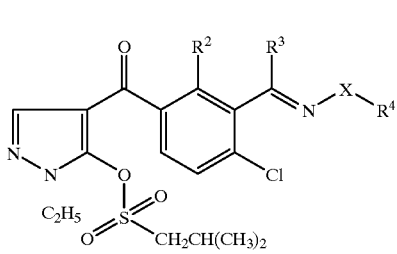

Ia87 the compounds Ia88, in particular the compounds Ia88.001–Ia88.180, which differ from the corresponding compounds Ia1.001–Ia1.180 by the fact that $R^{11}$ is n-propyl and $R^{12}$ is iso-butylsulfonyl:

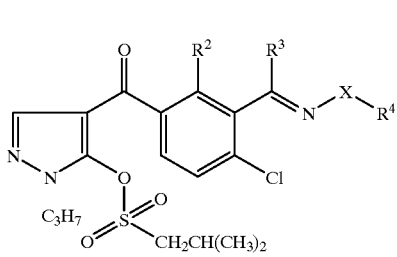

Ia88 the compounds Ia89, in particular the compounds Ia89.001–Ia89.180, which differ from the corresponding compounds Ia1.001–Ia1.180 by the fact that $R^{11}$ is n-butyl and $R^{12}$ is iso-butylsulfonyl:

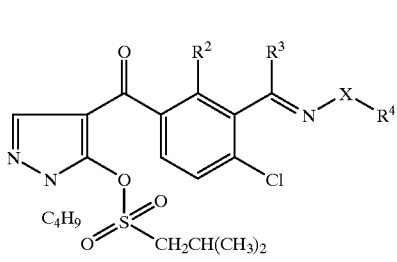

Ia89 the compounds Ia90, in particular the compounds Ia90.001–Ia90.180, which differ from the corresponding compounds Ia1.001–Ia1.180 by the fact that $R^{11}$ is iso-butyl and $R^{12}$ is iso-butylsulfonyl:

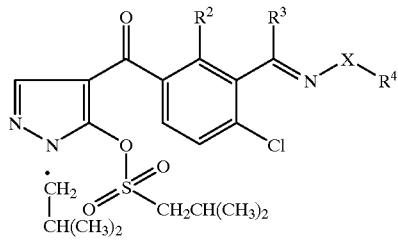

Ia90 the compounds Ia91, in particular the compounds Ia91.001–Ia91.180, which differ from the corresponding compounds Ia1.001–Ia1.180 by the fact that $R^{12}$ is sec-butylsulfonyl:

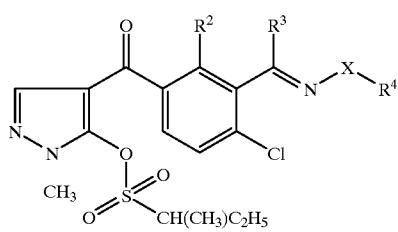

Ia91 the compounds Ia92, in particular the compounds Ia92.001–Ia92.180, which differ from the corresponding compounds Ia1.001–Ia1.180 by the fact that $R^{11}$ is ethyl and $R^{12}$ is sec-butylsulfonyl:

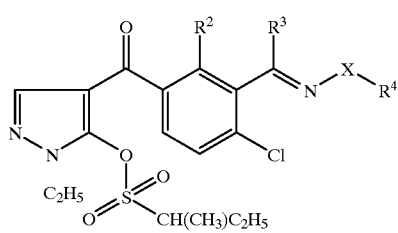

Ia92 the compounds Ia93, in particular the compounds Ia93.001–Ia93.180, which differ from the corresponding compounds Ia1.001–Ia1.180 by the fact that $R^{11}$ is n-propyl and $R^{12}$ is sec-butylsulfonyl:

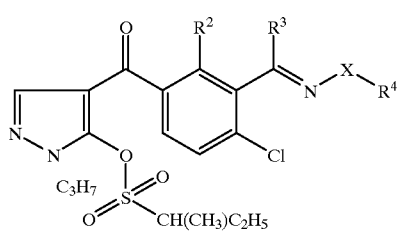

Ia93 the compounds Ia94, in particular the compounds Ia94.001–Ia94.180, which differ from the corresponding compounds Ia1.001–Ia1.180 by the fact that $R^{11}$ is n-butyl and $R^{12}$ is sec-butylsulfonyl:

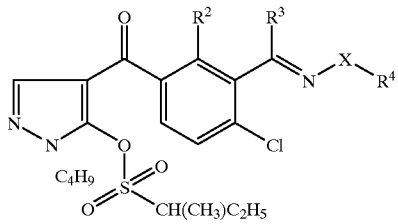

Ia94 the compounds Ia95, in particular the compounds Ia95.001–Ia95.180, which differ from the corresponding compounds Ia1.001–Ia1.180 by the fact that $R^{11}$ is iso-butyl and $R^{12}$ is sec-butylsulfonyl:

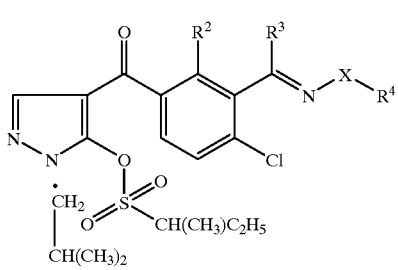

Ia95 the compounds Ia96, in particular the compounds Ia96.001–Ia96.180, which differ from the corresponding compounds Ia1.001–Ia1.180 by the fact that $R^{12}$ is trifluoromethylsulfonyl:

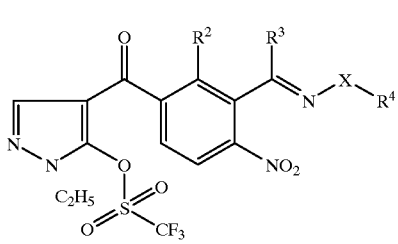

Ia96 the compounds Ia97, in particular the compounds Ia97.001–Ia97.180, which differ from the corresponding compounds Ia1.001–Ia1.180 by the fact that $R^{11}$ is ethyl and $R^{12}$ is trifluoromethylsulfonyl:

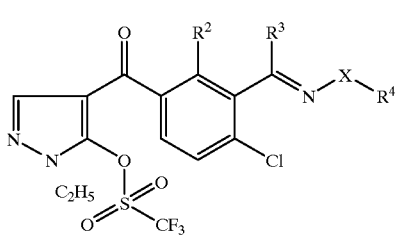

Ia97 the compounds Ia98, in particular the compounds Ia98.001–Ia98.180, which differ from the corresponding compounds Ia1.001–Ia1.180 by the fact that $R^{11}$ is n-propyl and $R^{12}$ is trifluoromethylsulfonyl:

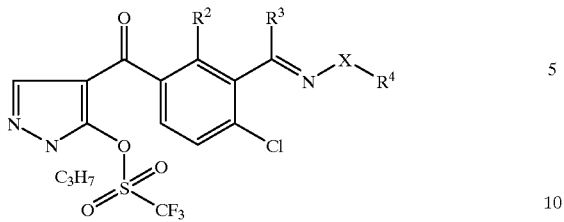

Ia98 the compounds Ia99, in particular the compounds Ia99.001–Ia99.180, which differ from the corresponding compounds Ia1.001–Ia1.180 by the fact that $R^{11}$ is n-butyl and $R^{12}$ is trifluoromethylsulfonyl:

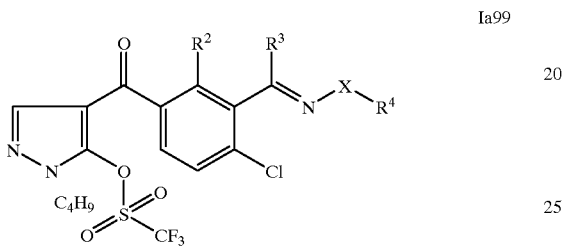

Ia99 the compounds Ia100, in particular the compounds Ia100.001–Ia100.180, which differ from the corresponding compounds Ia1.001–Ia1.180 by the fact that $R^{11}$ is iso-butyl and $R^{12}$ is trifluoromethylsulfonyl:

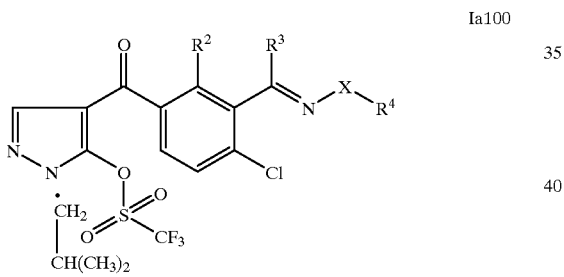

Ia100 the compounds Ia101, in particular the compounds Ia101.001–Ia101.180, which differ from the corresponding compounds Ia1.001–Ia1.180 by the fact that $R^{12}$ is phenylcarbonylmethyl:

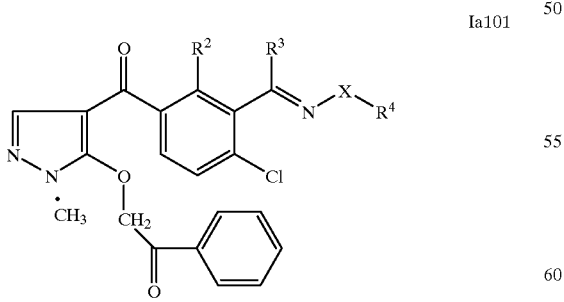

Ia101 the compounds Ia102, in particular the compounds Ia102.001–Ia102.180, which differ from the corresponding compounds Ia1.001–Ia1.180 by the fact that $R^{11}$ is ethyl and $R^{12}$ is phenylcarbonylmethyl:

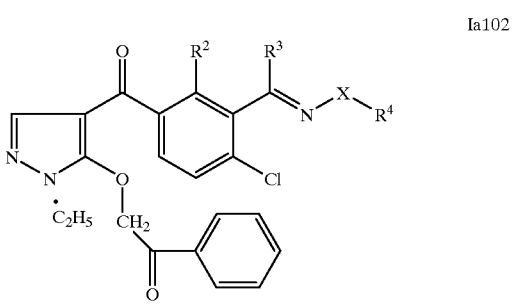

Ia102 the compounds Ia103, in particular the compounds Ia103.001–Ia103.180, which differ from the corresponding compounds Ia1.001–Ia1.180 by the fact that $R^{11}$ is n-propyl and $R^{12}$ is phenylcarbonylmethyl:

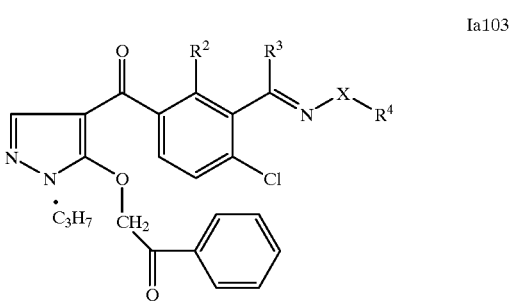

Ia103 the compounds Ia104, in particular the compounds Ia104.001–Ia104.180, which differ from the corresponding compounds Ia1.001–Ia1.180 by the fact that $R^{11}$ is n-butyl and $R^{12}$ is phenylcarbonylmethyl:

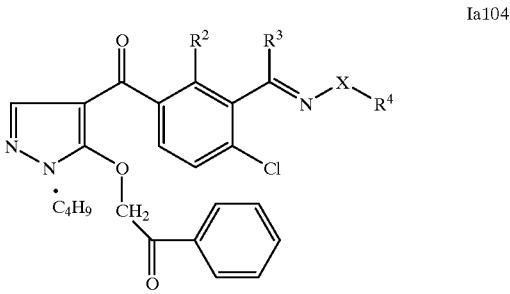

Ia104 the compounds Ia105, in particular the compounds Ia105.001–Ia105.180, which differ from the corresponding compounds Ia1.001–Ia1.180 by the fact that $R^{11}$ is iso-butyl and $R^{12}$ is phenylcarbonylmethyl:

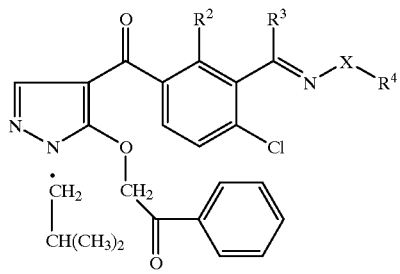

Ia105 the compounds Ia106, in particular the compounds Ia106.001–Ia106.180, which differ from the corresponding compounds Ia1.001–Ia1.180 by the fact that $R^{12}$ is phenylsulfonyl:

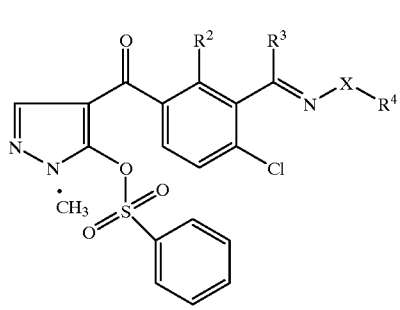

Ia106 the compounds Ia107, in particular the compounds Ia107.001–Ia107.180, which differ from the corresponding compounds Ia1.001–Ia1.180 by the fact that $R^{11}$ is ethyl and $R^{12}$ is phenylsulfonyl:

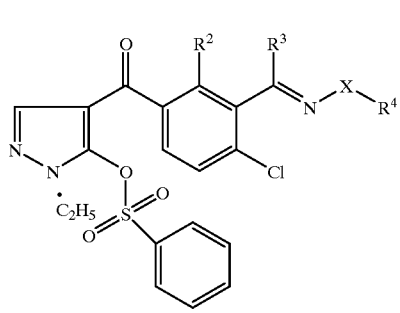

Ia107 the compounds Ia108, in particular the compounds Ia108.001–Ia108.180, which differ from the corresponding compounds Ia1.001–Ia1.180 by the fact that $R^{11}$ is n-propyl and $R^{12}$ is phenylsulfonyl:

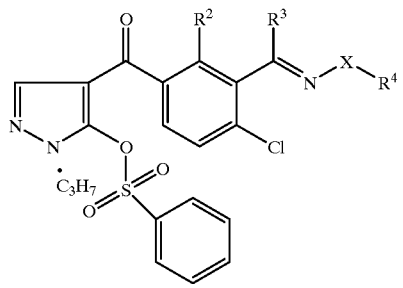

Ia108 the compounds Ia109, in particular the compounds Ia109.001–Ia109.180, which differ from the corresponding compounds Ia1.001–Ia1.180 by the fact that $R^{11}$ is n-butyl and $R^{12}$ is phenylsulfonyl:

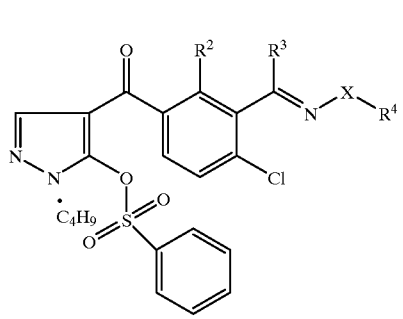

Ia109 the compounds Ia110, in particular the compounds Ia110.001–Ia110.180, which differ from the corresponding compounds Ia1.001–Ia1.180 by the fact that $R^{11}$ is iso-butyl and $R^{12}$ is phenylsulfonyl:

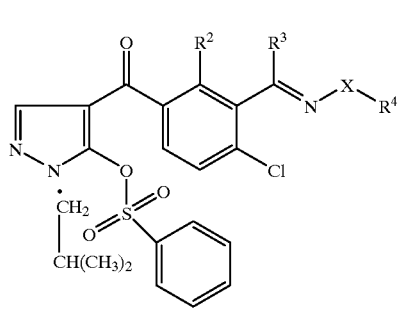

Ia110 the compounds Ia111, in particular the compounds Ia111.001–Ia111.180, which differ from the corresponding compounds Ia1.001–Ia1.180 by the fact that $R^{12}$ is 4-methylphenylsulfonyl:

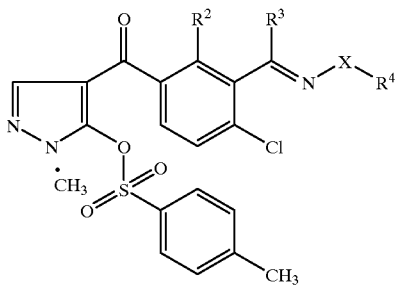

Ia111 the compounds Ia112, in particular the compounds Ia112.001–Ia112.180, which differ from the corresponding compounds Ia1.001–Ia1.180 by the fact that $R^{11}$ is ethyl and $R^{12}$ is 4-methylphenylsulfonyl:

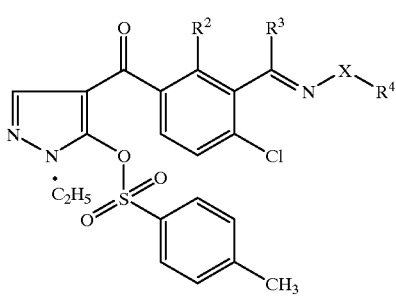

Ia112 the compounds Ia113, in particular the compounds Ia113.001–Ia113.180, which differ from the corresponding compounds Ia1.001–Ia1.180 by the fact that $R^{11}$ is n-propyl and $R^{12}$ is 4-methylphenylsulfonyl:

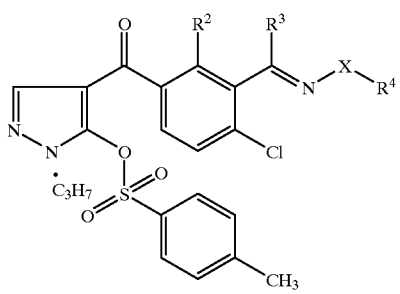

Ia113 the compounds Ia114, in particular the compounds Ia114.001–Ia114.180, which differ from the corresponding compounds Ia1.001–Ia1.180 by the fact that $R^{11}$ is n-butyl and $R^{12}$ is 4-methylphenylsulfonyl:

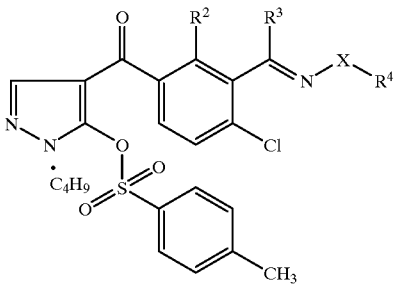

Ia114 the compounds Ia115, in particular the compounds Ia115.001–Ia115.180, which differ from the corresponding compounds Ia1.001–Ia1.180 by the fact that $R^{11}$ is iso-butyl and $R^{12}$ is 4-methylphenylsulfonyl:

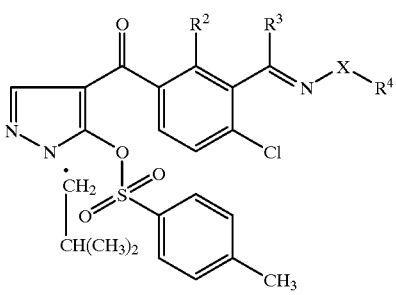

Ia115 the compounds Ia116, in particular the compounds Ia116.001–Ia116.180, which differ from the corresponding compounds Ia1.001–Ia1.180 by the fact that $R^1$ is nitro:

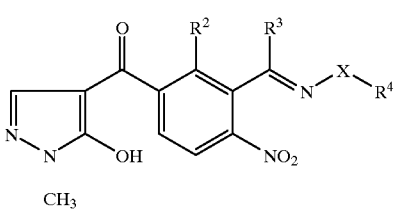

Ia116 the compounds Ia117, in particular the compounds Ia117.001–Ia117.180, which differ from the corresponding compounds Ia1.001–Ia1.180 by the fact that $R^1$ is nitro and $R^{11}$ is ethyl:

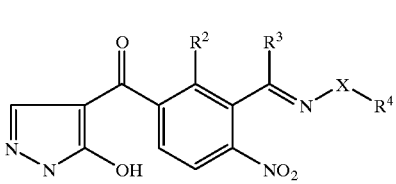

Ia117 the compounds Ia118, in particular the compounds Ia118.001–Ia118.180, which differ from the corresponding compounds Ia1.001–Ia1.180 by the fact that $R^1$ is nitro and $R^{11}$ is propyl:

Ia118

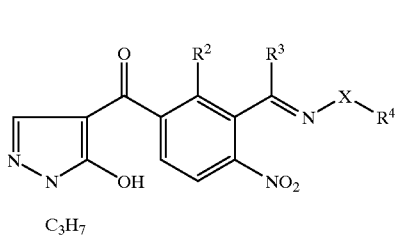

the compounds Ia119, in particular the compounds Ia119.001–Ia119.180, which differ from the corresponding compounds Ia1.001–Ia1.180 by the fact that $R^1$ is nitro and $R^{11}$ is n-butyl:

Ia119

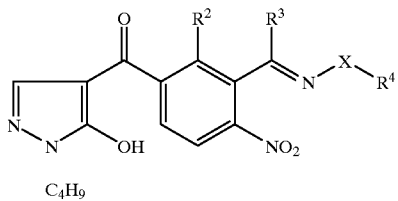

the compounds Ia120, in particular the compounds Ia120.001–Ia120.180, which differ from the corresponding compounds Ia1.001–Ia1.180 by the fact that $R^1$ is nitro and $R^{11}$ is iso-butyl:

Ia120

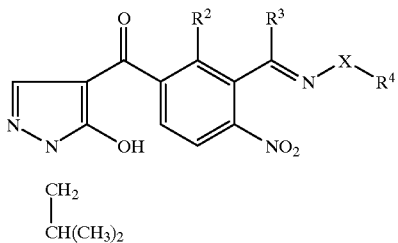

the compounds Ia121, in particular the compounds Ia121.001–Ia121.180, which differ from the corresponding compounds Ia1.001–Ia1.180 by the fact that $R^1$ is nitro and $R^{12}$ is methyl:

Ia121

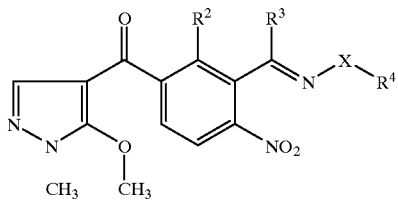

the compounds Ia122, in particular the compounds Ia122.001–Ia122.180, which differ from the corresponding compounds Ia1.001–Ia1.180 by the fact that $R^1$ is nitro, $R^{11}$ is ethyl and $R^{12}$ is methyl:

Ia122

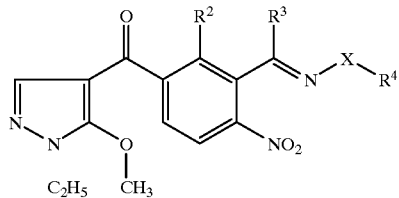

the compounds Ia123, in particular the compounds Ia123.001–Ia123.180, which differ from the corresponding compounds Ia1.001–Ia1.180 by the fact that $R^1$ is nitro, $R^{11}$ is n-propyl and $R^{12}$ is methyl:

Ia123

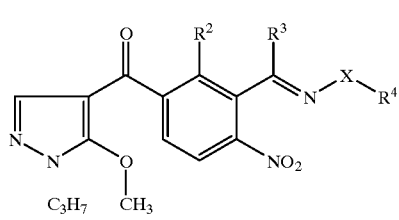

the compounds Ia124, in particular the compounds Ia124.001–Ia124.180, which differ from the corresponding compounds Ia1.001–Ia1.180 by the fact that $R^1$ is nitro, $R^{11}$ is n-butyl and $R^{12}$ is methyl:

Ia124

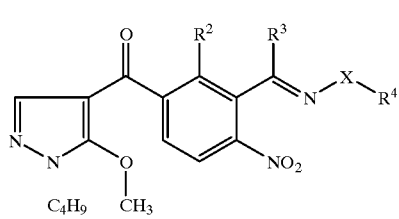

the compounds Ia125, in particular the compounds Ia125.001–Ia125.180, which differ from the corresponding compounds Ia1.001–Ia1.180 by the fact that $R^1$ is nitro, $R^{11}$ is iso-butyl and $R^{12}$ is methyl:

Ia125

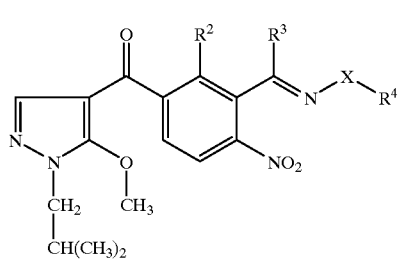

the compounds Ia126, in particular the compounds Ia126.001–Ia126.180, which differ from the corresponding compounds Ia1.001–Ia1.180 by the fact that $R^1$ is nitro and $R^{12}$ is ethyl:

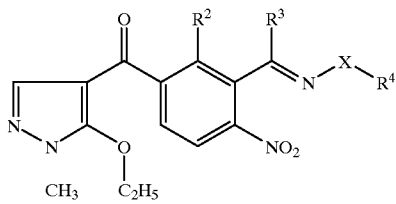
Ia126 the compounds Ia127, in particular the compounds Ia127.001–Ia127.180, which differ from the corresponding compounds Ia1.001–Ia1.180 by the fact that $R^1$ is nitro and $R^{11}$ and $R^{12}$ are ethyl:

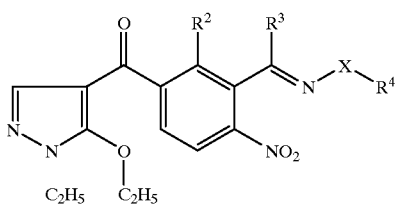
Ia127 the compounds Ia128, in particular the compounds Ia128.001–Ia128.180, which differ from the corresponding compounds Ia1.001–Ia1.180 by the fact that $R^1$ is nitro, $R^{11}$ is n-propyl and $R^{12}$ is ethyl:

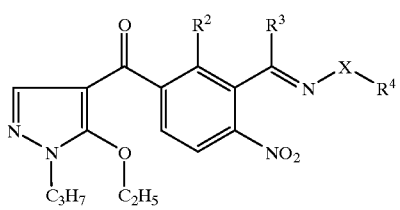
Ia128 the compounds Ia129, in particular the compounds Ia129.001–Ia129.180, which differ from the corresponding compounds Ia1.001–Ia1.180 by the fact that $R^1$ is nitro, $R^{11}$ is n-butyl and $R^{12}$ is ethyl:

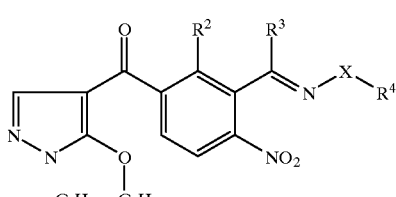
Ia129 the compounds Ia130, in particular the compounds Ia130.001–Ia130.180, which differ from the corresponding compounds Ia1.001–Ia1.180 by the fact that $R^1$ is nitro, $R^{11}$ is iso-butyl and $R^{12}$ is ethyl:

Ia130
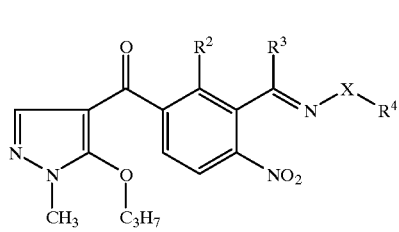

the compounds Ia131, in particular the compounds Ia131.001–Ia131.180, which differ from the corresponding compounds Ia1.001–Ia1.180 by the fact that $R^1$ is nitro and $R^{12}$ is n-propyl:

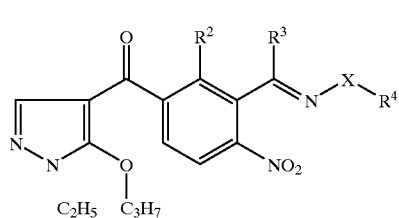
Ia131 the compounds Ia132, in particular the compounds Ia132.001–Ia132.180, which differ from the corresponding compounds Ia1.001–Ia1.180 by the fact that $R^1$ is nitro, $R^{11}$ is ethyl and $R^{12}$ is n-propyl:

Ia132 the compounds Ia133, in particular the compounds Ia133.001–Ia133.180, which differ from the corresponding compounds Ia1.001–Ia1.180 by the fact that $R^1$ is is [sic] nitro and $R^{11}$ and $R^{12}$ are n-propyl:

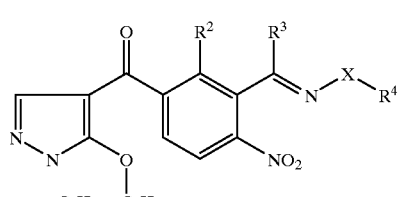
Ia133 the compounds Ia134, in particular the compounds Ia134.001–Ia134.180, which differ from the corresponding compounds Ia1.001–Ia1.180 by the fact that $R^1$ is nitro, $R^{11}$ is n-butyl and $R^{12}$ is n-propyl:

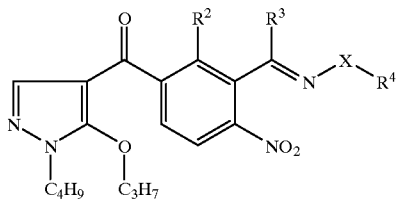

Ia134

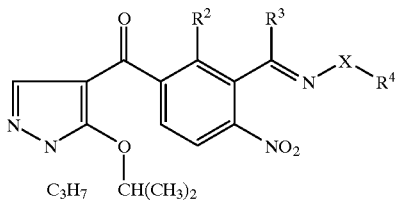

Ia138 the compounds Ia135, in particular the compounds Ia135.001–Ia135.180, which differ from the corresponding compounds Ia1.001–Ia1.180 by the fact that $R^1$ is nitro, $R^{11}$ is iso-butyl and $R^{12}$ is n-propyl:

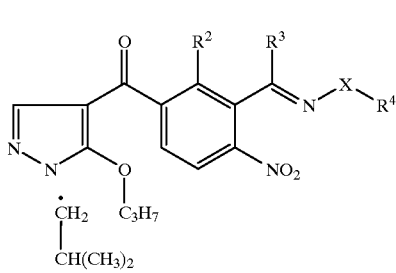

Ia135 the compounds Ia136, in particular the compounds Ia136.001–Ia136.180, which differ from the corresponding compounds Ia1.001–Ia1.180 by the fact that $R^1$ is nitro and $R^{12}$ is iso-propyl:

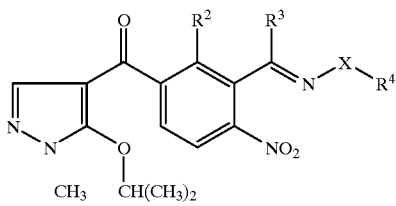

Ia136 the compounds Ia137, in particular the compounds Ia137.001–Ia137.180, which differ from the corresponding compounds Ia1.001–Ia1.180 by the fact that $R^1$ is nitro, $R^{11}$ is ethyl and $R^{12}$ is iso-propyl:

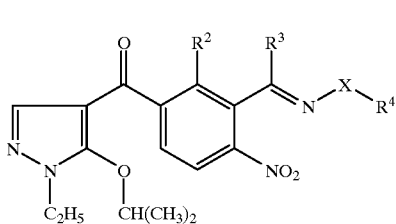

Ia137 the compounds Ia138, in particular the compounds Ia138.001–Ia318.180, which differ from the corresponding compounds Ia1.001–Ia1.180 by the fact that $R^1$ is nitro, $R^{11}$ is n-propyl and $R^{12}$ is iso-propyl:

the compounds Ia139, in particular the compounds Ia139.001–Ia139.180, which differ from the corresponding compounds Ia1.001–Ia1.180 by the fact that $R^1$ is nitro, $R^{11}$ is n-butyl and $R^{12}$ is iso-propyl:

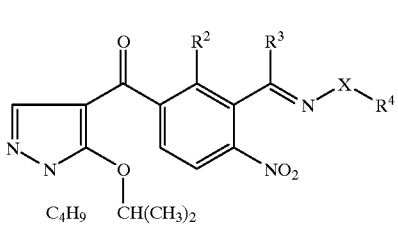

Ia139 the compounds Ia140, in particular the compounds Ia140.001–Ia140.180, which differ from the corresponding compounds Ia1.001–Ia1.180 by the fact that $R^1$ is nitro, $R^{11}$ is iso-butyl and $R^{12}$ is iso-propyl:

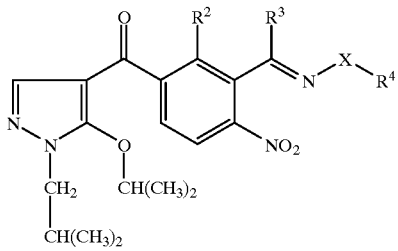

Ia140 the compounds Ia141, in particular the compounds Ia141.001–Ia141.180, which differ from the corresponding compounds Ia1.001–Ia1.180 by the fact that $R^1$ is nitro and $R^{12}$ is n-butyl:

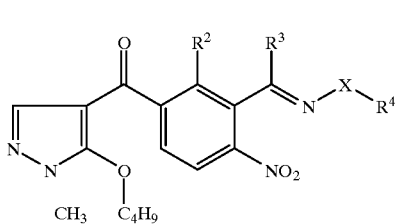

Ia141 the compounds Ia142, in particular the compounds Ia142.001–Ia142.180, which differ from the corresponding compounds Ia1.001–Ia1.180 by the fact that $R^1$ is nitro, $R^{11}$ is ethyl and $R^{12}$ is n-butyl:

Ia142

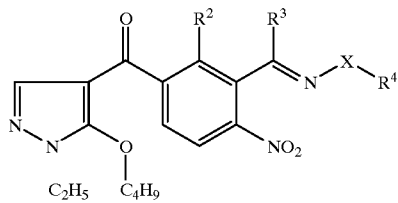

the compounds Ia143, in particular the compounds Ia143.001–Ia143.180, which differ from the corresponding compounds Ia1.001–Ia1.180 by the fact that $R^1$ is nitro, $R^{11}$ is n-propyl and $R^{12}$ is n-butyl:

Ia143

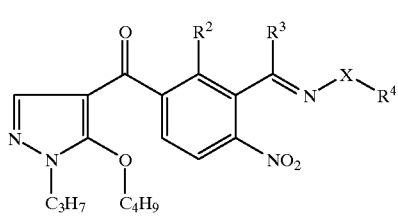

the compounds Ia144, in particular the compounds Ia144.001–Ia144.180, which differ from the corresponding compounds Ia1.001–Ia1.180 by the fact that $R^1$ is nitro and $R^{11}$ and $R^{12}$ are n-butyl:

Ia144

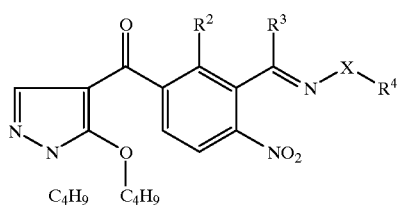

the compounds Ia145, in particular the compounds Ia145.001–Ia145.180, which differ from the corresponding compounds Ia1.001–Ia1.180 by the fact that $R^1$ is nitro, $R^{11}$ is iso-butyl and $R^{12}$ is n-butyl:

Ia145

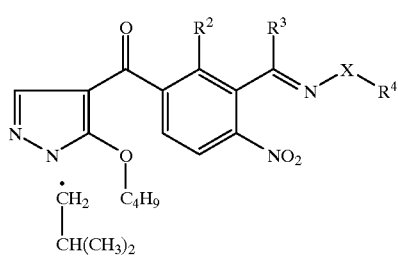

the compounds Ia146, in particular the compounds Ia146.001–Ia146.180, which differ from the corresponding compounds Ia1.001–Ia1.180 by the fact that $R^1$ is nitro and $R^{12}$ is sec-butyl:

Ia146

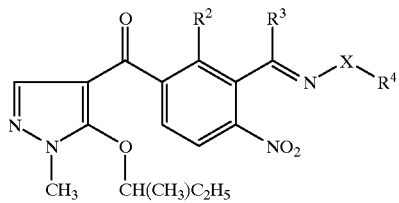

the compounds Ia147, in particular the compounds Ia147.001–Ia147.180, which differ from the corresponding compounds Ia1.001–Ia1.180 by the fact that $R^1$ is nitro, $R^{11}$ is ethyl and $R^{12}$ is sec-butyl:

Ia147

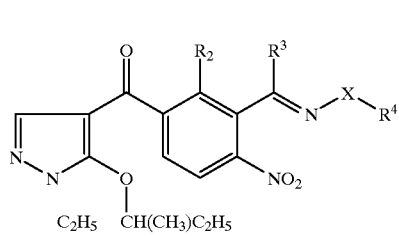

the compounds Ia148, in particular the compounds Ia148.001–Ia148.180, which differ from the corresponding compounds Ia1.001–Ia1.180 by the fact that $R^1$ is nitro, $R^{11}$ is n-propyl and $R^{12}$ is sec-butyl:

Ia148

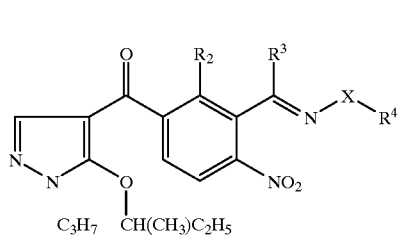

the compounds Ia149, in particular the compounds Ia149.001–Ia149.180, which differ from the corresponding compounds Ia1.001–Ia1.180 by the fact that $R^1$ is nitro, $R^{11}$ is n-butyl and $R^{12}$ is sec-butyl:

Ia149

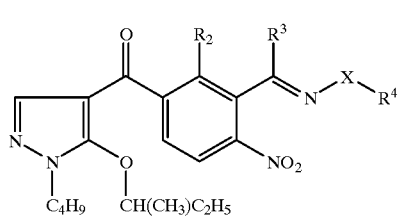

the compounds Ia150, in particular the compounds Ia150.001–Ia150.180, which differ from the corresponding compounds Ia1.001–Ia1.180 by the fact that $R^1$ is nitro, $R^{11}$ is iso-butyl and $R^{12}$ is sec-butyl:

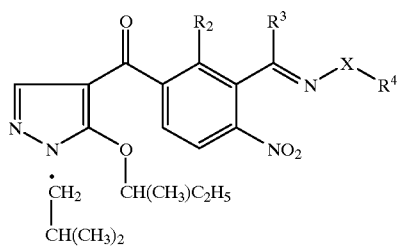
Ia150 the compounds Ia11, in particular the compounds Ia151.001–Ia151.180, which differ from the corresponding compounds Ia1.001–Ia1.180 by the fact that $R^1$ is nitro and $R^{12}$ is iso-butyl:

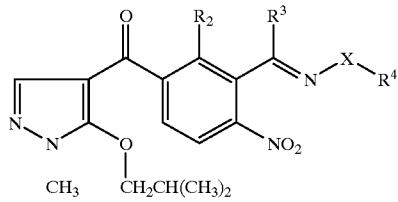
Ia151 the compounds Ia152, in particular the compounds Ia152.001–Ia152.180, which differ from the corresponding compounds Ia1.001–Ia1.180 by the fact that $R^1$ is nitro, $R^{11}$ is ethyl and $R^{12}$ is iso-butyl:

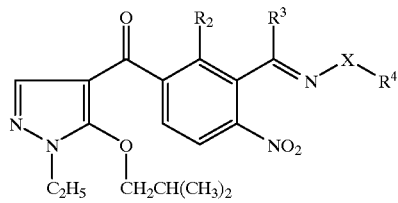
Ia152 the compounds Ia153, in particular the compounds Ia153.001–Ia153.180, which differ from the corresponding compounds Ia1.001–Ia1.180 by the fact that $R^1$ is nitro, $R^{11}$ is n-propyl and $R^{12}$ is iso-butyl:

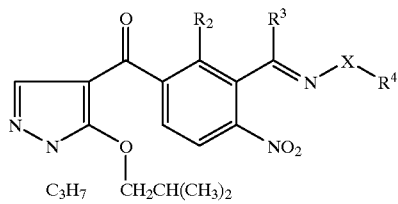
Ia153 the compounds Ia154, in particular the compounds Ia154.001–Ia154.180, which differ from the corresponding compounds Ia1.001–Ia1.180 by the fact that $R^1$ is nitro, $R^{11}$ is n-butyl and $R^{12}$ is iso-butyl:

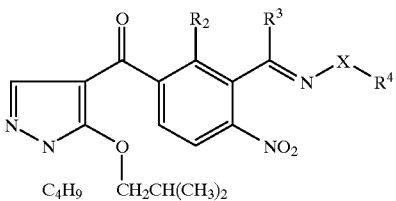
Ia154 the compounds Ia155, in particular the compounds Ia155.001–Ia154.180 [sic], which differ from the corresponding compounds Ia1.001–Ia1.180 by the fact that $R^1$ is nitro and $R^{11}$ and $R^{12}$ are iso-butyl:

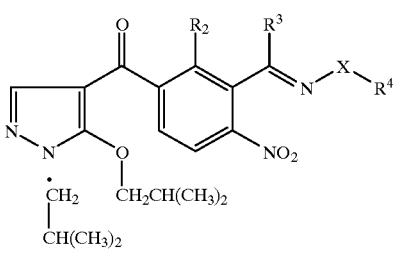
Ia155 the compounds Ia156, in particular the compounds Ia156.001–Ia156.180, which differ from the corresponding compounds Ia1.001–Ia1.180 by the fact that $R^1$ is nitro and $R^{12}$ is methylcarbonyl:

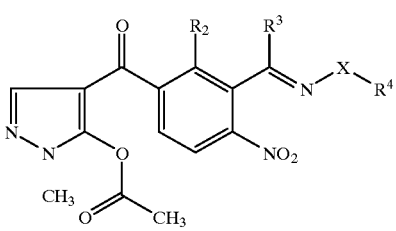
Ia156 the compounds Ia157, in particular the compounds Ia157.001–Ia157.180, which differ from the corresponding compounds Ia1.001–Ia1.180 by the fact that $R^1$ is nitro, $R^{11}$ is ethyl and $R^{12}$ is methylcarbonyl:

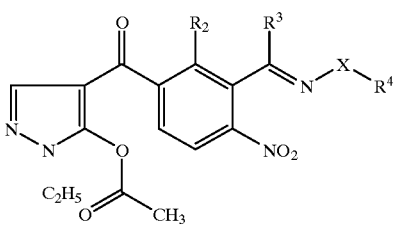
Ia157 the compounds Ia158, in particular the compounds Ia158.001–Ia158.180, which differ from the corresponding compounds Ia1.001–Ia1.180 by the fact that $R^1$ is nitro, $R^{11}$ is n-propyl and $R^{12}$ is methylcarbonyl:

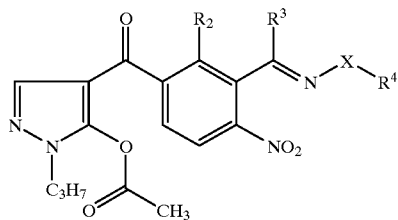
Ia158

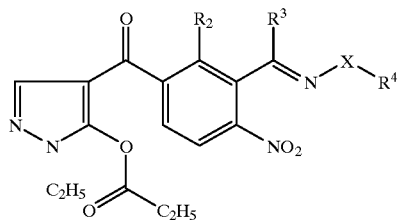
Ia162 the compounds Ia159, in particular the compounds Ia159.001–Ia159.180, which differ from the corresponding compounds Ia1.001–Ia1.180 by the fact that $R^1$ is nitro, $R^{11}$ is n-butyl and $R^{12}$ is methylcarbonyl:

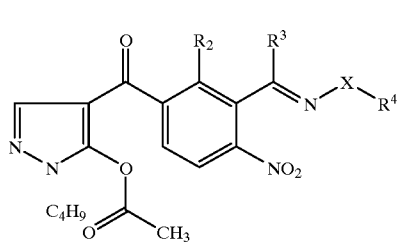
Ia159 the compounds Ia163, in particular the compounds Ia163.001–Ia163.180, which differ from the corresponding compounds Ia1.001–Ia1.180 by the fact that $R^1$ is nitro, $R^{11}$ is n-propyl and $R^{12}$ is ethylcarbonyl:

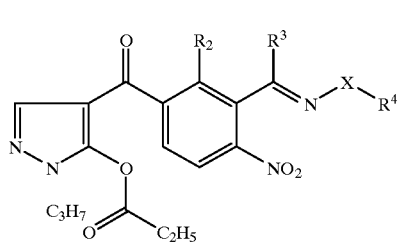
Ia163 the compounds Ia160, in particular the compounds Ia160.001–Ia160.180, which differ from the corresponding compounds Ia1.001–Ia1.180 by the fact that $R^1$ is nitro, $R^{11}$ is iso-butyl and $R^{12}$ is methylcarbonyl:

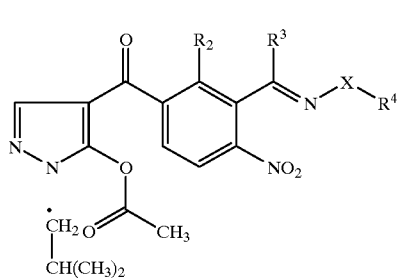
Ia160 the compounds Ia164, in particular the compounds Ia164.001–Ia164.180, which differ from the corresponding compounds Ia1.001–Ia1.180 by the fact that $R^1$ is nitro, $R^{11}$ is n-butyl and $R^{12}$ is ethylcarbonyl:

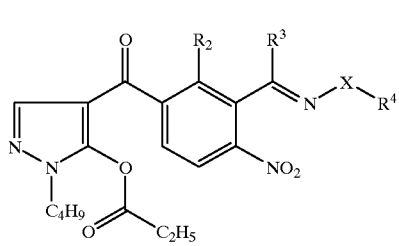
Ia164 the compounds Ia161, in particular the compounds Ia161.001–Ia160.180, which differ from the corresponding compounds Ia1.001–Ia1.180 by the fact that $R^1$ is nitro and $R^{12}$ is ethylcarbonyl:

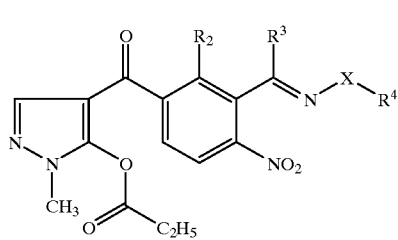
Ia161 the compounds Ia165, in particular the compounds Ia165.001–Ia165.180, which differ from the corresponding compounds Ia1.001–Ia1.180 by the fact that $R^1$ is nitro, $R^{11}$ is iso-butyl and $R^{12}$ is ethylcarbonyl:

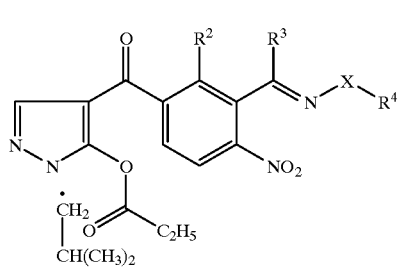
Ia165 the compounds Ia162, in particular the compounds Ia162.001–Ia162.180, which differ from the corresponding compounds Ia1.001–Ia1.180 by the fact that $R^1$ is nitro, $R^{11}$ is ethyl and $R^{12}$ is ethylcarbonyl:

the compounds Ia166, in particular the compounds Ia166.001–Ia166.180, which differ from the corresponding compounds Ia1.001–Ia1.180 by the fact that $R^1$ is nitro and $R^{12}$ is n-propylcarbonyl:

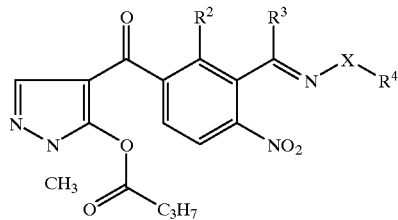

Ia166 the compounds Ia167, in particular the compounds Ia167.001–Ia167.180, which differ from the corresponding compounds Ia1.001–Ia1.180 by the fact that $R^1$ is nitro, $R^{11}$ is ethyl and $R^{12}$ is n-propylcarbonyl:

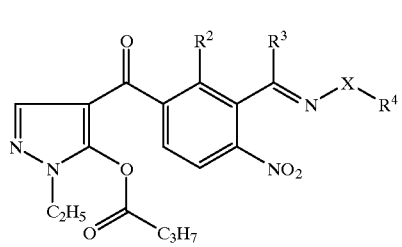

Ia167 the compounds Ia168, in particular the compounds Ia168.001–Ia168.180, which differ from the corresponding compounds Ia1.001–Ia1.180 by the fact that $R^1$ is nitro, $R^{11}$ is n-propyl and $R^{12}$ is n-propylcarbonyl:

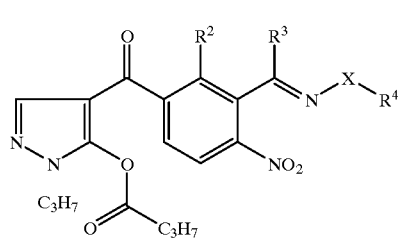

Ia168 the compounds Ia169, in particular the compounds Ia169.001–Ia169.180, which differ from the corresponding compounds Ia1.001–Ia1.180 by the fact that $R^1$ is nitro, $R^{11}$ is n-butyl and $R^{12}$ is n-propylcarbonyl:

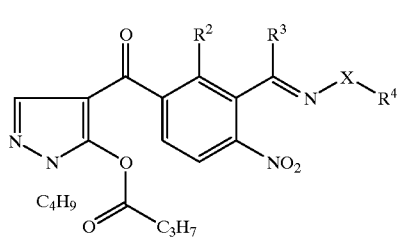

Ia169 the compounds Ia170, in particular the compounds Ia170.001–Ia170.180, which differ from the corresponding compounds Ia1.001–Ia1.180 by the fact that $R^1$ is nitro, $R^{11}$ is iso-butyl and $R^{12}$ is n-propylcarbonyl:

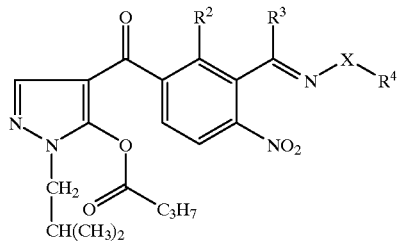

Ia170 the compounds Ia171, in particular the compounds Ia171.001–Ia171.180, which differ from the corresponding compounds Ia1.001–Ia1.180 by the fact that $R^1$ is nitro and $R^{12}$ is trifluoromethylcarbonyl:

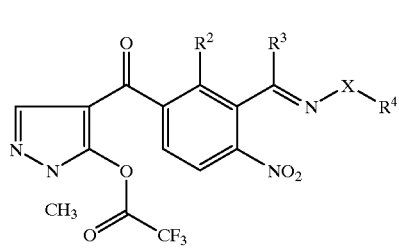

Ia171 the compounds Ia172, in particular the compounds Ia172.001–Ia172.180, which differ from the corresponding compounds Ia1.001–Ia1.180 by the fact that $R^1$ is nitro, $R^{11}$ is ethyl and $R^{12}$ is trifluoromethylcarbonyl:

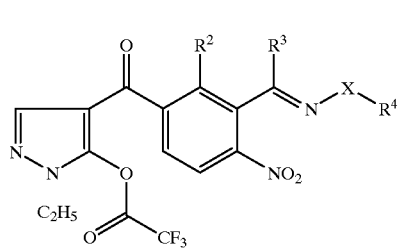

Ia172 the compounds Ia173, in particular the compounds Ia173.001–Ia173.180, which differ from the corresponding compounds Ia1.001–Ia1.180 by the fact that $R^1$ is nitro, $R^{11}$ is n-propyl and $R^{12}$ is trifluoromethylcarbonyl:

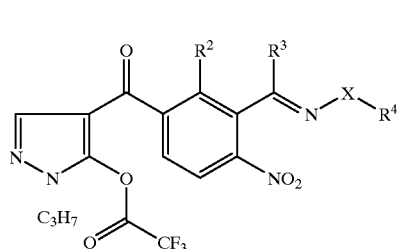

Ia173 the compounds Ia174, in particular the compounds Ia174.001–Ia174.180, which differ from the corresponding compounds Ia1.001–Ia1.180 by the fact that $R^1$ is nitro, $R^{11}$ is n-butyl and $R^{12}$ is trifluoromethylcarbonyl [sic]:

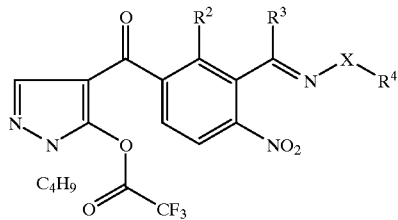

Ia174

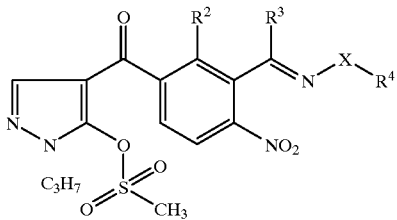

Ia178 the compounds Ia175, in particular the compounds Ia175.001–Ia175.180, which differ from the corresponding compounds Ia1.001–Ia1.180 by the fact that $R^1$ is nitro, $R^{11}$ is iso-butyl and $R^{12}$ is trifluoromethylcarbonyl:

the compounds Ia179, in particular the compounds Ia179.001–Ia179.180, which differ from the corresponding compounds Ia1.001–Ia1.180 by the fact that $R^1$ is nitro, $R^{11}$ is n-butyl and $R^{12}$ is methylsulfonyl:

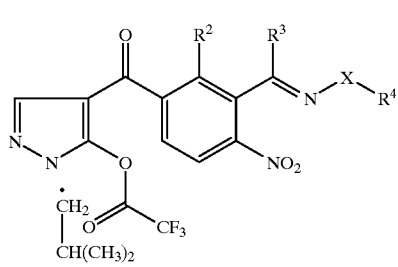

Ia175

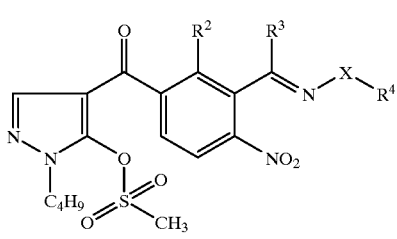

Ia179 the compounds Ia176, in particular the compounds Ia176.001–Ia176.180, which differ from the corresponding compounds Ia1.001–Ia1.180 by the fact that $R^1$ is nitro and $R^{12}$ is methylsulfonyl:

the compounds Ia180, in particular the compounds Ia180.001–Ia180.180, which differ from the corresponding compounds Ia1.001–Ia1.180 by the fact that $R^1$ is nitro, $R^{11}$ is iso-butyl and $R^{12}$ is methylsulfonyl:

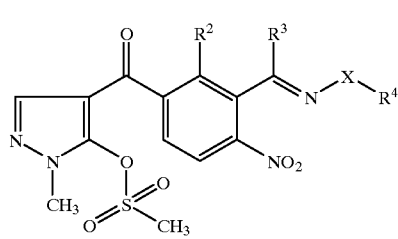

Ia176

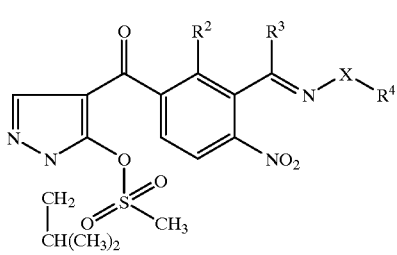

Ia180 the compounds Ia177, in particular the compounds Ia177.001–Ia177.180, which differ from the corresponding compounds Ia1.001–Ia1.180 by the fact that $R^1$ is nitro, $R^{11}$ is ethyl and $R^{12}$ is methylsulfonyl:

the compounds Ia181, in particular the compounds Ia181.001–Ia181.180, which differ from the corresponding compounds Ia1.001–Ia1.180 by the fact that $R^1$ is nitro and $R^{12}$ is ethylsulfonyl:

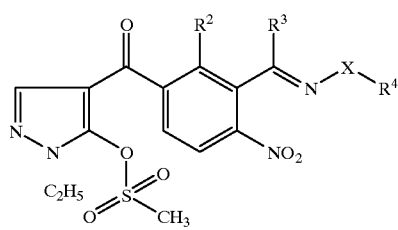

Ia177

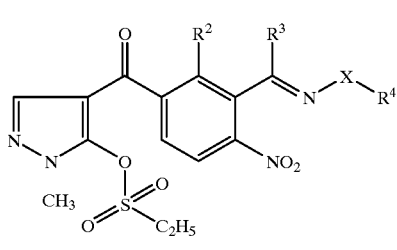

Ia181 the compounds Ia178, in particular the compounds Ia178.001–Ia178.180, which differ from the corresponding compounds Ia1.001–Ia1.180 by the fact that $R^1$ is nitro, $R^{11}$ is n-propyl and $R^{12}$ is methylsulfonyl:

the compounds Ia182, in particular the compounds Ia182.001–Ia182.180, which differ from the corresponding compounds Ia1.001–Ia1.180 by the fact that $R^1$ is nitro, $R^{11}$ is ethyl and $R^{12}$ is ethylsulfonyl:

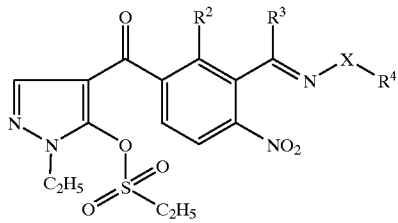

Ia182 the compounds Ia183, in particular the compounds Ia183.001–Ia183.180, which differ from the corresponding compounds Ia1.001–Ia1.180 by the fact that $R^1$ is nitro, $R^{11}$ is n-propyl and $R^{12}$ is ethylsulfonyl:

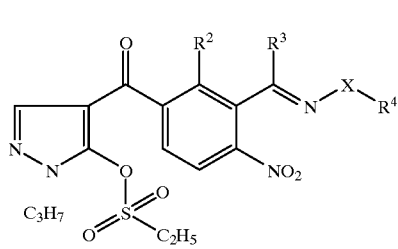

Ia183 the compounds Ia184, in particular the compounds Ia184.001–Ia184.180, which differ from the corresponding compounds Ia1.001–Ia1.180 by the fact that $R^1$ is nitro, $R^{11}$ is n-butyl and $R^{12}$ is ethylsulfonyl:

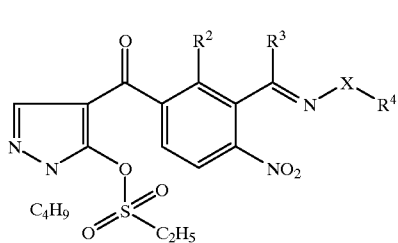

Ia184 the compounds Ia185, in particular the compounds Ia185.001–Ia185.180, which differ from the corresponding compounds Ia1.001–Ia1.180 by the fact that $R^1$ is nitro, $R^{11}$ is iso-butyl and $R^{12}$ is ethylsulfonyl:

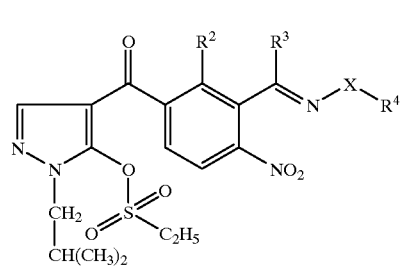

Ia185 the compounds Ia186, in particular the compounds Ia186.001–Ia186.180, which differ from the corresponding compounds Ia1.001–Ia1.180 by the fact that $R^1$ is nitro and $R^{12}$ is n-propylsulfonyl:

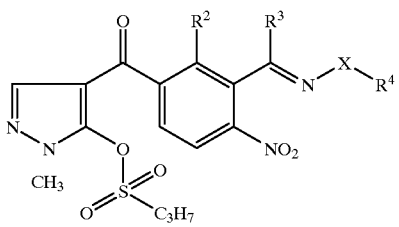

Ia186 the compounds Ia187, in particular the compounds Ia187.001–Ia187.180, which differ from the corresponding compounds Ia1.001–Ia1.180 by the fact that $R^1$ is nitro, $R^{11}$ is ethyl and $R^{12}$ is n-propylsulfonyl:

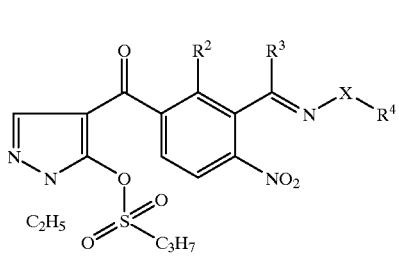

Ia187 the compounds Ia188, in particular the compounds Ia188.001–Ia188.180, which differ from the corresponding compounds Ia1.001–Ia1.180 by the fact that $R^1$ is nitro, $R^{11}$ is n-propyl and $R^{12}$ is n-propylsulfonyl:

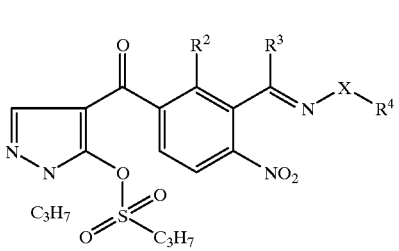

Ia188 the compounds Ia189, in particular the compounds Ia189.001–Ia189.180, which differ from the corresponding compounds Ia1.001–Ia1.180 by the fact that $R^1$ is nitro, $R^{11}$ is n-butyl and $R^{12}$ is n-propylsulfonyl:

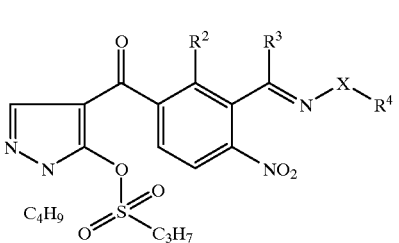

Ia189 the compounds Ia190, in particular the compounds Ia190.001–Ia190.180, which differ from the corresponding compounds Ia1.001–Ia1.180 by the fact that $R^1$ is nitro, $R^{11}$ is iso-butyl and $R^{12}$ is n-propylsulfonyl:

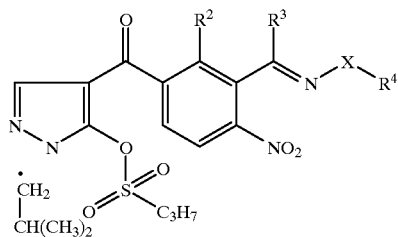

Ia190 the compounds Ia191, in particular the compounds Ia191.001–Ia191.180, which differ from the corresponding compounds Ia1.001–Ia1.180 by the fact that $R^1$ is nitro and $R^{12}$ is iso-propylsulfonyl:

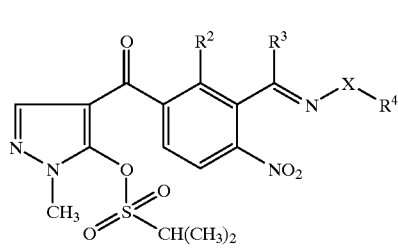

Ia191 the compounds Ia192, in particular the compounds Ia192.001–Ia192.180, which differ from the corresponding compounds Ia1.001–Ia1.180 by the fact that $R^1$ is nitro, $R^{11}$ is ethyl and $R^{12}$ is iso-propylsulfonyl:

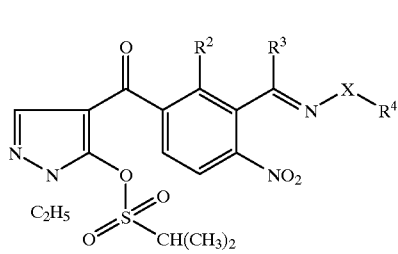

Ia192 the compounds Ia193, in particular the compounds Ia193.001–Ia193.180, which differ from the corresponding compounds Ia1.001–Ia1.180 by the fact that $R^1$ is nitro, $R^{11}$ is n-propyl and $R^{12}$ is iso-propylsulfonyl:

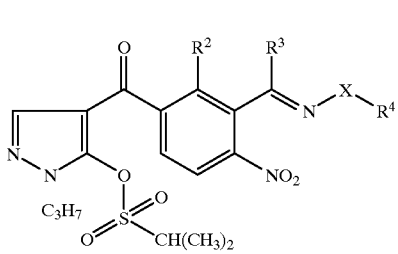

Ia193 the compounds Ia194, in particular the compounds Ia194.001–Ia194.180, which differ from the corresponding compounds Ia1.001–Ia1.180 by the fact that $R^1$ is nitro, $R^{11}$ is n-butyl and $R^{12}$ is iso-propylsulfonyl:

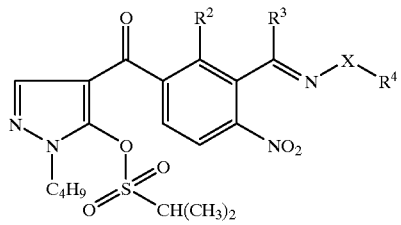

Ia194 the compounds Ia195, in particular the compounds Ia195.001–Ia195.180, which differ from the corresponding compounds Ia1.001–Ia1.180 by the fact that $R^1$ is nitro, $R^{11}$ is iso-butyl and $R^{12}$ is iso-propylsulfonyl:

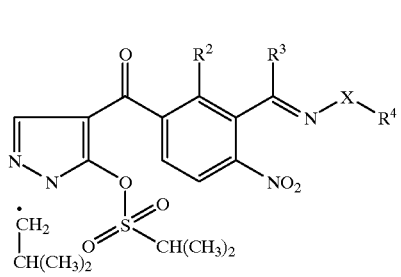

Ia195 the compounds Ia196, in particular the compounds Ia196.001–Ia196.180, which differ from the corresponding compounds Ia1.001–Ia1.180 by the fact that $R^1$ is nitro and $R^{12}$ is n-butylsulfonyl:

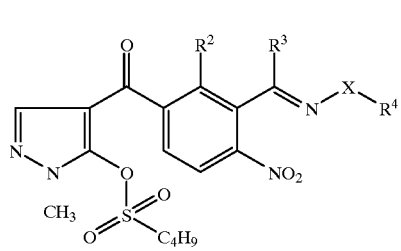

Ia196 the compounds Ia197, in particular the compounds Ia197.001–Ia197.180, which differ from the corresponding compounds Ia1.001–Ia1.180 by the fact that $R^1$ is nitro, $R^{11}$ is ethyl and $R^{12}$ is n-butylsulfonyl:

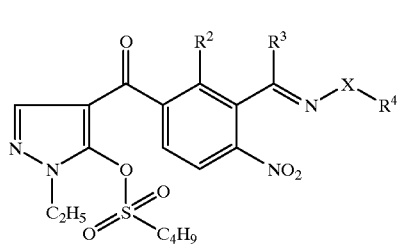

Ia197 the compounds Ia198, in particular the compounds Ia198.001–Ia198.180, which differ from the corresponding compounds Ia1.001–Ia1.180 by the fact that $R^1$ is nitro, $R^{11}$ is n-propyl and $R^{12}$ is n-butylsulfonyl:

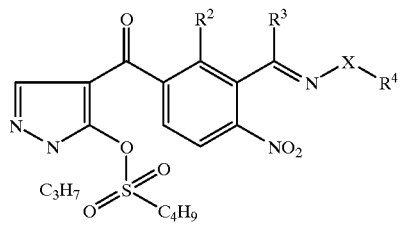
Ia198 the compounds Ia199, in particular the compounds Ia199.001–Ia199.180, which differ from the corresponding compounds Ia1.001–Ia1.180 by the fact that $R^1$ is nitro, $R^{11}$ is n-butyl and $R^{12}$ is n-butylsulfonyl:

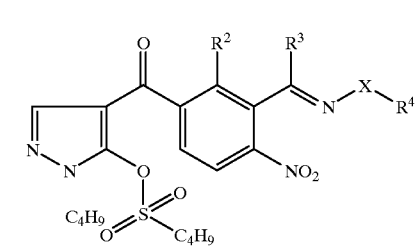
Ia199 the compounds Ia200, in particular the compounds Ia200.001–Ia200.180, which differ from the corresponding compounds Ia1.001–Ia1.180 by the fact that $R^1$ is nitro, $R^{11}$ is iso-butyl and $R^{12}$ is n-butylsulfonyl:

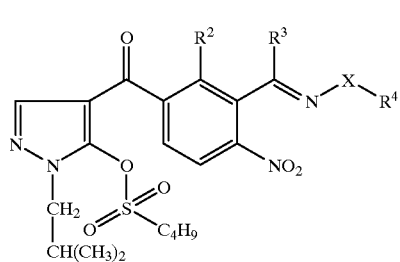
Ia200 the compounds Ia201, in particular the compounds Ia201.001–Ia201.180, which differ from the corresponding compounds Ia1.001–Ia1.180 by the fact that $R^1$ is nitro and $R^{12}$ is iso-butylsulfonyl:

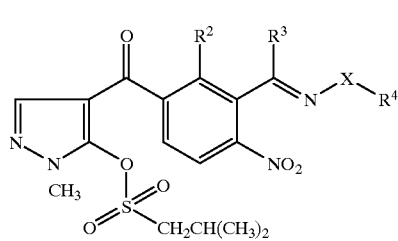
Ia201 the compounds Ia202, in particular the compounds Ia202.001–Ia202.180, which differ from the corresponding compounds Ia1.001–Ia1.180 by the fact that $R^1$ is nitro, $R^{11}$ is ethyl and $R^{12}$ is iso-butylsulfonyl:

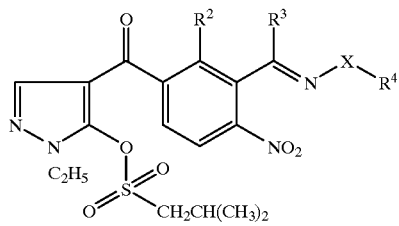
Ia202 the compounds Ia203, in particular the compounds Ia203.001–Ia203.180, which differ from the corresponding compounds Ia1.001–Ia1.180 by the fact that $R^1$ is nitro, $R^{11}$ is n-propyl and $R^{12}$ is iso-butylsulfonyl:

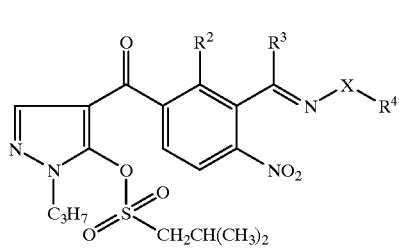
Ia203 the compounds Ia204, in particular the compounds Ia204.001–Ia204.180, which differ from the corresponding compounds Ia1.001–Ia1.180 by the fact that $R^1$ is nitro, $R^{11}$ is n-butyl and $R^{12}$ is iso-butylsulfonyl:

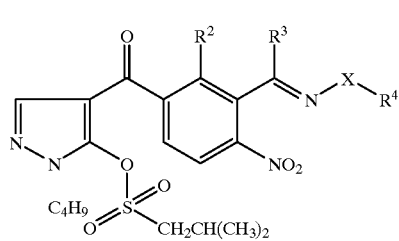
Ia204 the compounds Ia205, in particular the compounds Ia205.001–Ia205.180, which differ from the corresponding compounds Ia1.001–Ia1.180 by the fact that $R^1$ is nitro, $R^{11}$ is iso-butyl and $R^{12}$ is iso-butylsulfonyl:

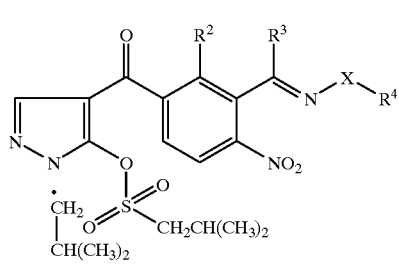
Ia205 the compounds Ia206, in particular the compounds Ia206.001–Ia2066.180 [sic], which differ from the corresponding compounds Ia1.001–Ia1.180 by the fact that $R^1$ is nitro and $R^{12}$ is sec-butylsulfonyl:

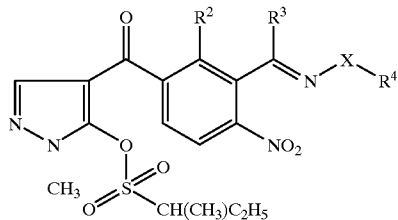
Ia206 the compounds Ia207, in particular the compounds Ia207.001–Ia207.180, which differ from the corresponding compounds Ia1.001–Ia1.180 by the fact that $R^1$ is nitro, $R^{11}$ is ethyl and $R^{12}$ is sec-butylsulfonyl:

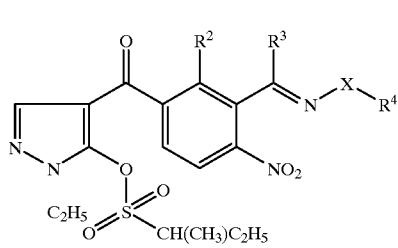
Ia207 the compounds Ia208, in particular the compounds Ia208.001–Ia208.180, which differ from the corresponding compounds Ia1.001–Ia1.180 by the fact that $R^1$ is nitro, $R^{11}$ is n-propyl and $R^{12}$ is sec-butylsulfonyl:

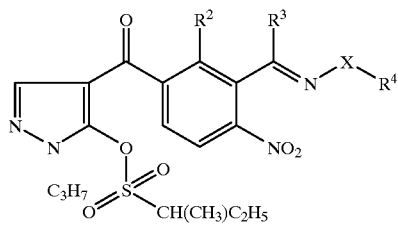
Ia208 the compounds Ia209, in particular the compounds Ia209.001–Ia209.180, which differ from the corresponding compounds Ia1.001–Ia1.180 by the fact that $R^1$ is nitro, $R^{11}$ is n-butyl and $R^{12}$ is sec-butylsulfonyl:

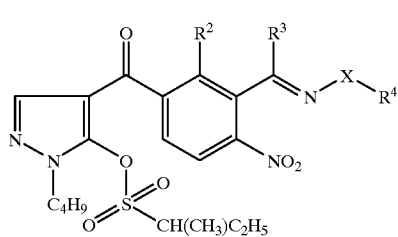
Ia209 the compounds Ia210, in particular the compounds Ia210.001–Ia210.180, which differ from the corresponding compounds Ia1.001–Ia1.180 by the fact that $R^1$ is nitro, $R^{11}$ is iso-butyl and $R^{12}$ is sec-butylsulfonyl:

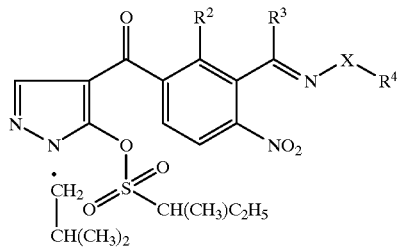
Ia210 the compounds Ia211, in particular the compounds Ia211.001–Ia211.180, which differ from the corresponding compounds Ia1.001–Ia1.180 by the fact that $R^1$ is nitro and $R^{12}$ is trifluoromethylsulfonyl:

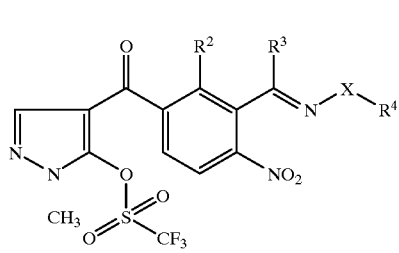
Ia211 the compounds Ia212, in particular the compounds Ia212.001–Ia212.180, which differ from the corresponding compounds Ia1.001–Ia1.180 by the fact that $R^1$ is nitro, $R^{11}$ is ethyl and $R^{12}$ is trifluoromethylsulfonyl:

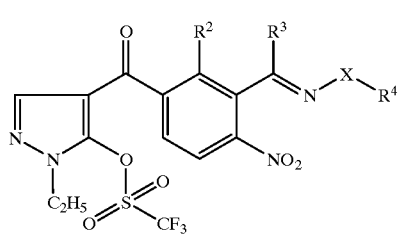
Ia212 the compounds Ia213, in particular the compounds Ia213.001–Ia213.180, which differ from the corresponding compounds Ia1.001–Ia1.180 by the fact that $R^1$ is nitro, $R^{11}$ is n-propyl and $R^{12}$ is trifluoromethylsulfonyl:

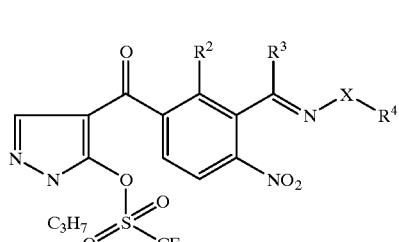
Ia213 the compounds Ia214, in particular the compounds Ia214.001–Ia214.180, which differ from the corresponding compounds Ia1.001–Ia1.180 by the fact that $R^1$ is nitro, $R^{11}$ is n-butyl and $R^{12}$ is trifluoromethylsulfonyl:

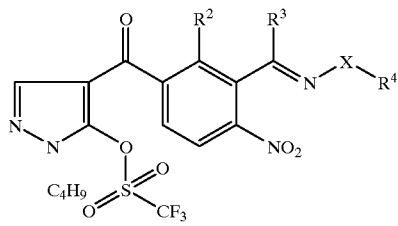

Ia214

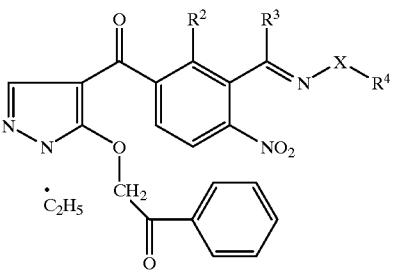

Ia217 the compounds Ia215, in particular the compounds Ia215.001–Ia125.180, which differ from the corresponding compounds Ia1.001–Ia1.180 by the fact that $R^1$ is nitro, $R^{11}$ is iso-butyl and $R^{12}$ is trifluoromethylsulfonyl:

the compounds Ia218, in particular the compounds Ia218.001–Ia218.180, which differ from the corresponding compounds Ia1.001–Ia1.180 by the fact that $R^1$ is nitro, $R^{11}$ is n-propyl and $R^{12}$ is phenylcarbonylmethyl:

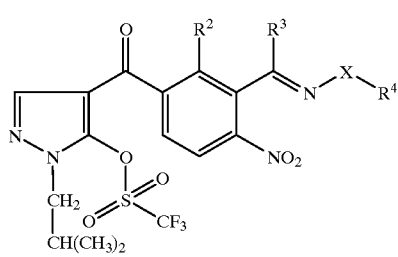

Ia215

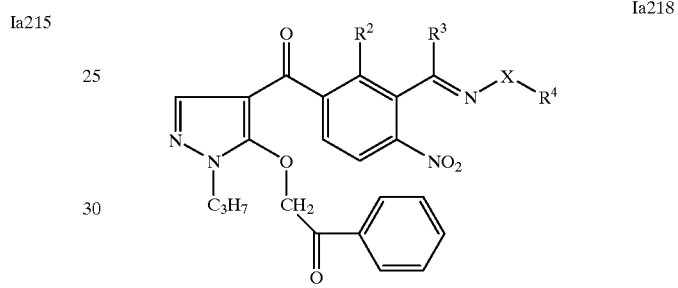

Ia218 the compounds Ia216, in particular the compounds Ia216.001–Ia216.180, which differ from the corresponding compounds Ia1.001–Ia1.180 by the fact that $R^1$ is nitro, $R^{11}$ is methyl and $R^{12}$ is phenylcarbonylmethyl:

the compounds Ia219, in particular the compounds Ia219.001–Ia219.180, which differ from the corresponding compounds Ia1.001–Ia1.180 by the fact that $R^1$ is nitro, $R^{11}$ is n-butyl and $R^{12}$ is phenylcarbonylmethyl:

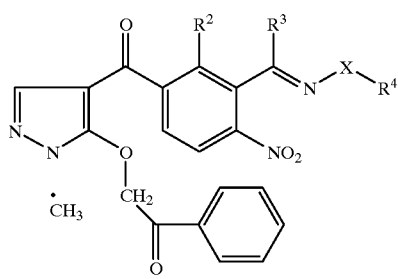

Ia216

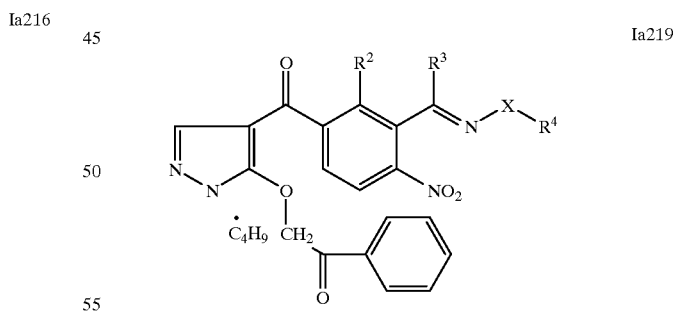

Ia219 the compounds Ia217, in particular the compounds Ia217.001–Ia217.180, which differ from the corresponding compounds Ia1.001–Ia1.180 by the fact that $R^1$ is nitro, $R^{11}$ is ethyl and $R^{12}$ is phenylcarbonylmethyl:

the compounds Ia220, in particular the compounds Ia220.001–Ia220.180, which differ from the corresponding compounds Ia1.001–Ia1.180 by the fact that $R^1$ is nitro, $R^{11}$ is iso-butyl and $R^{12}$ is phenylcarbonylmethyl:

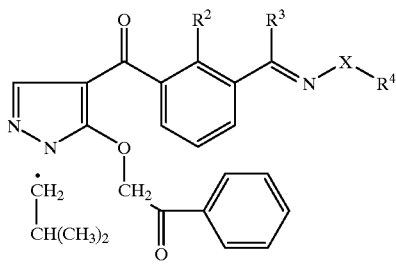

Ia220 the compounds Ia221, in particular the compounds Ia221.001–Ia221.180, which differ from the corresponding compounds Ia1.001–Ia1.180 by the fact that $R^1$ is nitro and $R^{12}$ is phenylsulfonyl:

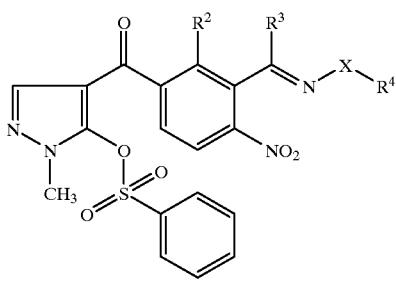

Ia221 the compounds Ia222, in particular the compounds Ia222.001–Ia222.180, which differ from the corresponding compounds Ia1.001–Ia1.180 by the fact that $R^1$ is nitro, $R^{11}$ is ethyl and $R^{12}$ is phenylsulfonyl:

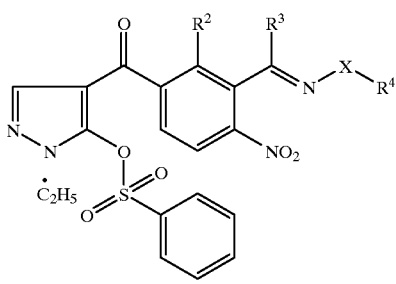

Ia222 the compounds Ia223, in particular the compounds Ia223.001–Ia223.180, which differ from the corresponding compounds Ia1.001–Ia1.180 by the fact that $R^1$ is nitro, $R^{11}$ is n-propyl and $R^{12}$ is phenylsulfonyl:

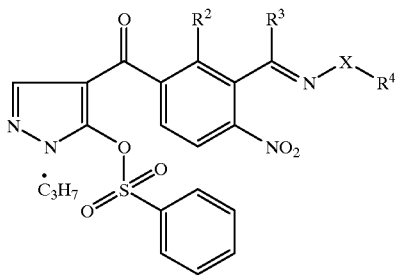

Ia223 the compounds Ia224, in particular the compounds Ia224.001–Ia224.180, which differ from the corresponding compounds Ia1.001–Ia1.180 by the fact that $R^1$ is nitro, $R^{11}$ is n-butyl and $R^{12}$ is phenylsulfonyl:

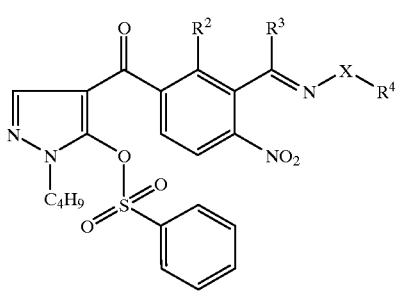

Ia224 the compounds Ia225, in particular the compounds Ia225.001–Ia225.180, which differ from the corresponding compounds Ia1.001–Ia1.180 by the fact that $R^1$ is nitro, $R^{11}$ is iso-butyl and $R^{12}$ is phenylsulfonyl:

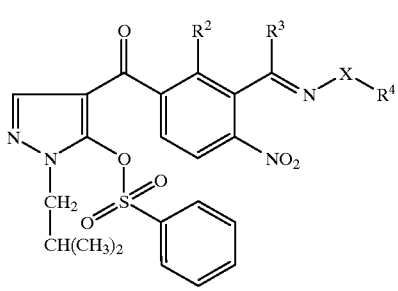

Ia225 the compounds Ia226, in particular the compounds Ia226.001–Ia226.180, which differ from the corresponding compounds Ia1.001–Ia1.180 by the fact that $R^1$ is nitro and $R^{12}$ is 4-methylphenylsulfonyl:

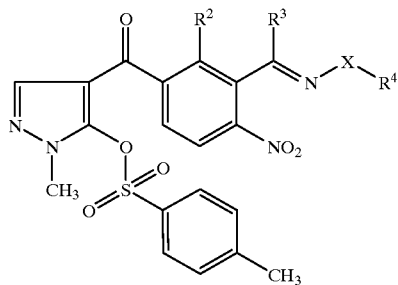

Ia226 the compounds Ia227, in particular the compounds Ia227.001–Ia227.180, which differ from the corresponding compounds Ia1.001–Ia1.180 by the fact that $R^1$ is nitro, $R^{11}$ is ethyl and $R^{12}$ is 4-methylphenylsulfonyl:

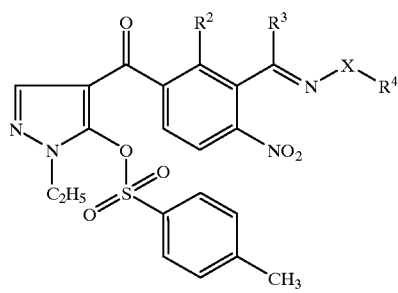

Ia227 the compounds Ia228, in particular the compounds Ia228.001–Ia228.180, which differ from the corresponding compounds Ia1.001–Ia1.180 by the fact that $R^1$ is nitro, $R^{11}$ is n-propyl and $R^{12}$ is 4-methylphenylsulfonyl:

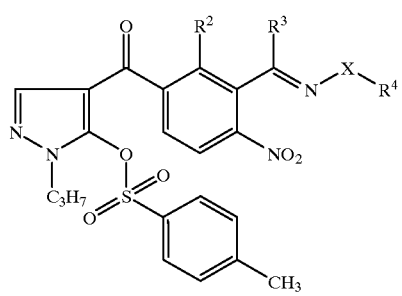

Ia228 the compounds Ia229, in particular the compounds Ia229.001–Ia229.180, which differ from the corresponding compounds Ia1.001–Ia1.180 by the fact that $R^1$ is nitro, $R^{11}$ is n-butyl and $R^{12}$ is 4-methylphenylsulfonyl:

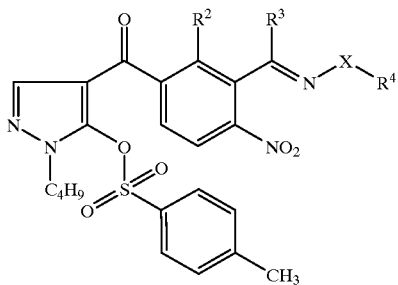

Ia229 the compounds Ia230, in particular the compounds Ia230.001–Ia230.180, which differ from the corresponding compounds Ia1.001–Ia1.180 by the fact that $R^1$ is nitro, $R^{11}$ is iso-butyl and $R^{12}$ is 4-methylphenylsulfonyl:

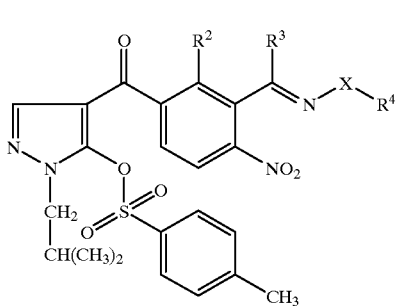

Ia230 the compounds Ia231, in particular the compounds Ia231.001–Ia231.180, which differ from the corresponding compounds Ia1.001–Ia1.180 by the fact that $R^1$ is methylsulfonyl:

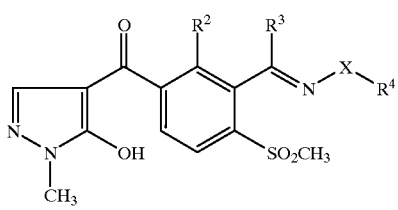

Ia231 the compounds Ia232, in particular the compounds Ia232.001–Ia232.180, which differ from the corresponding compounds Ia1.001–Ia1.180 by the fact that $R^1$ is methylsulfonyl and $R^{11}$ is ethyl:

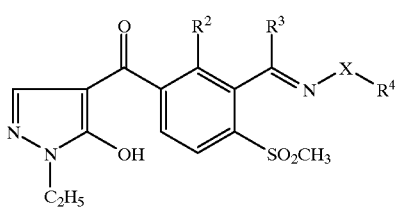

Ia232 the compounds Ia233, in particular the compounds Ia233.001–Ia233.180, which differ from the corresponding compounds Ia1.001–Ia1.180 by the fact that $R^1$ is methylsulfonyl and $R^{11}$ is n-propyl:

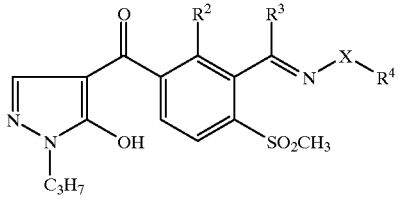
Ia233 the compounds Ia234, in particular the compounds Ia234.001–Ia234.180, which differ from the corresponding compounds Ia1.001–Ia1.180 by the fact that $R^1$ is methylsulfonyl and $R^{11}$ is n-butyl:

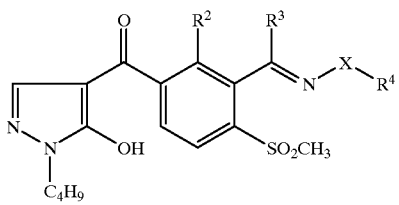
Ia234 the compounds Ia235, in particular the compounds Ia235.001–Ia235.180, which differ from the corresponding compounds Ia1.001–Ia1.180 by the fact that $R^1$ is methylsulfonyl and $R^{11}$ is iso-butyl:

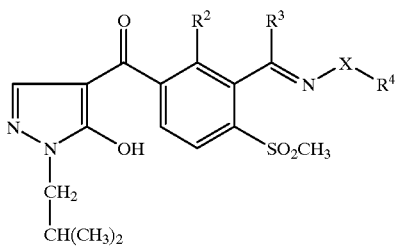
Ia235 the compounds Ia236, in particular the compounds Ia236.001–Ia236.180, which differ from the corresponding compounds Ia1.001–Ia1.180 by the fact that $R^1$ is methylsulfonyl and $R^{12}$ is methyl:

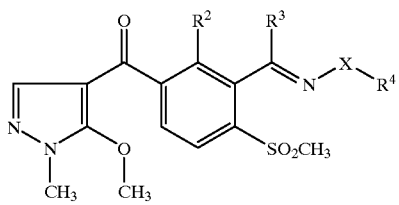
Ia236 the compounds Ia237, in particular the compounds Ia237.001–Ia237.180, which differ from the corresponding compounds Ia1.001–Ia1.180 by the fact that $R^1$ is methylsulfonyl, $R^{11}$ is ethyl and $R^{12}$ is methyl:

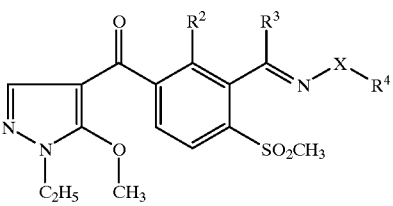
Ia237 the compounds Ia238, in particular the compounds Ia238.001–Ia238.180, which differ from the corresponding compounds Ia1.001–Ia1.180 by the fact that $R^1$ is methylsulfonyl, $R^{11}$ is n-propyl and $R^{12}$ is methyl:

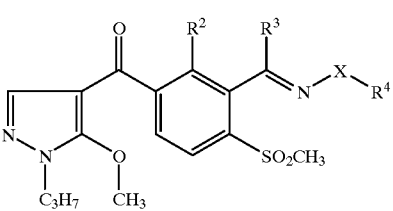
Ia238 the compounds Ia239, in particular the compounds Ia239.001–Ia239.180, which differ from the corresponding compounds Ia1.001–Ia1.180 by the fact that $R^1$ is methylsulfonyl, $R^{11}$ is n-butyl and $R^{12}$ is methyl:

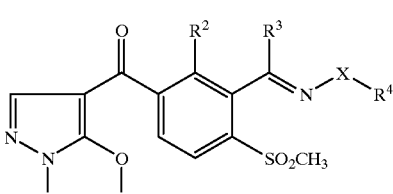
Ia239 the compounds Ia240, in particular the compounds Ia240.001–Ia240.180, which differ from the corresponding compounds Ia1.001–Ia1.180 by the fact that $R^1$ is methylsulfonyl, $R^{11}$ is iso-butyl and $R^{12}$ is methyl:

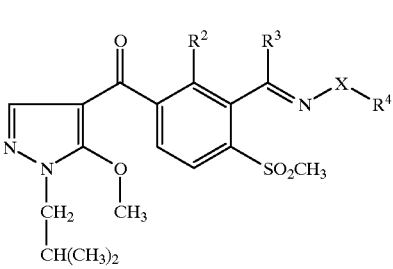
Ia240 the compounds Ia241, in particular the compounds Ia241.001–Ia241.180, which differ from the corresponding compounds Ia1.001–Ia1.180 by the fact that $R^1$ is methylsulfonyl and $R^{12}$ is ethyl:

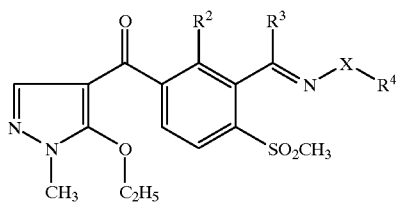

Ia241 the compounds Ia242, in particular the compounds Ia242.001–Ia242.180, which differ from the corresponding compounds Ia1.001–Ia1.180 by the fact that $R^1$ is methylsulfonyl and $R^{11}$ and $R^{12}$ is ethyl:

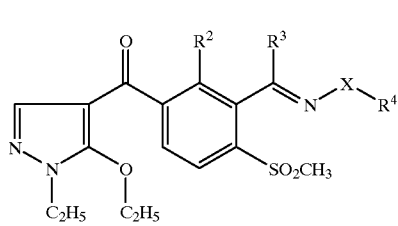

Ia242 the compounds Ia243, in particular the compounds Ia243.001–Ia243.180, which differ from the corresponding compounds Ia1.001–Ia1.180 by the fact that $R^1$ is methylsulfonyl, $R^{11}$ is n-propyl and $R^{12}$ is ethyl:

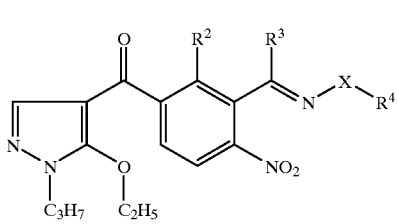

Ia243 the compounds Ia244, in particular the compounds Ia244.001–Ia244.180, which differ from the corresponding compounds Ia1.001–Ia1.180 by the fact that $R^1$ is methylsulfonyl, $R^{11}$ is n-butyl and $R^{12}$ is ethyl:

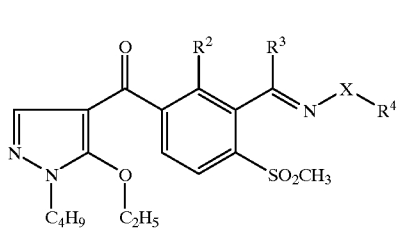

Ia244 the compounds Ia245, in particular the compounds Ia245.001–Ia245.180, which differ from the corresponding compounds Ia1.001–Ia1.180 by the fact that $R^1$ is methylsulfonyl, $R^{11}$ is iso-butyl and $R^{12}$ is ethyl:

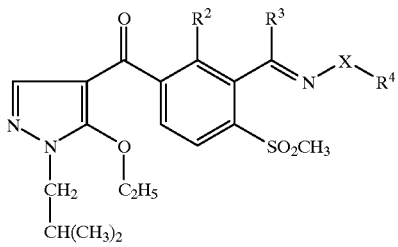

Ia245 the compounds Ia246, in particular the compounds Ia246.001–Ia246.180, which differ from the corresponding compounds Ia1.001–Ia1.180 by the fact that $R^1$ is methylsulfonyl and $R^{12}$ is n-propyl:

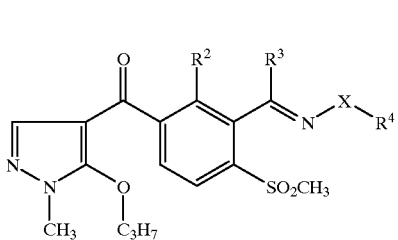

Ia246 the compounds Ia247, in particular the compounds Ia247.001–Ia247.180, which differ from the corresponding compounds Ia1.001–Ia1.180 by the fact that $R^1$ is methylsulfonyl $R^{11}$ is ethyl and $R^{12}$ is n-propyl:

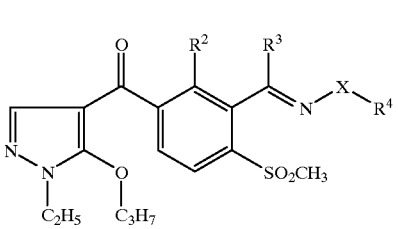

Ia247 the compounds Ia248, in particular the compounds Ia248.001–Ia248.180, which differ from the corresponding compounds Ia1.001–Ia1.180 by the fact that $R^1$ is methylsulfonyl and $R^{11}$ and $R^{12}$ are n-propyl:

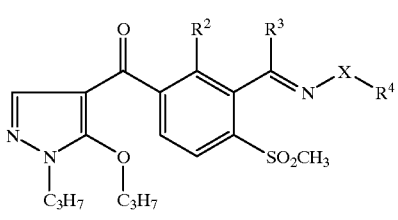

Ia248 the compounds Ia249, in particular the compounds Ia249.001–Ia249.180, which differ from the corresponding compounds Ia1.001–Ia1.180 by the fact that $R^1$ is methylsulfonyl, $R^{11}$ is n-butyl and $R^{12}$ is n-propyl:

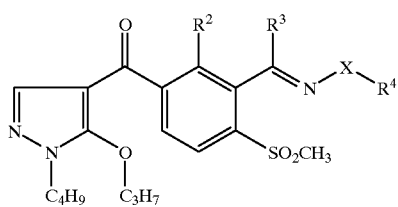
Ia249 the compounds Ia250, in particular the compounds Ia250.001–Ia250.180, which differ from the corresponding compounds Ia1.001–Ia1.180 by the fact that $R^1$ is methylsulfonyl, $R^{11}$ is iso-butyl and $R^{12}$ is n-propyl:

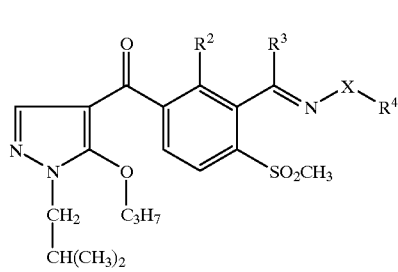
Ia250 the compounds Ia251, in particular the compounds Ia251.001–Ia251.180, which differ from the corresponding compounds Ia1.001–Ia1.180 by the fact that $R^1$ is methylsulfonyl and $R^{12}$ is iso-propyl:

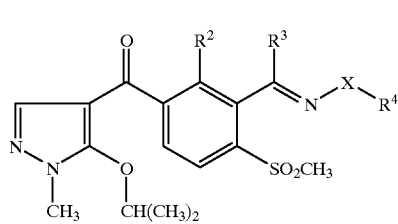
Ia251 the compounds Ia252, in particular the compounds Ia252.001–Ia252.180, which differ from the corresponding compounds Ia1.001–Ia1.180 by the fact that $R^1$ is methylsulfonyl, $R^{11}$ is ethyl and $R^{12}$ is iso-propyl:

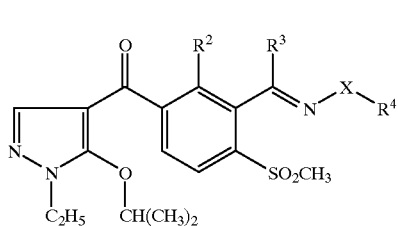
Ia252 the compounds Ia253, in particular the compounds Ia253.001–Ia253.180, which differ from the corresponding compounds Ia1.001–Ia1.180 by the fact that $R^1$ is methylsulfonyl, $R^{11}$ is n-propyl and $R^{12}$ is iso-propyl:

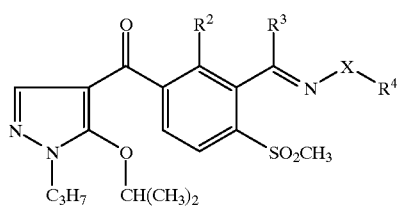
Ia253 the compounds Ia254, in particular the compounds Ia254.001–Ia254.180, which differ from the corresponding compounds Ia1.001–Ia1.180 by the fact that $R^1$ is methylsulfonyl, $R^{11}$ is n-butyl and $R^{12}$ is iso-propyl:

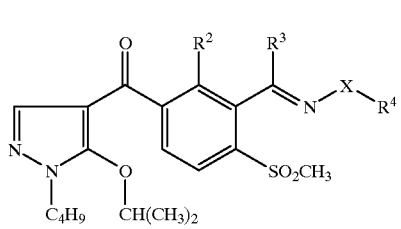
Ia254 the compounds Ia255, in particular the compounds Ia255.001–Ia255.180, which differ from the corresponding compounds Ia1.001–Ia1.180 by the fact that $R^1$ is methylsulfonyl, $R^{11}$ is iso-butyl and $R^{12}$ is iso-propyl:

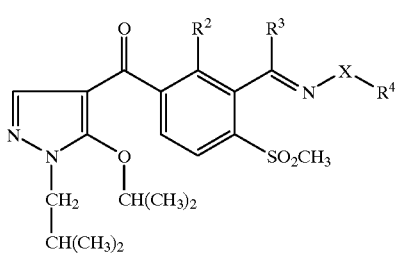
Ia255 the compounds Ia256, in particular the compounds Ia256.001–Ia256.180, which differ from the corresponding compounds Ia1.001–Ia1.180 by the fact that $R^1$ is methylsulfonyl and $R^{12}$ is n-butyl:

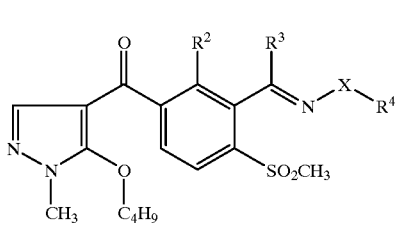
Ia256 the compounds Ia257, in particular the compounds Ia257.001–Ia257.180, which differ from the corresponding compounds Ia1.001–Ia1.180 by the fact that $R^1$ is methylsulfonyl, $R^{11}$ is ethyl and $R^{12}$ is n-butyl:

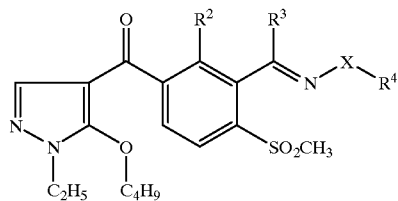
Ia257 the compounds Ia258, in particular the compounds Ia258.001–Ia258.180, which differ from the corresponding compounds Ia1.001–Ia1.180 by the fact that $R^1$ is methylsulfonyl, $R^{11}$ is n-propyl and $R^{12}$ is n-butyl:

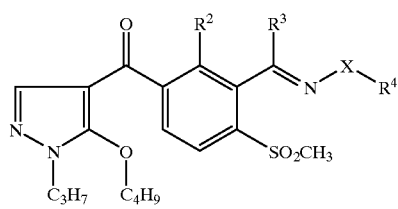
Ia258 the compounds Ia259, in particular the compounds Ia259.001–Ia259.180, which differ from the corresponding compounds Ia1.001–Ia1.180 by the fact that $R^1$ is methylsulfonyl and $R^{11}$ and $R^{12}$ are n-butyl:

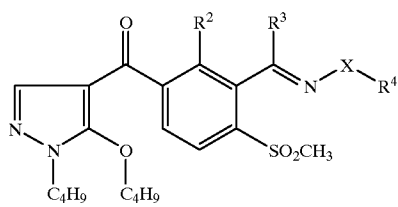
Ia259 the compounds Ia260, in particular the compounds Ia260.001–Ia260.180, which differ from the corresponding compounds Ia1.001–Ia1.180 by the fact that $R^1$ is methylsulfonyl, $R^{11}$ is iso-butyl and $R^{12}$ is n-butyl:

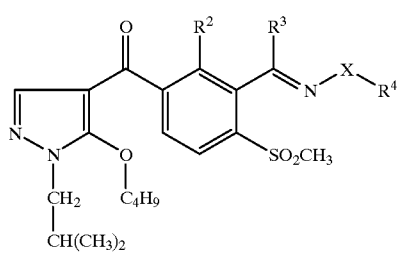
Ia260 the compounds Ia261, in particular the compounds Ia261.001–Ia261.180, which differ from the corresponding compounds Ia1.001–Ia1.180 by the fact that $R^1$ is methylsulfonyl and $R^{12}$ is sec-butyl:

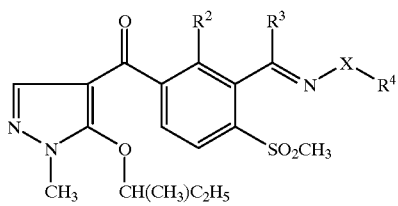
Ia261 the compounds Ia262, in particular the compounds Ia262.001–Ia262.180, which differ from the corresponding compounds Ia1.001–Ia1.180 by the fact that $R^1$ is methylsulfonyl, $R^{11}$ is ethyl and $R^{12}$ is sec-butyl:

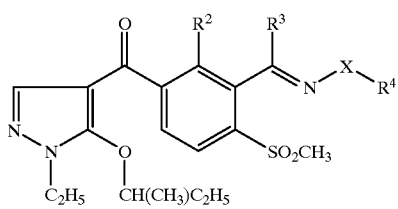
Ia262 the compounds Ia263, in particular the compounds Ia263.001–Ia263.180, which differ from the corresponding compounds Ia1.001–Ia1.180 by the fact that $R^1$ is methylsulfonyl, $R^{11}$ is n-propyl and $R^{12}$ is sec-butyl:

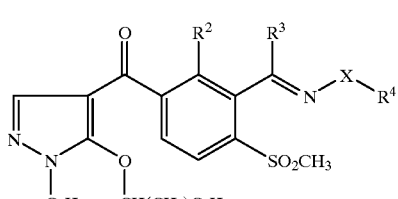
Ia263 the compounds Ia264, in particular the compounds Ia264.001–Ia264.180, which differ from the corresponding compounds Ia1.001–Ia1.180 by the fact that $R^1$ is methylsulfonyl, $R^{11}$ is n-butyl and $R^{12}$ is sec-butyl:

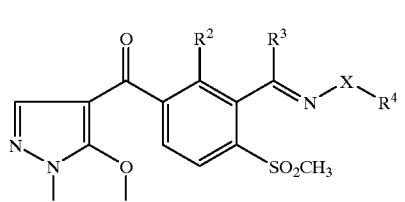
Ia264 the compounds Ia265, in particular the compounds Ia265.001–Ia265.180, which differ from the corresponding compounds Ia1.001–Ia1.180 by the fact that $R^1$ is methylsulfonyl, $R^{11}$ is iso-butyl and $R^{12}$ is sec-butyl:

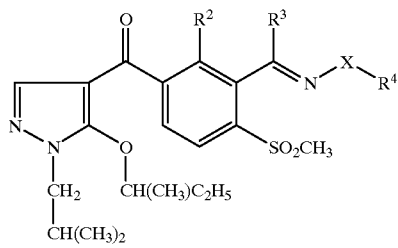
Ia265 the compounds Ia266, in particular the compounds Ia266.001–Ia266.180, which differ from the corresponding compounds Ia1.001–Ia1.180 by the fact that $R^1$ is methylsulfonyl and $R^{12}$ is iso-butyl:

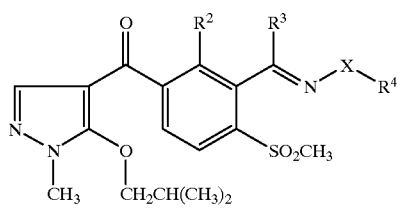
Ia266 the compounds Ia267, in particular the compounds Ia267.001–Ia267.180, which differ from the corresponding compounds Ia1.001–Ia1.180 by the fact that $R^1$ is methylsulfonyl, $R^{11}$ is ethyl and $R^{12}$ is iso-butyl:

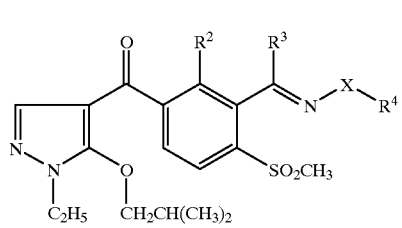
Ia267 the compounds Ia268, in particular the compounds Ia268.001–Ia268.180, which differ from the corresponding compounds Ia1.001–Ia1.180 by the fact that $R^1$ is methylsulfonyl, $R^{11}$ is n-propyl and $R^{12}$ is iso-butyl:

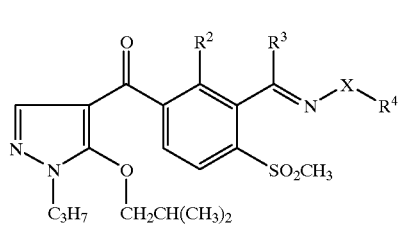
Ia268 the compounds Ia269, in particular the compounds Ia269.001–Ia269.180, which differ from the corresponding compounds Ia1.001–Ia1.180 by the fact that $R^1$ is methylsulfonyl, $R^{11}$ is n-butyl and $R^{12}$ is iso-butyl:

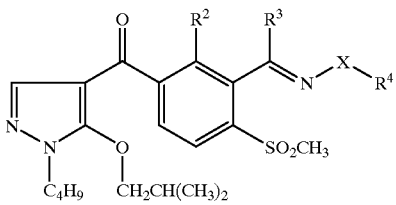
Ia269 the compounds Ia270, in particular the compounds Ia270.001–Ia270.180, which differ from the corresponding compounds Ia1.001–Ia1.180 by the fact that $R^1$ is methylsulfonyl and $R^{11}$ and $R^{12}$ are iso-butyl:

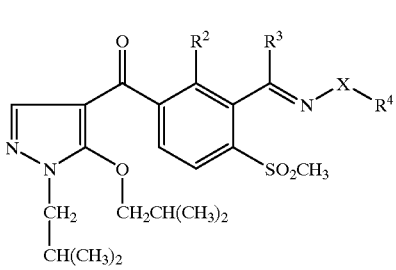
Ia270 the compounds Ia271, in particular the compounds Ia271.001–Ia271.180, which differ from the corresponding compounds Ia1.001–Ia1.180 by the fact that $R^1$ is methylsulfonyl and $R^{12}$ is methylcarbonyl:

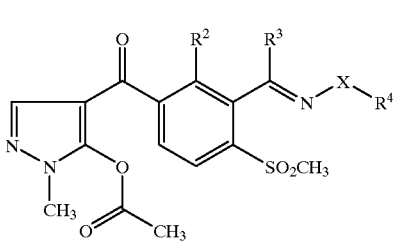
Ia271 the compounds Ia272, in particular the compounds Ia272.001–Ia272.180, which differ from the corresponding compounds Ia1.001–Ia1.180 by the fact that $R^1$ is methylsulfonyl, $R^{11}$ is ethyl and $R^{12}$ is methylcarbonyl:

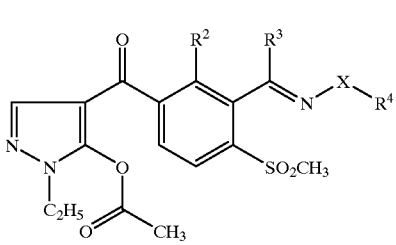
Ia272 the compounds Ia273, in particular the compounds Ia273.001–Ia273.180, which differ from the corresponding compounds Ia1.001–Ia1.180 by the fact that $R^1$ is methylsulfonyl, $R^{11}$ is n-propyl and $R^{12}$ is methylcarbonyl:

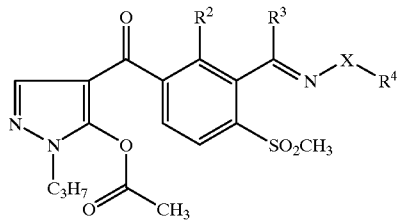

Ia273 the compounds Ia274, in particular the compounds Ia274.001–Ia274.180, which differ from the corresponding compounds Ia1.001–Ia1.180 by the fact that $R^1$ is methylsulfonyl, $R^{11}$ is n-butyl and $R^{12}$ is methylcarbonyl:

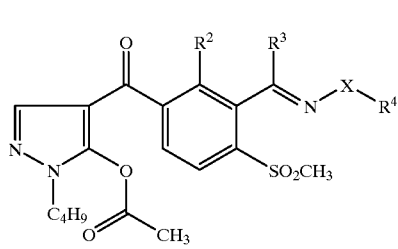

Ia274 the compounds Ia275, in particular the compounds Ia275.001–Ia275.180, which differ from the corresponding compounds Ia1.001–Ia1.180 by the fact that $R^1$ is methylsulfonyl, $R^{11}$ is iso-butyl and $R^{12}$ is methylcarbonyl:

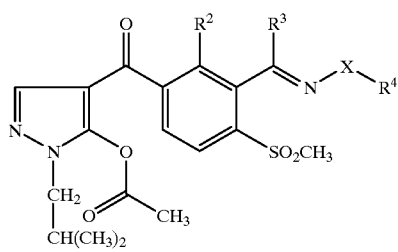

Ia275 the compounds Ia276, in particular the compounds Ia276.001–Ia276.180, which differ from the corresponding compounds Ia1.001–Ia1.180 by the fact that $R^1$ is methylsulfonyl and $R^{12}$ is ethylcarbonyl:

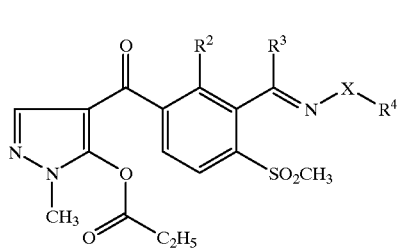

Ia276 the compounds Ia277, in particular the compounds Ia277.001–Ia277.180, which differ from the corresponding compounds Ia1.001–Ia1.180 by the fact that $R^1$ is methylsulfonyl, $R^{11}$ is ethyl and $R^{12}$ is ethylcarbonyl:

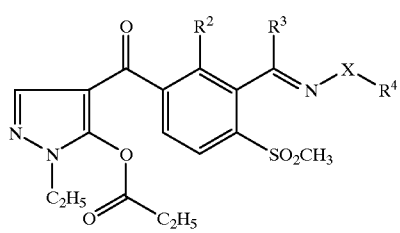

Ia277 the compounds Ia278, in particular the compounds Ia278.001–Ia278.180, which differ from the corresponding compounds Ia1.001–Ia1.180 by the fact that $R^1$ is methylsulfonyl, $R^{11}$ is n-propyl and $R^{12}$ is ethylcarbonyl:

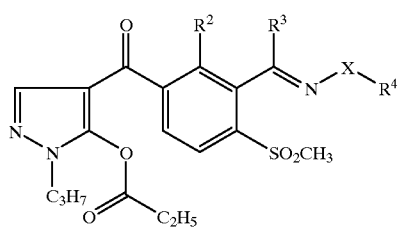

Ia278 the compounds Ia279, in particular the compounds Ia279.001–Ia279.180, which differ from the corresponding compounds Ia1.001–Ia1.180 by the fact that $R^1$ is methylsulfonyl, $R^{11}$ is n-butyl and $R^{12}$ is ethylcarbonyl:

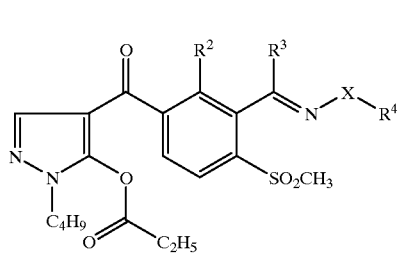

Ia279 the compounds Ia280, in particular the compounds Ia280.001–Ia280.180, which differ from the corresponding compounds Ia1.001–Ia1.180 by the fact that $R^1$ is methylsulfonyl, $R^{11}$ is iso-butyl and $R^{12}$ is ethylcarbonyl:

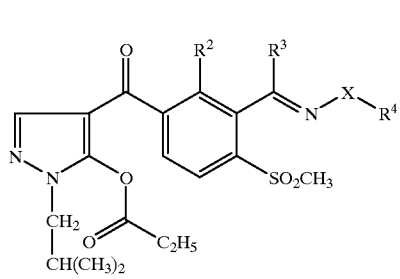

Ia280 the compounds Ia281, in particular the compounds Ia281.001–Ia281.180, which differ from the corresponding compounds Ia1.001–Ia1.180 by the fact that $R^1$ is methylsulfonyl and $R^{12}$ is n-propylcarbonyl:

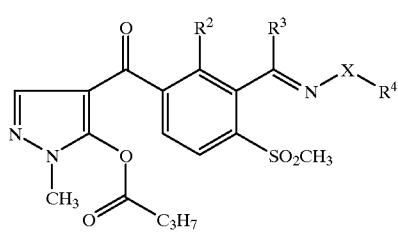

Ia281 the compounds Ia282, in particular the compounds Ia282.001–Ia282.180, which differ from the corresponding compounds Ia1.001–Ia1.180 by the fact that $R^1$ is methylsulfonyl, $R^{11}$ is ethyl and $R^{12}$ is n-propylcarbonyl:

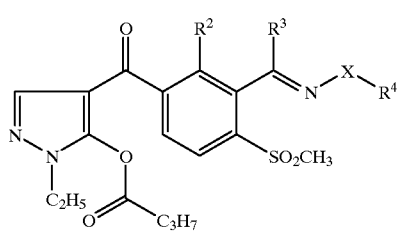

Ia282 the compounds Ia283, in particular the compounds Ia283.001–Ia283.180, which differ from the corresponding compounds Ia1.001–Ia1.180 by the fact that $R^1$ is methylsulfonyl, $R^{11}$ is n-propyl and $R^{12}$ is n-propylcarbonyl:

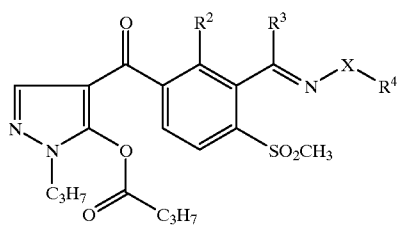

Ia283 the compounds Ia284, in particular the compounds Ia284.001–Ia284.180, which differ from the corresponding compounds Ia1.001–Ia1.180 by the fact that $R^1$ is methylsulfonyl, $R^{11}$ is n-butyl and $R^{12}$ is n-propylcarbonyl:

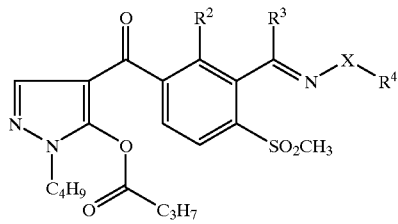

Ia284 the compounds Ia285, in particular the compounds Ia285.001–Ia285.180, which differ from the corresponding compounds Ia1.001–Ia1.180 by the fact that $R^1$ is methylsulfonyl, $R^{11}$ is iso-butyl and $R^{12}$ is n-propylcarbonyl:

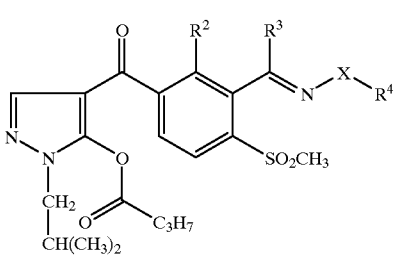

Ia285 the compounds Ia286, in particular the compounds Ia286.001–Ia286.180, which differ from the corresponding compounds Ia1.001–Ia1.180 by the fact that $R^1$ is methylsulfonyl and $R^{11}$ is trifluoromethylcarbonyl:

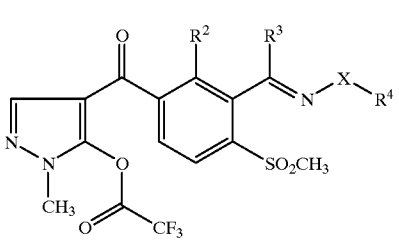

Ia286 the compounds Ia287, in particular the compounds Ia287.001–Ia287.180, which differ from the corresponding compounds Ia1.001–Ia1.180 by the fact that $R^1$ is methylsulfonyl, $R^{11}$ is ethyl and $R^{12}$ is trifluoromethylcarbonyl:

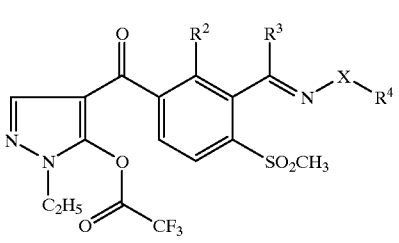

Ia287 the compounds Ia288, in particular the compounds Ia288.001–Ia288.180, which differ from the corresponding compounds Ia1.001–Ia1.180 by the fact that $R^1$ is methylsulfonyl, $R^{11}$ is n-propyl and $R^{12}$ is trifluoromethylcarbonyl:

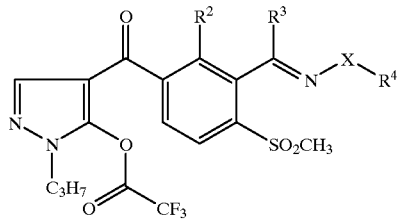
Ia288 the compounds Ia289, in particular the compounds Ia289.001–Ia289.180, which differ from the corresponding compounds Ia1.001–Ia1.180 by the fact that $R^1$ is methylsulfonyl, $R^{11}$ is n-butyl and $R^{12}$ is trifluoromethylcarbonyl:

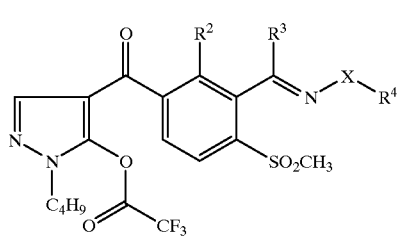
Ia289 the compounds Ia290, in particular the compounds Ia290.001–Ia290.180, which differ from the corresponding compounds Ia1.001–Ia1.180 by the fact that $R^1$ is methylsulfonyl, $R^{11}$ is iso-butyl and $R^{12}$ is trifluoromethylcarbonyl:

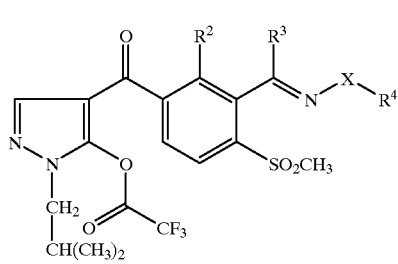
Ia290 the compounds Ia291, in particular the compounds Ia291.001–Ia291.180, which differ from the corresponding compounds Ia1.001–Ia1.180 by the fact that $R^1$ and $R^{12}$ are methylsulfonyl:

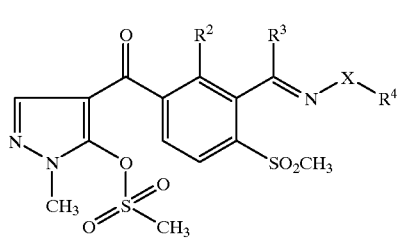
Ia291 the compounds Ia292, in particular the compounds Ia292.001–Ia292.180, which differ from the corresponding compounds Ia1.001–Ia1.180 by the fact that $R^1$ and $R^{12}$ are methylsulfonyl and $R^{11}$ is ethyl:

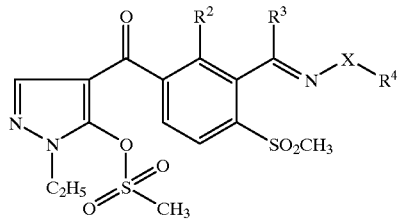
Ia292 the compounds Ia293, in particular the compounds Ia293.001–Ia293.180, which differ from the corresponding compounds Ia1.001–Ia1.180 by the fact that $R^1$ and $R^{12}$ are methylsulfonyl and $R^{11}$ is n-propyl:

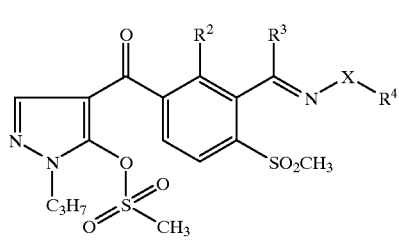
Ia293 the compounds Ia294, in particular the compounds Ia294.001–Ia294.180, which differ from the corresponding compounds Ia1.001–Ia1.180 by the fact that $R^1$ and $R^{12}$ are methylsulfonyl and $R^{11}$ is n-butyl:

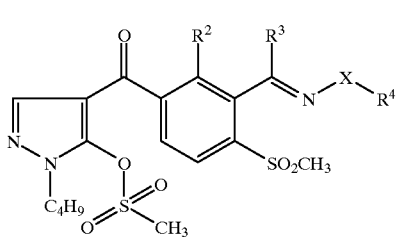
Ia294 the compounds Ia295, in particular the compounds Ia295.001–Ia295.180, which differ from the corresponding compounds Ia1.001–Ia1.180 by the fact that $R^1$ and $R^{12}$ are methylsulfonyl and $R^{11}$ is iso-butyl:

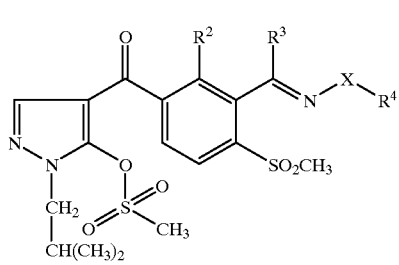
Ia295 the compounds Ia296, in particular the compounds Ia296.001–Ia296.180, which differ from the corresponding compounds Ia1.001–Ia1.180 by the fact that $R^1$ is methylsulfonyl and $R^{12}$ is ethylsulfonyl:

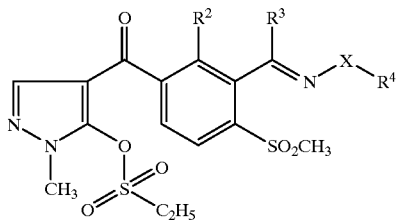

Ia296 the compounds Ia297, in particular the compounds Ia297.001–Ia297.180, which differ from the corresponding compounds Ia1.001–Ia1.180 by the fact that $R^1$ is methylsulfonyl, $R^{11}$ is ethyl and $R^{12}$ is ethylsulfonyl:

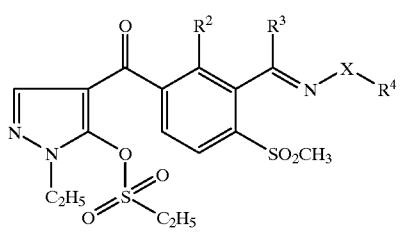

Ia297 the compounds Ia298, in particular the compounds Ia298.001–Ia298.180, which differ from the corresponding compounds Ia1.001–Ia1.180 by the fact that $R^1$ is methylsulfonyl, $R^{11}$ is n-propyl and $R^{12}$ is ethylsulfonyl:

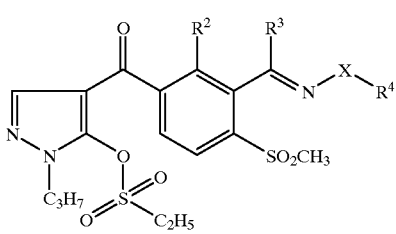

Ia298 the compounds Ia299, in particular the compounds Ia299.001–Ia299.180, which differ from the corresponding compounds Ia1.001–Ia1.180 by the fact that $R^1$ is methylsulfonyl, $R^{11}$ is n-butyl and $R^{12}$ is ethylsulfonyl:

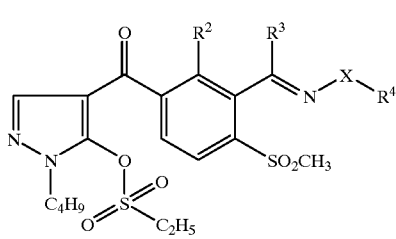

Ia299 the compounds Ia300, in particular the compounds Ia300.001–Ia300.180, which differ from the corresponding compounds Ia1.001–Ia1.180 by the fact that $R^1$ is methylsulfonyl, $R^{11}$ is iso-butyl and $R^{12}$ is ethylsulfonyl:

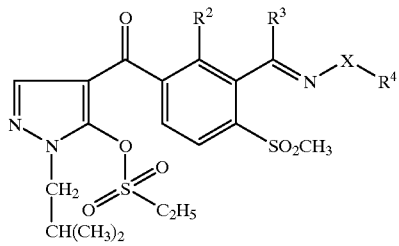

Ia300 the compounds Ia301, in particular the compounds Ia301.001–Ia301.180, which differ from the corresponding compounds Ia1.001–Ia1.180 by the fact that $R^1$ is methylsulfonyl and $R^{12}$ is n-propylsulfonyl:

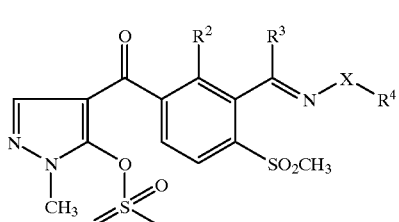

Ia301 the compounds Ia302, in particular the compounds Ia302.001–Ia302.180, which differ from the corresponding compounds Ia1.001–Ia1.180 by the fact that $R^1$ is methylsulfonyl, $R^{11}$ is ethyl and $R^{12}$ is n-propylsulfonyl:

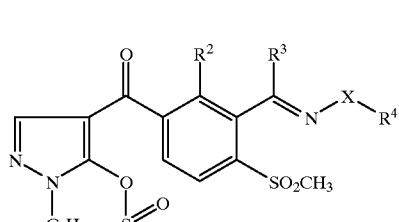

Ia302 the compounds Ia303, in particular the compounds Ia303.001–Ia303.180, which differ from the corresponding compounds Ia1.001–Ia1.180 by the fact that $R^1$ is methylsulfonyl, $R^{11}$ is n-propyl and $R^{12}$ is n-propylsulfonyl:

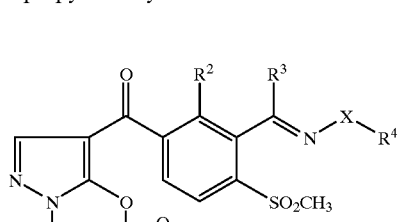

Ia303 the compounds Ia304, in particular the compounds Ia304.001–Ia304.180, which differ from the corresponding compounds Ia1.001–Ia1.180 by the fact that $R^1$ is methylsulfonyl, $R^{11}$ is n-butyl and $R^{12}$ is n-propylsulfonyl:

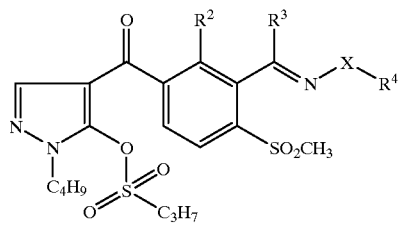

Ia304 the compounds Ia305, in particular the compounds Ia305.001–Ia305.180, which differ from the corresponding compounds Ia1.001–Ia1.180 by the fact that $R^1$ is methylsulfonyl, $R^{11}$ is iso-butyl and $R^{12}$ is n-propylsulfonyl:

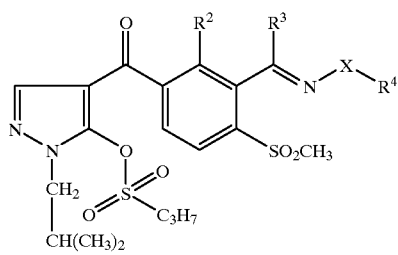

Ia305 the compounds Ia306, in particular the compounds Ia306.001–Ia306.180, which differ from the corresponding compounds Ia1.001–Ia1.180 by the fact that $R^1$ is methylsulfonyl and $R^{12}$ is iso-propylsulfonyl:

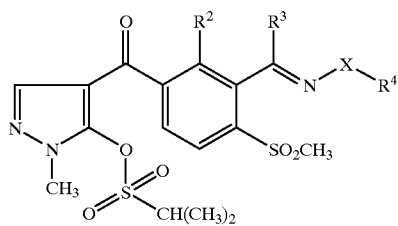

Ia306 the compounds Ia307, in particular the compounds Ia307.001–Ia307.180, which differ from the corresponding compounds Ia1.001–Ia1.180 by the fact that $R^1$ is methylsulfonyl, $R^{11}$ is ethyl and $R^{12}$ is iso-propylsulfonyl:

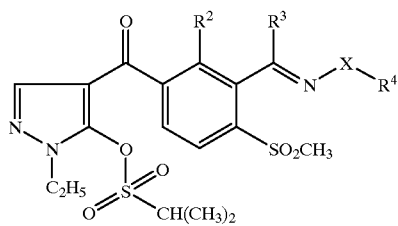

Ia307 the compounds Ia308, in particular the compounds Ia308.001–Ia308.180, which differ from the corresponding compounds Ia1.001–Ia1.180 by the fact that $R^1$ is methylsulfonyl, $R^{11}$ is n-propyl and $R^{12}$ is iso-propylsulfonyl:

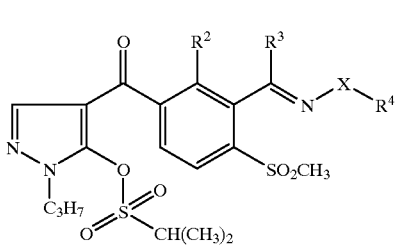

Ia308 the compounds Ia309, in particular the compounds Ia309.001–Ia309.180, which differ from the corresponding compounds Ia1.001–Ia1.180 by the fact that $R^1$ is methylsulfonyl, $R^{11}$ is n-butyl and $R^{12}$ is iso-propylsulfonyl:

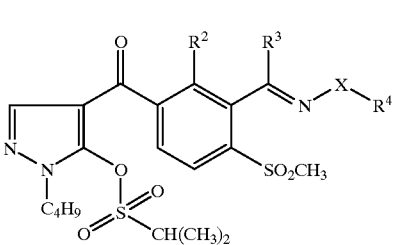

Ia309 the compounds Ia310, in particular the compounds Ia310.001–Ia310.180, which differ from the corresponding compounds Ia1.001–Ia1.180 by the fact that $R^1$ is methylsulfonyl, $R^{11}$ is iso-butyl and $R^{12}$ is iso-propylsulfonyl:

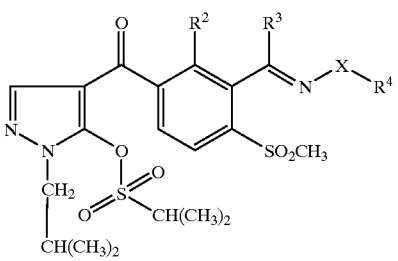

Ia310 the compounds Ia311, in particular the compounds Ia311.001–Ia311.180, which differ from the corresponding compounds Ia1.001–Ia1.180 by the fact that $R^1$ is methylsulfonyl and $R^{12}$ is n-butylsulfonyl:

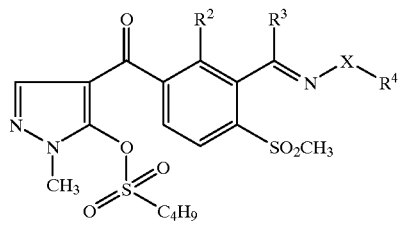

Ia311 the compounds Ia312.001–Ia312.180, which differ from the corresponding compounds Ia1.001–Ia1.180 by the fact that $R^1$ is methylsulfonyl, $R^{11}$ is ethyl and $R^{12}$ is n-butylsulfonyl:

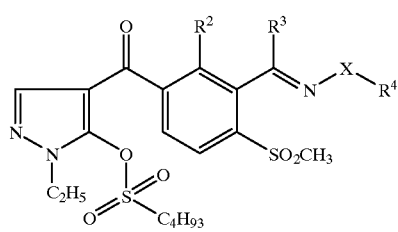

Ia312 the compounds Ia313, in particular the compounds Ia313.001–Ia313.180, which differ from the corresponding compounds Ia1.001–Ia1.180 by the fact that $R^1$ is methylsulfonyl, $R^{11}$ is n-propyl and $R^{12}$ is n-butylsulfonyl:

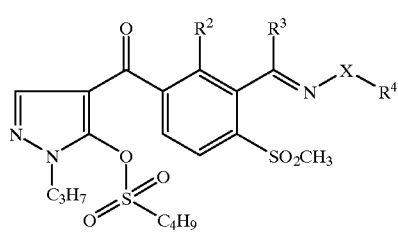

Ia313 the compounds Ia314, in particular the compounds Ia314.001–Ia314.180, which differ from the corresponding compounds Ia1.001–Ia1.180 by the fact that $R^1$ is methylsulfonyl, $R^{11}$ is n-butyl and $R^{12}$ is n-butylsulfonyl:

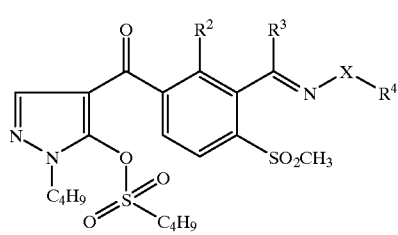

Ia314 the compounds Ia315, in particular the compounds Ia315.001–Ia315.180, which differ from the corresponding compounds Ia1.001–Ia1.180 by the fact that $R^1$ is methylsulfonyl, $R^{11}$ is iso-butyl and $R^{12}$ is n-butylsulfonyl:

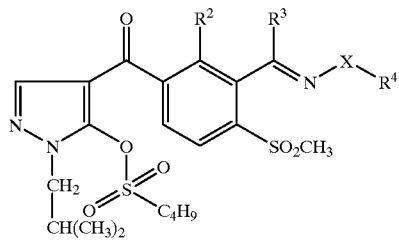

Ia315 the compounds Ia316, in particular the compounds Ia316.001–Ia316.180, which differ from the corresponding compounds Ia1.001–Ia1.180 by the fact that $R^1$ is methylsulfonyl and $R^{12}$ is iso-butylsulfonyl:

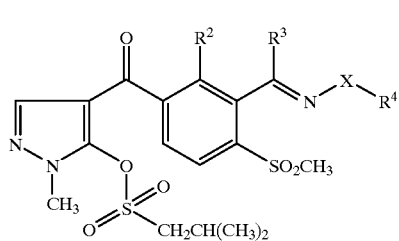

Ia316 the compounds Ia317, in particular the compounds Ia317.001–Ia317.180, which differ from the corresponding compounds Ia1.001–Ia1.180 by the fact that $R^1$ is methylsulfonyl, $R^{11}$ is ethyl and $R^{12}$ is iso-butylsulfonyl:

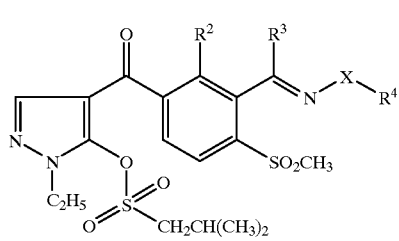

Ia317 the compounds Ia318, in particular the compounds Ia318.001–Ia318.180, which differ from the corresponding compounds Ia1.001–Ia1.180 by the fact that $R^1$ is methylsulfonyl, $R^{11}$ is n-propyl and $R^{12}$ is iso-butylsulfonyl:

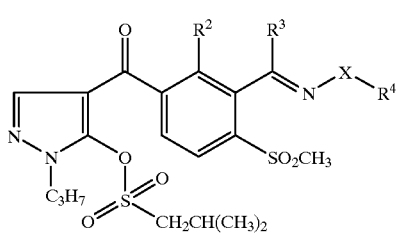

Ia318 the compounds Ia319, in particular the compounds Ia319.001–Ia319.180, which differ from the corresponding compounds Ia1.001–Ia1.180 by the fact that $R^1$ is methylsulfonyl, $R^{11}$ is n-butyl and $R^{12}$ is iso-butylsulfonyl:

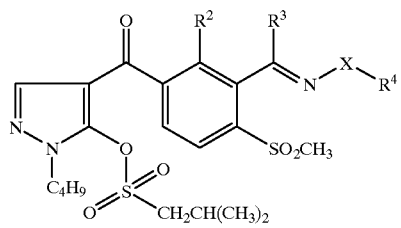

Ia319 the compounds Ia320, in particular the compounds Ia320.001–Ia320.180, which differ from the corresponding compounds Ia1.001–Ia1.180 by the fact that $R^1$ is methylsulfonyl, $R^{11}$ is iso-butyl and $R^{12}$ is iso-butylsulfonyl:

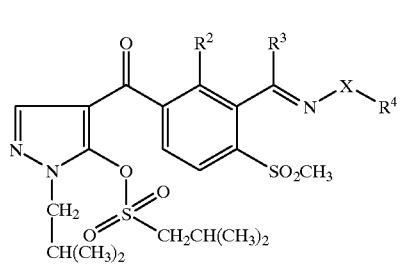

Ia320 the compounds Ia321, in particular the compounds Ia321.001–Ia321.180, which differ from the corresponding compounds Ia1.001–Ia1.180 by the fact that $R^1$ is methylsulfonyl and $R^{12}$ is sec-butylsulfonyl:

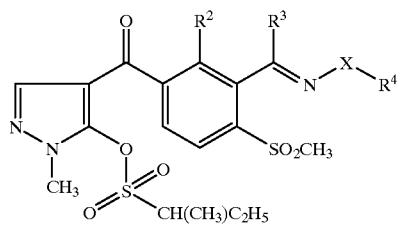

Ia321 the compounds Ia322, in particular the compounds Ia322.001–Ia322.180, which differ from the corresponding compounds Ia1.001–Ia1.180 by the fact that $R^1$ is methylsulfonyl, $R^{11}$ is ethyl and $R^{12}$ is sec-butylsulfonyl:

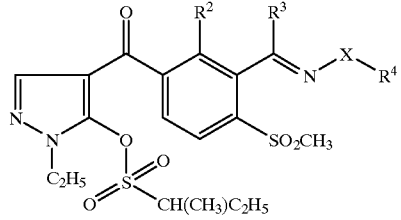

Ia322 the compounds Ia323, in particular the compounds Ia323.001–Ia323.180, which differ from the corresponding compounds Ia1.001–Ia1.180 by the fact that $R^1$ is methylsulfonyl, $R^{11}$ is is [sic] n-propyl and $R^{12}$ is sec-butylsulfonyl:

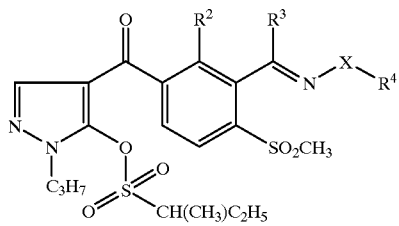

Ia323 the compounds Ia324, in particular the compounds Ia324.001–Ia324.180, which differ from the corresponding compounds Ia1.001–Ia1.180 by the fact that $R^1$ is methylsulfonyl, $R^{11}$ is n-butyl and $R^{12}$ is sec-butylsulfonyl:

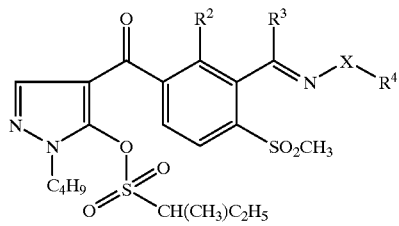

Ia324 the compounds Ia325, in particular the compounds Ia325.001–Ia325.180, which differ from the corresponding compounds Ia1.001–Ia1.180 by the fact that $R^1$ is methylsulfonyl, $R^{11}$ is iso-butyl and $R^{12}$ is sec-butylsulfonyl:

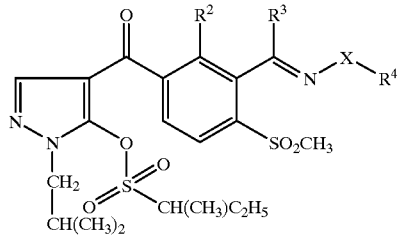

Ia325 the compounds Ia326, in particular the compounds Ia326.001–Ia326.180, which differ from the corresponding compounds Ia1.001–Ia1.180 by the fact that $R^1$ is methylsulfonyl and $R^{12}$ is trifluoromethylsulfonyl:

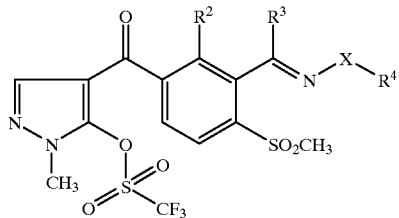

Ia326 the compounds Ia327, in particular the compounds Ia327.001–Ia327.180, which differ from the corresponding compounds Ia1.001–Ia1.180 by the fact that R$^1$ is methylsulfonyl, R$^{11}$ is ethyl and R$^{12}$ is trifluoromethylsulfonyl:

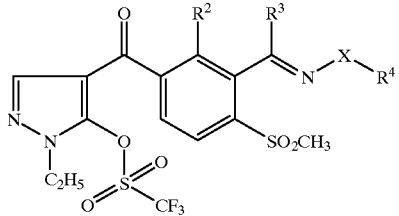

Ia327 the compounds Ia328, in particular the compounds Ia328.001–Ia328.180, which differ from the corresponding compounds Ia1.001–Ia1.180 by the fact that R$^1$ is methylsulfonyl, R$^{11}$ is n-propyl and R$^{12}$ is trifluoromethylsulfonyl:

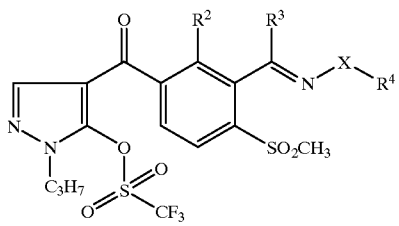

Ia328 the compounds Ia329, in particular the compounds Ia329.001–Ia329.180, which differ from the corresponding compounds Ia1.001–Ia1.180 by the fact that R$^1$ is methylsulfonyl, R$^{11}$ is n-butyl and R$^{12}$ is trifluoromethylsulfonyl:

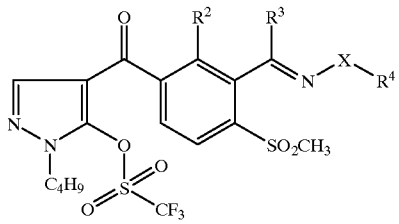

Ia329 the compounds Ia330, in particular the compounds Ia330.001–Ia330.180, which differ from the corresponding compounds Ia1.001–Ia1.180 by the fact that R$^1$ is methylsulfonyl, R$^{11}$ is iso-butyl and R$^{12}$ is trifluoromethylsulfonyl:

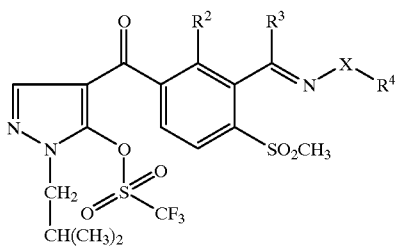

Ia330 the compounds Ia331, in particular the compounds Ia331.001–Ia331.180, which differ from the corresponding compounds Ia1.001–Ia1.180 by the fact that R$^1$ is methylsulfonyl and R$^{12}$ is phenylcarbonylmethyl:

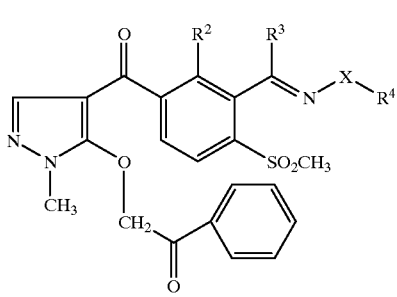

Ia331 the compounds Ia332, in particular the compounds Ia332.001–Ia332.180, which differ from the corresponding compounds Ia1.001–Ia1.180 by the fact that R$^1$ is methylsulfonyl, R$^{11}$ is ethyl and R$^{12}$ is phenylcarbonylmethyl:

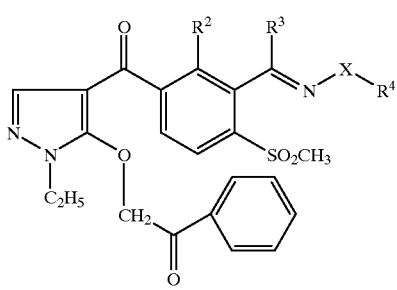

Ia332 the compounds Ia333, in particular the compounds Ia333.001–Ia333.180, which differ from the corresponding compounds Ia1.001–Ia1.180 by the fact that R$^1$ is methylsulfonyl, R$^{11}$ is n-propyl and R$^{12}$ is phenylcarbonylmethyl:

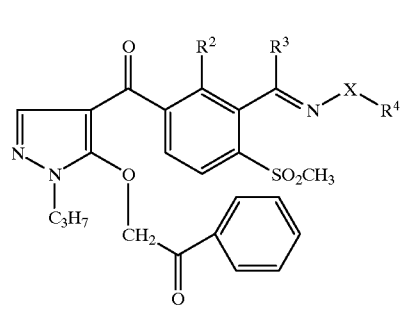

Ia333 the compounds Ia334, in particular the compounds Ia334.001–Ia334.180, which differ from the corresponding compounds Ia1.001–Ia1.180 by the fact that $R^1$ is methylsulfonyl, $R^{11}$ is n-butyl and $R^{12}$ is phenylcarbonylmethyl:

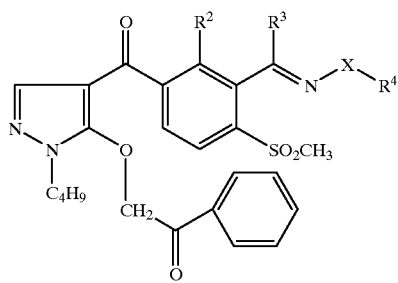

Ia334 the compounds Ia335, in particular the compounds Ia335.001–Ia335.180, which differ from the corresponding compounds Ia1.001–Ia1.180 by the fact that $R^1$ is methylsulfonyl, $R^{11}$ is iso-butyl and $R^{12}$ is phenylcarbonylmethyl:

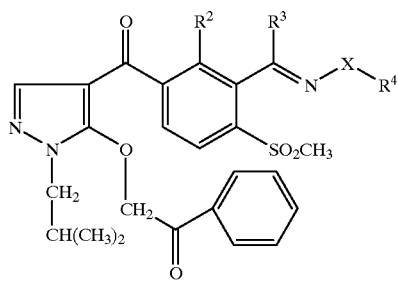

Ia335 the compounds Ia336, in particular the compounds Ia336.001–Ia336.180, which differ from the corresponding compounds Ia1.001–Ia1.180 by the fact that $R^1$ is methylsulfonyl and $R^{12}$ is phenylsulfonyl:

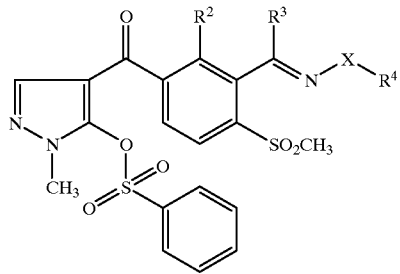

Ia336 le;2qthe compounds Ia337, in particular the compounds Ia337.001–Ia337.180, which differ from the corresponding compounds Ia1.001–Ia1.180 by the fact that $R^1$ is methylsulfonyl, $R^{11}$ is ethyl and $R^{12}$ is phenylsulfonyl:

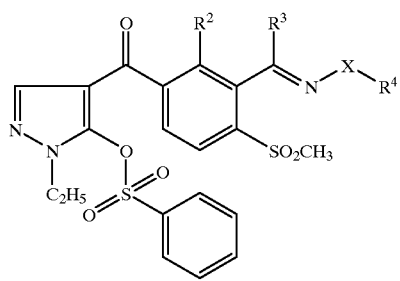

Ia337 the compounds Ia338, in particular the compounds Ia338.001–Ia338.180, which differ from the corresponding compounds Ia1.001–Ia1.180 by the fact that $R^1$ is methylsulfonyl, $R^{11}$ is n-propyl and $R^{12}$ is phenylsulfonyl:

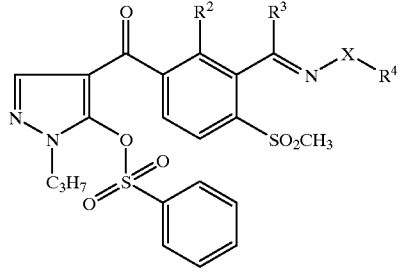

Ia338 the compounds Ia339, in particular the compounds Ia339.001–Ia339.180, which differ from the corresponding compounds Ia1.001–Ia1.180 by the fact that $R^1$ is methylsulfonyl, $R^{11}$ is n-butyl and $R^{12}$ is phenylsulfonyl:

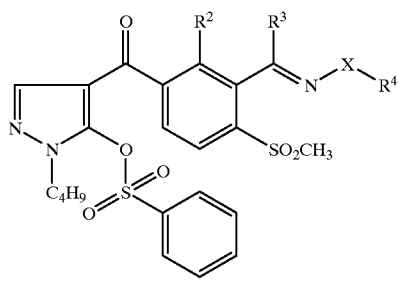

Ia339 the compounds Ia340, in particular the compounds Ia340.001–Ia340.180, which differ from the corresponding compounds Ia1.001–Ia1.180 by the fact that $R^1$ is methylsulfonyl, $R^{11}$ is iso-butyl and $R^{12}$ is phenylsulfonyl:

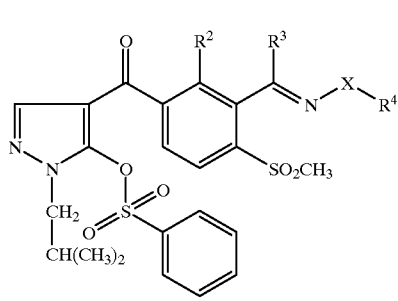

Ia340 the compounds Ia341, in particular the compounds Ia341.001–Ia341.180, which differ from the corresponding compounds Ia1.001–Ia1.180 by the fact that $R^1$ is methylsulfonyl and $R^{12}$ is 4-methylphenylsulfonyl:

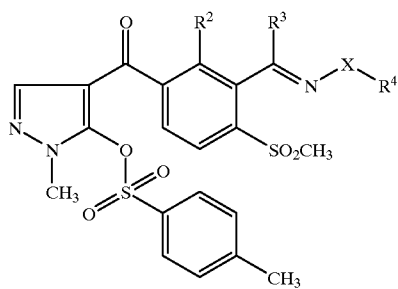

Ia341 the compounds Ia342, in particular the compounds Ia342.001–Ia342.180, which differ from the corresponding compounds Ia1.001–Ia1.180 by the fact that $R^1$ is methylsulfonyl, $R^{11}$ is ethyl and $R^{12}$ is 4-methylphenylsulfonyl:

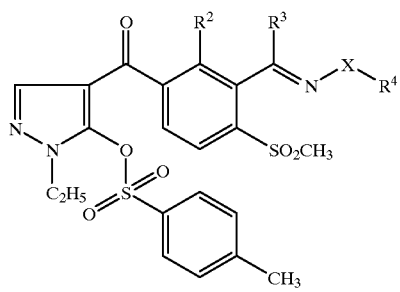

Ia342 the compounds Ia343, in particular the compounds Ia343.001–Ia343.180, which differ from the corresponding compounds Ia1.001–Ia1.180 by the fact that $R^1$ is methylsulfonyl, $R^{11}$ is n-propyl and $R^{12}$ is 4-methylphenylsulfonyl:

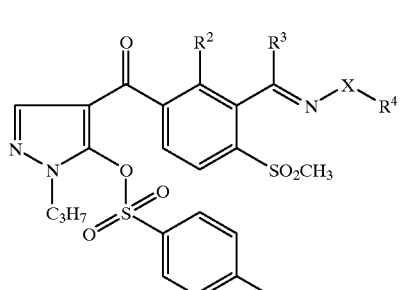

Ia343 the compounds Ia344, in particular the compounds Ia344.001–Ia344.180, which differ from the corresponding compounds Ia1.001–Ia1.180 by the fact that $R^1$ is methylsulfonyl, $R^{11}$ is n-butyl and $R^{12}$ is 4-methylphenylsulfonyl:

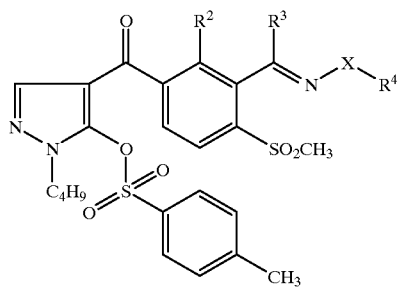

Ia344 the compounds Ia345, in particular the compounds Ia345.001–Ia345.180, which differ from the corresponding compounds Ia1.001–Ia1.180 by the fact that $R^1$ is methylsulfonyl, $R^{11}$ is iso-butyl and $R^{12}$ is 4-methylphenylsulfonyl:

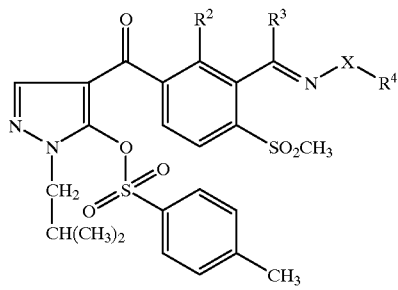

Ia345 the compounds Ia346, in particular the compounds Ia346.001–Ia346.180, which differ from the corresponding compounds Ia1.001–Ia1.180 by the fact that $R^{13}$ is methyl:

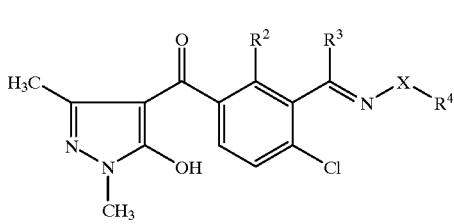

Ia346 the compounds Ia347, in particular the compounds Ia347.001–Ia347.180, which differ from the corresponding compounds Ia1.001–Ia1.180 by the fact that $R^{11}$ is ethyl and $R^{13}$ is methyl:

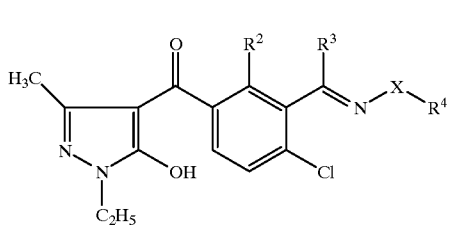

Ia347 the compounds Ia348, in particular the compounds Ia348.001–Ia348.180, which differ from the corresponding compounds Ia1.001–Ia1.180 by the fact that $R^{11}$ is n-propyl and $R^{13}$ is methyl:

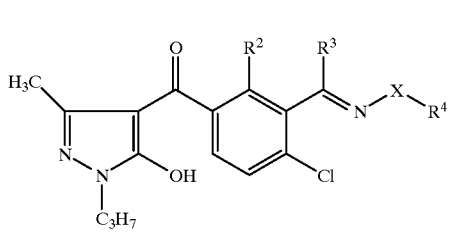

Ia348 the compounds Ia349, in particular the compounds Ia349.001–Ia349.180, which differ from the corresponding compounds Ia1.001–Ia1.180 by the fact that $R^{11}$ is n-butyl and $R^{13}$ is methyl:

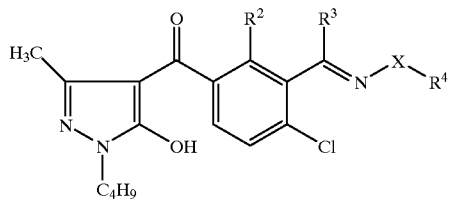

Ia349 the compounds Ia350, in particular the compounds Ia350.001–Ia350.180, which differ from the corresponding compounds Ia1.001–Ia1.180 by the fact that $R^{11}$ is iso-butyl and $R^{13}$ is methyl:

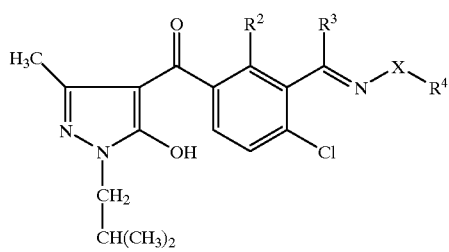

Ia350 the compounds Ia351, in particular the compounds Ia351.001–Ia351.180, which differ from the corresponding compounds Ia1.001–Ia1.180 by the fact that $R^{12}$ and $R^{13}$ are methyl:

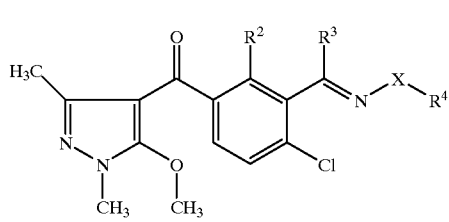

Ia351 the compounds Ia352, in particular the compounds Ia352.001–Ia352.180, which differ from the corresponding compounds Ia1.001–Ia1.180 by the fact that $R^{11}$ is ethyl and $R^{12}$ and $R^{13}$ are methyl:

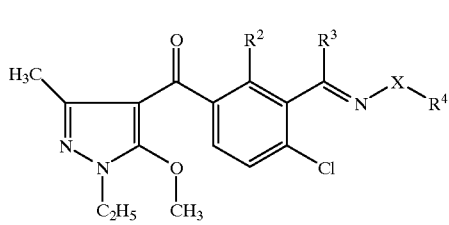

Ia352 the compounds Ia353, in particular the compounds Ia353.001–Ia353.180, which differ from the corresponding compounds Ia1.001–Ia1.180 by the fact that $R^{11}$ is n-propyl and $R^{12}$ and $R^{13}$ are methyl:

Ia353

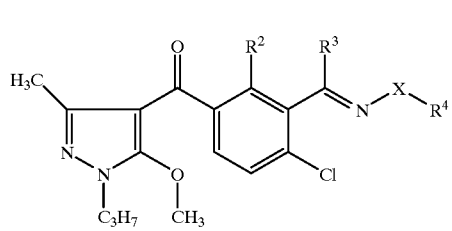

the compounds Ia354, in particular the compounds Ia354.001–Ia354.180, which differ from the corresponding compounds Ia1.001–Ia1.180 by the fact that $R^{11}$ is n-butyl and $R^{12}$ and $R^{13}$ are methyl:

Ia354

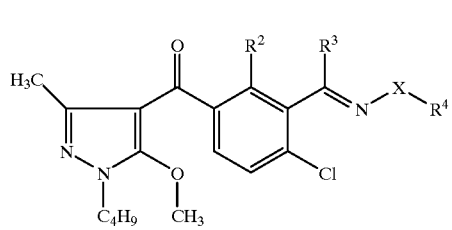

the compounds Ia355, in particular the compounds Ia355.001–Ia355.180, which differ from the corresponding compounds Ia1.001–Ia1.180 by the fact that $R^{11}$ is iso-butyl and $R^{12}$ and $R^{13}$ are methyl:

Ia355

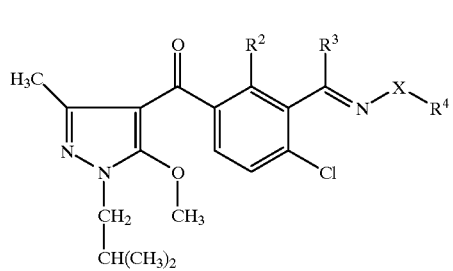

the compounds Ia356, in particular the compounds Ia356.001–Ia356.180, which differ from the corresponding compounds Ia1.001–Ia1.180 by the fact that $R^{12}$ is ethyl and $R^{13}$ is methyl:

Ia356

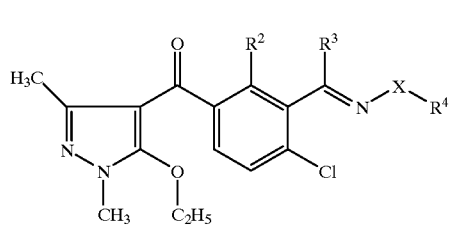

the compounds Ia357, in particular the compounds Ia357.001–Ia357.180, which differ from the corresponding compounds Ia1.001–Ia1.180 by the fact that $R^{11}$ and $R^{12}$ are ethyl and $R^{13}$ is methyl:

Ia357

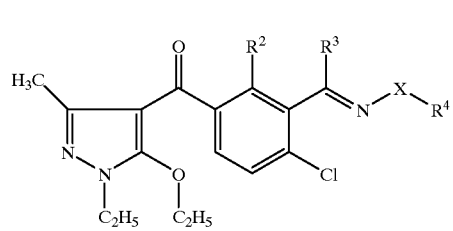

the compounds Ia358, in particular the compounds Ia358.001–Ia358.180, which differ from the corresponding compounds Ia1.001–Ia1.180 by the fact that $R^{11}$ is n-propyl, $R^{12}$ is ethyl and $R^{13}$ is methyl:

Ia358

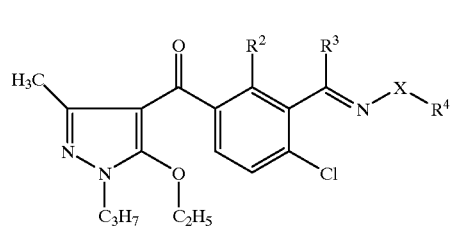

the compounds Ia359, in particular the compounds Ia359.001–Ia359.180, which differ from the corresponding compounds Ia1.001–Ia1.180 by the fact that $R^{11}$ is n-butyl, $R^{12}$ is ethyl and $R^{13}$ is methyl:

Ia359

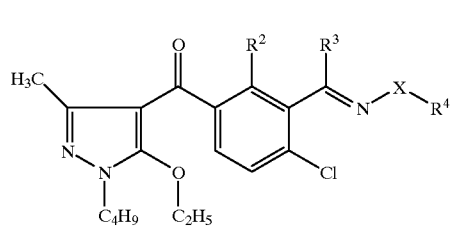

the compounds Ia360, in particular the compounds Ia360.001–Ia360.180, which differ from the corresponding compounds Ia1.001–Ia1.180 by the fact that $R^{11}$ is iso-butyl, $R^{12}$ is ethyl and $R^{13}$ is methyl:

Ia360

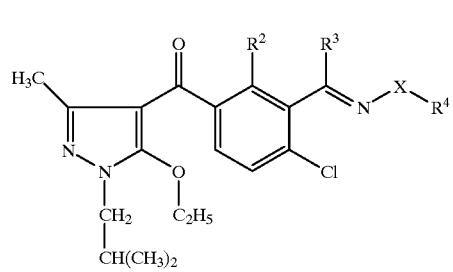

the compounds Ia361, in particular the compounds Ia361.001–Ia361.180, which differ from the corresponding compounds Ia1.001–Ia1.180 by the fact that $R^{11}$ is n-propyl and $R^{13}$ is methyl:

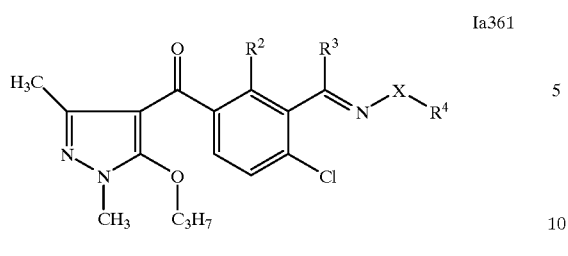

Ia361 the compounds Ia362, in particular the compounds Ia362.001–Ia362.180, which differ from the corresponding compounds Ia1.001–Ia1.180 by the fact that $R^{11}$ is ethyl, $R^{12}$ is n-propyl and $R^{13}$ is methyl:

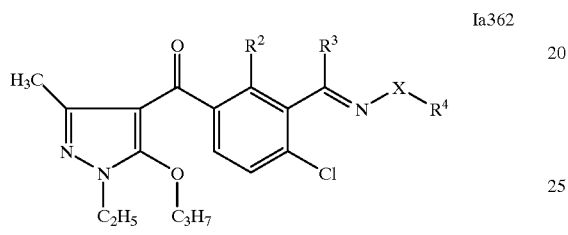

Ia362 the compounds Ia363, in particular the compounds Ia363.001–Ia363.180, which differ from the corresponding compounds Ia1.001–Ia1.180 by the fact that $R^{11}$ and $R^{12}$ are n-propyl and $R^{13}$ is methyl:

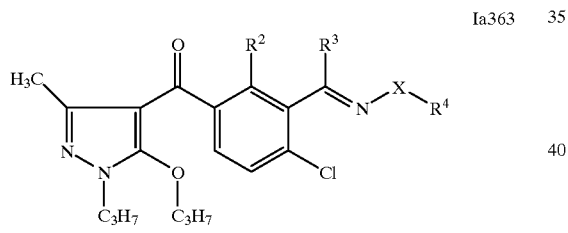

Ia363 the compounds Ia364, in particular the compounds Ia364.001–Ia364.180, which differ from the corresponding compounds Ia1.001–Ia1.180 by the fact that $R^{11}$ is n-butyl, $R^{12}$ is n-propyl and $R^{13}$ is methyl:

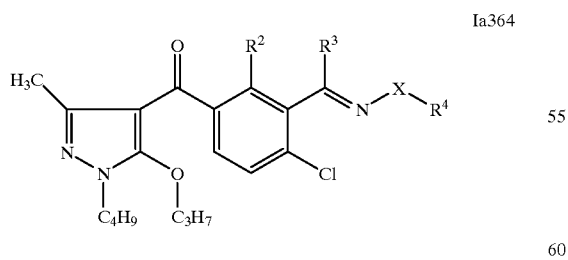

Ia364 the compounds Ia365, in particular the compounds Ia365.001–Ia365.180, which differ from the corresponding compounds Ia1.001–Ia1.180 by the fact that $R^{11}$ is iso-butyl, $R^{12}$ is n-propyl and $R^{13}$ is methyl:

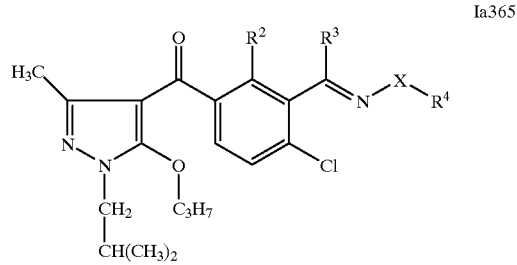

Ia365 the compounds Ia366, in particular the compounds Ia366.001–Ia366.180, which differ from the corresponding compounds Ia1.001–Ia1.180 by the fact that $R^{12}$ is iso-propyl and $R^{13}$ is methyl:

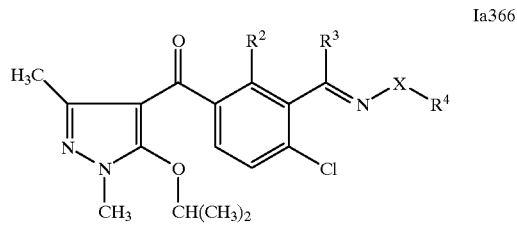

Ia366 the compounds Ia367, in particular the compounds Ia367.001–Ia367.180, which differ from the corresponding compounds Ia1.001–Ia1.180 by the fact that $R^{11}$ is ethyl, $R^{12}$ is iso-propyl and $R^{13}$ is methyl:

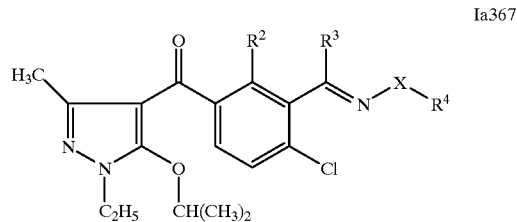

Ia367 the compounds Ia368, in particular the compounds Ia368.001–Ia368.180, which differ from the corresponding compounds Ia1.001–Ia1.180 by the fact that $R^{11}$ is n-propyl, $R^{12}$ is iso-propyl and $R^{13}$ is methyl:

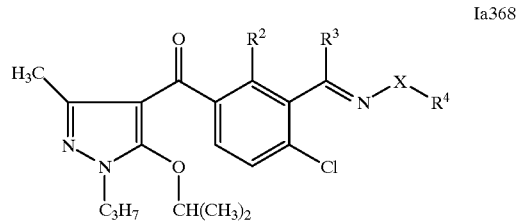

Ia368 the compounds Ia369, in particular the compounds Ia369.001–Ia369.180, which differ from the corresponding compounds Ia1.001–Ia1.180 by the fact that $R^{11}$ is n-butyl, $R^{12}$ is iso-propyl and $R^{13}$ is methyl:

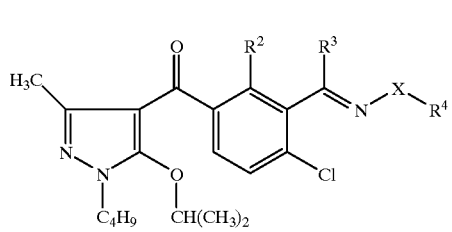

Ia369 the compounds Ia370, in particular the compounds Ia370.001–Ia370.180, which differ from the corresponding compounds Ia1.001–Ia1.180 by the fact that $R^{11}$ is iso-butyl, $R^{12}$ is iso-propyl and $R^{13}$ is methyl:

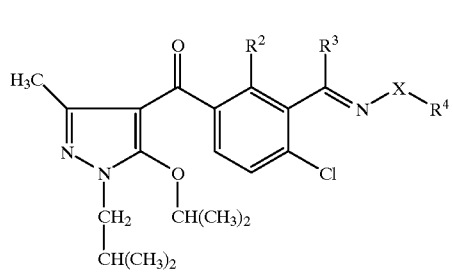

Ia370 the compounds Ia371, in particular the compounds Ia371.001–Ia371.180, which differ from the corresponding compounds Ia1.001–Ia1.180 by the fact that $R^{12}$ is n-butyl and $R^{13}$ is methyl:

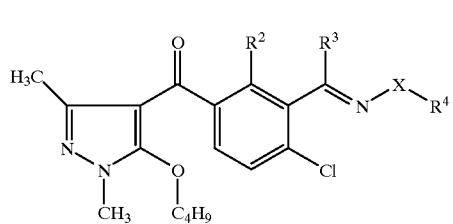

Ia371 the compounds Ia372, in particular the compounds Ia372.001–Ia372.180, which differ from the corresponding compounds Ia1.001–Ia1.180 by the fact that $R^{11}$ is ethyl, $R^{12}$ is n-butyl and $R^{13}$ is methyl:

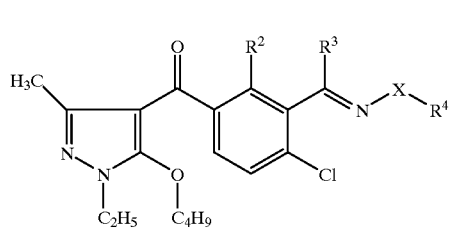

Ia372 the compounds Ia373, in particular the compounds Ia373.001–Ia373.180, which differ from the corresponding compounds Ia1.001–Ia1.180 by the fact that $R^{11}$ is n-propyl, $R^{12}$ is n-butyl and $R^{13}$ is methyl:

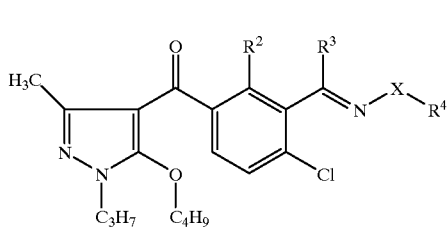

Ia373 the compounds Ia374, in particular the compounds Ia374.001–Ia374.180, which differ from the corresponding compounds Ia1.001–Ia1.180 by the fact that $R^{11}$ and $R^{12}$ are n-butyl and $R^{13}$ is methyl:

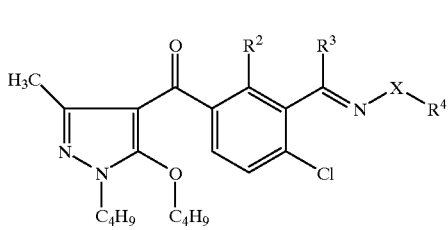

Ia374 the compounds Ia375, in particular the compounds Ia375.001–Ia375.180, which differ from the corresponding compounds Ia1.001–Ia1.180 by the fact that $R^{11}$ is iso-butyl, $R^{12}$ is n-butyl and $R^{13}$ is methyl:

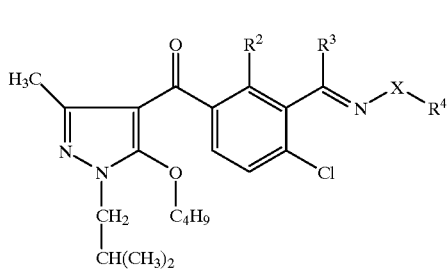

Ia375 the compounds Ia376, in particular the compounds Ia376.001–Ia376.180, which differ from the corresponding compounds Ia1.001–Ia1.180 by the fact that $R^{12}$ is sec-butyl and $R^{13}$ is methyl:

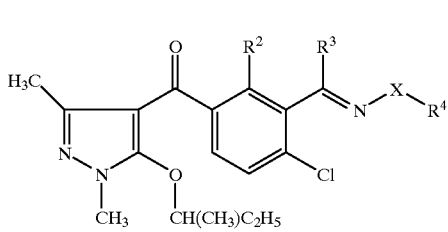

Ia376 the compounds Ia377, in particular the compounds Ia377.001–Ia377.180, which differ from the corresponding compounds Ia1.001–Ia1.180 by the fact that $R^{11}$ is ethyl, $R^{12}$ is sec-butyl and $R^{13}$ is methyl:

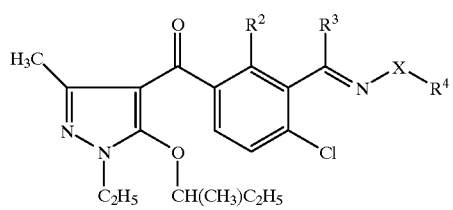

Ia377 the compounds Ia378, in particular the compounds Ia378.001–Ia378.180, which differ from the corresponding compounds Ia1.001–Ia1.180 by the fact that $R^{11}$ is n-propyl, $R^{12}$ is sec-butyl and $R^{13}$ is methyl:

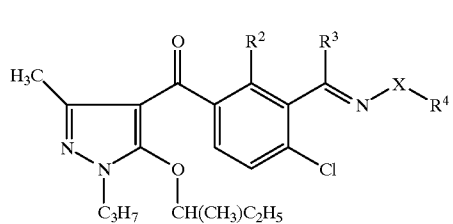

Ia378 the compounds Ia379, in particular the compounds Ia379.001–Ia379.180, which differ from the corresponding compounds Ia1.001–Ia1.180 by the fact that $R^{11}$ is n-butyl, $R^{12}$ is sec-butyl and $R^{13}$ is methyl:

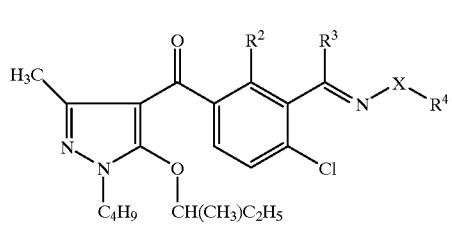

Ia379 the compounds Ia380, in particular the compounds Ia380.001–Ia380.180, which differ from the corresponding compounds Ia1.001–Ia1.180 by the fact that $R^{11}$ is iso-butyl, $R^{12}$ is sec-butyl and $R^{13}$ is methyl:

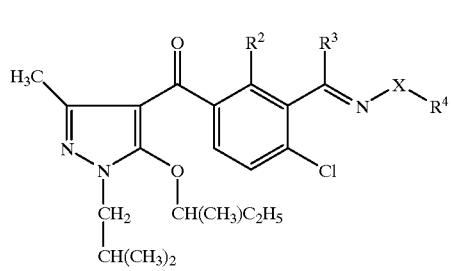

Ia380 the compounds Ia381, in particular the compounds Ia381.001–Ia381.180, which differ from the corresponding compounds Ia1.001–Ia1.180 by the fact that $R^{12}$ is iso-butyl and $R^{13}$ is methyl:

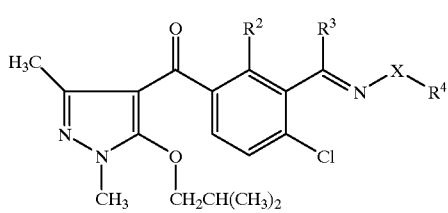

Ia381 the compounds Ia382, in particular the compounds Ia382.001–Ia382.180, which differ from the corresponding compounds Ia1.001–Ia1.180 by the fact that $R^{11}$ is ethyl, $R^{12}$ is iso-butyl and $R^{13}$ is methyl:

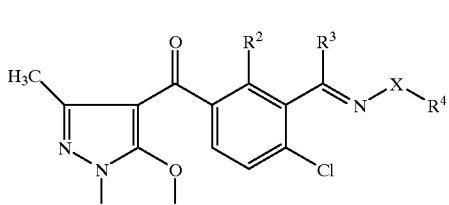

Ia382 the compounds Ia383, in particular the compounds Ia383.001–Ia383.180, which differ from the corresponding compounds Ia1.001–Ia1.180 by the fact that $R^{11}$ is n-propyl, $R^{12}$ is iso-butyl and $R^{13}$ is methyl:

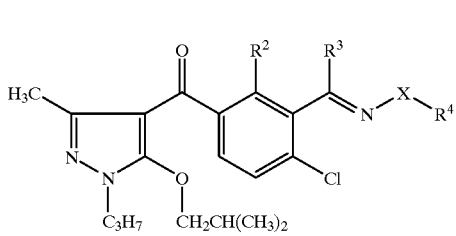

Ia383 the compounds Ia384, in particular the compounds Ia384.001–Ia384.180, which differ from the corresponding compounds Ia1.001–Ia1.180 by the fact that $R^{11}$ is n-butyl, $R^{12}$ is iso-butyl and $R^{13}$ is methyl:

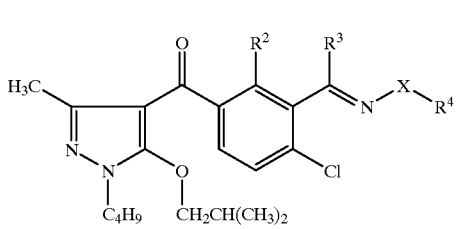

Ia384 the compounds Ia385, in particular the compounds Ia385.001–Ia385.180, which differ from the corresponding compounds Ia1.001–Ia1.180 by the fact that $R^{11}$ and $R^{12}$ are iso-butyl and $R^{13}$ is methyl:

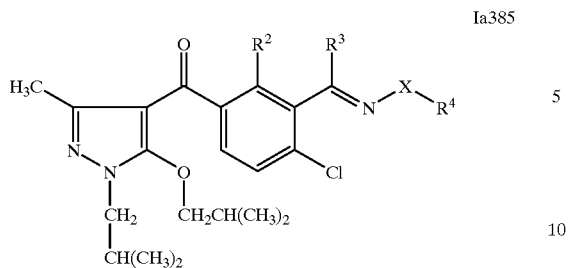
Ia385 the compounds Ia386, in particular the compounds Ia386.001–Ia386.180, which differ from the corresponding compounds Ia1.001–Ia1.180 by the fact that $R^{12}$ is methylcarbonyl and $R^{13}$ is methyl:

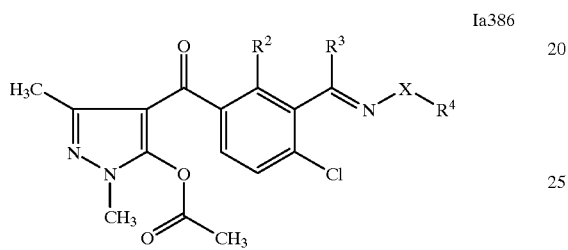
Ia386 the compounds Ia387, in particular the compounds Ia387.001–Ia387.180, which differ from the corresponding compounds Ia1.001–Ia1.180 by the fact that $R^{11}$ is ethyl, $R^{12}$ is methylcarbonyl and $R^{13}$ is methyl:

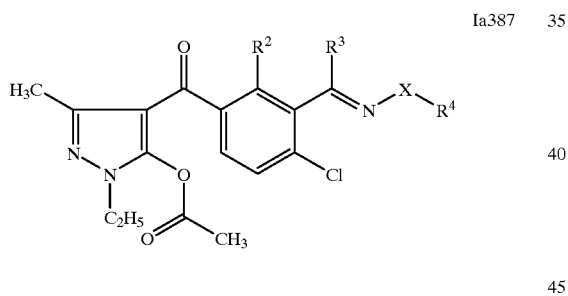
Ia387 the compounds Ia388, in particular the compounds Ia388.001–Ia388.180, which differ from the corresponding compounds Ia1.001–Ia1.180 by the fact that $R^{11}$ is n-propyl, $R^{12}$ is methylcarbonyl and $R^{13}$ is methyl:

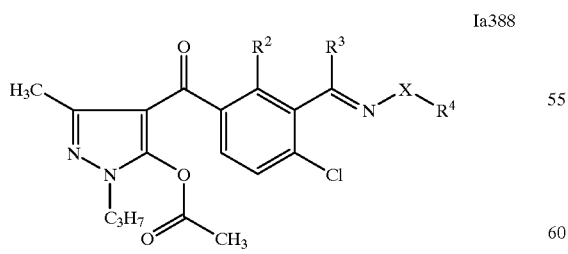
Ia388 the compounds Ia389, in particular the compounds Ia389.001–Ia389.180, which differ from the corresponding compounds Ia1.001–Ia1.180 by the fact that $R^{11}$ is n-butyl, $R^{12}$ is methylcarbonyl and $R^{13}$ is methyl:

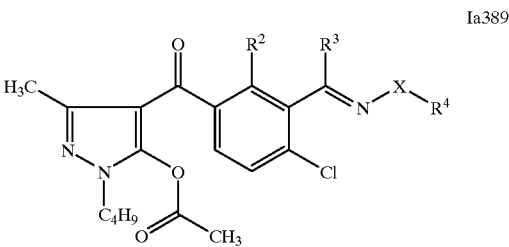
Ia389 the compounds Ia390, in particular the compounds Ia390.001–Ia390.180, which differ from the corresponding compounds Ia1.001–Ia1.180 by the fact that $R^{11}$ is iso-butyl, $R^{12}$ is methylcarbonyl and $R^{13}$ is methyl:

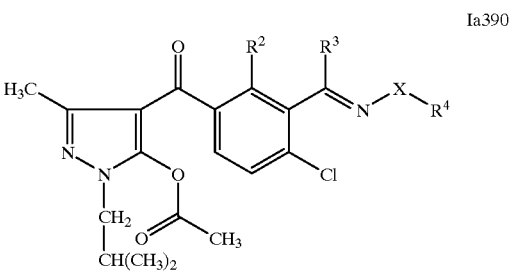
Ia390 the compounds Ia391, in particular the compounds Ia391.001–Ia391.180, which differ from the corresponding compounds Ia1.001–Ia1.180 by the fact that $R^{11}$ is ethylcarbonyl and $R^{13}$ is methyl:

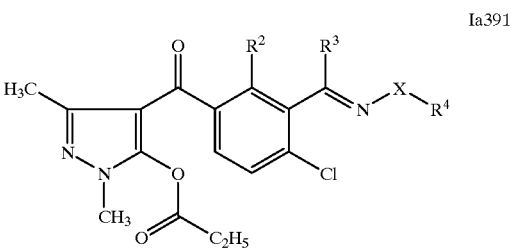
Ia391 the compounds Ia392, in particular the compounds Ia392.001–Ia392.180, which differ from the corresponding compounds Ia1.001–Ia1.180 by the fact that $R^{11}$ is ethyl, $R^{12}$ is ethylcarbonyl and $R^{13}$ is methyl:

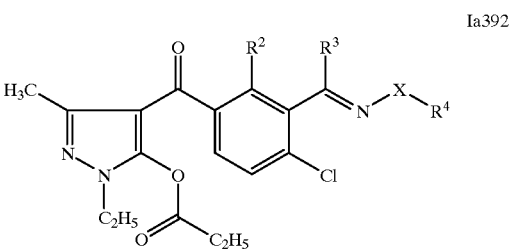
Ia392 the compounds Ia393, in particular the compounds Ia393.001–Ia393.180, which differ from the corresponding compounds Ia1.001–Ia1.180 by the fact that $R^{11}$ is n-propyl, $R^{12}$ is ethylcarbonyl and $R^{13}$ is methyl:

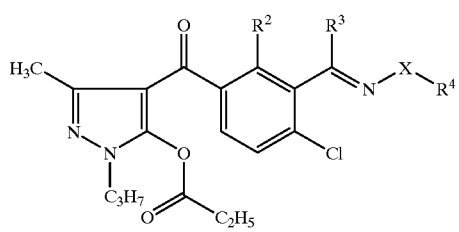

the compounds Ia394, in particular the compounds Ia394.001–Ia394.180, which differ from the corresponding compounds Ia1.001–Ia1.180 by the fact that $R^{11}$ is n-butyl, $R^{12}$ is ethylcarbonyl and $R^{13}$ is methyl:

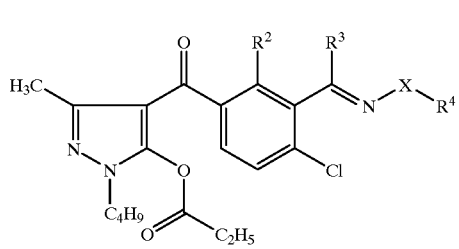

the compounds Ia395, in particular the compounds Ia395.001–Ia395.180, which differ from the corresponding compounds Ia1.001–Ia1.180 by the fact that $R^{11}$ is iso-butyl, $R^{12}$ is ethylcarbonyl and $R^{13}$ is methyl:

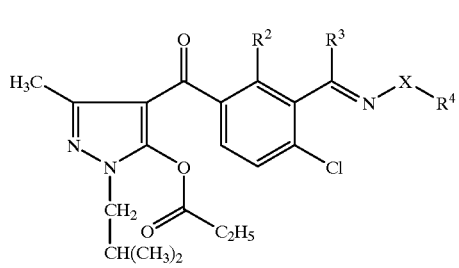

the compounds Ia396, in particular the compounds Ia396.001–Ia396.180, which differ from the corresponding compounds Ia1.001–Ia1.180 by the fact that $R^{12}$ is phenylsulfonyl and $R^{13}$ is methyl:

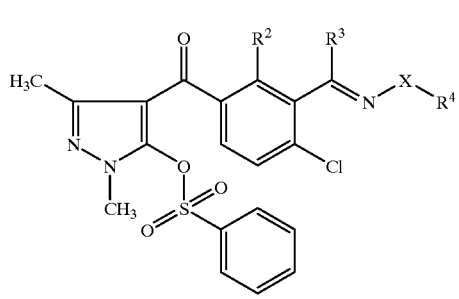

the compounds Ia397, in particular the compounds Ia397.001–Ia397.180, which differ from the corresponding compounds Ia1.001–Ia1.180 by the fact that $R^{11}$ is ethyl, $R^{12}$ is phenylsulfonyl and $R^{13}$ is methyl:

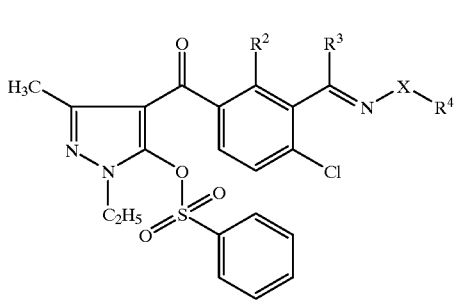

the compounds Ia398, in particular the compounds Ia398.001–Ia398.180, which differ from the corresponding compounds Ia1.001–Ia1.180 by the fact that $R^{11}$ is n-propyl, $R^{12}$ is phenylsulfonyl and $R^{13}$ is methyl:

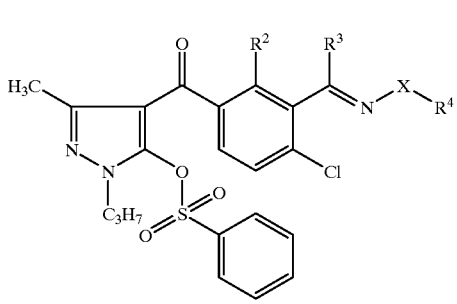

the compounds Ia399, in particular the compounds Ia399.001–Ia399.180, which differ from the corresponding compounds Ia1.001–Ia1.180 by the fact that $R^{11}$ is n-butyl, $R^{12}$ is phenylsulfonyl and $R^{13}$ is methyl:

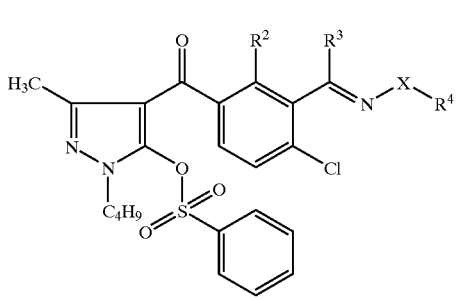

the compounds Ia400, in particular the compounds Ia400.001–Ia400.180, which differ from the corresponding compounds Ia1.001–Ia1.180 by the fact that $R^{11}$ is iso-butyl, $R^{12}$ is phenylsulfonyl and $R^{13}$ is methyl:

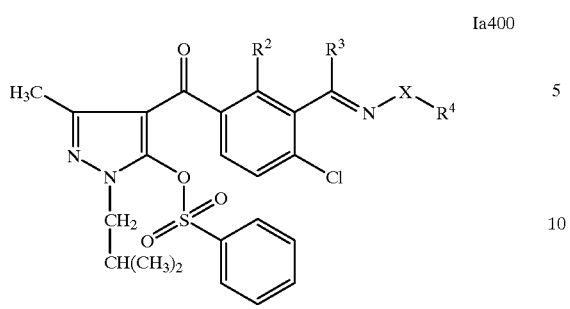
Ia400 the compounds Ia401, in particular the compounds Ia401.001–Ia402.180 [sic], which differ from the corresponding compounds Ia1.001–Ia1.180 by the fact that $R^{12}$ is 4-methylphenylsulfonyl and $R^{13}$ is methyl:

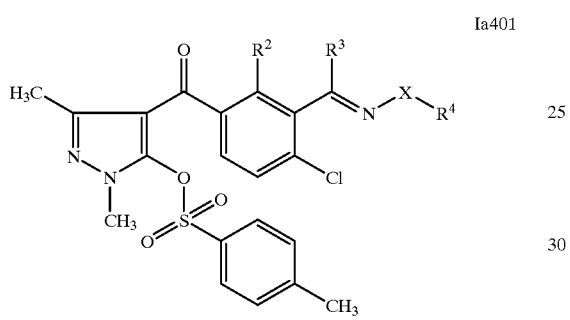
Ia401 the compounds Ia402, in particular the compounds Ia402.001–Ia402.180, which differ from the corresponding compounds Ia1.001–Ia1.180 by the fact that $R^{11}$ is ethyl, $R^{12}$ is 4-methylphenylsulfonyl and $R^{13}$ is methyl:

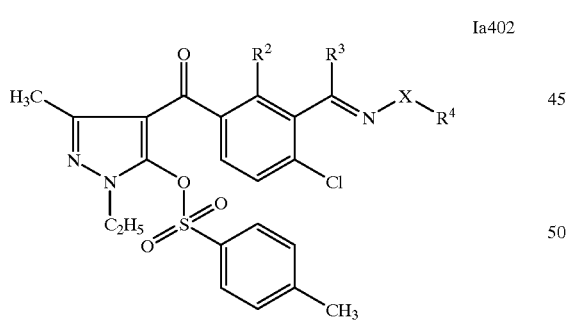
Ia402 the compounds Ia403, in particular the compounds Ia403.001–Ia403.180, which differ from the corresponding compounds Ia1.001–Ia1.180 by the fact that $R^{11}$ is n-propyl, $R^{12}$ is 4-methylphenylsulfonyl and $R^{13}$ is methyl:

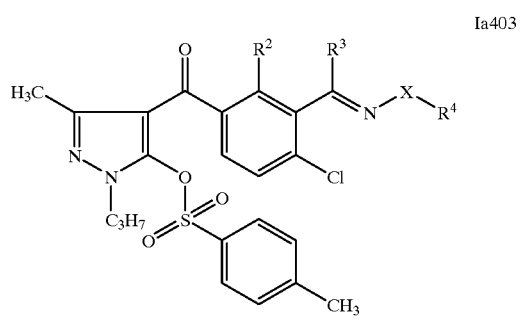
Ia403 the compounds Ia404, in particular the compounds Ia404.001–Ia404.180, which differ from the corresponding compounds Ia1.001–Ia1.180 by the fact that $R^{11}$ is n-butyl, $R^{12}$ is 4-methylphenylsulfonyl and $R^{13}$ is methyl:

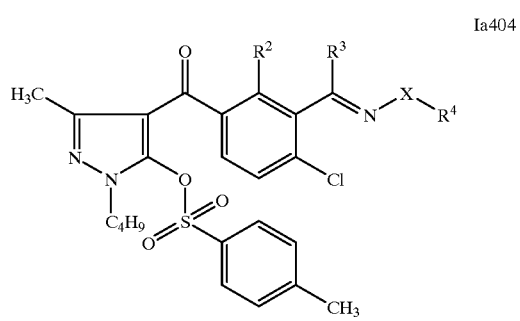
Ia404 the compounds Ia405, in particular the compounds Ia405.001–Ia405.180, which differ from the corresponding compounds Ia1.001–Ia1.180 by the fact that $R^{11}$ is iso-butyl, $R^{12}$ is 4-methylphenylsulfonyl and $R^{13}$ is methyl:

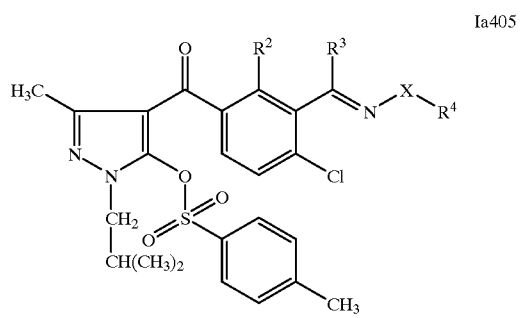
Ia405 the compounds Ia406, in particular the compounds Ia406.001–Ia406.180, which differ from the corresponding compounds Ia1.001–Ia1.180 by the fact that $R^{12}$ is n-propylcarbonyl and $R^{13}$ is methyl:

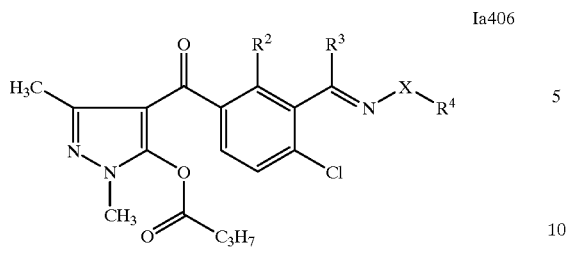

Ia406 the compounds Ia407, in particular the compounds Ia407.001–Ia407.180, which differ from the corresponding compounds Ia1.001–Ia1.180 by the fact that $R^{11}$ is ethyl, $R^{12}$ is n-propylcarbonyl and $R^{13}$ is methyl:

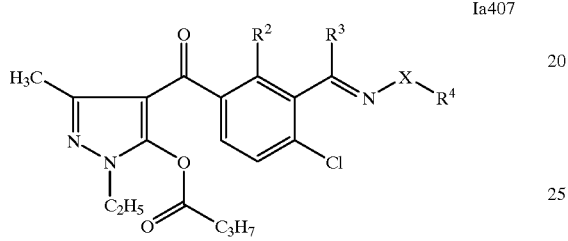

Ia407 the compounds Ia408, in particular the compounds Ia408.001–Ia408.180, which differ from the corresponding compounds Ia1.001–Ia1.180 by the fact that $R^{11}$ is n-propyl, $R^{12}$ is n-propylcarbonyl and $R^{13}$ is methyl:

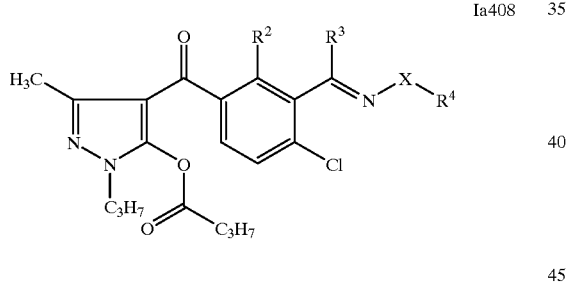

Ia408 the compounds Ia409, in particular the compounds Ia409.001–Ia409.180, which differ from the corresponding compounds Ia1.001–Ia1.180 by the fact that $R^{11}$ is n-butyl, $R^{12}$ is n-propylcarbonyl and $R^{13}$ is methyl:

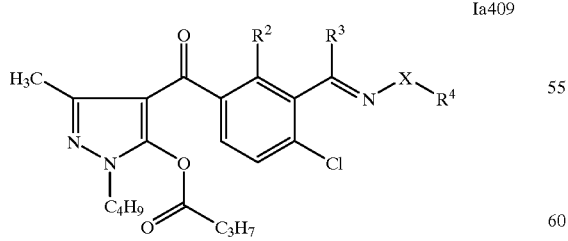

Ia409 the compounds Ia410, in particular the compounds Ia410.001–Ia410.180, which differ from the corresponding compounds Ia1.001–Ia1.180 by the fact that $R^{11}$ is iso-butyl, $R^{12}$ is n-propylcarbonyl and $R^{13}$ is methyl:

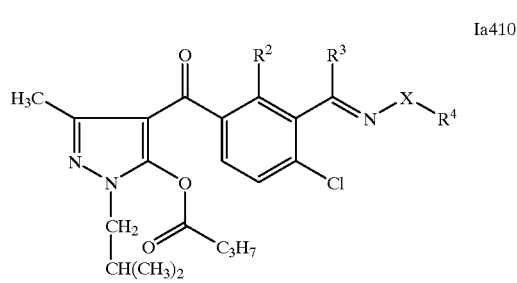

Ia410 the compounds Ia411, in particular the compounds Ia411.001–Ia411.180, which differ from the corresponding compounds Ia1.001–Ia1.180 by the fact that $R^{12}$ is trifluoromethylcarbonyl and $R^{13}$ is methyl:

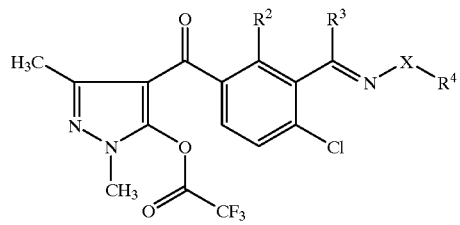

Ia411 the compounds Ia412, in particular the compounds Ia412.001–Ia412.180, which differ from the corresponding compounds Ia1.001–Ia1.180 by the fact that $R^{11}$ is ethyl, $R^{12}$ is trifluoromethylcarbonyl and $R^{13}$ is methyl:

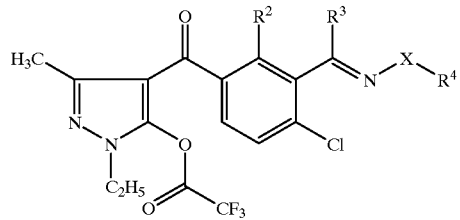

Ia412 the compounds Ia413, in particular the compounds Ia413.001–Ia413.180, which differ from the corresponding compounds Ia1.001–Ia1.180 by the fact that $R^{11}$ is n-propyl, $R^{12}$ is trifluoromethylcarbonyl and $R^{13}$ is methyl:

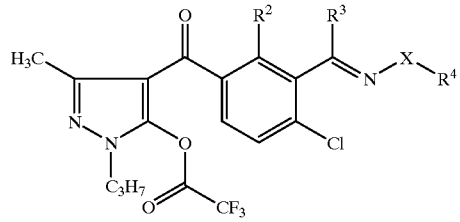

Ia413 the compounds Ia414, in particular the compounds Ia414.001–Ia414.180, which differ from the corresponding compounds Ia1.001–Ia1.180 by the fact that $R^{11}$ is n-butyl, $R^{12}$ is trifluoromethylcarbonyl and $R^{13}$ is methyl:

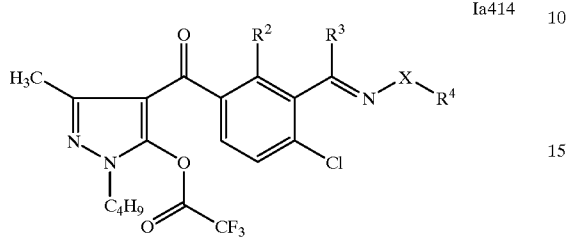

the compounds Ia415, in particular the compounds Ia415.001–Ia415.180, which differ from the corresponding compounds Ia1.001–Ia1.180 by the fact that $R^{11}$ is iso-butyl, $R^{12}$ is trifluoromethylcarbonyl and $R^{13}$ is methyl:

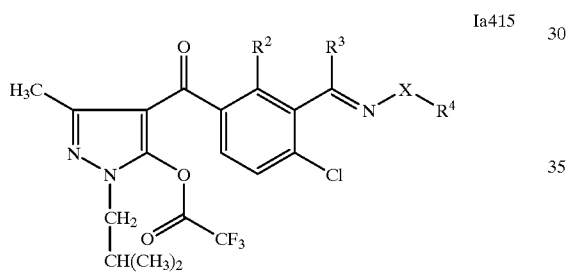

the compounds Ia416, in particular the compounds Ia416.001–Ia416.180, which differ from the corresponding compounds Ia1.001–Ia1.180 by the fact that $R^{12}$ is methylsulfonyl and $R^{13}$ is methyl:

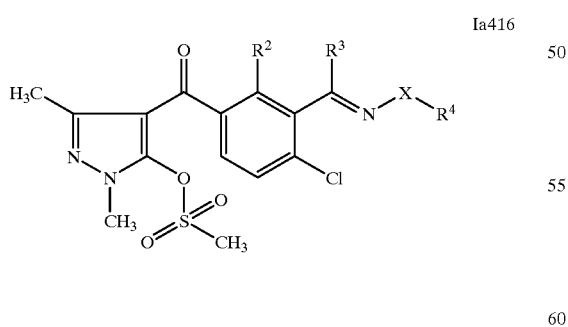

the compounds Ia417, in particular the compounds Ia417.001–Ia417.180, which differ from the corresponding compounds Ia1.001–Ia1.180 by the fact that $R^{11}$ is ethyl, $R^{12}$ is methylsulfonyl and $R^{13}$ is methyl:

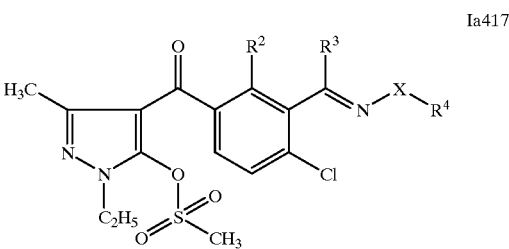

the compounds Ia418, in particular the compounds Ia418.001–Ia418.180, which differ from the corresponding compounds Ia1.001–Ia1.180 by the fact that $R^{11}$ is n-propyl, $R^{12}$ is methylsulfonyl and $R^{13}$ is methyl:

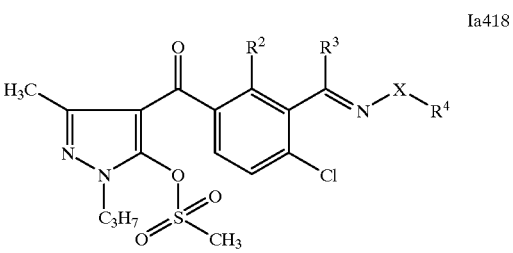

the compounds Ia419, in particular the compounds Ia419.001–Ia419.180, which differ from the corresponding compounds Ia1.001–Ia1.180 by the fact that $R^{11}$ is n-butyl, $R^{12}$ is methylsulfonyl and $R^{13}$ is methyl:

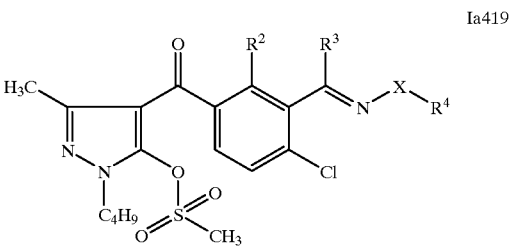

the compounds Ia420, in particular the compounds Ia420.001–Ia420.180, which differ from the corresponding compounds Ia1.001–Ia1.180 by the fact that $R^{11}$ is iso-butyl, $R^{12}$ is methylsulfonyl and $R^{13}$ is methyl:

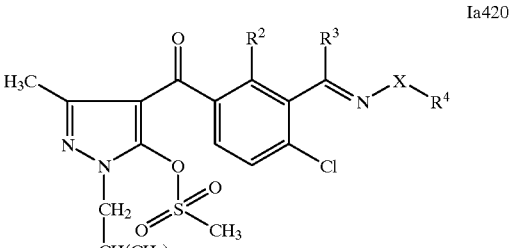

the compounds Ia421, in particular the compounds Ia421.001–Ia421.180, which differ from the corresponding compounds Ia1.001–Ia1.180 by the fact that $R^{12}$ is ethylsulfonyl and $R^{13}$ is methyl:

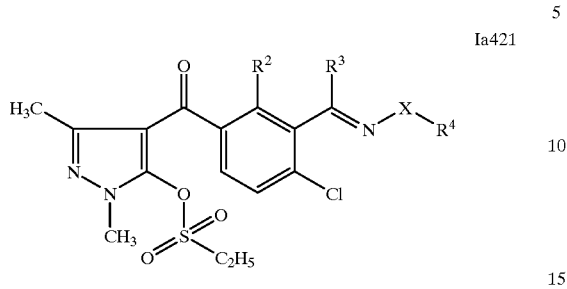
Ia421 the compounds Ia422, in particular the compounds Ia422.001–Ia422.180, which differ from the corresponding compounds Ia1.001–Ia1.180 by the fact that $R^{11}$ is ethyl, $R^{12}$ is ethylsulfonyl and $R^{13}$ is methyl:

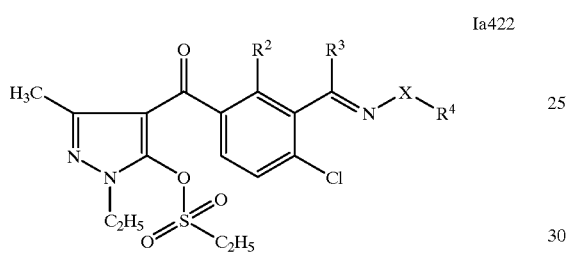
Ia422 the compounds Ia423, in particular the compounds Ia423.001–Ia423.180, which differ from the corresponding compounds Ia1.001–Ia1.180 by the fact that $R^{11}$ is n-propyl, $R^{12}$ is ethylsulfonyl and $R^{13}$ is methyl:

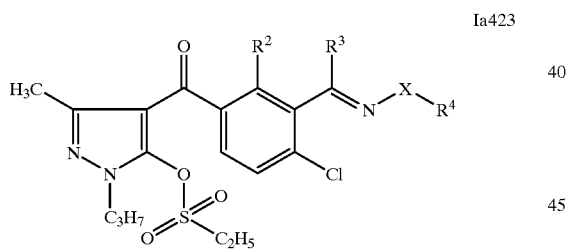
Ia423 the compounds Ia424, in particular the compounds Ia424.001–Ia424.180, which differ from the corresponding compounds Ia1.001–Ia1.180 by the fact that $R^{11}$ is n-butyl, $R^{12}$ is ethylsulfonyl and $R^{13}$ is methyl:

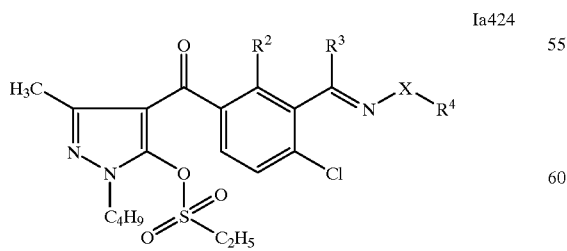
Ia424 the compounds Ia425, in particular the compounds Ia425.001–Ia425.180, which differ from the corresponding compounds Ia1.001–Ia1.180 by the fact that $R^{11}$ is iso-butyl, $R^{12}$ is ethylsulfonyl and $R^{13}$ is methyl:

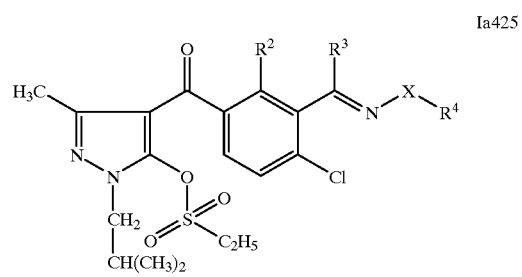
Ia425 the compounds Ia426, in particular the compounds Ia426.001–Ia426.180, which differ from the corresponding compounds Ia1.001–Ia1.180 by the fact that $R^{12}$ is n-propylsulfonyl and $R^{13}$ is methyl:

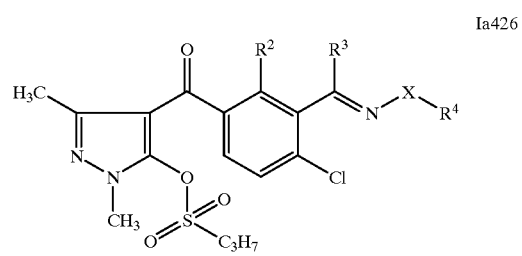
Ia426 the compounds Ia427, in particular the compounds Ia427.001–Ia427.180, which differ from the corresponding compounds Ia1.001–Ia1.180 by the fact that $R^{11}$ is ethyl, $R^{12}$ is n-propylsulfonyl and $R^{13}$ is methyl:

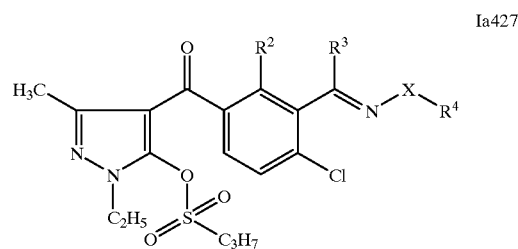
Ia427 the compounds Ia428, in particular the compounds Ia428.001–Ia428.180, which differ from the corresponding compounds Ia1.001–Ia1.180 by the fact that $R^{11}$ is n-propyl, $R^{12}$ is n-propylsulfonyl and $R^{13}$ is methyl:

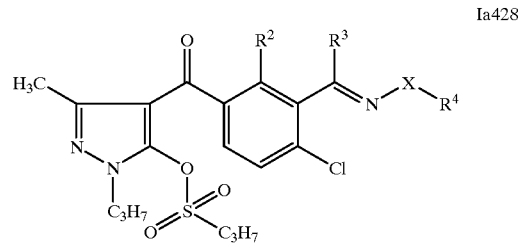
Ia428 the compounds Ia429, in particular the compounds Ia429.001–Ia429.180, which differ from the corresponding compounds Ia1.001–Ia1.180 by the fact that $R^{11}$ is n-butyl, $R^{12}$ is n-propylsulfonyl and $R^{13}$ is methyl:

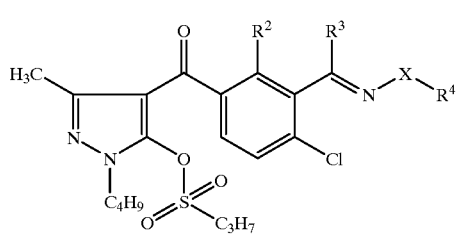

Ia429 the compounds Ia430, in particular the compounds Ia430.001–Ia430.180, which differ from the corresponding compounds Ia1.001–Ia1.180 by the fact that $R^{11}$ is iso-butyl, $R^{12}$ is propylsulfonyl and $R^{13}$ is methyl:

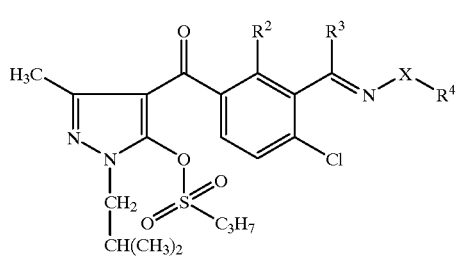

Ia430 the compounds Ia431, in particular the compounds Ia431.001–Ia431.180, which differ from the corresponding compounds Ia1.001–Ia1.180 by the fact that $R^{12}$ is iso-propylsulfonyl and $R^{13}$ is methyl:

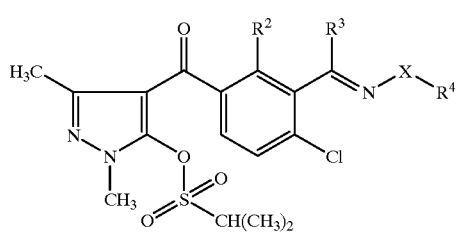

Ia431 the compounds Ia432, in particular the compounds Ia432.001–Ia432.180, which differ from the corresponding compounds Ia1.001–Ia1.180 by the fact that $R^{11}$ is ethyl, $R^{12}$ is iso-propylsulfonyl and $R^{13}$ is methyl:

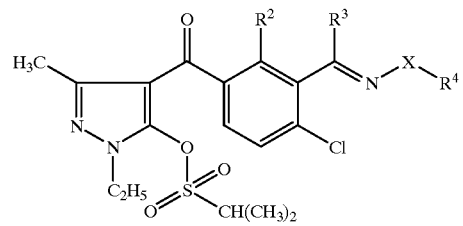

Ia432 the compounds Ia433, in particular the compounds Ia433.001–Ia433.180, which differ from the corresponding compounds Ia1.001–Ia1.180 by the fact that $R^{11}$ is n-propyl, $R^{12}$ is iso-propylsulfonyl and $R^{13}$ is methyl:

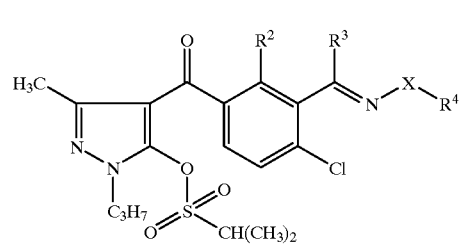

Ia433 the compounds Ia434, in particular the compounds Ia434.001–Ia434.180, which differ from the corresponding compounds Ia1.001–Ia1.180 by the fact that $R^{11}$ is n-butyl, $R^{12}$ is iso-propylsulfonyl and $R^{13}$ is methyl:

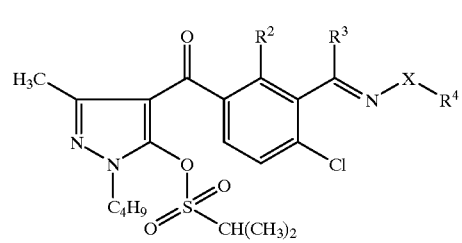

Ia434 the compounds Ia435, in particular the compounds Ia435.001–Ia435.180, which differ from the corresponding compounds Ia1.001–Ia1.180 by the fact that $R^{11}$ is iso-butyl, $R^{12}$ is iso-propylsulfonyl and $R^{13}$ is methyl:

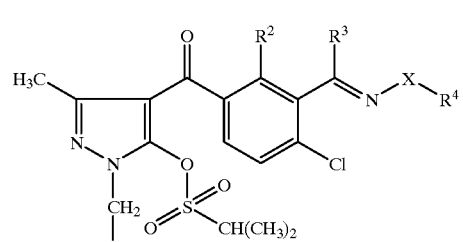

Ia435 the compounds Ia436, in particular the compounds Ia436.001–Ia436.180, which differ from the corresponding compounds Ia1.001–Ia1.180 by the fact that $R^{12}$ is n-butylsulfonyl and $R^{13}$ is methyl:

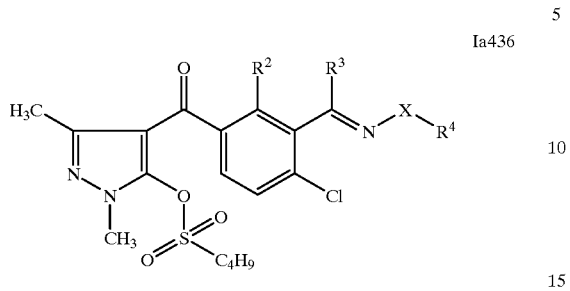
Ia436 the compounds Ia437, in particular the compounds Ia437.001–Ia437.180, which differ from the corresponding compounds Ia1.001–Ia1.180 by the fact that $R^{11}$ is ethyl, $R^{12}$ is n-butylsulfonyl and $R^{13}$ is methyl:

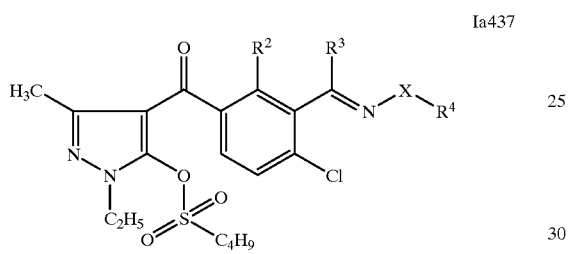
Ia437 the compounds Ia438, in particular the compounds Ia438.001–Ia438.180, which differ from the corresponding compounds Ia1.001–Ia1.180 by the fact that $R^{11}$ is n-propyl, $R^{12}$ is n-butylsulfonyl and $R^{13}$ is methyl:

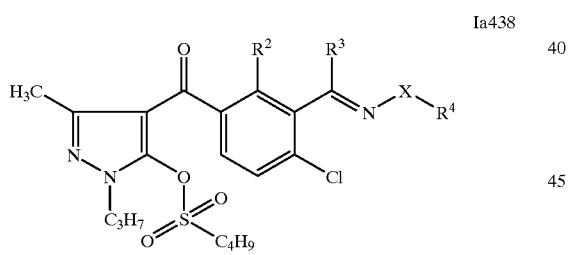
Ia438 the compounds Ia439, in particular the compounds Ia439.001–Ia439.180, which differ from the corresponding compounds Ia1.001–Ia1.180 by the fact that $R^{11}$ is n-butyl, $R^{12}$ is n-butylsulfonyl and $R^{13}$ is methyl:

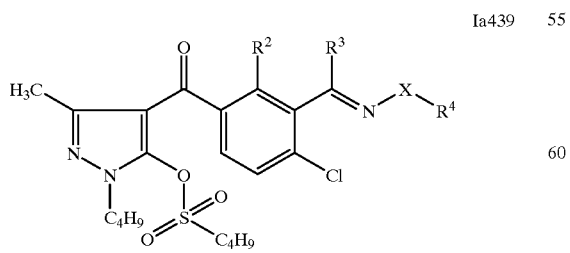
Ia439 the compounds Ia440, in particular the compounds Ia440.001–Ia440.180, which differ from the corresponding compounds Ia1.001–Ia1.180 by the fact that $R^{11}$ is iso-butyl, $R^{12}$ is n-butylsulfonyl and $R^{13}$ is methyl:

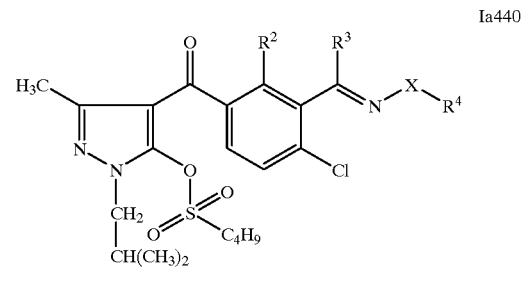
Ia440 the compounds Ia441, in particular the compounds Ia441.001–Ia441.180, which differ from the corresponding compounds Ia1.001–Ia1.180 by the fact that $R^{12}$ is iso-butylsulfonyl and $R^{13}$ is methyl:

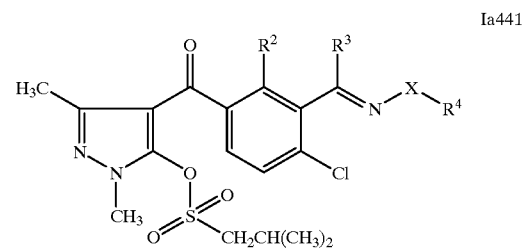
Ia441 the compounds Ia442, in particular the compounds Ia442.001–Ia442.180, which differ from the corresponding compounds Ia1.001–Ia1.180 by the fact that $R^{11}$ is ethyl, $R^{12}$ is iso-butylsulfonyl and $R^{13}$ is methyl:

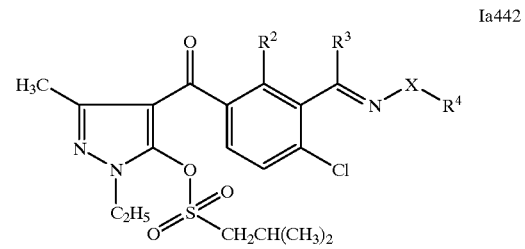
Ia442 the compounds Ia443, in particular the compounds Ia443.001–Ia443.180, which differ from the corresponding compounds Ia1.001–Ia1.180 by the fact that $R^{11}$ is n-propyl, $R^{12}$ is iso-butylsulfonyl and $R^{13}$ is methyl:

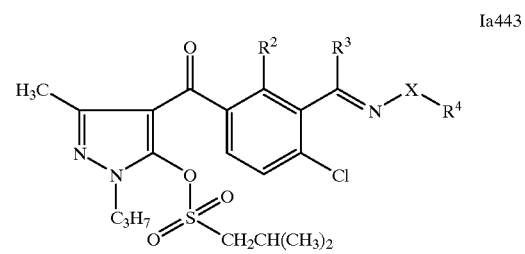
Ia443 the compounds Ia444, in particular the compounds Ia444.001–Ia444.180, which differ from the corresponding compounds Ia1.001–Ia1.180 by the fact that $R^{11}$ is n-butyl, $R^{12}$ is iso-butylsulfonyl and $R^{13}$ is methyl:

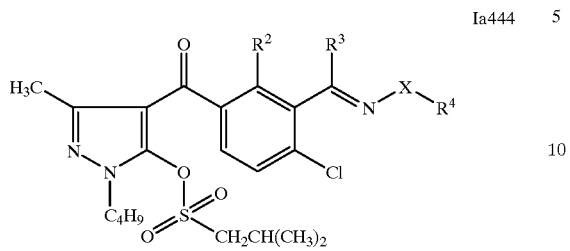
Ia444 the compounds Ia445, in particular the compounds Ia445.001–Ia445.180, which differ from the corresponding compounds Ia1.001–Ia1.180 by the fact that $R^{11}$ is iso-butyl, $R^{12}$ is iso-butylsulfonyl and $R^{13}$ is methyl:

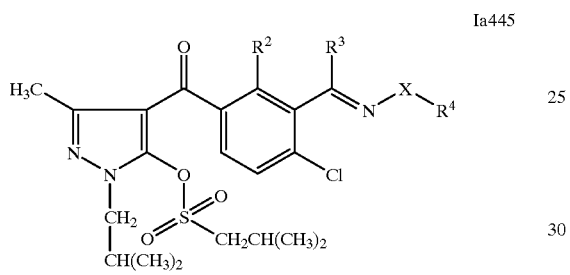
Ia445 the compounds Ia446, in particular the compounds Ia446.001–Ia446.180, which differ from the corresponding compounds Ia1.001–Ia1.180 by the fact that $R^{12}$ is sec-butylsulfonyl and $R^{13}$ is methyl:

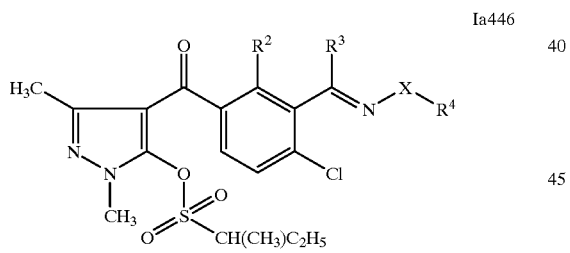
Ia446 the compounds Ia447, in particular the compounds Ia447.001–Ia447.180, which differ from the corresponding compounds Ia1.001–Ia1.180 by the fact that $R^{11}$ is ethyl, $R^{12}$ is sec-butylsulfonyl and $R^{13}$ is methyl:

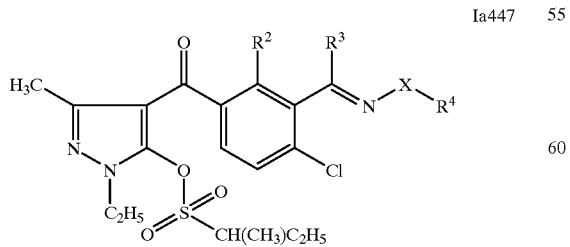
Ia447 the compounds Ia448, in particular the compounds Ia448.001–Ia448.180, which differ from the corresponding compounds Ia1.001–Ia1.180 by the fact that $R^{11}$ is n-propyl, $R^{12}$ is sec-butylsulfonyl and $R^{13}$ is methyl:

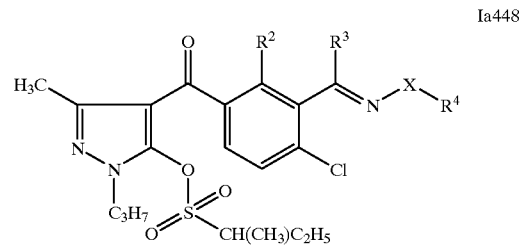
Ia448 the compounds Ia449, in particular the compounds Ia449.001–Ia449.180, which differ from the corresponding compounds Ia1.001–Ia1.180 by the fact that $R^{11}$ is n-butyl, $R^{12}$ is sec-butylsulfonyl and $R^{13}$ is methyl:

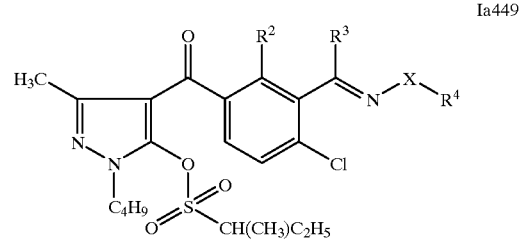
Ia449 the compounds Ia450, in particular the compounds Ia450.001–Ia450.180, which differ from the corresponding compounds Ia1.001–Ia1.180 by the fact that $R^{11}$ is iso-butyl, $R^{12}$ is sec-butylsulfonyl and $R^{13}$ is methyl:

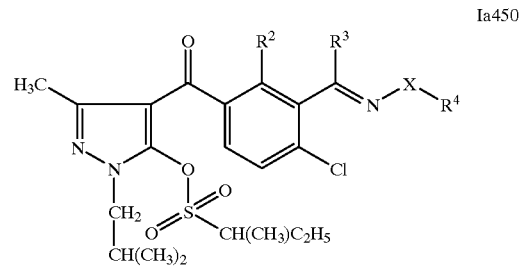
Ia450 the compounds Ia451, in particular the compounds Ia451.001–Ia451.180, which differ from the corresponding compounds Ia1.001–Ia1.180 by the fact that $R^{12}$ is trifluoromethylsulfonyl and $R^{13}$ is methyl:

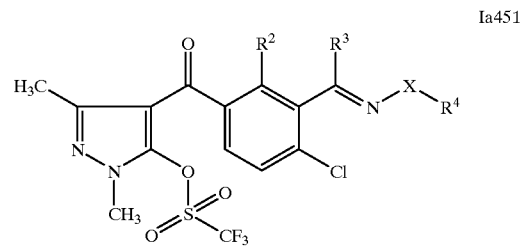
Ia451 the compounds Ia452, in particular the compounds Ia452.001–Ia452.180, which differ from the corresponding compounds Ia1.001–Ia1.180 by the fact that $R^{11}$ is ethyl, $R^{12}$ is trifluoromethylsulfonyl and $R^{13}$ is methyl:

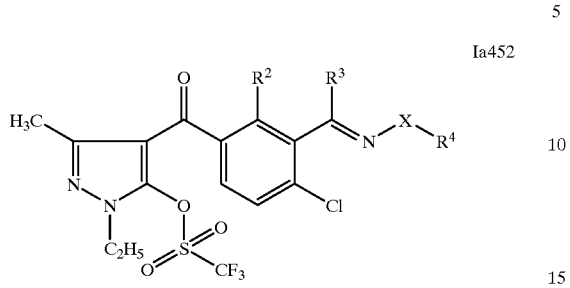
Ia452 the compounds Ia453, in particular the compounds Ia453.001–Ia453.180, which differ from the corresponding compounds Ia1.001–Ia1.180 by the fact that $R^{11}$ is n-propyl, $R^{12}$ is trifluoromethylsulfonyl and $R^{13}$ is methyl:

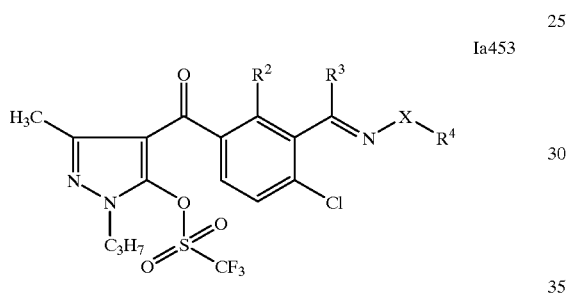
Ia453 the compounds Ia454, in particular the compounds Ia454.001–Ia454.180, which differ from the corresponding compounds Ia1.001–Ia1.180 by the fact that $R^{11}$ is n-butyl, $R^{12}$ is trifluoromethylsulfonyl and $R^{13}$ is methyl:

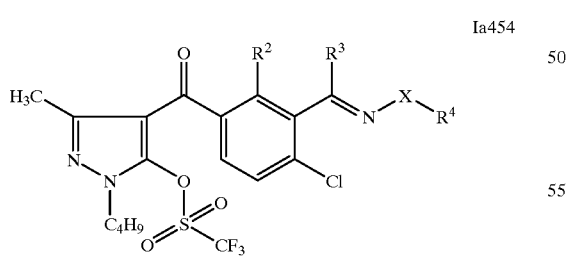
Ia454 the compounds Ia455, in particular the compounds Ia455.001–Ia455.180, which differ from the corresponding compounds Ia1.001–Ia1.180 by the fact that $R^{11}$ is iso-butyl, $R^{12}$ is trifluoromethylsulfonyl and $R^{13}$ is methyl:

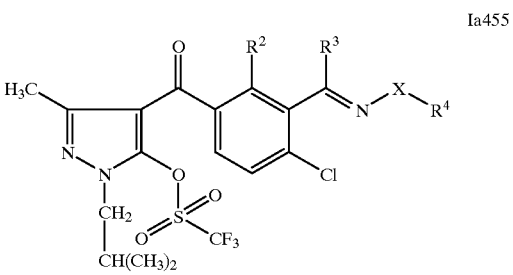
Ia455 the compounds Ia456, in particular the compounds Ia456.001–Ia456.180, which differ from the corresponding compounds Ia1.001–Ia1.180 by the fact that $R^{11}$ and $R^{13}$ are methyl and $R^{12}$ is phenylcarbonylmethyl:

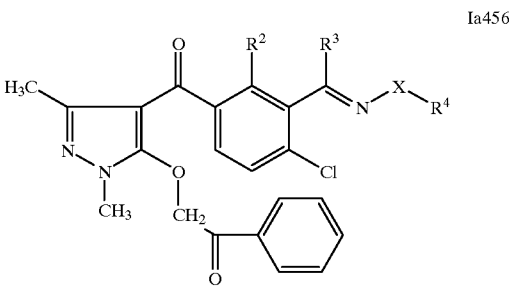
Ia456 the compounds Ia457, in particular the compounds Ia457.001–Ia457.180, which differ from the corresponding compounds Ia1.001–Ia1.180 by the fact that $R^{11}$ is ethyl, $R^{12}$ is phenylcarbonylmethyl and $R^{13}$ is methyl:

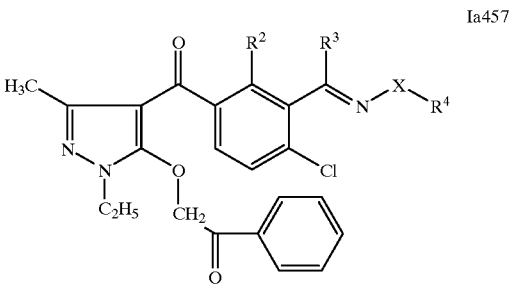
Ia457 the compounds Ia458, in particular the compounds Ia458.001–Ia458.180, which differ from the corresponding compounds Ia1.001–Ia1.180 by the fact that $R^{11}$ is n-propyl, $R^{12}$ is phenylcarbonylmethyl and $R^{13}$ is methyl:

Ia458

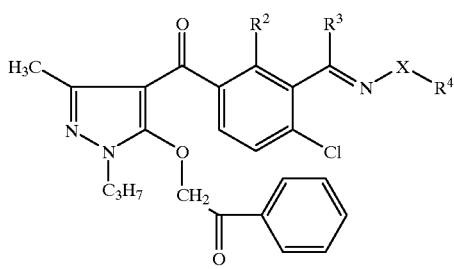

the compounds Ia459, in particular the compounds Ia459.001–Ia459.180, which differ from the corresponding compounds Ia1.001–Ia1.180 by the fact that $R^{11}$ is n-butyl, $R^{12}$ is phenylcarbonylmethyl and $R^{13}$ is methyl:

Ia459

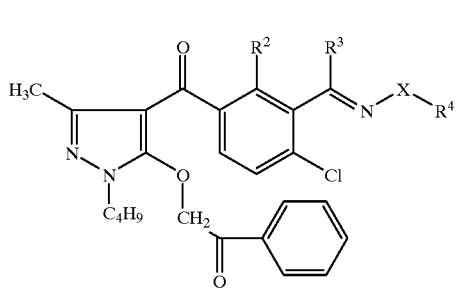

the compounds Ia460, in particular the compounds Ia460.001–Ia460.180, which differ from the corresponding compounds Ia1.001–Ia1.180 by the fact that $R^{11}$ is iso-butyl, $R^{12}$ is phenylcarbonylmethyl and $R^{13}$ is methyl:

Ia460

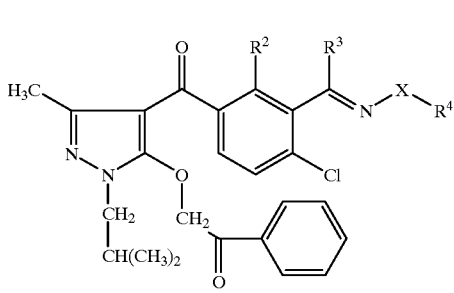

the compounds Ia461, in particular the compounds Ia461.001–Ia461.180, which differ from the corresponding compounds Ia1.001–Ia1.180 by the fact that $R^1$ is nitro and $R^{13}$ is methyl:

Ia461

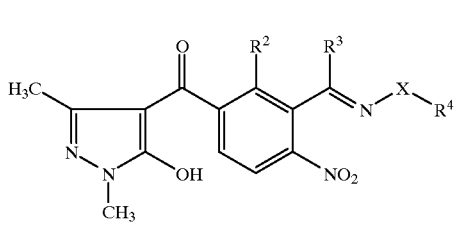

the compounds Ia462, in particular the compounds Ia462.001–Ia462.180, which differ from the corresponding compounds Ia1.001–Ia1.180 by the fact that $R^1$ is nitro, $R^{11}$ is ethyl and $R^{13}$ is methyl:

Ia462

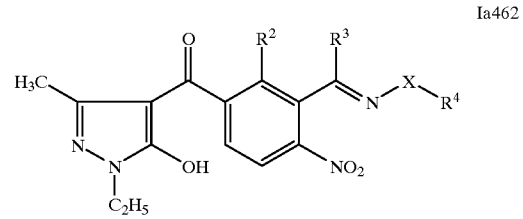

the compounds Ia463, in particular the compounds Ia463.001–Ia463.180, which differ from the corresponding compounds Ia1.001–Ia1.180 by the fact that $R^1$ is nitro, $R^{11}$ is n-propyl and $R^{13}$ is methyl:

Ia463

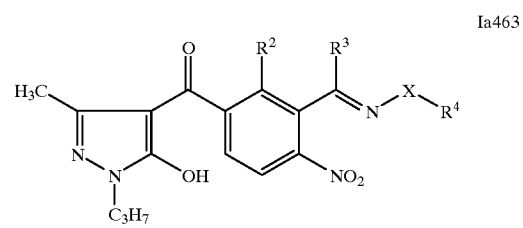

the compounds Ia464, in particular the compounds Ia464.001–Ia464.180, which differ from the corresponding compounds Ia1.001–Ia1.180 by the fact that $R^1$ is nitro, $R^{11}$ is n-butyl and $R^{13}$ is methyl:

Ia464

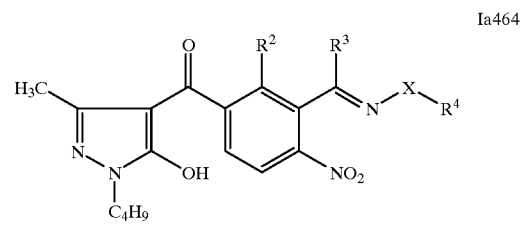

the compounds Ia465, in particular the compounds Ia465.001–Ia465.180, which differ from the corresponding compounds Ia1.001–Ia1.180 by the fact that $R^1$ is nitro, $R^{11}$ is iso-butyl and $R^{13}$ is methyl:

Ia465

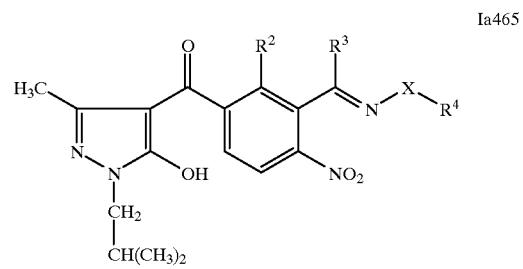

the compounds Ia466, in particular the compounds Ia466.001–Ia466.180, which differ from the corresponding compounds Ia1.001–Ia1.180 by the fact that $R^1$ is nitro and $R^{12}$ and $R^{13}$ are methyl:

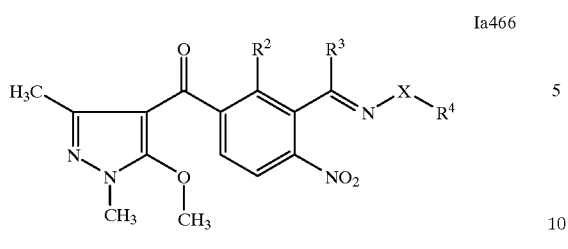

Ia466 the compounds Ia467, in particular the compounds Ia467.001–Ia467.180, which differ from the corresponding compounds Ia1.001–Ia1.180 by the fact that $R^1$ is nitro, $R^{11}$ is ethyl and $R^{12}$ and $R^{13}$ are methyl:

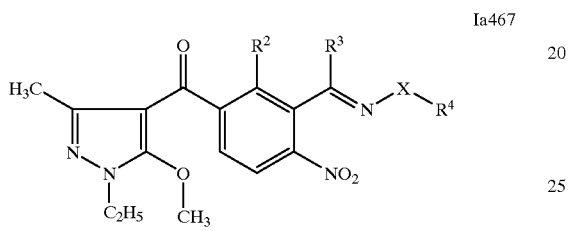

Ia467 the compounds Ia468, in particular the compounds Ia468.001–Ia468.180, which differ from the corresponding compounds Ia1.001–Ia1.180 by the fact that $R^1$ is nitro, $R^{11}$ is n-propyl and $R^{12}$ and $R^{13}$ are methyl:

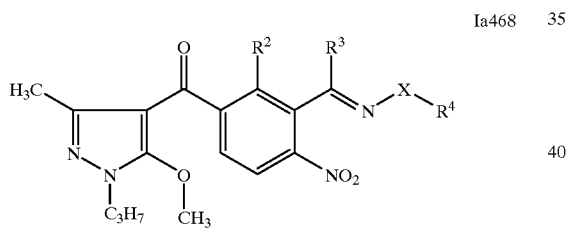

Ia468 the compounds Ia469, in particular the compounds Ia469.001–Ia469.180, which differ from the corresponding compounds Ia1.001–Ia1.180 by the fact that $R^1$ is nitro, $R^{11}$ is n-butyl and $R^{12}$ and $R^{13}$ are methyl:

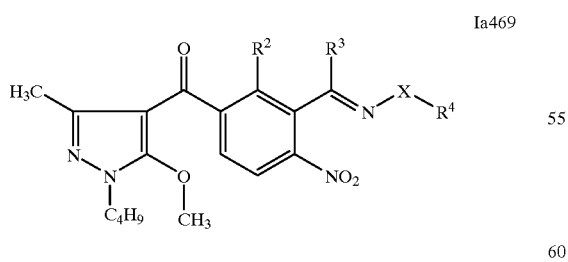

Ia469 the compounds Ia470, in particular the compounds Ia470.001–Ia470.180, which differ from the corresponding compounds Ia1.001–Ia1.180 by the fact that $R^1$ is nitro, $R^{11}$ is iso-butyl and $R^{12}$ and $R^{13}$ are methyl:

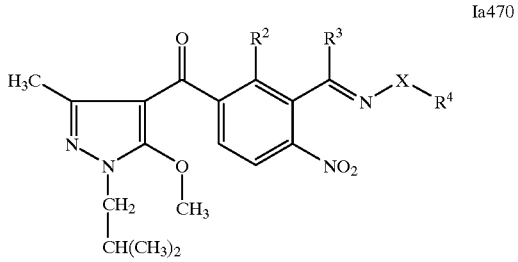

Ia470 the compounds Ia471, in particular the compounds Ia471.001–Ia471.180, which differ from the corresponding compounds Ia1.001–Ia1.180 by the fact that $R^1$ is nitro, $R^{12}$ is ethyl and $R^{13}$ is methyl:

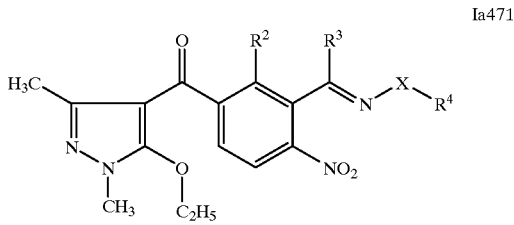

Ia471 the compounds Ia472, in particular the compounds Ia472.001–Ia472.180, which differ from the corresponding compounds Ia1.001–Ia1.180 by the fact that $R^1$ is nitro, $R^{11}$ and $R^{12}$ are ethyl and $R^{13}$ is methyl:

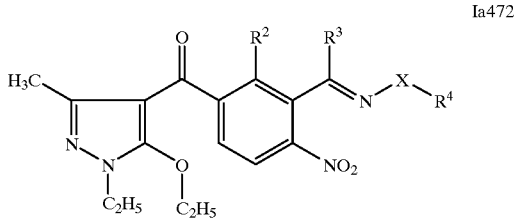

Ia472 the compounds Ia473, in particular the compounds Ia473.001–Ia473.180, which differ from the corresponding compounds Ia1.001–Ia1.180 by the fact that $R^1$ is nitro, $R^{11}$ is n-propyl, $R^{12}$ is ethyl and $R^{13}$ is methyl:

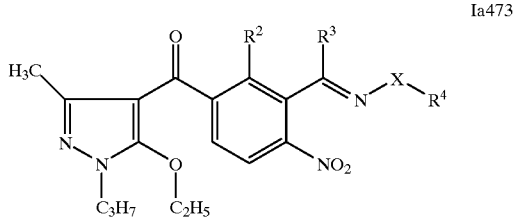

Ia473 the compounds Ia474, in particular the compounds Ia474.001–Ia474.180, which differ from the corresponding compounds Ia1.001–Ia1.180 by the fact that $R^1$ is nitro, $R^{11}$ is n-butyl, $R^{12}$ is ethyl and $R^{13}$ is methyl:

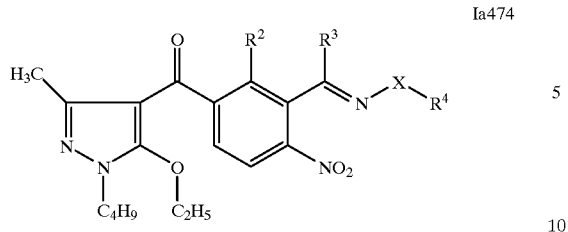
Ia474

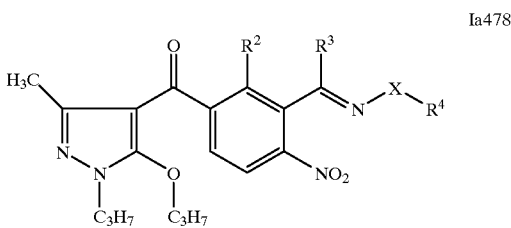
Ia478 the compounds Ia475, in particular the compounds Ia475.001–Ia475.180, which differ from the corresponding compounds Ia1.001–Ia1.180 by the fact that $R^1$ is nitro, $R^{11}$ is iso-butyl, $R^{12}$ is ethyl and $R^{13}$ is methyl:

the compounds Ia479, in particular the compounds Ia479.001–Ia479.180, which differ from the corresponding compounds Ia1.001–Ia1.180 by the fact that $R^1$ is nitro, $R^{11}$ is n-butyl, $R^{12}$ is n-propyl and $R^{13}$ is methyl:

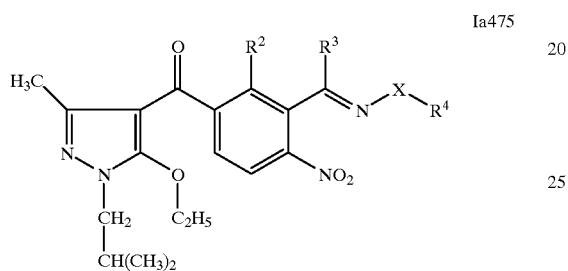
Ia475

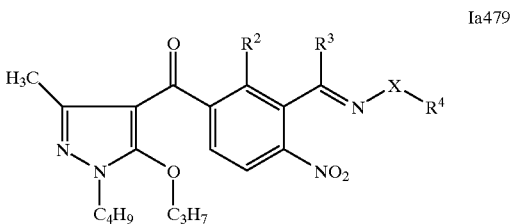
Ia479 the compounds Ia476, in particular the compounds Ia476.001–Ia476.180, which differ from the corresponding compounds Ia1.001–Ia1.180 by the fact that $R^1$ is nitro, $R^{12}$ is n-propyl and $R^{13}$ is methyl:

the compounds Ia480, in particular the compounds Ia480.001–Ia480.180, which differ from the corresponding compounds Ia1.001–Ia1.180 by the fact that $R^1$ is nitro, $R^{11}$ is iso-butyl, $R^{12}$ is n-propyl and $R^{13}$ is methyl:

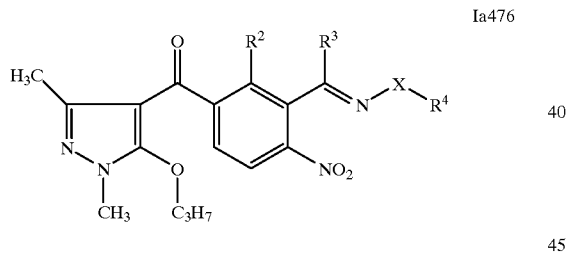
Ia476

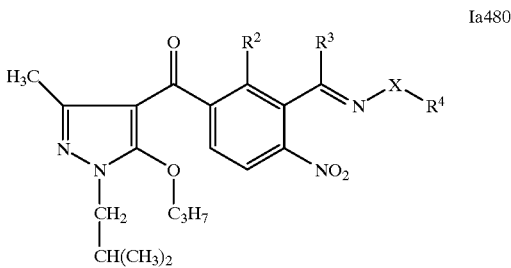
Ia480 the compounds Ia477, in particular the compounds Ia477.001–Ia477.180, which differ from the corresponding compounds Ia1.001–Ia1.180 by the fact that $R^1$ is nitro, $R^{11}$ is ethyl, $R^{12}$ is n-propyl and $R^{13}$ is methyl:

the compounds Ia481, in particular the compounds Ia481.001–Ia481.180, which differ from the corresponding compounds Ia1.001–Ia1.180 by the fact that $R^1$ is nitro, $R^{12}$ is iso-propyl and $R^{13}$ is methyl:

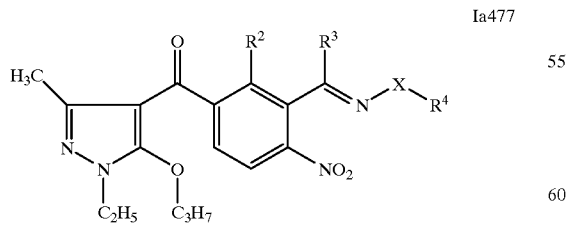
Ia477

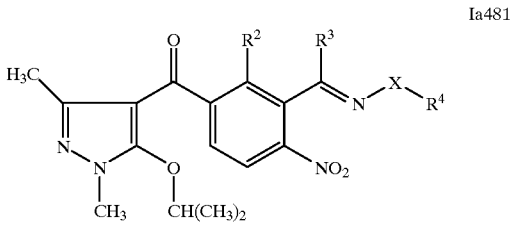
Ia481 the compounds Ia478, in particular the compounds Ia478.001–Ia478.180, which differ from the corresponding compounds Ia1.001–Ia1.180 by the fact that $R^1$ is nitro, $R^{11}$ and $R^{12}$ are n-propyl and $R^{13}$ is methyl:

the compounds Ia482, in particular the compounds Ia482.001–Ia482.180, which differ from the corresponding compounds Ia1.001–Ia1.180 by the fact that $R^1$ is nitro, $R^{11}$ is ethyl, $R^{12}$ is iso-propyl and $R^{13}$ is methyl:

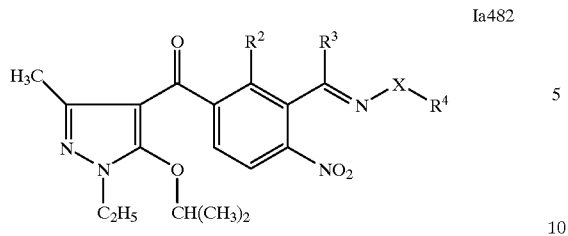

Ia482 the compounds Ia483, in particular the compounds Ia483.001–Ia483.180, which differ from the corresponding compounds Ia1.001–Ia1.180 by the fact that $R^1$ is nitro, $R^{11}$ is n-propyl, $R^{12}$ is iso-propyl and $R^{13}$ is methyl:

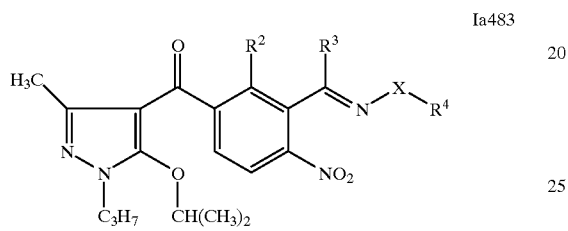

Ia483 the compounds Ia484, in particular the compounds Ia484.001–Ia484.180, which differ from the corresponding compounds Ia1.001–Ia1.180 by the fact that $R^1$ is nitro, $R^{11}$ is n-butyl, $R^{12}$ is iso-propyl and $R^{13}$ is methyl:

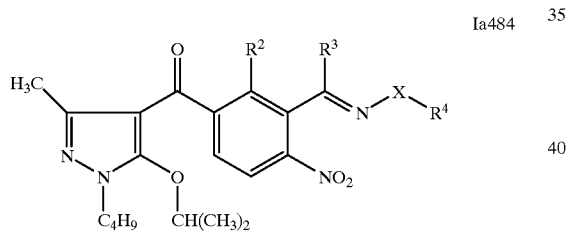

Ia484 the compounds Ia485, in particular the compounds Ia485.001–Ia485.180, which differ from the corresponding compounds Ia1.001–Ia1.180 by the fact that $R^1$ is nitro, $R^{11}$ is iso-butyl, $R^{12}$ is iso-propyl and $R^{13}$ is methyl:

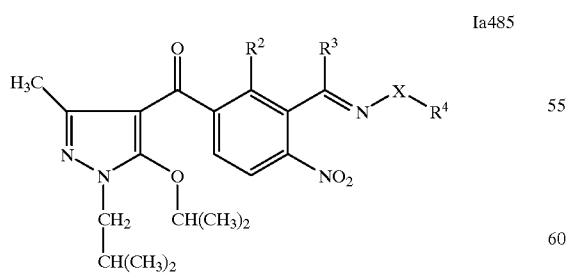

Ia485 the compounds Ia486, in particular the compounds Ia486.001–Ia486.180, which differ from the corresponding compounds Ia1.001–Ia1.180 by the fact that $R^1$ is nitro, $R^{12}$ is n-butyl and $R^{13}$ is methyl:

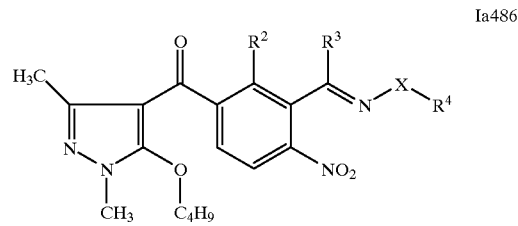

Ia486 the compounds Ia487, in particular the compounds Ia487.001–Ia487.180, which differ from the corresponding compounds Ia1.001–Ia1.180 by the fact that $R^1$ is nitro, $R^{11}$ is ethyl, $R^{12}$ is n-butyl and $R^{13}$ is methyl:

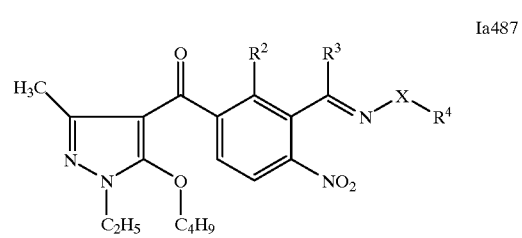

Ia487 the compounds Ia488, in particular the compounds Ia488.001–Ia488.180, which differ from the corresponding compounds Ia1.001–Ia1.180 by the fact that $R^1$ is nitro, $R^{11}$ is n-propyl, $R^{12}$ is n-butyl and $R^{13}$ is methyl:

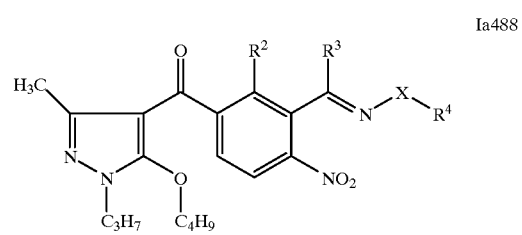

Ia488 the compounds Ia489, in particular the compounds Ia489.001–Ia489.180, which differ from the corresponding compounds Ia1.001–Ia1.180 by the fact that $R^1$ is nitro, $R^{11}$ and $R^{12}$ are n-butyl and $R^{13}$ is methyl:

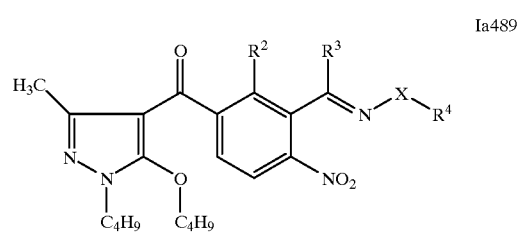

Ia489 the compounds Ia490, in particular the compounds Ia490.001–Ia490.180, which differ from the corresponding compounds Ia1.001–Ia1.180 by the fact that $R^1$ is nitro, $R^{11}$ is iso-butyl, $R^{12}$ is n-butyl and $R^{13}$ is methyl:

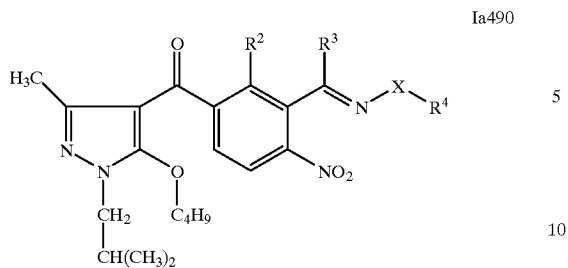

Ia490 the compounds Ia491, in particular the compounds Ia491.001–Ia491.180, which differ from the corresponding compounds Ia1.001–Ia1.180 by the fact that $R^1$ is nitro, $R^{12}$ is sec-butyl and $R^{13}$ is methyl:

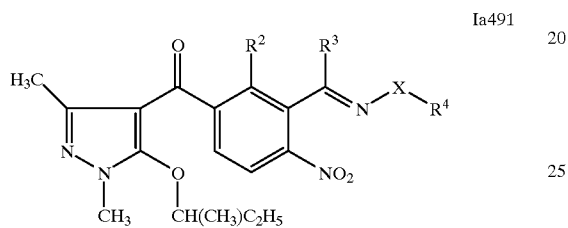

Ia491 the compounds Ia492, in particular the compounds Ia492.001–Ia492.180, which differ from the corresponding compounds Ia1.001–Ia1.180 by the fact that $R^1$ is nitro, $R^{11}$ is ethyl, $R^{12}$ is sec-butyl and $R^{13}$ is methyl:

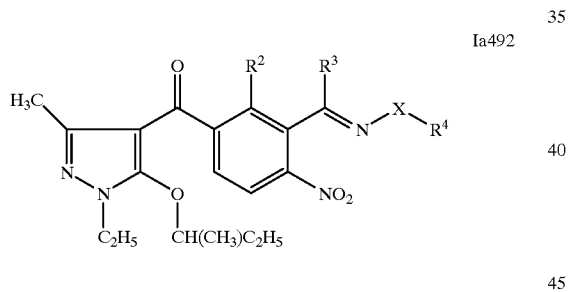

Ia492 the compounds Ia493, in particular the compounds Ia493.001–Ia493.180, which differ from the corresponding compounds Ia1.001–Ia1.180 by the fact that $R^1$ is nitro, $R^{11}$ is n-propyl, $R^{12}$ is sec-butyl and $R^{13}$ is methyl:

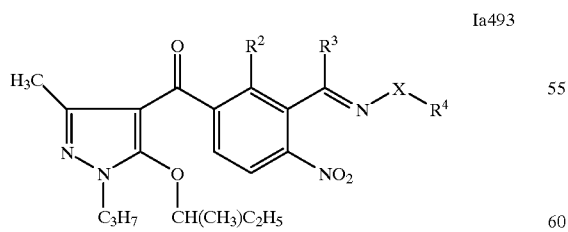

Ia493 the compounds Ia494, in particular the compounds Ia494.001–Ia494.180, which differ from the corresponding compounds Ia1.001–Ia1.180 by the fact that $R^1$ is nitro, $R^{11}$ is n-butyl, $R^{12}$ is sec-butyl and $R^{13}$ is methyl:

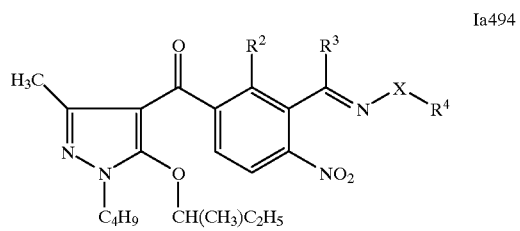

Ia494 the compounds Ia495, in particular the compounds Ia495.001–Ia495.180, which differ from the corresponding compounds Ia1.001–Ia1.180 by the fact that $R^1$ is nitro, $R^{11}$ is iso-butyl, $R^{12}$ is sec-butyl and $R^{13}$ is methyl:

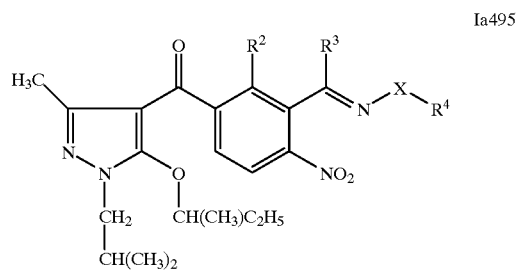

Ia495 the compounds Ia496, in particular the compounds Ia496.001–Ia496.180, which differ from the corresponding compounds Ia1.001–Ia1.180 by the fact that $R^1$ is nitro, $R^{12}$ is iso-butyl and $R^{13}$ is methyl:

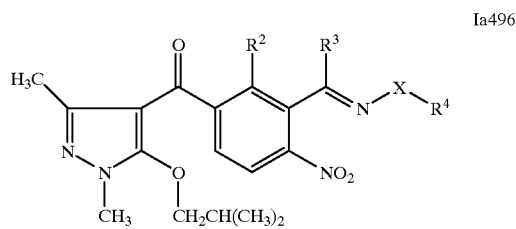

Ia496 the compounds Ia497, in particular the compounds Ia497.001–Ia497.180, which differ from the corresponding compounds Ia1.001–Ia1.180 by the fact that $R^1$ is nitro, $R^{11}$ is ethyl, $R^{12}$ is iso-butyl and $R^{13}$ is methyl:

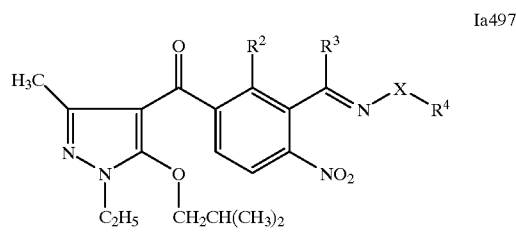

Ia497 the compounds Ia498, in particular the compounds Ia498.001–Ia498.180, which differ from the corresponding compounds Ia1.001–Ia1.180 by the fact that $R^1$ is nitro, $R^{11}$ is n-propyl, $R^{12}$ is iso-butyl and $R^{13}$ is methyl:

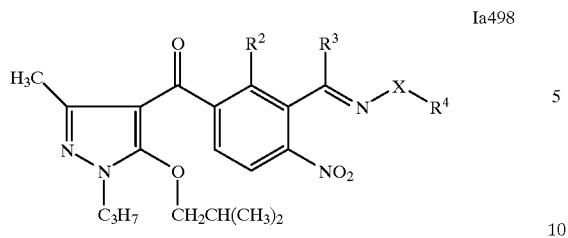

the compounds Ia499, in particular the compounds Ia499.001–Ia499.180, which differ from the corresponding compounds Ia1.001–Ia1.180 by the fact that $R^1$ is nitro, $R^{11}$ is n-butyl, $R^{12}$ is iso-butyl and $R^{13}$ is methyl:

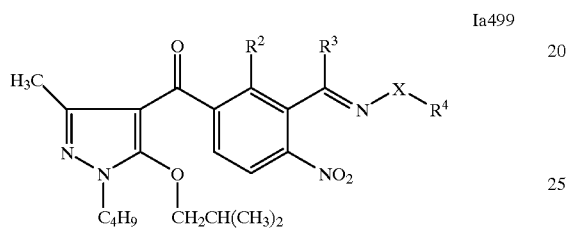

the compounds Ia500, in particular the compounds Ia500.001–Ia500.180, which differ from the corresponding compounds Ia1.001–Ia1.180 by the fact that $R^1$ is nitro, $R^{11}$ and $R^{12}$ are iso-butyl and $R^{13}$ is methyl:

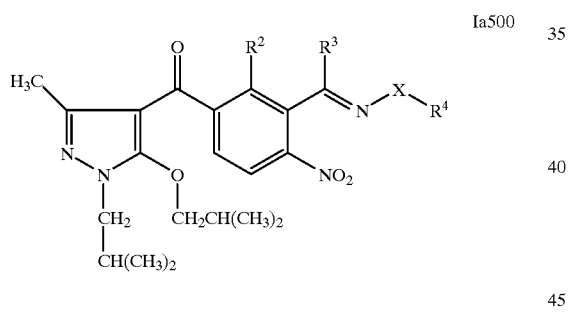

the compounds Ia501, in particular the compounds Ia501.001–Ia501.180, which differ from the corresponding compounds Ia1.001–Ia1.180 by the fact that $R^1$ is nitro, $R^{12}$ is methylcarbonyl and $R^{13}$ is methyl:

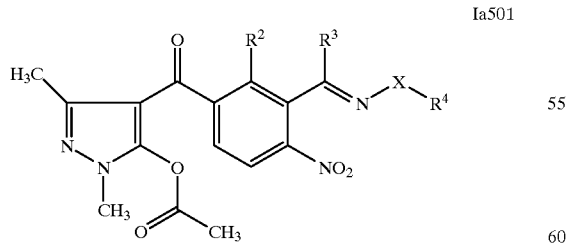

the compounds Ia502, in particular the compounds Ia502.001–Ia502.180, which differ from the corresponding compounds Ia1.001–Ia1.180 by the fact that $R^1$ is nitro, $R^{11}$ is ethyl, $R^{12}$ is methylcarbonyl and $R^{13}$ is methyl:

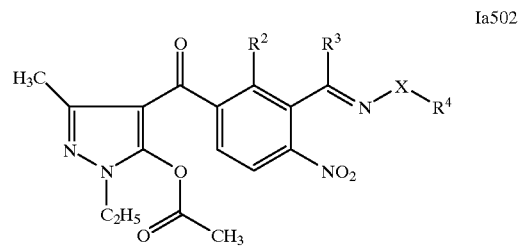

the compounds Ia503, in particular the compounds Ia503.001–Ia503.180, which differ from the corresponding compounds Ia1.001–Ia1.180 by the fact that $R^1$ is nitro, $R^{11}$ is n-propyl, $R^{12}$ is methylcarbonyl and $R^{13}$ is methyl:

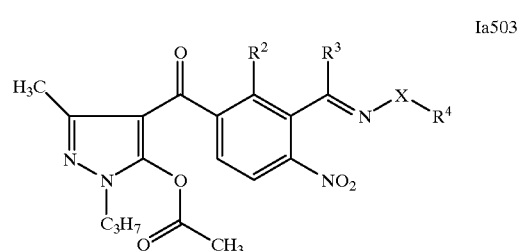

the compounds Ia504, in particular the compounds Ia504.001–Ia504.180, which differ from the corresponding compounds Ia1.001–Ia1.180 by the fact that $R^1$ is nitro, $R^{11}$ is n-butyl, $R^{12}$ is methylcarbonyl and $R^{13}$ is methyl:

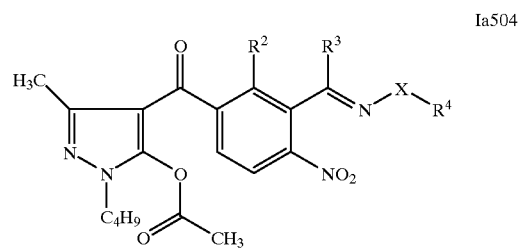

the compounds Ia505, in particular the compounds Ia505.001–Ia505.180, which differ from the corresponding compounds Ia1.001–Ia1.180 by the fact that $R^1$ is nitro, $R^{11}$ is iso-butyl, $R^{12}$ is methylcarbonyl and $R^{13}$ is methyl:

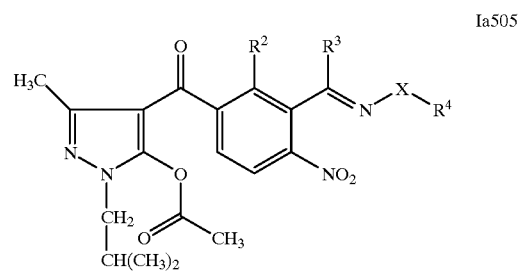

the compounds Ia506, in particular the compounds Ia506.001–Ia506.180, which differ from the corresponding compounds Ia1.001–Ia1.180 by the fact that $R^1$ is nitro, $R^{12}$ is ethylcarbonyl and $R^{13}$ is methyl:

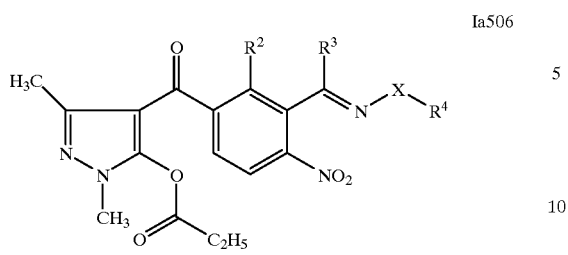

Ia506 the compounds Ia507, in particular the compounds Ia507.001–Ia507.180, which differ from the corresponding compounds Ia1.001–Ia1.180 by the fact that $R^1$ is nitro, $R^{11}$ is ethyl, $R^{12}$ is ethylcarbonyl and $R^{13}$ is methyl:

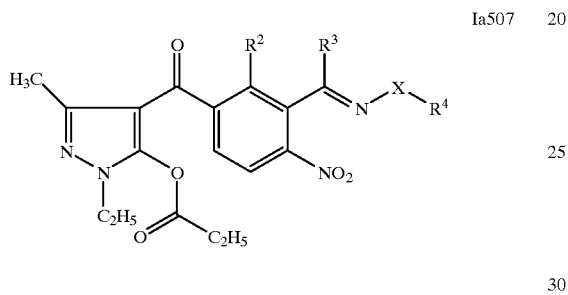

Ia507 the compounds Ia508, in particular the compounds Ia508.001–Ia508.180, which differ from the corresponding compounds Ia1.001–Ia1.180 by the fact that $R^1$ is nitro, $R^{11}$ is n-propyl, $R^{12}$ is ethylcarbonyl and $R^{13}$ is methyl:

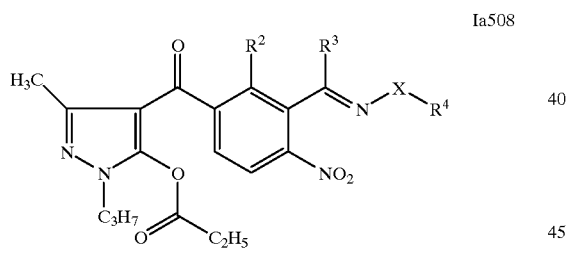

Ia508 the compounds Ia509, in particular the compounds Ia509.001–Ia509.180, which differ from the corresponding compounds Ia1.001–Ia1.180 by the fact that $R^1$ is nitro, $R^{11}$ is n-butyl, $R^{12}$ is ethylcarbonyl and $R^{13}$ is methyl:

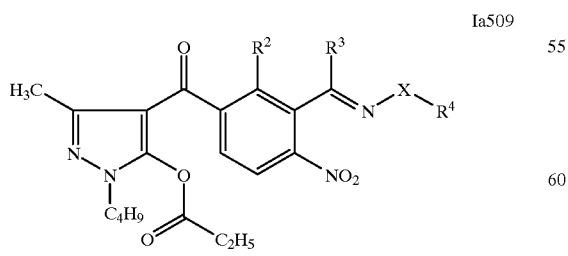

Ia509 the compounds Ia510, in particular the compounds Ia510.001–Ia510.180, which differ from the corresponding compounds Ia1.001–Ia1.180 by the fact that $R^1$ is nitro, $R^{11}$ is iso-butyl, $R^{12}$ is ethylcarbonyl and $R^{13}$ is methyl:

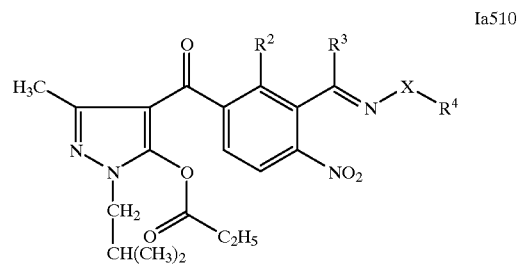

Ia510 the compounds Ia511, in particular the compounds Ia511.001–Ia511.180, which differ from the corresponding compounds Ia1.001–Ia1.180 by the fact that $R^1$ is nitro, $R^{12}$ is n-propylcarbonyl and $R^{13}$ is methyl:

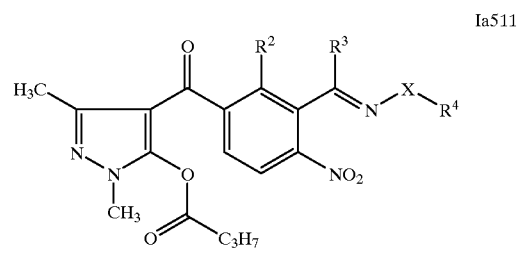

Ia511 the compounds Ia512, in particular the compounds Ia512.001–Ia512.180, which differ from the corresponding compounds Ia1.001–Ia1.180 by the fact that $R^1$ is nitro, $R^{11}$ is ethyl, $R^{12}$ is n-propylcarbonyl and $R^{13}$ is methyl:

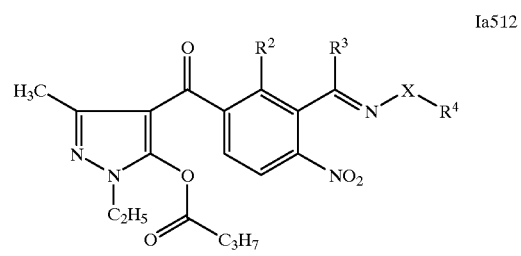

Ia512 the compounds Ia513, in particular the compounds Ia513.001–Ia513.180, which differ from the corresponding compounds Ia1.001–Ia1.180 by the fact that $R^1$ is nitro, $R^{11}$ is n-propyl, $R^{12}$ is n-propylcarbonyl and $R^{13}$ is methyl:

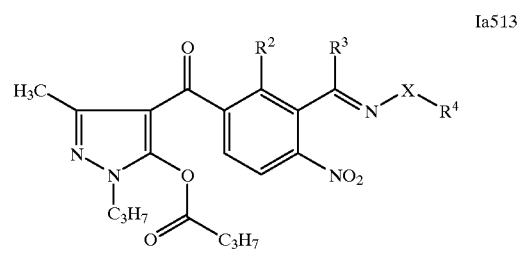

Ia513 the compounds Ia514, in particular the compounds Ia514.001–Ia514.180, which differ from the corresponding compounds Ia1.001–Ia1.180 by the fact that $R^1$ is nitro, $R^{11}$ is n-butyl, $R^{12}$ is n-propylcarbonyl and $R^{13}$ is methyl:

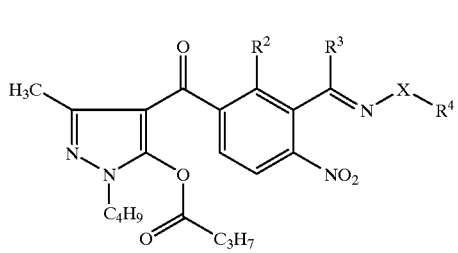

Ia514 the compounds Ia515, in particular the compounds Ia515.001–Ia515.180, which differ from the corresponding compounds Ia1.001–Ia1.180 by the fact that $R^1$ is nitro, $R^{11}$ is iso-butyl, $R^{12}$ is n-propylcarbonyl and $R^{13}$ is methyl:

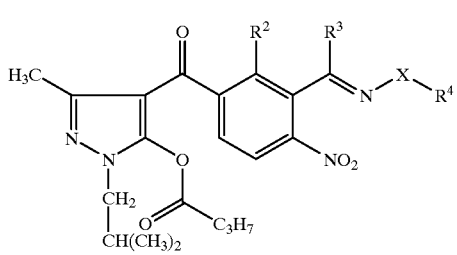

Ia515 the compounds Ia516, in particular the compounds Ia516.001–Ia516.180, which differ from the corresponding compounds Ia1.001–Ia1.180 by the fact that $R^1$ is nitro, $R^{12}$ is trifluoromethylcarbonyl and $R^{13}$ is methyl:

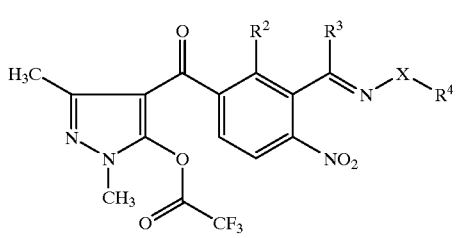

Ia516 the compounds Ia517, in particular the compounds Ia517.001–Ia517.180, which differ from the corresponding compounds Ia1.001–Ia1.180 by the fact that $R^1$ is nitro, $R^{11}$ is ethyl, $R^{12}$ is trifluoromethylcarbonyl and $R^{13}$ is methyl:

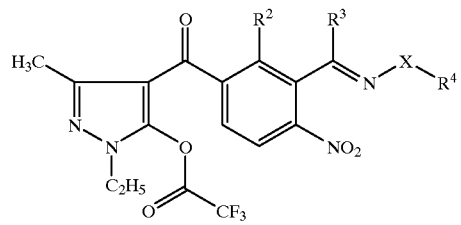

Ia517 the compounds Ia518, in particular the compounds Ia518.001–Ia518.180, which differ from the corresponding compounds Ia1.001–Ia1.180 by the fact that $R^1$ is nitro, $R^{11}$ is n-propyl, $R^{12}$ is trifluoromethylcarbonyl and $R^{13}$ is methyl:

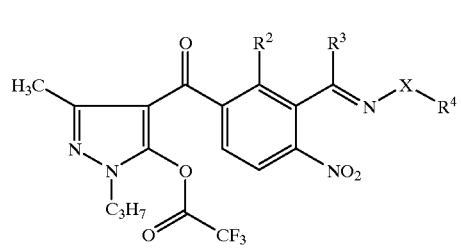

Ia518 the compounds Ia519, in particular the compounds Ia519.001–Ia519.180, which differ from the corresponding compounds Ia1.001–Ia1.180 by the fact that $R^1$ is nitro, $R^{11}$ is n-butyl, $R^{12}$ is trifluoromethylcarbonyl and $R^{13}$ is methyl:

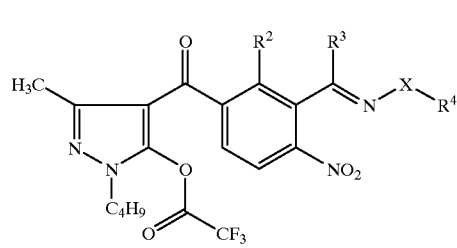

Ia519 the compounds Ia520, in particular the compounds Ia520.001–Ia520.180, which differ from the corresponding compounds Ia1.001–Ia1.180 by the fact that $R^1$ is nitro, $R^{11}$ is iso-butyl, $R^{12}$ is trifluoromethylcarbonyl and $R^{13}$ is methyl:

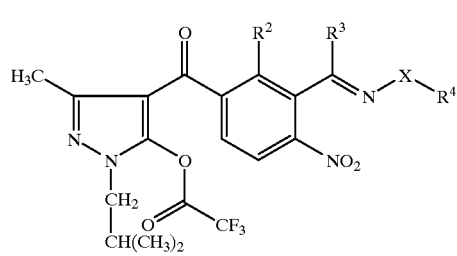

Ia520 the compounds Ia521, in particular the compounds Ia521.001–Ia521.180, which differ from the corresponding compounds Ia1.001–Ia1.180 by the fact that $R^1$ is nitro, $R^{12}$ is methylsulfonyl and $R^{13}$ is methyl:

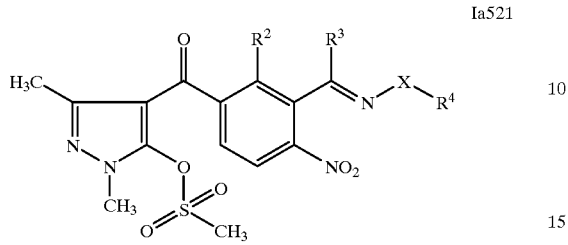
Ia521 the compounds Ia522, in particular the compounds Ia522.001–Ia522.180, which differ from the corresponding compounds Ia1.001–Ia1.180 by the fact that $R^1$ is nitro, $R^{11}$ is ethyl, $R^{12}$ is methylsulfonyl and $R^{13}$ is methyl:

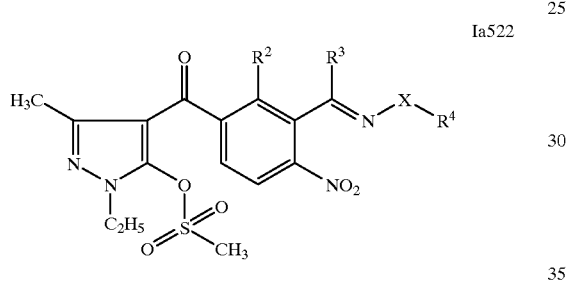
Ia522 the compounds Ia523, in particular the compounds Ia523.001–Ia523.180, which differ from the corresponding compounds Ia1.001–Ia1.180 by the fact that $R^1$ is nitro, $R^{11}$ is n-propyl, $R^{12}$ is methylsulfonyl and $R^{13}$ is methyl:

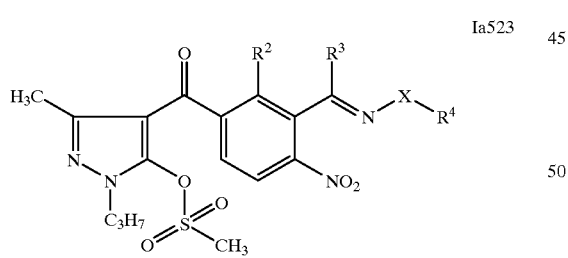
Ia523 the compounds Ia524, in particular the compounds Ia524.001–Ia524.180, which differ from the corresponding compounds Ia1.001–Ia1.180 by the fact that $R^1$ is nitro, $R^{11}$ is n-butyl, $R^{12}$ is methylsulfonyl and $R^{13}$ is methyl:

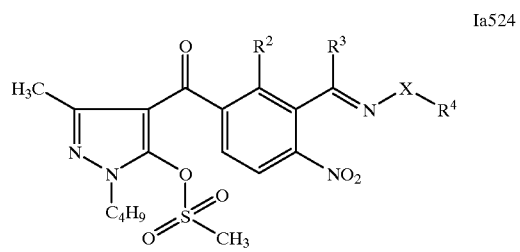
Ia524 the compounds Ia525, in particular the compounds Ia525.001–Ia525.180, which differ from the corresponding compounds Ia1.001–Ia1.180 by the fact that $R^1$ is nitro, $R^{11}$ is iso-butyl, $R^{12}$ is methylsulfonyl and $R^{13}$ is methyl:

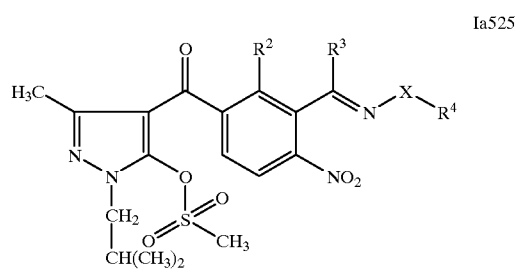
Ia525 the compounds Ia526, in particular the compounds Ia526.001–Ia526.180, which differ from the corresponding compounds Ia1.001–Ia1.180 by the fact that $R^1$ is nitro, $R^{12}$ is ethylsulfonyl and $R^{13}$ is methyl:

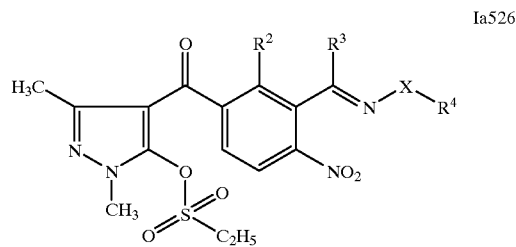
Ia526 the compounds Ia527, in particular the compounds Ia527.001–Ia527.180, which differ from the corresponding compounds Ia1.001–Ia1.180 by the fact that $R^1$ is nitro, $R^{11}$ is ethyl, $R^{12}$ is ethylsulfonyl and $R^{13}$ is methyl:

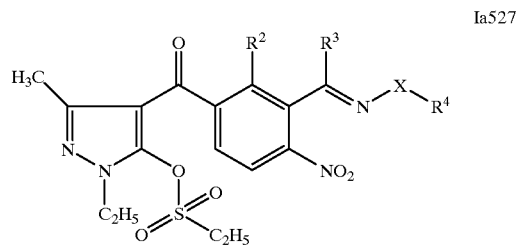
Ia527 the compounds Ia528, in particular the compounds Ia528.001–Ia528.180, which differ from the corresponding compounds Ia1.001–Ia1.180 by the fact that $R^1$ is nitro, $R^{11}$ is n-propyl, $R^{12}$ is ethylsulfonyl and $R^{13}$ is methyl:

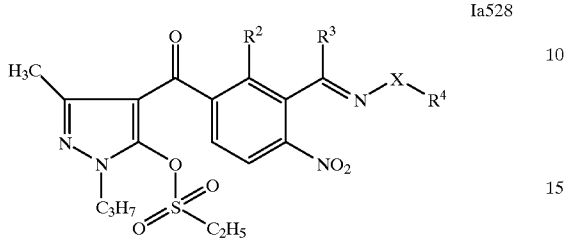

Ia528 the compounds Ia529, in particular the compounds Ia529.001–Ia529.180, which differ from the corresponding compounds Ia1.001–Ia1.180 by the fact that $R^1$ is nitro, $R^{11}$ is n-butyl, $R^{12}$ is ethylsulfonyl and $R^{13}$ is methyl:

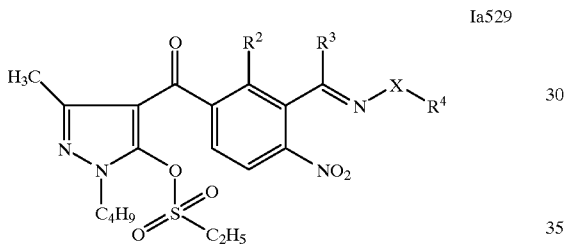

Ia529 the compounds Ia530, in particular the compounds Ia530.001–Ia530.180, which differ from the corresponding compounds Ia1.001–Ia1.180 by the fact that $R^1$ is nitro, $R^{11}$ is iso-butyl, $R^{12}$ is ethylsulfonyl and $R^{13}$ is methyl:

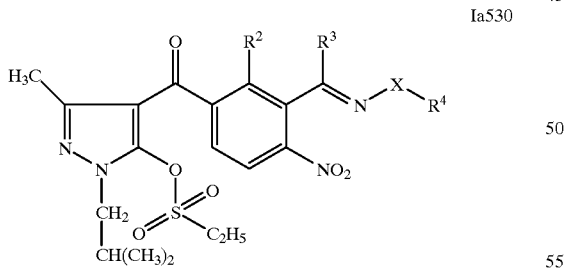

Ia530 the compounds Ia531, in particular the compounds Ia531.001–Ia531.180, which differ from the corresponding compounds Ia1.001–Ia1.180 by the fact that $R^1$ is nitro, $R^{12}$ is n-propylsulfonyl and $R^{13}$ is methyl:

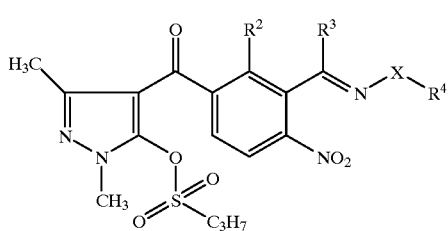

Ia531 the compounds Ia532, in particular the compounds Ia532.001–Ia532.180, which differ from the corresponding compounds Ia1.001–Ia1.180 by the fact that $R^1$ is nitro, $R^{11}$ is ethyl, $R^{12}$ is n-propylsulfonyl and $R^{13}$ is methyl:

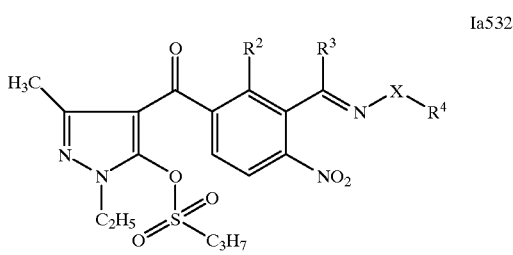

Ia532 the compounds Ia533, in particular the compounds Ia533.001–Ia533.180, which differ from the corresponding compounds Ia1.001–Ia1.180 by the fact that $R^1$ is nitro, $R^{11}$ is n-propyl, $R^{12}$ is n-propylsulfonyl and $R^{13}$ is methyl:

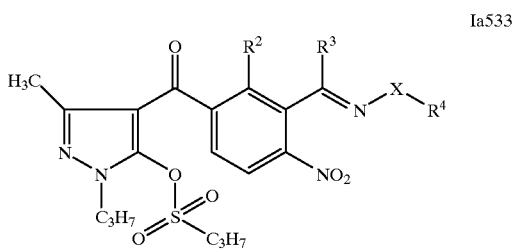

Ia533 the compounds Ia534, in particular the compounds Ia534.001–Ia534.180, which differ from the corresponding compounds Ia1.001–Ia1.180 by the fact that $R^1$ is nitro, $R^{11}$ is n-butyl, $R^{12}$ is n-propylsulfonyl and $R^{13}$ is methyl:

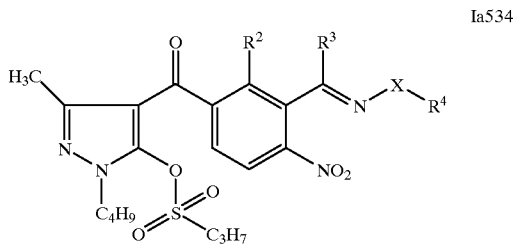

Ia534 the compounds Ia535, in particular the compounds Ia535.001–Ia535.180, which differ from the corresponding compounds Ia1.001–Ia1.180 by the fact that $R^1$ is nitro, $R^{11}$ is iso-butyl, $R^{12}$ is n-propylsulfonyl and $R^{13}$ is methyl:

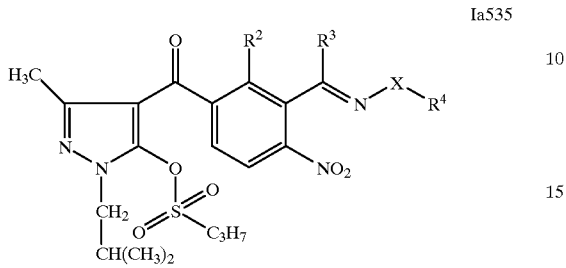

Ia535 the compounds Ia536, in particular the compounds Ia536.001–Ia536.180, which differ from the corresponding compounds Ia1.001–Ia1.180 by the fact that $R^1$ is nitro, $R^{12}$ is iso-propylsulfonyl and $R^{13}$ is methyl:

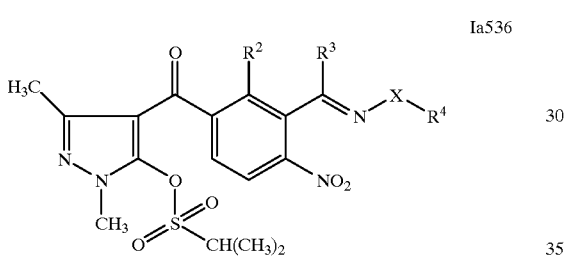

Ia536 the compounds Ia537, in particular the compounds Ia537.001–Ia537.180, which differ from the corresponding compounds Ia1.001–Ia1.180 by the fact that $R^1$ is nitro, $R^{11}$ is ethyl, $R^{12}$ is iso-propylsulfonyl and $R^{13}$ is methyl:

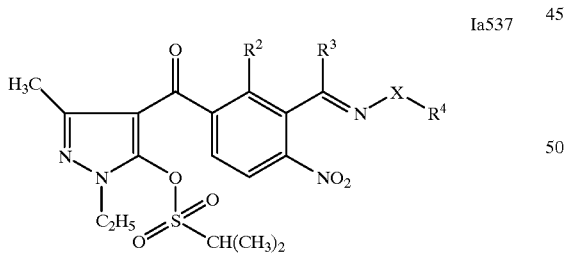

Ia537 the compounds Ia538, in particular the compounds Ia538.001–Ia538.180, which differ from the corresponding compounds Ia1.001–Ia1.180 by the fact that $R^1$ is nitro, $R^{11}$ is n-propyl, $R^{12}$ is iso-propylsulfonyl and $R^{13}$ is methyl:

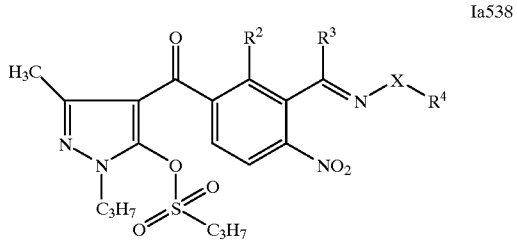

Ia538 the compounds Ia539, in particular the compounds Ia539.001–Ia539.180, which differ from the corresponding compounds Ia1.001–Ia1.180 by the fact that $R^1$ is nitro, $R^{11}$ is n-butyl, $R^{12}$ is iso-propylsulfonyl and $R^{13}$ is methyl:

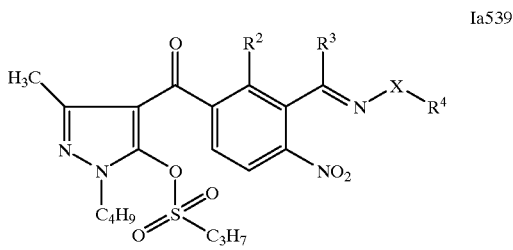

Ia539 the compounds Ia540, in particular the compounds Ia540.001–Ia540.180, which differ from the corresponding compounds Ia1.001–Ia1.180 by the fact that $R^1$ is nitro, $R^{11}$ is iso-butyl, $R^{12}$ is iso-propylsulfonyl and $R^{13}$ is methyl:

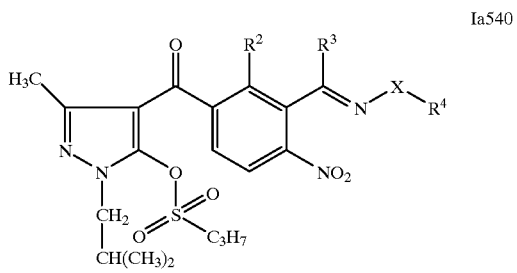

Ia540 the compounds Ia541, in particular the compounds Ia541.001–Ia541.180, which differ from the corresponding compounds Ia1.001–Ia1.180 by the fact that $R^1$ is nitro, $R^{12}$ is n-butylsulfonyl and $R^{13}$ is methyl:

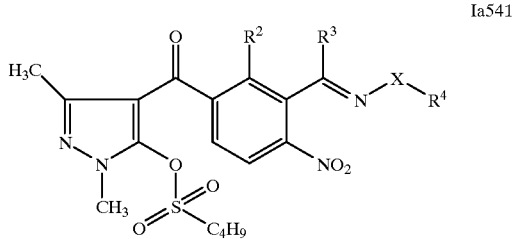

Ia541 the compounds Ia542, in particular the compounds Ia542.001–Ia542.180, which differ from the corresponding compounds Ia1.001–Ia1.180 by the fact that $R^1$ is nitro, $R^{11}$ is ethyl, $R^{12}$ is n-butylsulfonyl and $R^{13}$ is methyl:

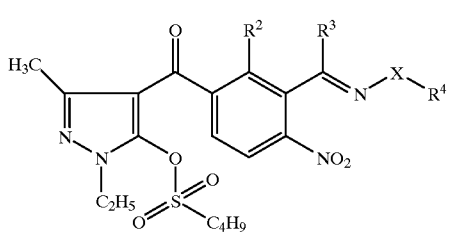

Ia542 the compounds Ia543, in particular the compounds Ia543.001–Ia543.180, which differ from the corresponding compounds Ia1.001–Ia1.180 by the fact that $R^1$ is nitro, $R^{11}$ is n-propyl, $R^{12}$ is n-butylsulfonyl and $R^{13}$ is methyl:

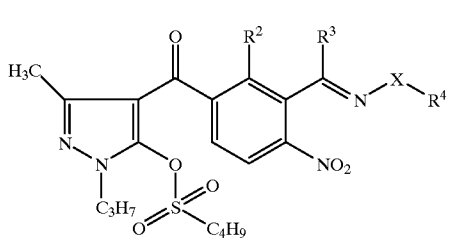

Ia543 the compounds Ia544, in particular the compounds Ia544.001–Ia544.180, which differ from the corresponding compounds Ia1.001–Ia1.180 by the fact that $R^1$ is nitro, $R^{11}$ is n-butyl, $R^{12}$ is n-butylsulfonyl and $R^{13}$ is methyl:

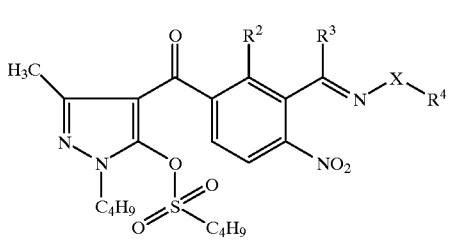

Ia544 the compounds Ia545, in particular the compounds Ia545.001–Ia545.180, which differ from the corresponding compounds Ia1.001–Ia1.180 by the fact that $R^1$ is nitro, $R^{11}$ is iso-butyl, $R^{12}$ is n-butylsulfonyl and $R^{13}$ is methyl:

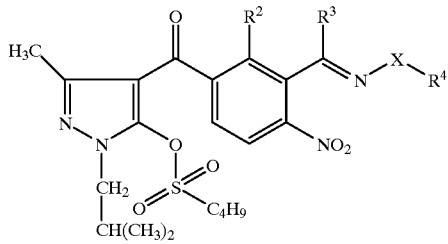

Ia545 the compounds Ia546, in particular the compounds Ia546.001–Ia546.180, which differ from the corresponding compounds Ia1.001–Ia1.180 by the fact that $R^1$ is nitro, $R^{12}$ is iso-butylsulfonyl and $R^{13}$ is methyl:

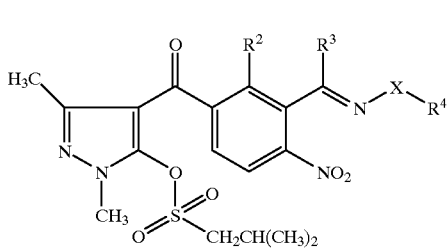

Ia546 the compounds Ia547, in particular the compounds Ia547.001–Ia547.180, which differ from the corresponding compounds Ia1.001–Ia1.180 by the fact that $R^1$ is nitro, $R^{11}$ is ethyl, $R^{12}$ is iso-butylsulfonyl and $R^{13}$ is methyl:

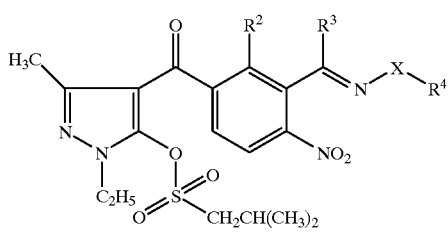

Ia547 the compounds Ia548, in particular the compounds Ia548.001–Ia548.180, which differ from the corresponding compounds Ia1.001–Ia1.180 by the fact that $R^1$ is nitro, $R^{11}$ is n-propyl, $R^{12}$ is iso-butylsulfonyl and $R^{13}$ is methyl:

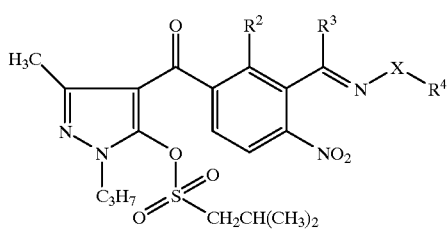

Ia548 the compounds Ia549, in particular the compounds Ia549.001–Ia549.180, which differ from the corresponding compounds Ia1.001–Ia1.180 by the fact that $R^1$ is nitro, $R^{11}$ is n-butyl, $R^{12}$ is iso-butylsulfonyl and $R^{13}$ is methyl:

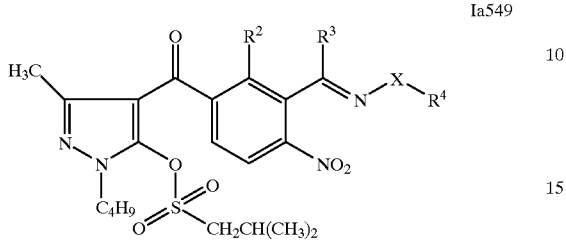

Ia549 the compounds Ia550, in particular the compounds Ia550.001–Ia550.180, which differ from the corresponding compounds Ia1.001–Ia1.180 by the fact that $R^1$ is nitro, $R^{11}$ is iso-butyl, $R^{12}$ is iso-butylsulfonyl and $R^{13}$ is methyl:

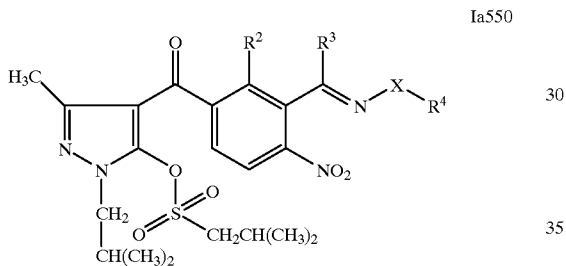

Ia550 the compounds Ia551, in particular the compounds Ia551.001–Ia551.180, which differ from the corresponding compounds Ia1.001–Ia1.180 by the fact that $R^1$ is nitro, $R^{12}$ is sec-butylsulfonyl and $R^{13}$ is methyl:

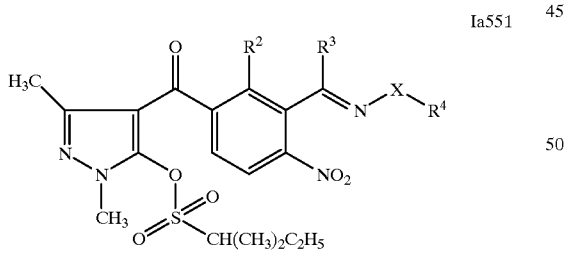

Ia551 the compounds Ia552, in particular the compounds Ia552.001–Ia552.180, which differ from the corresponding compounds Ia1.001–Ia1.180 by the fact that $R^1$ is nitro, $R^{11}$ is ethyl, $R^{12}$ is sec-butylsulfonyl and $R^{13}$ is methyl:

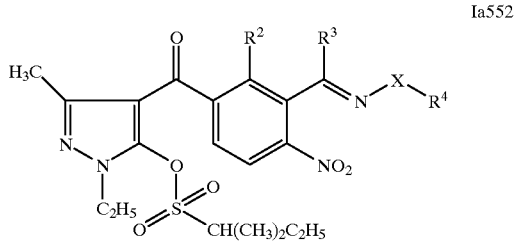

Ia552 the compounds Ia553, in particular the compounds Ia553.001–Ia553.180, which differ from the corresponding compounds Ia1.001–Ia1.180 by the fact that $R^1$ is nitro, $R^{11}$ is n-propyl, $R^{12}$ is sec-butylsulfonyl and $R^{13}$ is methyl:

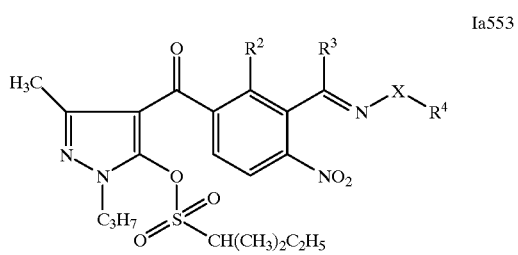

Ia553 the compounds Ia554, in particular the compounds Ia554.001–Ia554.180, which differ from the corresponding compounds Ia1.001–Ia1.180 by the fact that $R^1$ is nitro, $R^{11}$ is n-butyl, $R^{12}$ is sec-butylsulfonyl and $R^{13}$ is methyl:

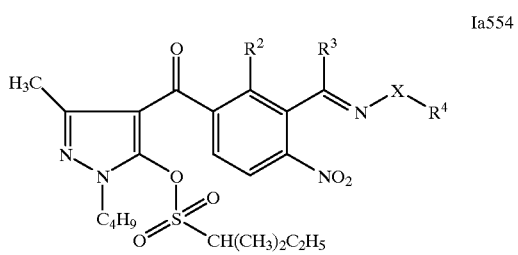

Ia554 the compounds Ia555, in particular the compounds Ia555.001–Ia555.180, which differ from the corresponding compounds Ia1.001–Ia1.180 by the fact that $R^1$ is nitro, $R^{11}$ is iso-butyl, $R^{12}$ is sec-butylsulfonyl and $R^{13}$ is methyl:

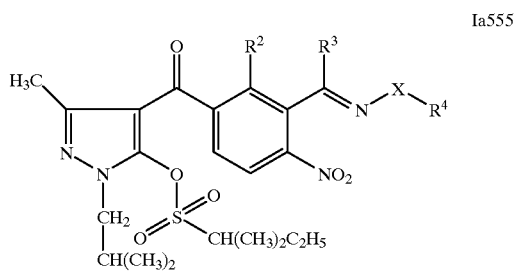

Ia555 the compounds Ia556, in particular the compounds Ia556.001–Ia556.180, which differ from the corresponding compounds Ia1.001–Ia1.180 by the fact that $R^1$ is nitro, $R^{12}$ is trifluoromethylsulfonyl and $R^{13}$ is methyl:

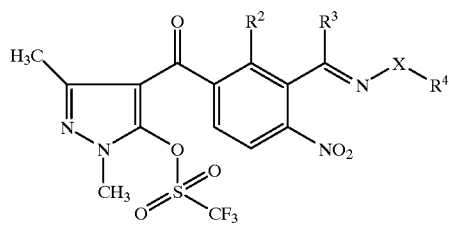

Ia556 the compounds Ia557, in particular the compounds Ia557.001–Ia557.180, which differ from the corresponding compounds Ia1.001–Ia1.180 by the fact that $R^1$ is nitro, $R^{11}$ is ethyl, $R^{12}$ is trifluoromethylsulfonyl and $R^{13}$ is methyl:

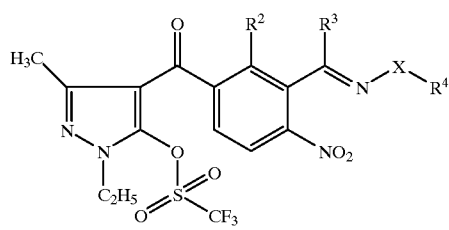

Ia557 the compounds Ia558, in particular the compounds Ia558.001–Ia558.180, which differ from the corresponding compounds Ia1.001–Ia1.180 by the fact that $R^1$ is nitro, $R^{11}$ is n-propyl, $R^{12}$ is trifluoromethylsulfonyl and $R^{13}$ is methyl:

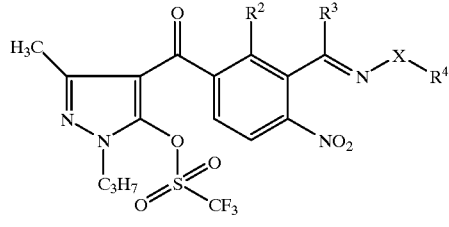

Ia558 the compounds Ia559, in particular the compounds Ia559.001–Ia559.180, which differ from the corresponding compounds Ia1.001–Ia1.180 by the fact that $R^1$ is nitro, $R^{11}$ is n-butyl, $R^{12}$ is trifluoromethylsulfonyl and $R^{13}$ is methyl:

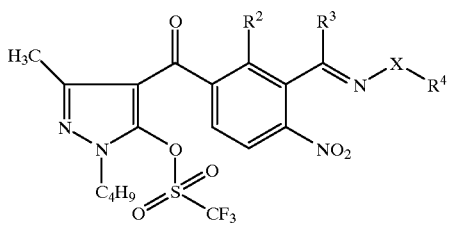

Ia559 the compounds Ia560, in particular the compounds Ia560.001–Ia560.180, which differ from the corresponding compounds Ia1.001–Ia1.180 by the fact that $R^1$ is nitro, $R^{11}$ is iso-butyl, $R^{12}$ is trifluoromethylsulfonyl and $R^{13}$ is methyl:

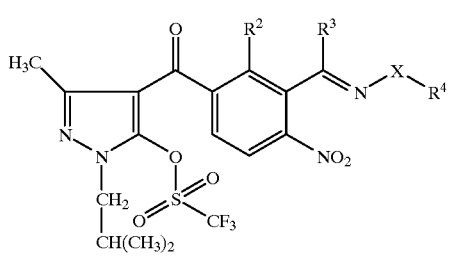

Ia560 the compounds Ia561, in particular the compounds Ia561.001–Ia561.180, which differ from the corresponding compounds Ia1.001–Ia1.180 by the fact that $R^1$ is nitro, $R^{11}$ is methyl, $R^{12}$ is phenylcarbonylmethyl and $R^{13}$ is methyl:

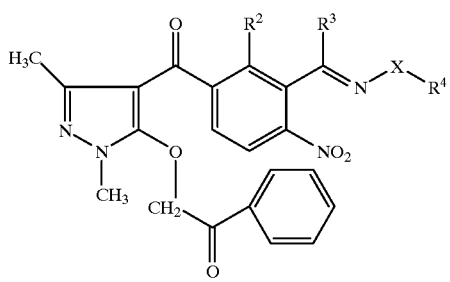

Ia561 the compounds Ia562, in particular the compounds Ia562.001–Ia562.180, which differ from the corresponding compounds Ia1.001–Ia1.180 by the fact that $R^1$ is nitro, $R^{11}$ is ethyl, $R^{12}$ is phenylcarbonylmethyl and $R^{13}$ is methyl:

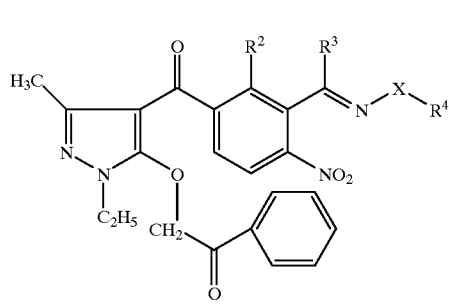

Ia562 the compounds Ia563, in particular the compounds Ia563.001–Ia563.180, which differ from the corresponding compounds Ia1.001–Ia1.180 by the fact that $R^1$ is nitro, $R^{11}$ is n-propyl, $R^{12}$ is phenylcarbonylmethyl and $R^{13}$ is methyl:

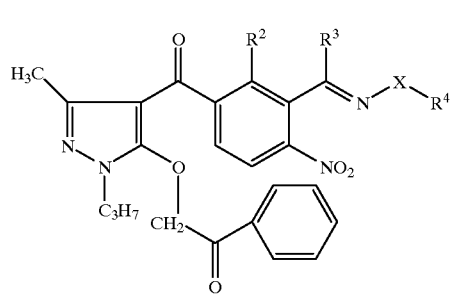

Ia563 the compounds Ia564, in particular the compounds Ia564.001–Ia564.180, which differ from the corresponding compounds Ia1.001–Ia1.180 by the fact that $R^1$ is nitro, $R^{11}$ is n-butyl, $R^{12}$ is phenylcarbonylmethyl and $R^{13}$ is methyl:

M

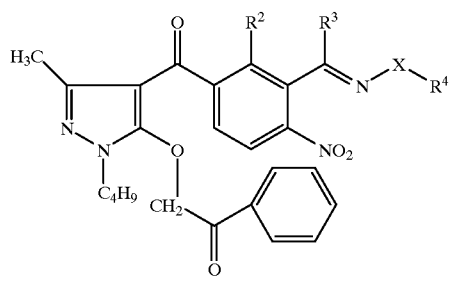

Ia564 the compounds Ia565, in particular the compounds Ia565.001–Ia565.180, which differ from the corresponding compounds Ia1.001–Ia1.180 by the fact that $R^1$ is nitro, $R^{11}$ is iso-butyl, $R^{12}$ is phenylcarbonylmethyl and $R^{13}$ is methyl:

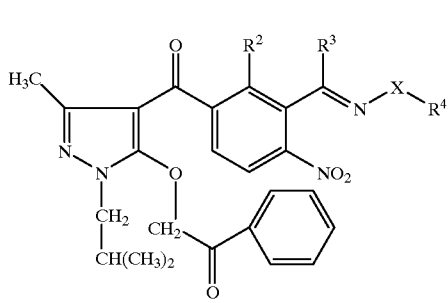

Ia565 the compounds Ia566, in particular the compounds Ia566.001–Ia566.180, which differ from the corresponding compounds Ia1.001–Ia1.180 by the fact that $R^1$ is nitro, $R^{12}$ is phenylsulfonyl and $R^{13}$ is methyl:

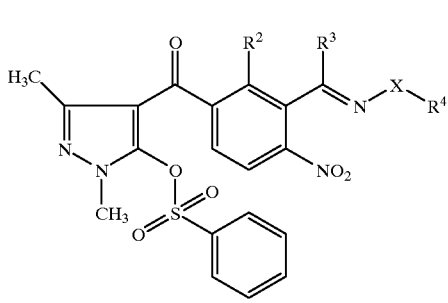

Ia566 the compounds Ia567, in particular the compounds Ia567.001–Ia567.180, which differ from the corresponding compounds Ia1.001–Ia1.180 by the fact that $R^1$ is nitro, $R^{11}$ is ethyl, $R^{12}$ is phenylsulfonyl and $R^{13}$ is methyl:

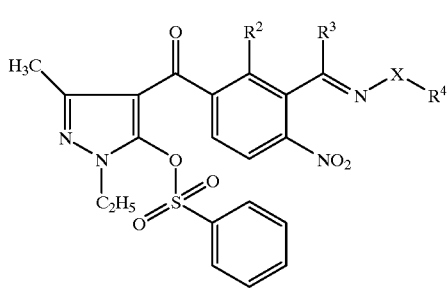

Ia567 the compounds Ia568, in particular the compounds Ia568.001–Ia568.180, which differ from the corresponding compounds Ia1.001–Ia1.180 by the fact that $R^1$ is nitro, $R^{11}$ is ethyl [sic], $R^{12}$ is phenylsulfonyl and $R^{13}$ is methyl:

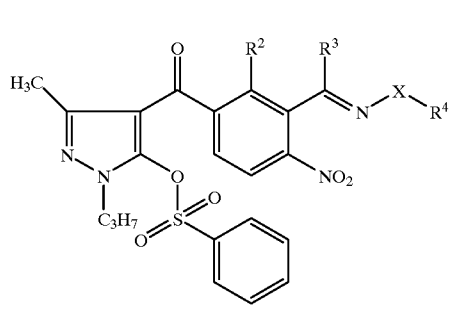

Ia568

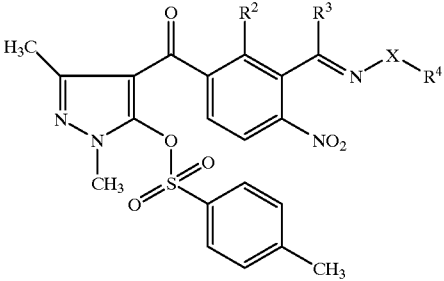

Ia571 the compounds Ia569, in particular the compounds Ia569.001–Ia569.180, which differ from the corresponding compounds Ia1.001–Ia1.180 by the fact that $R^1$ is nitro, $R^{11}$ is n-butyl, $R^{12}$ is phenylsulfonyl and $R^{13}$ is methyl:

the compounds Ia572, in particular the compounds Ia572.001–Ia572.180, which differ from the corresponding compounds Ia1.001–Ia1.180 by the fact that $R^1$ is nitro, $R^{11}$ is ethyl, $R^{12}$ is 4-methylphenylsulfonyl and $R^{13}$ is methyl:

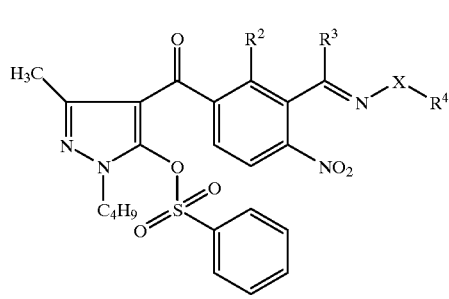

Ia569

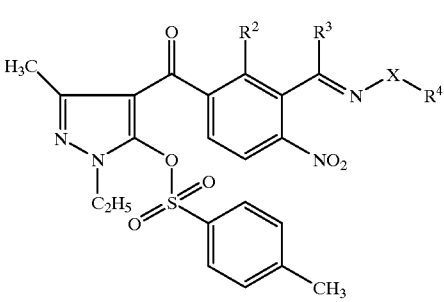

Ia572 the compounds Ia570, in particular the compounds Ia570.001–Ia570.180, which differ from the corresponding compounds Ia1.001–Ia1.180 by the fact that $R^1$ is nitro, $R^{11}$ is iso-butyl, $R^{12}$ is phenylsulfonyl and $R^{13}$ is methyl:

the compounds Ia573, in particular the compounds Ia573.001–Ia573.180, which differ from the corresponding compounds Ia1.001–Ia1.180 by the fact that $R^1$ is nitro, $R^{11}$ is n-propyl, $R^{12}$ is 4-methylphenylsulfonyl and $R^{13}$ is methyl:

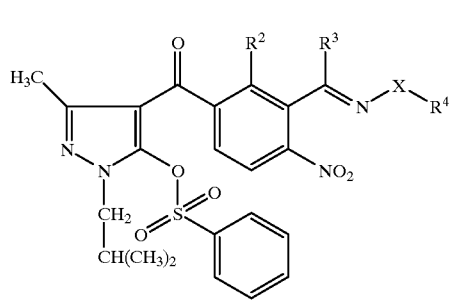

Ia570

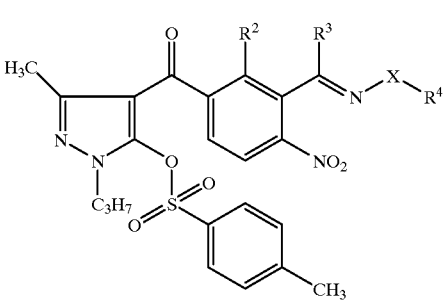

Ia573 the compounds Ia571, in particular the compounds Ia571.001–Ia571.180, which differ from the corresponding compounds Ia1.001–Ia1.180 by the fact that $R^1$ is nitro, $R^{12}$ is 4-methylphenylsulfonyl and $R^{13}$ is methyl:

the compounds Ia574, in particular the compounds Ia574.001–Ia574.180, which differ from the corresponding compounds Ia1.001–Ia1.180 by the fact that $R^1$ is nitro, $R^{11}$ is n-butyl, $R^{12}$ is 4-methylphenylsulfonyl and $R^{13}$ is methyl:

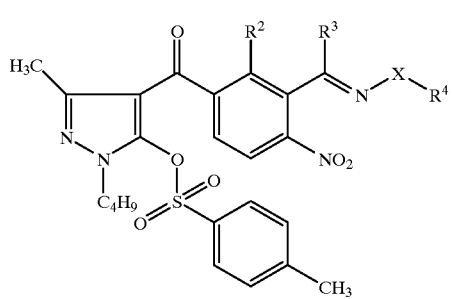
Ia574 the compounds Ia575, in particular the compounds Ia575.001–Ia575.180, which differ from the corresponding compounds Ia1.001–Ia1.180 by the fact that $R^1$ is nitro, $R^{11}$ is iso-butyl, $R^{12}$ is 4-methylphenylsulfonyl and $R^{13}$ is methyl:

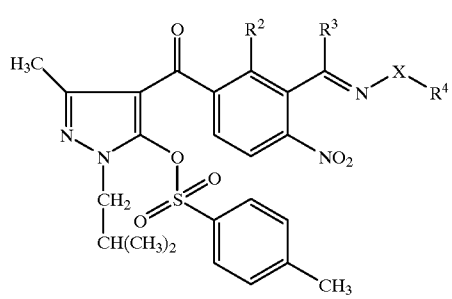
Ia575 the compounds Ia576, in particular the compounds Ia576.001–Ia576.180, which differ from the corresponding compounds Ia1.001–Ia1.180 by the fact that $R^1$ is methylsulfonyl and $R^{13}$ is methyl:

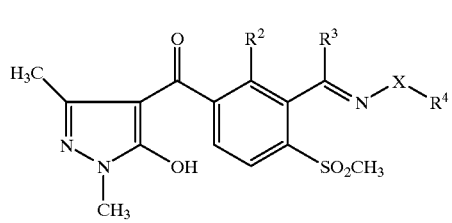
Ia576 the compounds Ia577, in particular the compounds Ia577.001–Ia577.180, which differ from the corresponding compounds Ia1.001–Ia1.180 by the fact that $R^1$ is methylsulfonyl, $R^{11}$ is ethyl and $R^{12}$ [sic] is methyl:

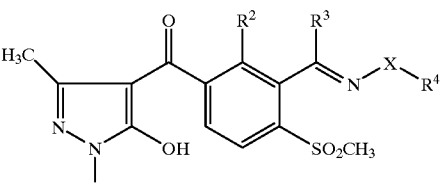
Ia577 the compounds Ia578, in particular the compounds Ia578.001–Ia578.180, which differ from the corresponding compounds Ia1.001–Ia1.180 by the fact that $R^1$ is methylsulfonyl, $R^{11}$ is n-propyl and $R^{13}$ is methyl:

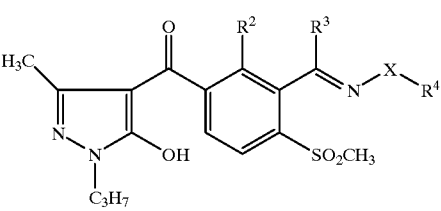
Ia578 the compounds Ia579, in particular the compounds Ia579.001–Ia579.180, which differ from the corresponding compounds Ia1.001–Ia1.180 by the fact that $R^1$ is methylsulfonyl, $R^{11}$ is n-butyl and $R^{13}$ is methyl:

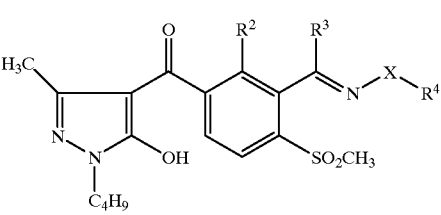
Ia579 the compounds Ia580, in particular the compounds Ia580.001–Ia580.180, which differ from the corresponding compounds Ia1.001–Ia1.180 by the fact that $R^1$ is methylsulfonyl, $R^{11}$ is iso-butyl and $R^{13}$ is methyl:

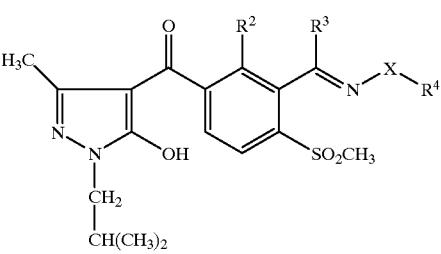
Ia580 the compounds Ia581, in particular the compounds Ia581.001–Ia581.180, which differ from the corresponding compounds Ia1.001–Ia1.180 by the fact that $R^1$ is methylsulfonyl and $R^{12}$ and $R^{13}$ are methyl:

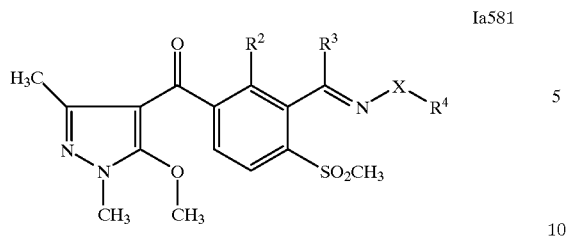
Ia581 the compounds Ia582, in particular the compounds Ia582.001–Ia582.180, which differ from the corresponding compounds Ia1.001–Ia1.180 by the fact that $R^1$ is methylsulfonyl, $R^{11}$ is ethyl and $R^{12}$ and $R^{13}$ are methyl:

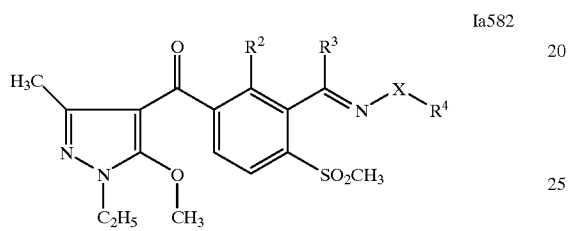
Ia582 the compounds Ia583, in particular the compounds Ia583.001–Ia583.180, which differ from the corresponding compounds Ia1.001–Ia1.180 by the fact that $R^1$ is methylsulfonyl, $R^{11}$ is n-propyl and $R^{12}$ and $R^{13}$ are methyl:

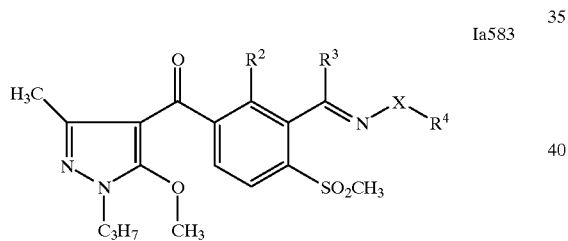
Ia583 the compounds Ia584, in particular the compounds Ia584.001–Ia584.180, which differ from the corresponding compounds Ia1.001–Ia1.180 by the fact that $R^1$ is methylsulfonyl, $R^{11}$ is n-butyl and $R^{12}$ and $R^{13}$ are methyl:

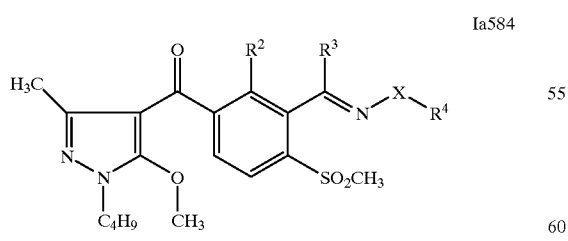
Ia584 the compounds Ia585, in particular the compounds Ia585.001–Ia585.180, which differ from the corresponding compounds Ia1.001–Ia1.180 by the fact that $R^1$ is methylsulfonyl, $R^{11}$ is iso-butyl and $R^{12}$ and $R^{13}$ are methyl:

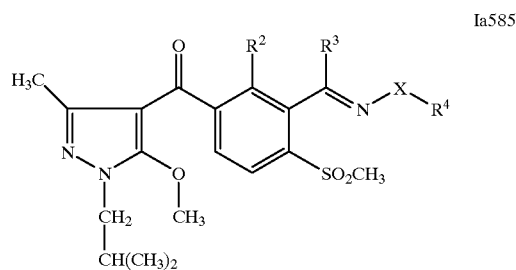
Ia585 the compounds Ia586, in particular the compounds Ia586.001–Ia586.180, which differ from the corresponding compounds Ia1.001–Ia1.180 by the fact that $R^1$ is methylsulfonyl, $R^{12}$ is ethyl and $R^{13}$ is methyl:

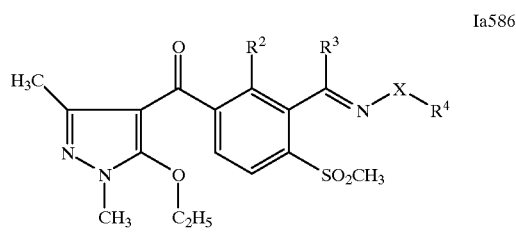
Ia586 the compounds Ia587, in particular the compounds Ia587.001–Ia587.180, which differ from the corresponding compounds Ia1.001–Ia1.180 by the fact that $R^1$ is methylsulfonyl, $R^{11}$ and $R^{12}$ are ethyl and $R^{13}$ is methyl:

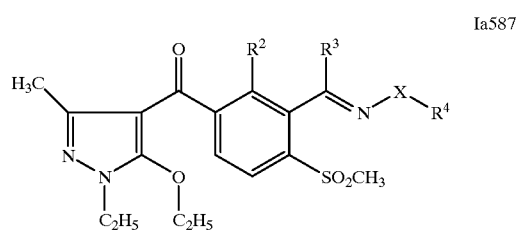
Ia587 the compounds Ia588, in particular the compounds Ia588.001–Ia588.180, which differ from the corresponding compounds Ia1.001–Ia1.180 by the fact that $R^1$ is methylsulfonyl, $R^{11}$ is n-propyl, $R^{12}$ is ethyl and $R^{13}$ is methyl:

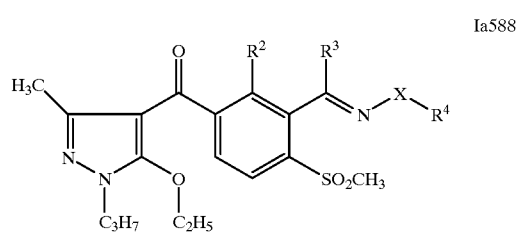
Ia588 the compounds Ia589, in particular the compounds Ia589.001–Ia589.180, which differ from the corresponding compounds Ia1.001–Ia1.180 by the fact that $R^1$ is methylsulfonyl, $R^{11}$ is n-butyl, $R^{12}$ is ethyl and $R^{13}$ is methyl:

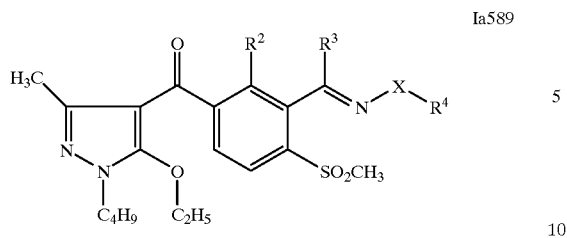

Ia589 the compounds Ia590, in particular the compounds Ia590.001–Ia590.180, which differ from the corresponding compounds Ia1.001–Ia1.180 by the fact that $R^1$ is methylsulfonyl, $R^{11}$ is iso-butyl, $R^{12}$ is ethyl and $R^{13}$ is methyl:

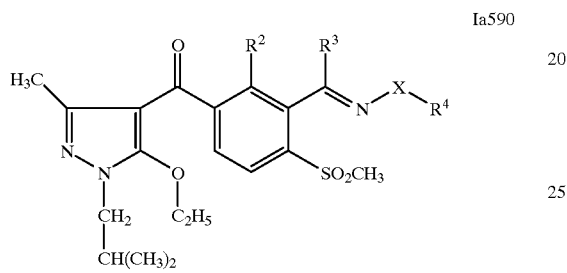

Ia590 the compounds Ia591, in particular the compounds Ia591.001–Ia591.180, which differ from the corresponding compounds Ia1.001–Ia1.180 by the fact that $R^1$ is methylsulfonyl, $R^{12}$ is n-propyl and $R^{13}$ is methyl:

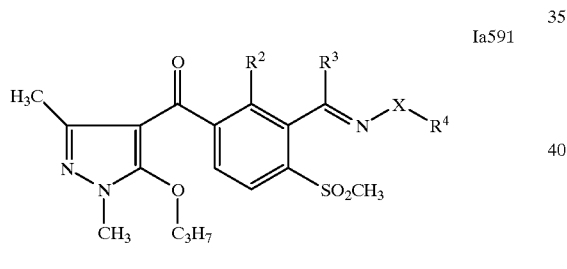

Ia591 the compounds Ia592, in particular the compounds Ia592.001–Ia592.180, which differ from the corresponding compounds Ia1.001–Ia1.180 by the fact that $R^1$ is methylsulfonyl, $R^{11}$ is ethyl, $R^{12}$ is n-propyl and $R^{13}$ is methyl:

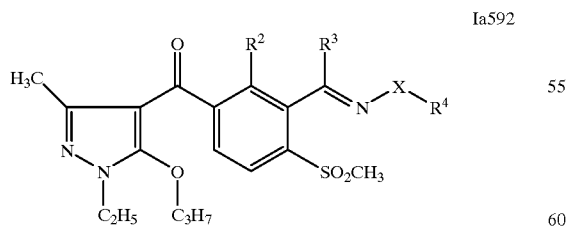

Ia592 the compounds Ia593, in particular the compounds Ia593.001–Ia593.180, which differ from the corresponding compounds Ia1.001–Ia1.180 by the fact that $R^1$ is methylsulfonyl, $R^{11}$ and $R^{12}$ are n-propyl and $R^{13}$ is methyl:

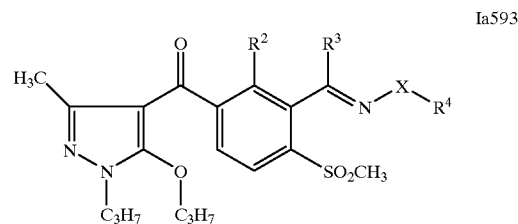

Ia593 the compounds Ia594, in particular the compounds Ia594.001–Ia594.180, which differ from the corresponding compounds Ia1.001–Ia1.180 by the fact that $R^1$ is methylsulfonyl, $R^{11}$ is n-butyl, $R^{12}$ is n-propyl and $R^{13}$ is methyl:

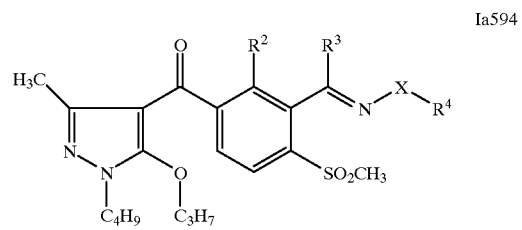

Ia594 the compounds Ia595, in particular the compounds Ia595.001–Ia595.180, which differ from the corresponding compounds Ia1.001–Ia1.180 by the fact that $R^1$ is methylsulfonyl, $R^{11}$ is iso-butyl, $R^{12}$ is n-propyl and $R^{13}$ is methyl:

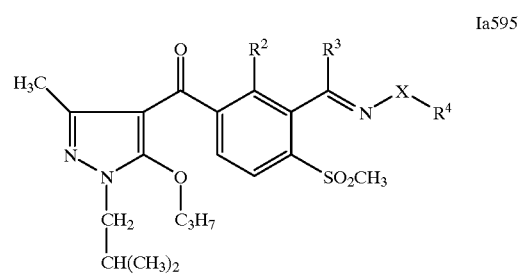

Ia595 the compounds Ia596, in particular the compounds Ia596.001–Ia596.180, which differ from the corresponding compounds Ia1.001–Ia1.180 by the fact that $R^1$ is methylsulfonyl, $R^{12}$ is iso-propyl and $R^{13}$ is methyl:

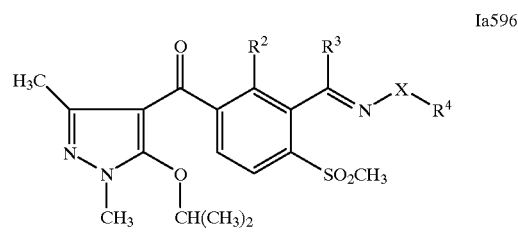

Ia596 the compounds Ia597, in particular the compounds Ia597.001–Ia597.180, which differ from the corresponding compounds Ia1.001–Ia1.180 by the fact that $R^1$ is methylsulfonyl, $R^{11}$ is ethyl, $R^{12}$ is iso-propyl and $R^{13}$ is methyl:

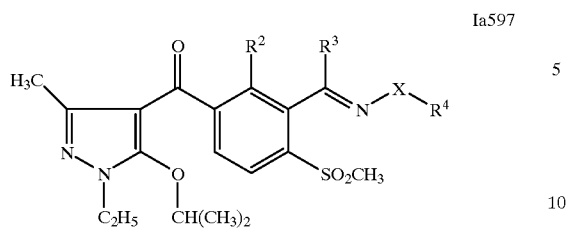
Ia597 the compounds Ia598, in particular the compounds Ia598.001–Ia598.180, which differ from the corresponding compounds Ia1.001–Ia1.180 by the fact that $R^1$ is methylsulfonyl, $R^{11}$ is n-propyl, $R^{12}$ is iso-propyl and $R^{13}$ is methyl:

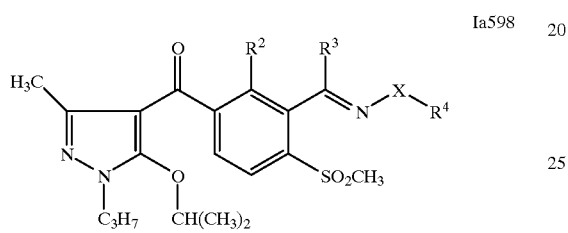
Ia598 the compounds Ia599, in particular the compounds Ia599.001–Ia599.180, which differ from the corresponding compounds Ia1.001–Ia1.180 by the fact that $R^1$ is methylsulfonyl, $R^{11}$ is n-butyl, $R^{12}$ is iso-propyl and $R^{13}$ is methyl:

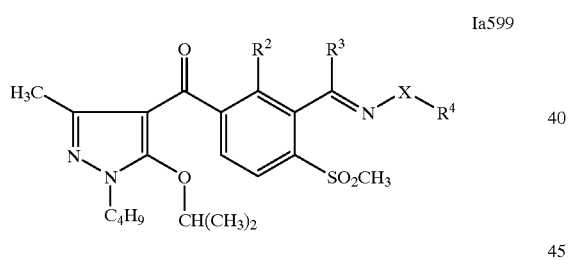
Ia599 the compounds Ia600, in particular the compounds Ia600.001–Ia600.180, which differ from the corresponding compounds Ia1.001–Ia1.180 by the fact that $R^1$ is methylsulfonyl, $R^{11}$ is iso-butyl, $R^{12}$ is iso-propyl and $R^{13}$ is methyl:

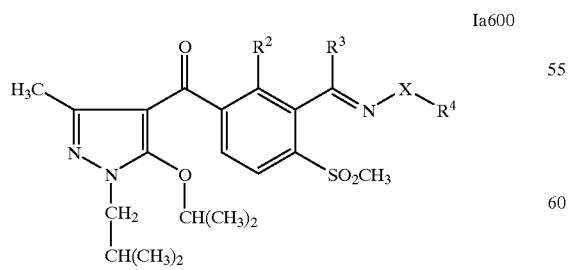
Ia600 the compounds Ia601, in particular the compounds Ia601.001–Ia601.180, which differ from the corresponding compounds Ia1.001–Ia1.180 by the fact that $R^1$ is methylsulfonyl, $R^{12}$ is n-butyl and $R^{13}$ is methyl:

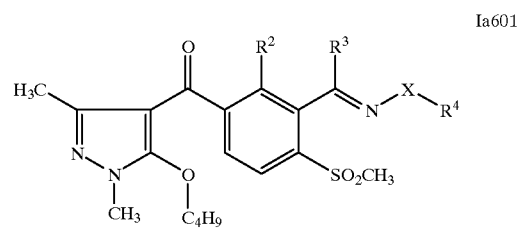
Ia601 the compounds Ia602, in particular the compounds Ia602.001–Ia602.180, which differ from the corresponding compounds Ia1.001–Ia1.180 by the fact that $R^1$ is methylsulfonyl, $R^{11}$ is ethyl, $R^{12}$ is n-butyl and $R^{13}$ is methyl:

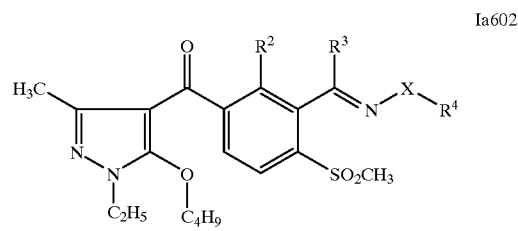
Ia602 the compounds Ia603, in particular the compounds Ia603.001–Ia603.180, which differ from the corresponding compounds Ia1.001–Ia1.180 by the fact that $R^1$ is methylsulfonyl, $R^{11}$ is n-propyl, $R^{12}$ is n-butyl and $R^{13}$ is methyl:

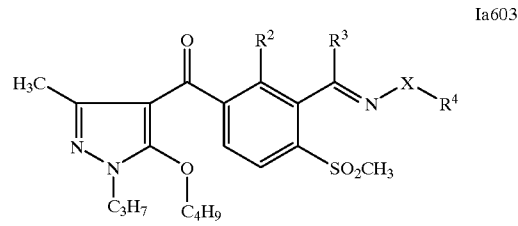
Ia603 the compounds Ia604, in particular the compounds Ia604.001–Ia604.180, which differ from the corresponding compounds Ia1.001–Ia1.180 by the fact that $R^1$ is methylsulfonyl, $R^{11}$ and $R^{12}$ are n-butyl and $R^{13}$ is methyl:

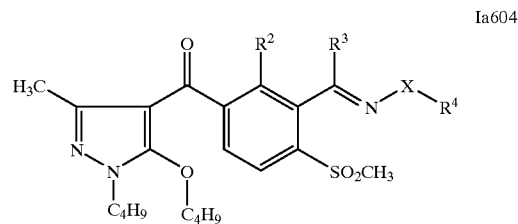
Ia604 the compounds Ia605, in particular the compounds Ia605.001–Ia605.180, which differ from the corresponding compounds Ia1.001–Ia1.180 by the fact that $R^1$ is methylsulfonyl, $R^{11}$ is iso-butyl, $R^{12}$ is n-butyl and $R^{13}$ is methyl:

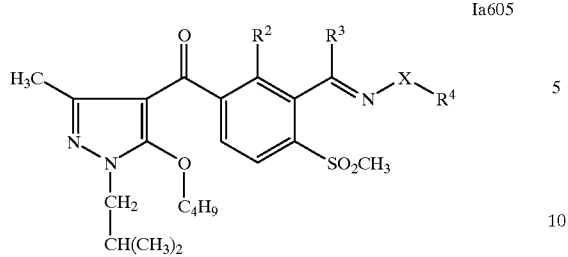

Ia605 the compounds Ia606, in particular the compounds Ia606.001–Ia606.180, which differ from the corresponding compounds Ia1.001–Ia1.180 by the fact that $R^1$ is methylsulfonyl, $R^{12}$ is sec-butyl and $R^{13}$ is methyl:

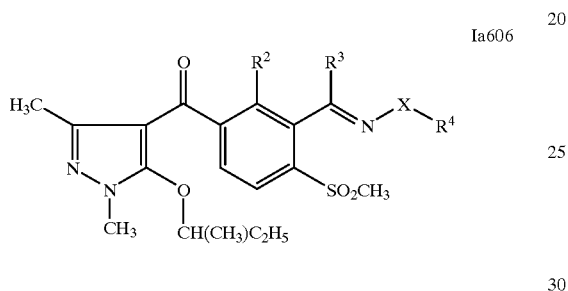

Ia606 the compounds Ia607, in particular the compounds Ia607.001–Ia607.180, which differ from the corresponding compounds Ia1.001–Ia1.180 by the fact that $R^1$ is methylsulfonyl, $R^{11}$ is ethyl, $R^{12}$ is sec-butyl and $R^{13}$ is methyl:

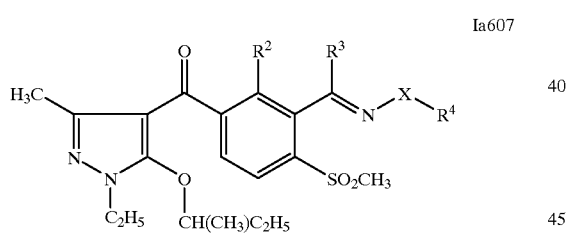

Ia607 the compounds Ia608, in particular the compounds Ia608.001–Ia608.180, which differ from the corresponding compounds Ia1.001–Ia1.180 by the fact that $R^1$ is methylsulfonyl, $R^{11}$ is n-propyl, $R^{12}$ is sec-butyl and $R^{13}$ is methyl:

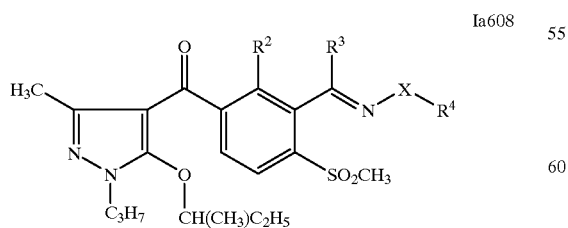

Ia608 the compounds Ia609, in particular the compounds Ia609.001–Ia609.180, which differ from the corresponding compounds Ia1.001–Ia1.180 by the fact that $R^1$ is methylsulfonyl, $R^{11}$ is n-butyl, $R^{12}$ is sec-butyl and $R^{13}$ is methyl:

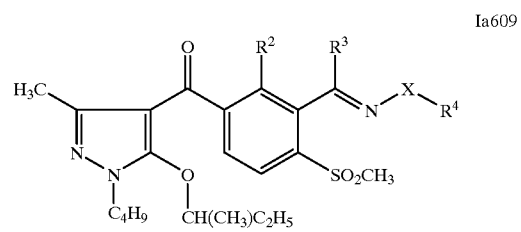

Ia609 the compounds Ia610, in particular the compounds Ia610.001–Ia610.180, which differ from the corresponding compounds Ia1.001–Ia1.180 by the fact that $R^1$ is methylsulfonyl, $R^{11}$ is iso-butyl, $R^{12}$ is sec-butyl and $R^{13}$ is methyl:

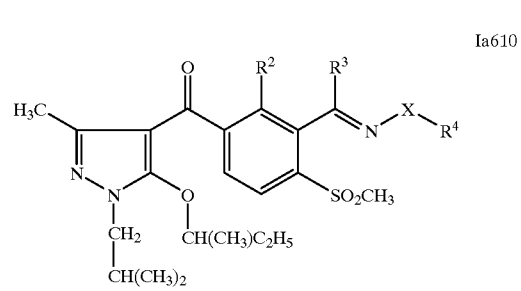

Ia610 the compounds Ia611, in particular the compounds Ia611.001–Ia611.180, which differ from the corresponding compounds Ia1.001–Ia1.180 by the fact that $R^1$ is methylsulfonyl, $R^{12}$ is iso-butyl and $R^{13}$ is methyl:

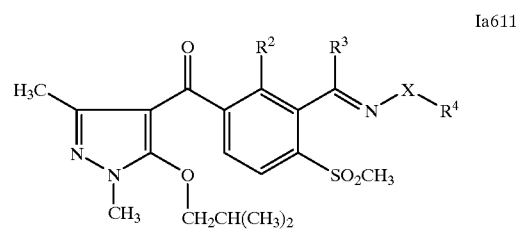

Ia611 the compounds Ia612, in particular the compounds Ia612.001–Ia612.180, which differ from the corresponding compounds Ia1.001–Ia1.180 by the fact that $R^1$ is methylsulfonyl, $R^{11}$ is ethyl, $R^{12}$ is iso-butyl and $R^{13}$ is methyl:

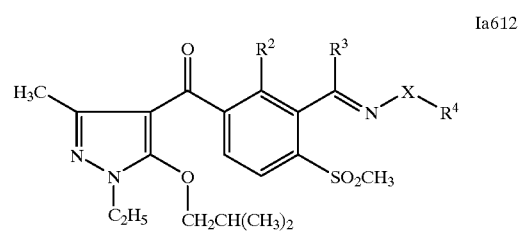

Ia612 the compounds Ia613, in particular the compounds Ia613.001–Ia613.180, which differ from the corresponding compounds Ia1.001–Ia1.180 by the fact that $R^1$ is methylsulfonyl, $R^{11}$ is n-propyl, $R^{12}$ is iso-butyl and $R^{13}$ is methyl:

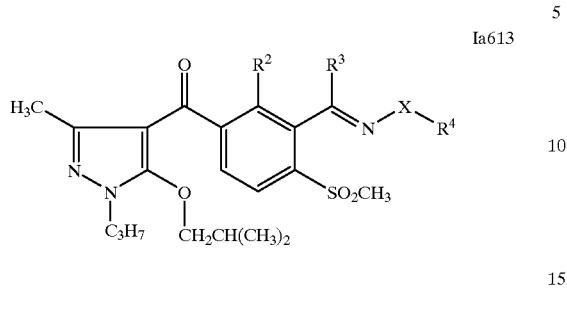

Ia613 the compounds Ia614, in particular the compounds Ia614.001–Ia614.180, which differ from the corresponding compounds Ia1.001–Ia1.180 by the fact that $R^1$ is methylsulfonyl, $R^{11}$ is n-butyl, $R^{12}$ is iso-butyl and $R^{13}$ is methyl:

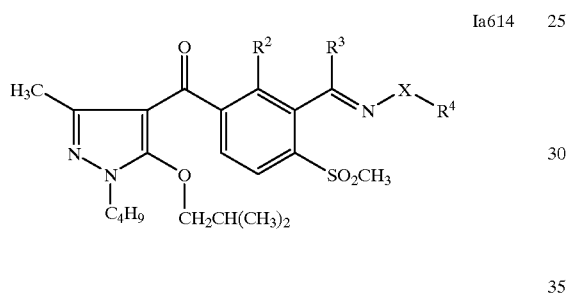

Ia614 the compounds Ia615, in particular the compounds Ia615.001–Ia615.180, which differ from the corresponding compounds Ia1.001–Ia1.180 by the fact that $R^1$ is methylsulfonyl, $R^{11}$ and $R^{12}$ are iso-butyl and $R^{13}$ is methyl:

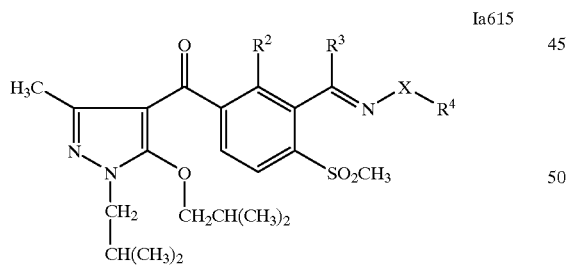

Ia615 the compounds Ia616, in particular the compounds Ia616.001–Ia616.180, which differ from the corresponding compounds Ia1.001–Ia1.180 by the fact that $R^1$ is methylsulfonyl, $R^{12}$ is methylcarbonyl and $R^{13}$ is methyl:

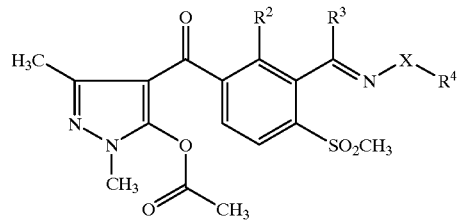

Ia616 the compounds Ia617, in particular the compounds Ia617.001–Ia617.180, which differ from the corresponding compounds Ia1.001–Ia1.180 by the fact that $R^1$ is methylsulfonyl, $R^{11}$ is ethyl, $R^{12}$ is methylcarbonyl and $R^{13}$ is methyl:

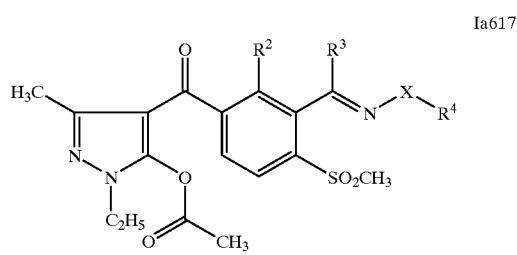

Ia617 the compounds Ia618, in particular the compounds Ia618.001–Ia618.180, which differ from the corresponding compounds Ia1.001–Ia1.180 by the fact that $R^1$ is methylsulfonyl, $R^{11}$ is n-propyl, $R^{12}$ is methylcarbonyl and $R^{13}$ is methyl:

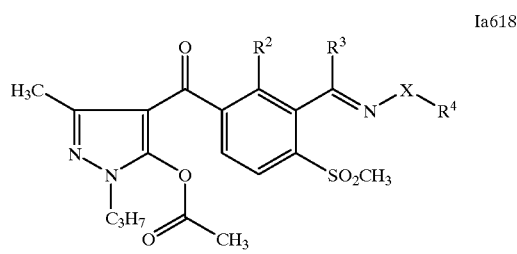

Ia618 the compounds Ia619, in particular the compounds Ia619.001–Ia619.180, which differ from the corresponding compounds Ia1.001–Ia1.180 by the fact that $R^1$ is methylsulfonyl, $R^{11}$ is n-butyl, $R^{12}$ is methylcarbonyl and $R^{13}$ is methyl:

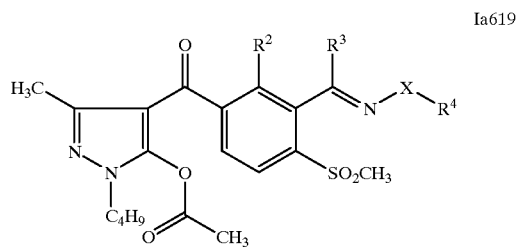

Ia619 the compounds Ia620, in particular the compounds Ia620.001–Ia620.180, which differ from the corresponding compounds Ia1.001–Ia1.180 by the fact that $R^1$ is methylsulfonyl, $R^{11}$ is iso-butyl, $R^{12}$ is methylcarbonyl and $R^{13}$ is methyl:

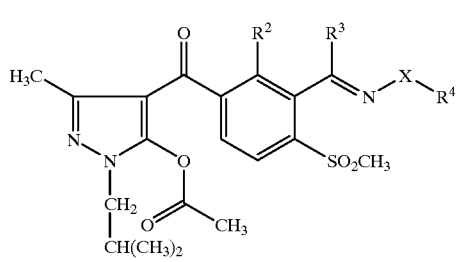

Ia620 the compounds Ia621, in particular the compounds Ia621.001–Ia621.180, which differ from the corresponding compounds Ia1.001–Ia1.180 by the fact that $R^1$ is methylsulfonyl, $R^{12}$ is ethylcarbonyl and $R^{13}$ is methyl:

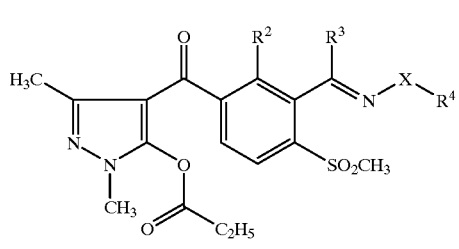

Ia621 the compounds Ia622, in particular the compounds Ia622.001–Ia622.180, which differ from the corresponding compounds Ia1.01–Ia1.180 by the fact that $R^1$ is methylsulfonyl, $R^{13}$ is ethyl, $R^{12}$ is ethylcarbonyl and $R^{13}$ is methyl:

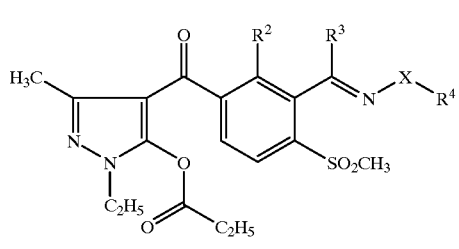

Ia622 the compounds Ia623, in particular the compounds Ia623.001–Ia623.180, which differ from the corresponding compounds Ia1.001–Ia1.180 by the fact that $R^1$ is methylsulfonyl, $R^{11}$ is n-propyl, $R^{12}$ is ethylcarbonyl and $R^{13}$ is methyl:

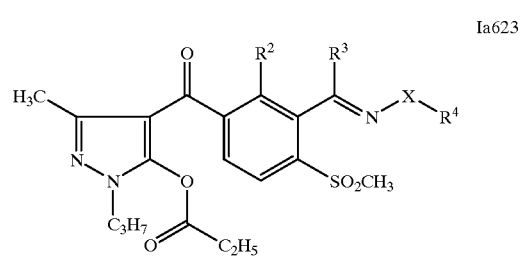

Ia623 the compounds Ia624, in particular the compounds Ia624.001–Ia624.180, which differ from the corresponding compounds Ia1.001–Ia1.180 by the fact that $R^1$ is methylsulfonyl, $R^{11}$ is n-butyl, $R^{12}$ is ethylcarbonyl and $R^{13}$ is methyl:

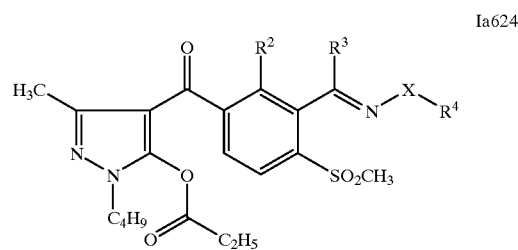

Ia624 the compounds Ia625, in particular the compounds Ia625.001–Ia625.180, which differ from the corresponding compounds Ia1.001–Ia1.180 by the fact that $R^1$ is methylsulfonyl, $R^{11}$ is iso-butyl, $R^{12}$ is ethylcarbonyl and $R^{13}$ is methyl:

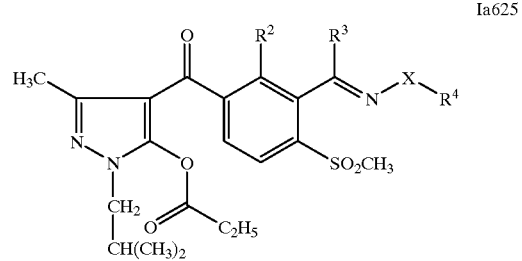

Ia625 the compounds Ia626, in particular the compounds Ia626.001–Ia626.180, which differ from the corresponding compounds Ia1.001–Ia1.180 by the fact that $R^1$ is methylsulfonyl, $R^{12}$ is n-propylcarbonyl and $R^{13}$ is methyl:

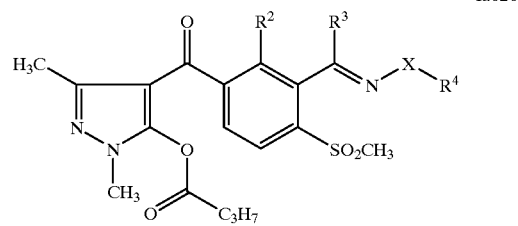

Ia626 the compounds Ia627, in particular the compounds Ia627.001–Ia627.180, which differ from the corresponding compounds Ia1.001–Ia1.180 by the fact that $R^1$ is methylsulfonyl, $R^{11}$ is ethyl, $R^{12}$ is n-propylcarbonyl and $R^{13}$ is methyl:

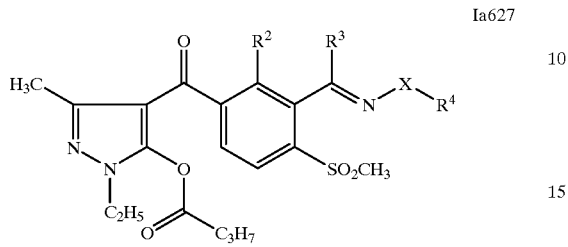

Ia627 the compounds Ia628, in particular the compounds Ia628.001–Ia628.180, which differ from the corresponding compounds Ia1.001–Ia1.180 by the fact that $R^1$ is methylsulfonyl, $R^{11}$ is n-propyl, $R^{12}$ is n-propylcarbonyl and $R^{13}$ is methyl:

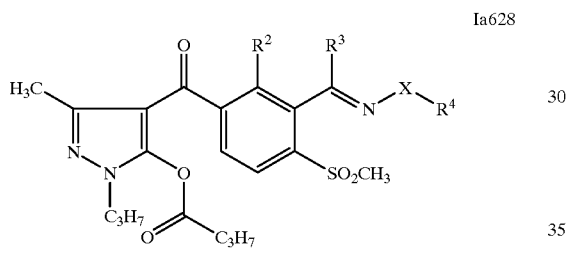

Ia628 the compounds Ia629, in particular the compounds Ia629.001–Ia629.180, which differ from the corresponding compounds Ia1.001–Ia1.180 by the fact that $R^1$ is methylsulfonyl, $R^{11}$ is n-butyl, $R^{12}$ is n-propylcarbonyl and $R^{13}$ is methyl:

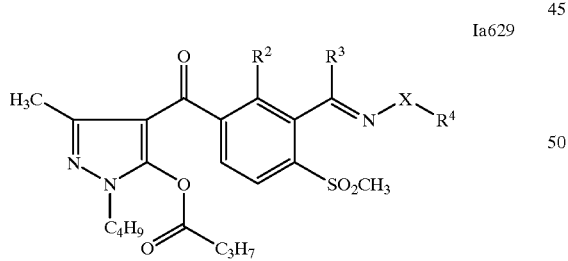

Ia629 the compounds Ia630, in particular the compounds Ia630.001–Ia630.180, which differ from the corresponding compounds Ia1.001–Ia1.180 by the fact that $R^1$ is methylsulfonyl, $R^{11}$ is iso-butyl, $R^{12}$ is n-propylcarbonyl and $R^{13}$ is methyl:

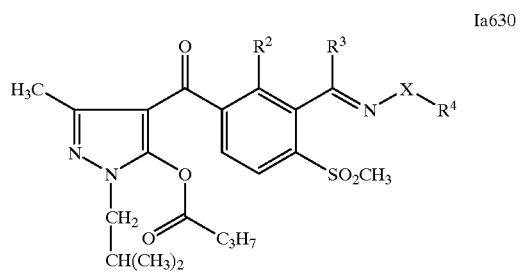

Ia630 the compounds Ia631, in particular the compounds Ia631.001–Ia631.180, which differ from the corresponding compounds Ia1.001–Ia1.180 by the fact that $R^1$ is methylsulfonyl, $R^{12}$ is trifluoromethylcarbonyl and $R^{13}$ is methyl:

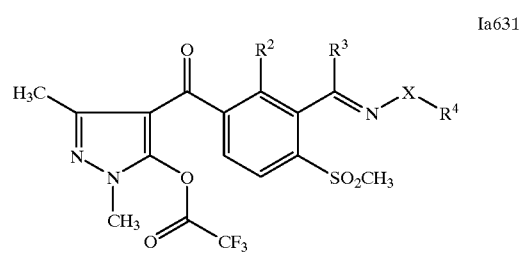

Ia631 the compounds Ia632, in particular the compounds Ia632.001–Ia632.180, which differ from the corresponding compounds Ia1.001–Ia1.180 by the fact that $R^1$ is methylsulfonyl, $R^{11}$ is ethyl, $R^{12}$ is trifluoromethyl- carbonyl and $R^{13}$ is methyl:

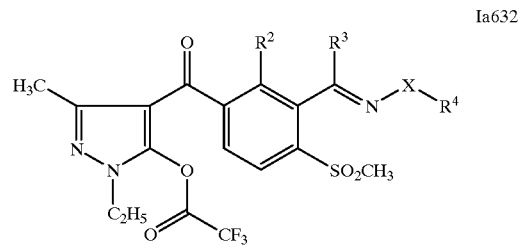

Ia632 the compounds Ia633, in particular the compounds Ia633.001–Ia633.180, which differ from the corresponding compounds Ia1.001–Ia1.180 by the fact that $R^1$ is methylsulfonyl, $R^{11}$ is n-propyl, $R^{12}$ is trifluoromethylcarbonyl and $R^{13}$ is methyl:

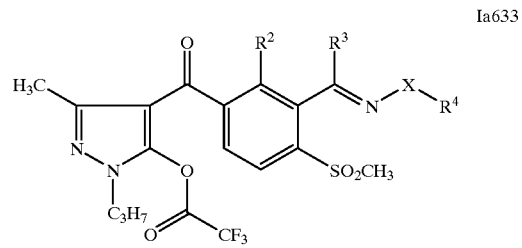

Ia633 the compounds Ia634, in particular the compounds Ia634.001–Ia634.180, which differ from the corresponding compounds Ia1.001–Ia1.180 by the fact that $R^1$ is methylsulfonyl, $R^{11}$ is n-butyl, $R^{12}$ is trifluoromethylcarbonyl and $R^{13}$ is methyl:

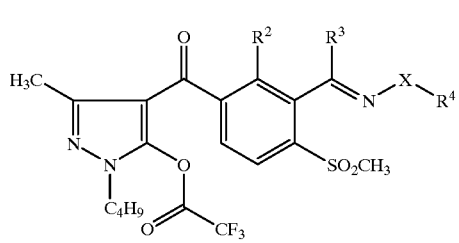

Ia634 the compounds Ia635, in particular the compounds Ia635.001–Ia635.180, which differ from the corresponding compounds Ia1.001–Ia1.180 by the fact that $R^1$ is methylsulfonyl, $R^{11}$ is iso-butyl, $R^{12}$ is trifluoromethylcarbonyl and $R^{13}$ is methyl:

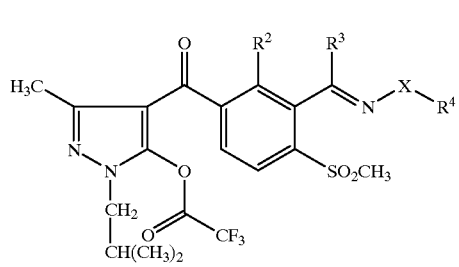

Ia635 the compounds Ia636, in particular the compounds Ia636.001–Ia636.180, which differ from the corresponding compounds Ia1.001–Ia1.180 by the fact that $R^1$ and $R^{12}$ are methylsulfonyl and $R^{13}$ is methyl:

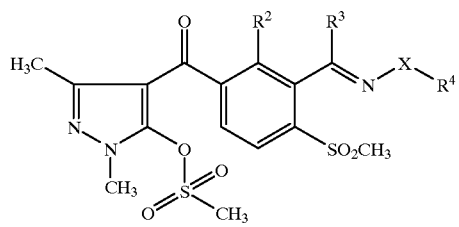

Ia636 the compounds Ia637, in particular the compounds Ia637.001–Ia637.180, which differ from the corresponding compounds Ia1.001–Ia1.180 by the fact that $R^1$ and $R^{12}$ are methylsulfonyl, $R^{11}$ is ethyl and $R^{13}$ is methyl:

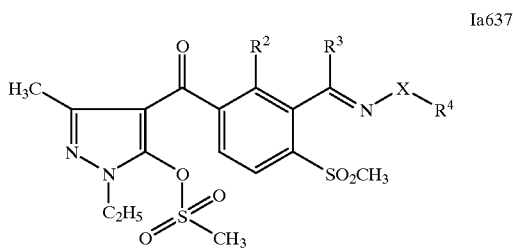

Ia637 the compounds Ia638, in particular the compounds Ia638.001–Ia638.180, which differ from the corresponding compounds Ia1.001–Ia1.180 by the fact that $R^1$ and $R^{12}$ are methylsulfonyl, $R^{11}$ is n-propyl and $R^{13}$ is methyl:

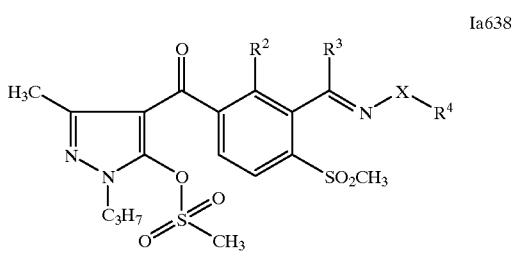

Ia638 the compounds Ia639, in particular the compounds Ia639.001–Ia639.180, which differ from the corresponding compounds Ia1.001–Ia1.180 by the fact that $R^1$ and $R^{12}$ are methylsulfonyl, $R^{11}$ is n-butyl and $R^{13}$ is methyl:

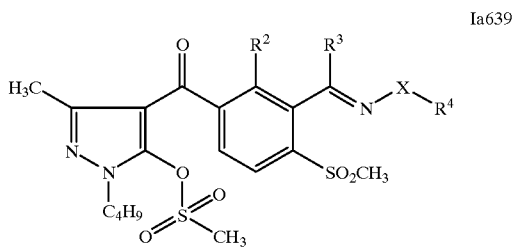

Ia639 the compounds Ia640, in particular the compounds Ia640.001–Ia640.180, which differ from the corresponding compounds Ia1.001–Ia1.180 by the fact that $R^1$ and $R^{12}$ are methylsulfonyl, $R^{11}$ is iso-butyl and $R^{13}$ is methyl:

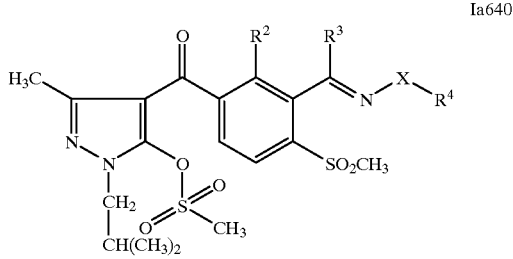

Ia640 the compounds Ia641, in particular the compounds Ia641.001–Ia641.180, which differ from the corresponding compounds Ia1.001–Ia1.180 by the fact that $R^1$ is methylsulfonyl, $R^{12}$ is ethylsulfonyl and $R^{13}$ is methyl:

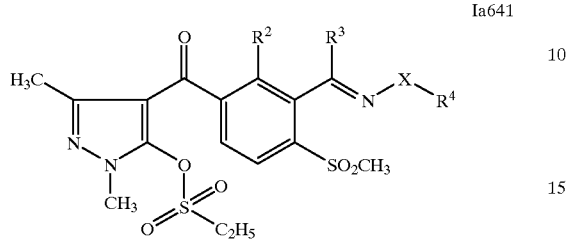
Ia641 the compounds Ia642, in particular the compounds Ia642.001–Ia642.180, which differ from the corresponding compounds Ia1.001–Ia1.180 by the fact that $R^1$ is methylsulfonyl, $R^{11}$ is ethyl, $R^{12}$ is ethylsulfonyl and $R^{13}$ is methyl:

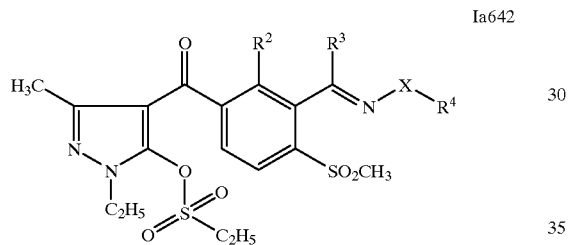
Ia642 the compounds Ia643, in particular the compounds Ia643.001–Ia643.180, which differ from the corresponding compounds Ia1.001–Ia1.180 by the fact that $R^1$ is methylsulfonyl, $R^{11}$ is n-propyl, $R^{12}$ is ethylsulfonyl and $R^{13}$ is methyl:

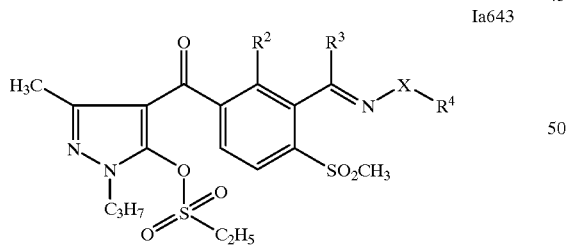
Ia643 the compounds Ia644, in particular the compounds Ia644.001–Ia644.180, which differ from the corresponding compounds Ia1.001–Ia1.180 by the fact that $R^1$ is methylsulfonyl, $R^{11}$ is n-butyl, $R^{12}$ is ethylsulfonyl and $R^{13}$ is methyl:

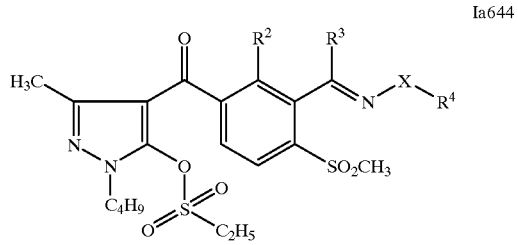
Ia644 the compounds Ia645, in particular the compounds Ia645.001–Ia645.180, which differ from the corresponding compounds Ia1.001–Ia1.180 by the fact that $R^1$ is methylsulfonyl, $R^{11}$ is iso-butyl, $R^{12}$ is ethylsulfonyl and $R^{13}$ is methyl:

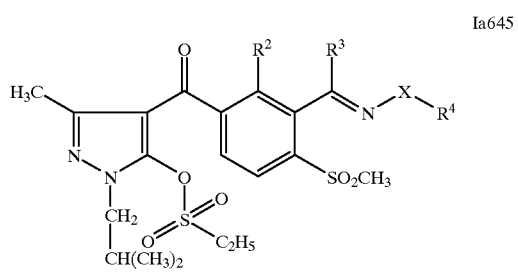
Ia645 the compounds Ia646, in particular the compounds Ia646.001–Ia646.180, which differ from the corresponding compounds Ia1.001–Ia1.180 by the fact that $R^1$ is methylsulfonyl, $R^{12}$ is n-propylsulfonyl and $R^{13}$ is methyl:

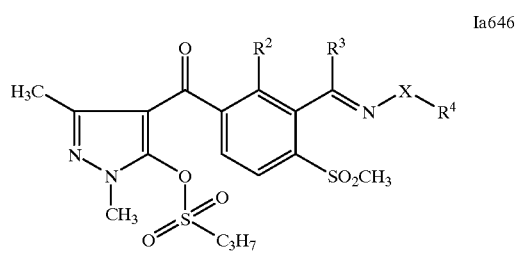
Ia646 the compounds Ia647, in particular the compounds Ia647.001–Ia647.180, which differ from the corresponding compounds Ia1.001–Ia1.180 by the fact that $R^1$ is methylsulfonyl, $R^{11}$ is ethyl, $R^{12}$ is n-propylsulfonyl and $R^{13}$ is methyl:

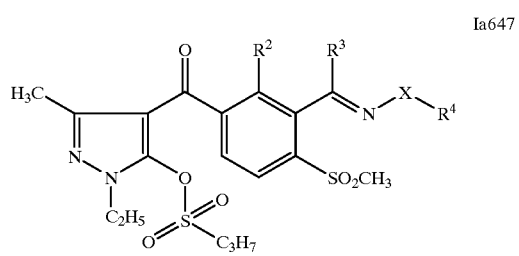
Ia647 the compounds Ia648, in particular the compounds Ia648.001–Ia648.180, which differ from the corresponding compounds Ia1.001–Ia1.180 by the fact that $R^1$ is methylsulfonyl, $R^{11}$ is n-propyl, $R^{12}$ is n-propylsulfonyl and $R^{13}$ is methyl:

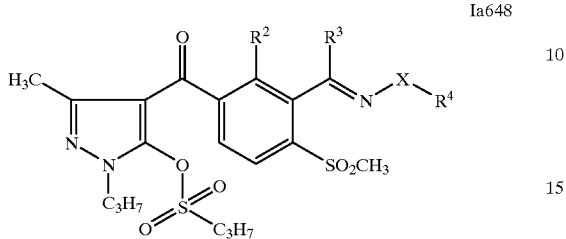

Ia648 the compounds Ia649, in particular the compounds Ia649.001–Ia649.180, which differ from the corresponding compounds Ia1.001–Ia1.180 by the fact that $R^1$ is methylsulfonyl, $R^{11}$ is n-butyl, $R^{12}$ is n-propylsulfonyl and $R^{13}$ is methyl:

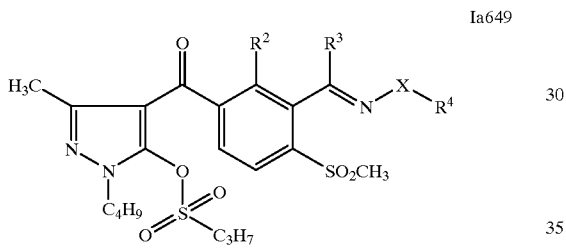

Ia649 the compounds Ia650, in particular the compounds Ia650.001–Ia650.180, which differ from the corresponding compounds Ia1.001–Ia1.180 by the fact that $R^1$ is methylsulfonyl, $R^1$ is iso-butyl, $R^{12}$ is n-propylsulfonyl and $R^{13}$ is methyl:

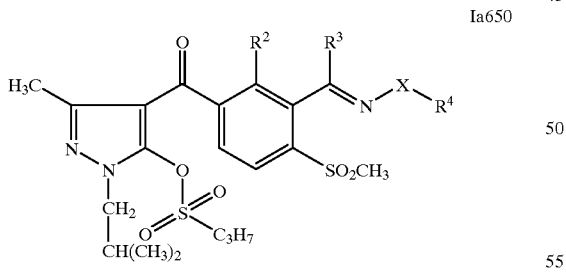

Ia650 the compounds Ia651, in particular the compounds Ia651.001–Ia651.180, which differ from the corresponding compounds Ia1.001–Ia1.180 by the fact that $R^1$ is methylsulfonyl, $R^{12}$ is iso-propylsulfonyl and $R^{13}$ is methyl:

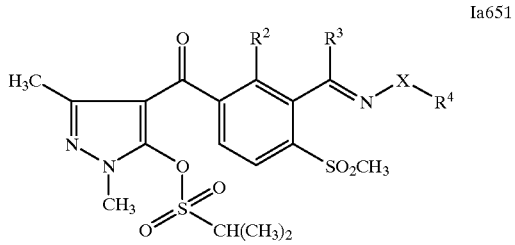

Ia651 the compounds Ia652, in particular the compounds Ia652.001–Ia652.180, which differ from the corresponding compounds Ia1.001–Ia1.180 by the fact that $R^1$ is methylsulfonyl, $R^{11}$ is ethyl, $R^{12}$ is iso-propylsulfonyl and $R^{13}$ is methyl:

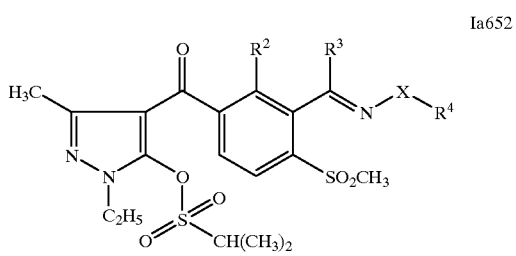

Ia652 the compounds Ia653, in particular the compounds Ia653.001–Ia653.180, which differ from the corresponding compounds Ia1.001–Ia1.180 by the fact that $R^1$ is methylsulfonyl, $R^{11}$ is n-propyl, $R^{12}$ is iso-propylsulfonyl and $R^{13}$ is methyl:

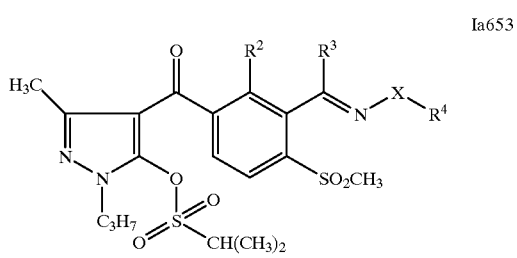

Ia653 the compounds Ia654, in particular the compounds Ia654.001–Ia654.180, which differ from the corresponding compounds Ia1.001–Ia1.180 by the fact that $R^1$ is methylsulfonyl, $R^{11}$ is n-butyl, $R^{12}$ is iso-propylsulfonyl and $R^{13}$ is methyl:

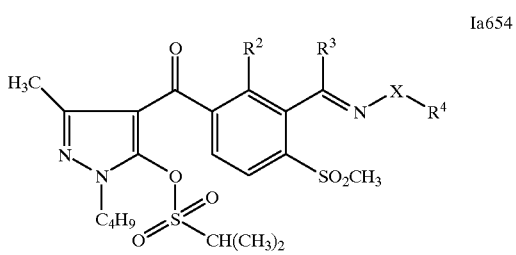

Ia654 the compounds Ia655, in particular the compounds Ia655.001–Ia655.180, which differ from the corresponding compounds Ia1.001–Ia1.180 by the fact that $R^1$ is methylsulfonyl, $R^{11}$ is iso-butyl, $R^{12}$ is iso-propylsulfonyl and $R^{13}$ is methyl:

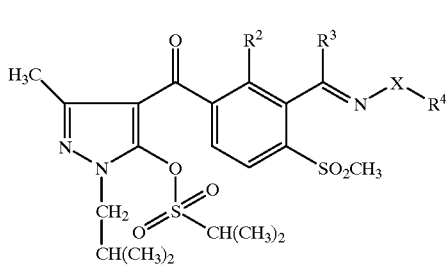

the compounds Ia656, in particular the compounds Ia656.001–Ia656.180, which differ from the corresponding compounds Ia1.001–Ia1.180 by the fact that $R^1$ is methylsulfonyl, $R^{12}$ is n-butylsulfonyl and $R^{13}$ is methyl:

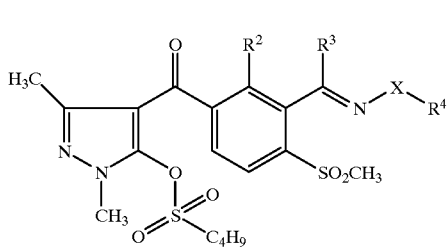

the compounds Ia657, in particular the compounds Ia657.001–Ia657.180, which differ from the corresponding compounds Ia1.001–Ia1.180 by the fact that $R^1$ is methylsulfonyl, $R^{11}$ is ethyl, $R^{12}$ is n-butylsulfonyl and $R^{13}$ is methyl:

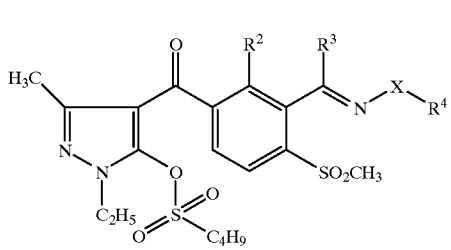

the compounds Ia658, in particular the compounds Ia658.001–Ia658.180, which differ from the corresponding compounds Ia1.001–Ia1.180 by the fact that $R^1$ is methylsulfonyl, $R^{11}$ is n-propyl, $R^{12}$ is n-butylsulfonyl and $R^{13}$ is methyl:

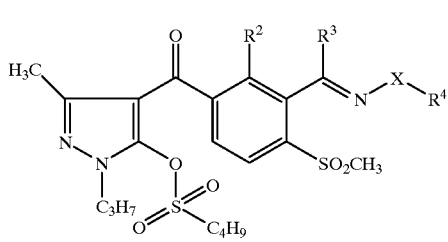

the compounds Ia659, in particular the compounds Ia659.001–Ia659.180, which differ from the corresponding compounds Ia1.001–Ia1.180 by the fact that $R^1$ is methylsulfonyl, $R^{11}$ is n-butyl, $R^{12}$ is n-butylsulfonyl and $R^{13}$ is methyl:

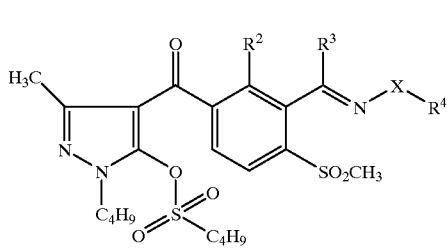

the compounds Ia660, in particular the compounds Ia660.001–Ia660.180, which differ from the corresponding compounds Ia1.001–Ia1.180 by the fact that $R^1$ is methylsulfonyl, $R^{11}$ is iso-butyl, $R^{12}$ is n-butylsulfonyl and $R^{13}$ is methyl:

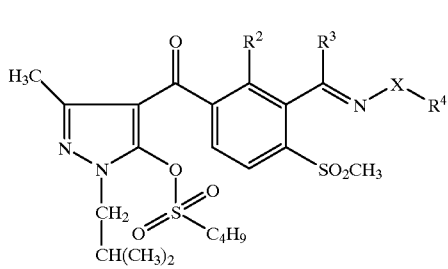

the compounds Ia661, in particular the compounds Ia661.001–Ia661.180, which differ from the corresponding compounds Ia1.001–Ia1.180 by the fact that $R^1$ is methylsulfonyl, $R^{12}$ is iso-butylsulfonyl and $R^{13}$ is methyl:

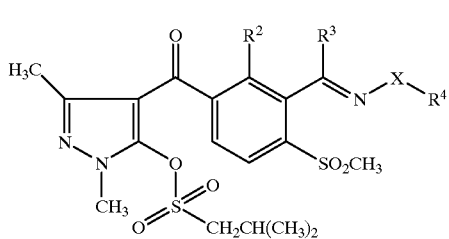

the compounds Ia662, in particular the compounds Ia662.001–Ia662.180, which differ from the corresponding compounds Ia1.001–Ia1.180 by the fact that $R^1$ is methylsulfonyl, $R^{11}$ is ethyl, $R^{12}$ is iso-butylsulfonyl and $R^{13}$ is methyl:

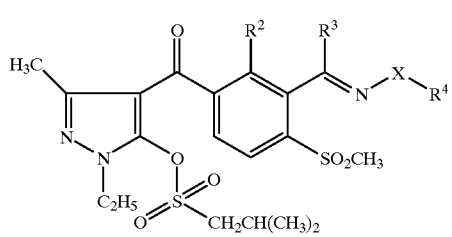

Ia662 the compounds Ia663, in particular the compounds Ia663.001–Ia663.180, which differ from the corresponding compounds Ia1.001–Ia1.180 by the fact that $R^1$ is methylsulfonyl, $R^{11}$ is n-propyl, $R^{12}$ is iso-butylsulfonyl and $R^{13}$ is methyl:

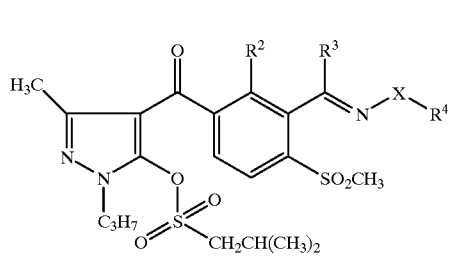

Ia663 the compounds Ia664, in particular the compounds Ia664.001–Ia664.180, which differ from the corresponding compounds Ia1.001–Ia1.180 by the fact that $R^1$ is methylsulfonyl, $R^{11}$ is n-butyl, $R^{12}$ is iso-butylsulfonyl and $R^{13}$ is methyl:

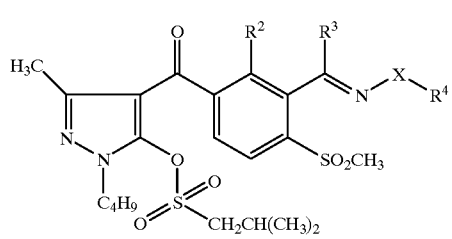

Ia664 the compounds Ia665, in particular the compounds Ia665.001–Ia665.180, which differ from the corresponding compounds Ia1.001–Ia1.180 by the fact that $R^1$ is methylsulfonyl, $R^{11}$ is iso-butyl, $R^{12}$ is iso-butylsulfonyl and $R^{13}$ is methyl:

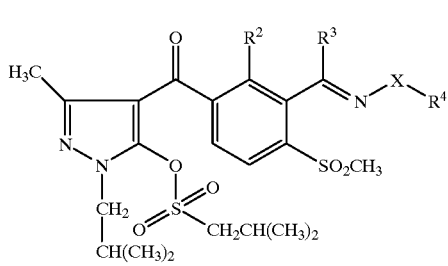

Ia665 the compounds Ia666, in particular the compounds Ia666.001–Ia666.180, which differ from the corresponding compounds Ia1.001–Ia1.180 by the fact that $R^1$ is methylsulfonyl, $R^{12}$ is sec-butylsulfonyl and $R^{13}$ is methyl:

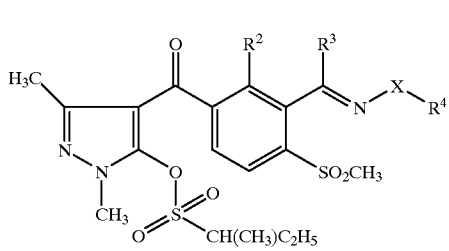

Ia666 the compounds Ia667, in particular the compounds Ia667.001–Ia667.180, which differ from the corresponding compounds Ia1.001–Ia1.180 by the fact that $R^1$ is methylsulfonyl, $R^{11}$ is ethyl, $R^{12}$ is sec-butylsulfonyl and $R^{13}$ is methyl:

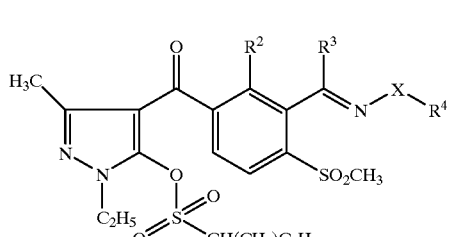

Ia667 the compounds Ia668, in particular the compounds Ia668.001–Ia668.180, which differ from the corresponding compounds Ia1.001–Ia1.180 by the fact that $R^1$ is methylsulfonyl, $R^{11}$ is n-propyl, $R^{12}$ is sec-butylsulfonyl and $R^{13}$ is methyl:

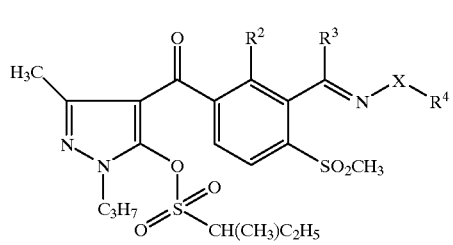

Ia668 the compounds Ia669, in particular the compounds Ia669.001–Ia669.180, which differ from the corresponding compounds Ia1.001–Ia1.180 by the fact that $R^1$ is methylsulfonyl, $R^{11}$ is n-butyl, $R^{12}$ is sec-butylsulfonyl and $R^{13}$ is methyl:

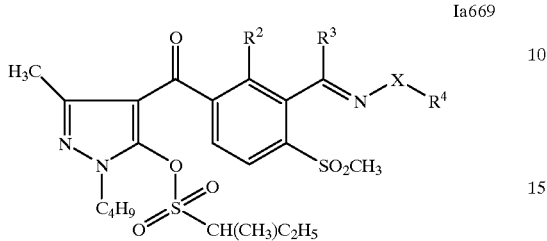

the compounds Ia670, in particular the compounds Ia670.001–Ia670.180, which differ from the corresponding compounds Ia1.001–Ia1.180 by the fact that $R^1$ is methylsulfonyl, $R^{11}$ is iso-butyl, $R^{12}$ is sec-butylsulfonyl and $R^{13}$ is methyl:

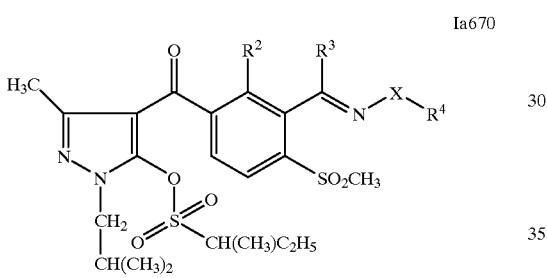

the compounds Ia671, in particular the compounds Ia671.001–Ia671.180, which differ from the corresponding compounds Ia1.001–Ia1.180 by the fact that $R^1$ is methylsulfonyl, $R^{12}$ is trifluoromethylsulfonyl and $R^{13}$ is methyl:

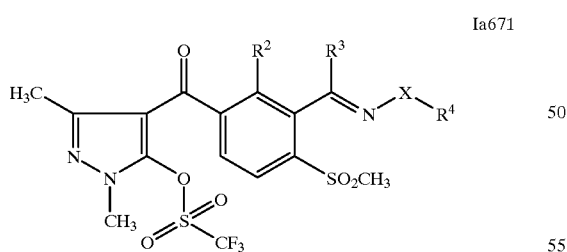

the compounds Ia672, in particular the compounds Ia672.001–Ia672.180, which differ from the corresponding compounds Ia1.001–Ia1.180 by the fact that $R^1$ is methylsulfonyl, $R^{11}$ is ethyl, $R^{12}$ is trifluoromethylsulfonyl and $R^{13}$ is methyl:

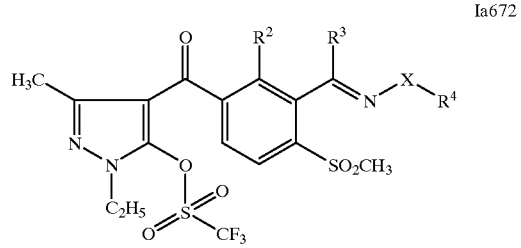

the compounds Ia673, in particular the compounds Ia673.001–Ia673.180, which differ from the corresponding compounds Ia1.001–Ia1.180 by the fact that $R^1$ is methylsulfonyl, $R^{11}$ is n-propyl, $R^{12}$ is trifluoromethylsulfonyl and $R^{13}$ is methyl:

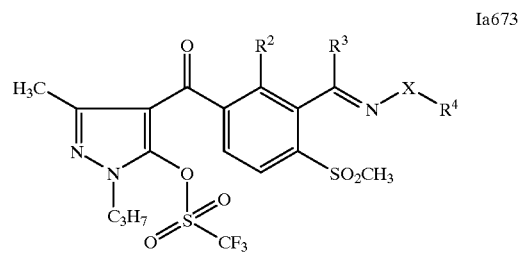

the compounds Ia674, in particular the compounds Ia674.001–Ia674.180, which differ from the corresponding compounds Ia1.001–Ia1.180 by the fact that $R^1$ is methylsulfonyl, $R^{11}$ is n-butyl, $R^{12}$ is trifluoromethylsulfonyl and $R^{13}$ is methyl:

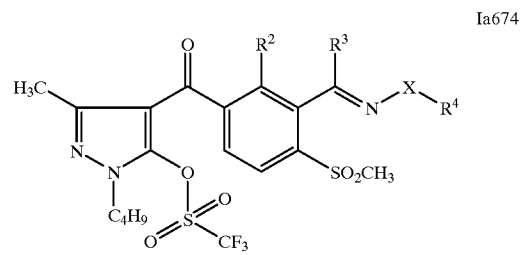

the compounds Ia675, in particular the compounds Ia675.001–Ia675.180, which differ from the corresponding compounds Ia1.001–Ia1.180 by the fact that $R^1$ is methylsulfonyl, $R^{11}$ is iso-butyl, $R^{12}$ is trifluoromethylsulfonyl and $R^{13}$ is methyl:

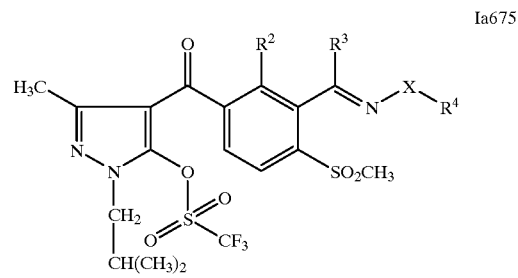

the compounds Ia676, in particular the compounds Ia676.001–Ia676.180, which differ from the corresponding compounds Ia1.001–Ia1.180 by the fact that $R^1$ is methylsulfonyl, $R^{11}$ is methyl, $R^{12}$ is phenylcarbonylmethyl and $R^{13}$ is methyl:

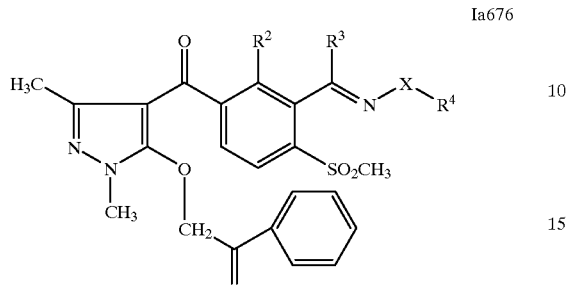

the compounds Ia677, in particular the compounds Ia677.001–Ia677.180, which differ from the corresponding compounds Ia1.001–Ia1.180 by the fact that $R^1$ is methylsulfonyl, $R^{11}$ is ethyl, $R^{12}$ is phenylcarbonylmethyl and $R^{13}$ is methyl:

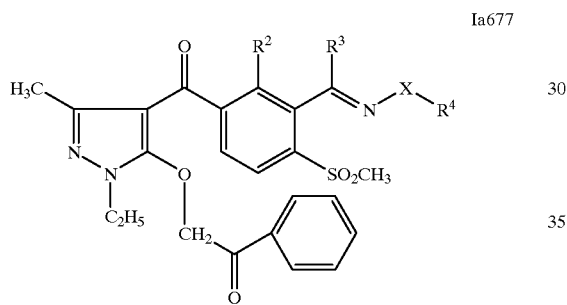

the compounds Ia678, in particular the compounds Ia678.001–Ia678.180, which differ from the corresponding compounds Ia1.001–Ia1.180 by the fact that $R^1$ is methylsulfonyl, $R^{11}$ is n-propyl, $R^{12}$ is phenylcarbonyl-methyl and $R^{13}$ is methyl:

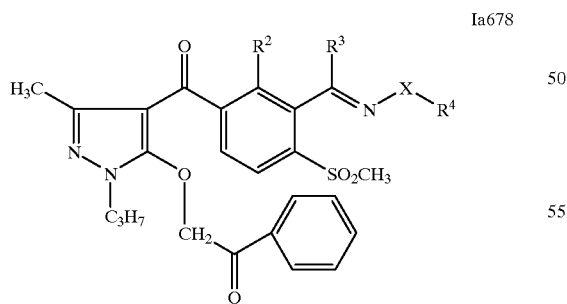

the compounds Ia679, in particular the compounds Ia679.001–Ia679.180, which differ from the corresponding compounds Ia1.001–Ia1.180 by the fact that $R^1$ is methylsulfonyl, $R^{11}$ is n-butyl, $R^{12}$ is phenylcarbonylmethyl and $R^{13}$ is methyl:

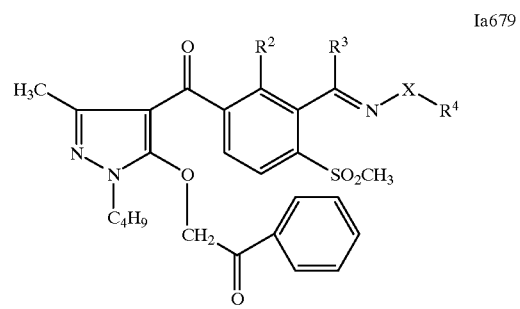

the compounds Ia680, in particular the compounds Ia680.001–Ia680.180, which differ from the corresponding compounds Ia1.001–Ia1.180 by the fact that $R^1$ is methylsulfonyl, $R^{11}$ is iso-butyl, $R^{12}$ is phenylcarbonylmethyl and $R^{13}$ is methyl:

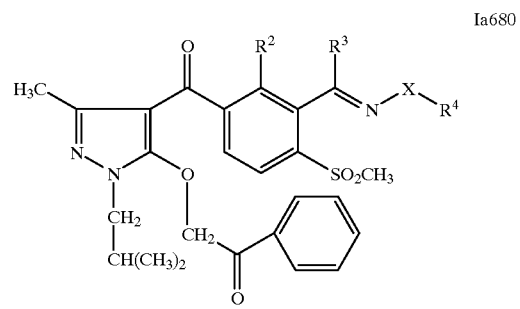

the compounds Ia681, in particular the compounds Ia681.001–Ia681.180, which differ from the corresponding compounds Ia1.001–Ia1.180 by the fact that $R^1$ is methylsulfonyl, $R^{12}$ is phenylsulfonyl and $R^{13}$ is methyl:

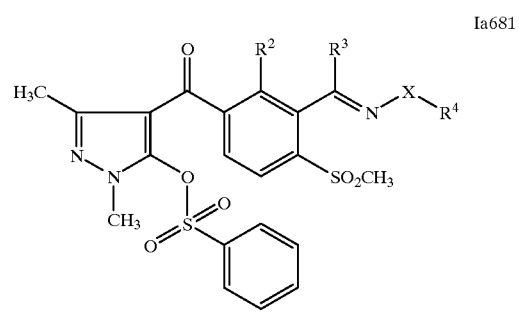

the compounds Ia682, in particular the compounds Ia682.001–Ia682.180, which differ from the corresponding compounds Ia1.001–Ia1.180 by the fact that $R^1$ is methylsulfonyl, $R^{11}$ is ethyl, $R^{12}$ is phenylsulfonyl and $R^{13}$ is methyl:

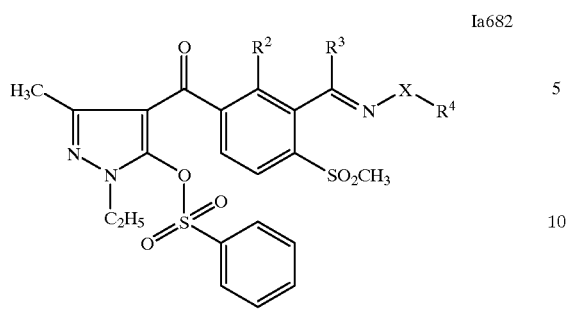

Ia682 the compounds Ia683, in particular the compounds Ia683.001–Ia683.180, which differ from the corresponding compounds Ia1.001–Ia1.180 by the fact that $R^1$ is methylsulfonyl, $R^{11}$ is n-propyl, $R^{12}$ is phenylsulfonyl and $R^{13}$ is methyl:

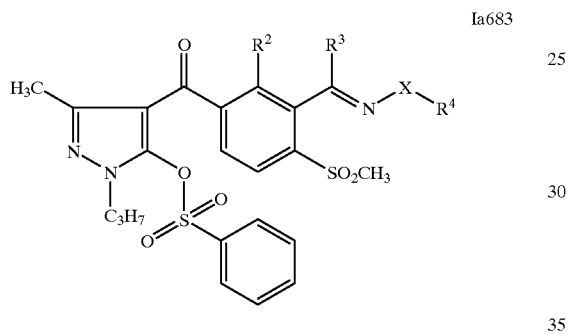

Ia683 the compounds Ia684, in particular the compounds Ia684.001–Ia684.180, which differ from the corresponding compounds Ia1.001–Ia1.180 by the fact that $R^1$ is methylsulfonyl, $R^{11}$ is n-butyl, $R^{12}$ is phenylsulfonyl and $R^{13}$ is methyl:

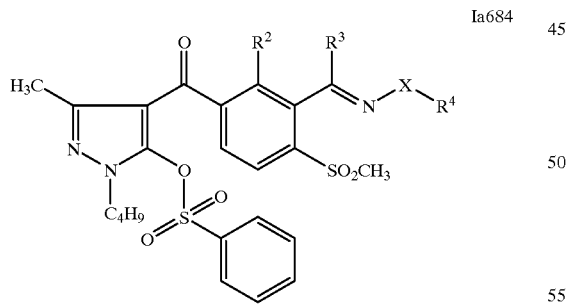

Ia684 the compounds Ia685, in particular the compounds Ia685.001–Ia685.180, which differ from the corresponding compounds Ia1.001–Ia1.180 by the fact that $R^1$ is methylsulfonyl, $R^{11}$ is iso-butyl, $R^{12}$ is phenylsulfonyl and $R^{13}$ is methyl:

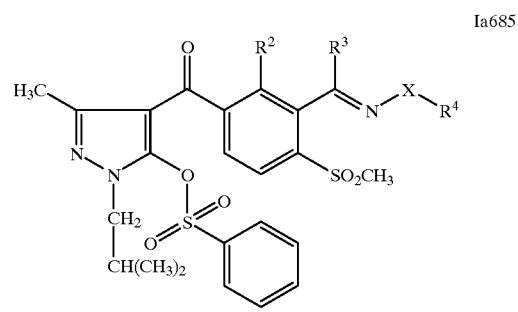

Ia685 the compounds Ia686, in particular the compounds Ia686.001–Ia686.180, which differ from the corresponding compounds Ia1.001–Ia1.180 by the fact that $R^1$ is methylsulfonyl, $R^{12}$ is 4-methylphenylsulfonyl and $R^{13}$ is methyl:

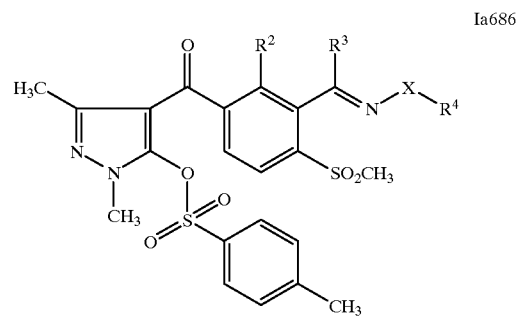

Ia686 the compounds Ia687, in particular the compounds Ia687.001–Ia687.180, which differ from the corresponding compounds Ia1.001–Ia1.180 by the fact that $R^1$ is methylsulfonyl, $R^{11}$ is ethyl, $R^{12}$ is 4-methylphenylsulfonyl and $R^{13}$ is methyl:

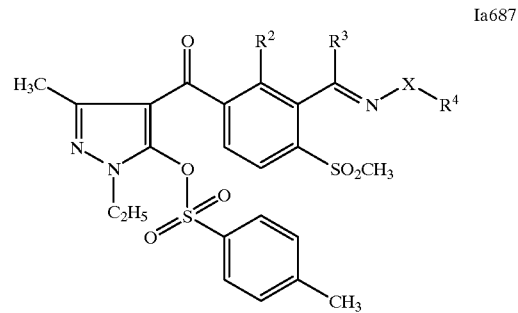

Ia687 the compounds Ia688, in particular the compounds Ia688.001–Ia688.180, which differ from the corresponding compounds Ia1.001–Ia1.180 by the fact that $R^1$ is methylsulfonyl, $R^{11}$ is n-propyl, $R^{12}$ is 4-methylphenylsulfonyl and $R^{13}$ is methyl:

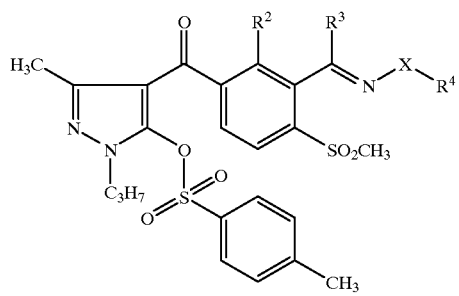

Ia688 the compounds Ia689, in particular the compounds Ia689.001–Ia689.180, which differ from the corresponding compounds Ia1.001–Ia1.180 by the fact that $R^1$ is methylsulfonyl, $R^{11}$ is n-butyl, $R^{12}$ is 4-methylphenylsulfonyl and $R^{13}$ is methyl:

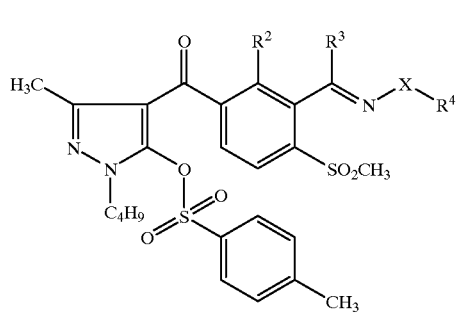

Ia689 the compounds Ia690, in particular the compounds Ia690.001–Ia690.180, which differ from the corresponding compounds Ia1.001–Ia1.180 by the fact that $R^1$ is methylsulfonyl, $R^{11}$ is iso-butyl, $R^{12}$ is 4-methylphenylsulfonyl and $R^{13}$ is methyl:

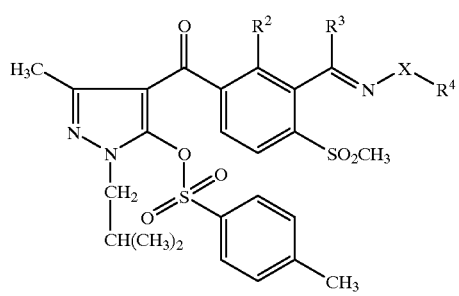

Ia690

Very particular extraordinary preference is given to the compounds of the formula Ia' (=I, where $R^1$ is bonded in position 4 of the phenyl ring and $R^2$ in position 2 of the phenyl ring)

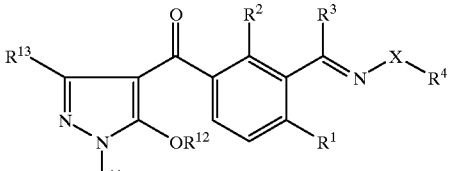

Ia' where
$R^1$ is halogen or $C_1$–$C_4$-alkylsulfonyl;
$R^2$ is halogen or $C_1$–$C_4$-alkyl, in particular halogen;
$R^3$ is hydrogen or $C_1$–$C_4$-alkyl, in particular hydrogen;
$R^4$ is $C_1$–$C_6$-alkyl, $C_3$–$C_6$-alkynyl, it being possible for these two substituents to be partially or fully halogenated and/or to contain one to three of the following groups: phenyl or hetaryl, it being possible for these, in turn, to be partially or fully halogenated;
X is oxygen;
$R^{11}$ is $C_1$–$C_6$-alkyl;
$R^{12}$ is hydrogen;
$R^{13}$ is hydrogen.

The 4-benzoylpyrazoles of the formula I can be obtained by various routes, for example by the following processes:
Process A:
Reaction of pyrazoles of the formula II where $R^{12}$=H with an activated carboxylic acid IIIα or a carboxylic acid IIIβ which is preferably activated in situ, to give the acylation product IV, followed by a rearrangement reaction.

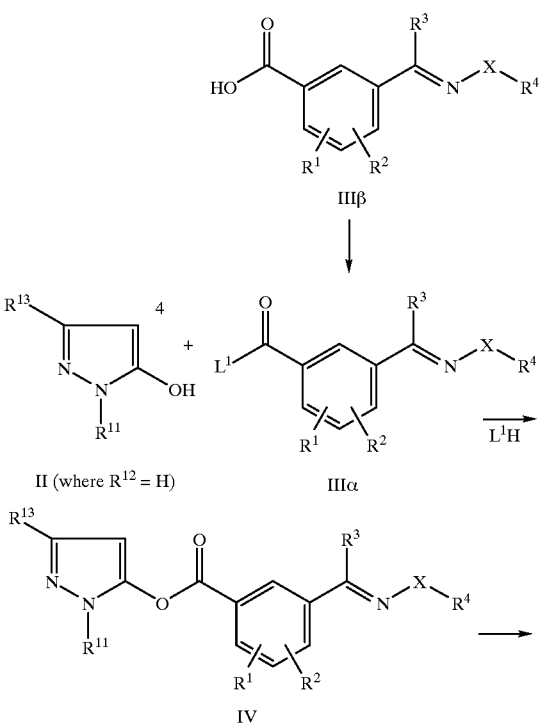

-continued

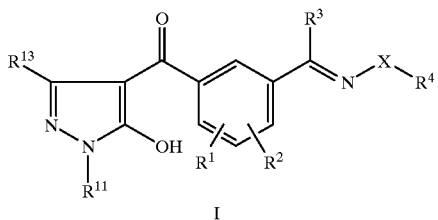

I $L^1$ is a nucleophilically displaceable leaving group, such as halogen, eg. bromine, chlorine, hetaryl, eg. imidazolyl, pyridyl, carboxylate, eg. acetate, trifluoroacetate and the like.

The activated carboxylic acid can be employed directly, as in the case of the carboxylic acid halides, or prepared in situ, eg. with dicyclocarbodiimide, triphenylphosphine/azodicarboxylic ester, 2-pyridine disulfite/triphenylphosphine, carbonyldiimidazole and the like.

If appropriate, it may be advantageous to carry out the acylation reaction in the presence of a base. The reactants and the auxiliary base are expediently employed in equimolar amounts. Under certain circumstances, a slight excess of the auxiliary base, for example 1.2 to 1.5 mol equivalents, based on II, may be advantageous.

Suitable auxiliary bases are tertiary alkylamines, pyridine or alkali metal carbonates. Examples of solvents which can be used are chlorinated hydrocarbons, such as methylene chloride, 1,2-dichloroethane, aromatic hydrocarbons such as toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide, or esters such as ethyl acetate or mixtures of these.

If carboxylic acid halides are employed as activated carboxylic acid component, it may be expedient to cool the reaction mixture to 0–10° C. when adding this reactant. The mixture is subsequently stirred at 20–100° C., preferably at 25–50° C., until the reaction is complete. Work-up is carried out in the customary manner, for example the reaction mixture is poured into water and the product of value is extracted. Solvents which are especially suitable for this purpose are methylene chloride, diethyl ether and ethyl acetate. After the organic phase has been dried and the solvent has been numbered, the ester of the formula IV is purified, preferably by chromatography. Alternatively, it is possible to employ the crude enol ester of the formula IV for the rearrangement reaction without further purification.

The rearrangement of the enol sters [sic] of the formula IV to give the compounds of the formula I is expediently carried out at from 20 to 40° C. in a solvent and in the presence of a base and, if appropriate, in the presence of a cyano compound.

Examples of solvents which can be used are acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates such as sodium carbonate, potassium carbonate, which are preferably employed in equimolar amounts or up to a four-fold excess, based on the ester. Triethylamine or alkali metal carbonates are preferably used.

Suitable cyano compounds are inorganic cyanides such as sodium cyanide, potassium cyanide and organic cyano compounds such as acetone cyanohydrin, trimethylsily [sic] cyanide. They are employed in an amount of 1 to 50 mol percent, based on the ester. Acetone cyanohydrin or trimethylsilyl cyanide are preferably employed, for example in an amount of 5 to 15, preferably 10, mol percent based on the ester.

Substances which are especially preferably employed are alkali metal carbonates such as potassium carbonate in acetonitrile or dioxane.

Work-up can be effected in a manner known per se. For example, the reaction mixture is acidified with dilute mineral acid, such as 5% strength hydrochloric acid or sulfuric acid, [lacuna] extracted with an organic solvent, eg. methylene chloride, ethyl acetate. The organic extract [sic] can be extracted with 5–10% strength alkali metal carbonate solution, eg. sodium carbonate or potassium carbonate solution. The aqueous phase is acidified, and the precipitate which forms is filtered off with suction and/or extracted with methylene chloride or ethyl acetate, dried and concentrated.

(Examples of the synthesis of esters from hydroxypyrazoles and of the rearrangement of the esters are mentioned for example in EP-A 282 944 or U.S. Pat. No. 4,643,757).

Process B:

Reaction of 4-benzoylpyrazoles of the formula I where $R^{12}$=H with a compound of the formula V (where $R^{12} \neq H$):

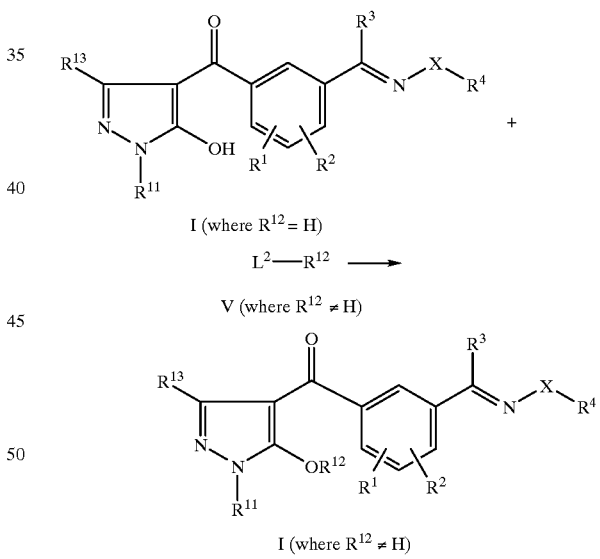

$L^2$ is a nucleophilically displaceable leaving group such as halogen, eg. bromine, chlorine, hetaryl, eg. imidazolyl, pyridyl, carboxylate, eg. acetate, trifluoroacetate, sulfonate, eg. mesylate, triflate and the like.

The compounds of the formula V can be employed directly, for example in the case of the alkyl halides, carboxylic acid halides, sulfonyl halides, carboxylic anhydrides and sulfonic anhydrides, or prepared in situ, for example activated carboxylic acids (by means of carboxylic acid and dicyclohexylcarbodiimide, carbonyldiimidazole and the like).

As a rule, the starting compounds are employed in an equimolar ratio. However, it may also be advantageous to employ one or the other component in an excess.

Where appropriate, it may be advantageous to carry out the reaction in the presence of a base. The reactants and the auxiliary base are expediently employed in equimolar amounts in this case. Under certain circumstances, an excess of the auxiliary base, for example 1.5 to 3 mol equivalents, based on II, may be advantageous.

Suitable auxiliary bases are tertiary alkylamines such as triethylamine, pyridine, alkali metal carbonates, eg. sodium carbonate, potassium carbonate and alkali metal hydrides, eg. sodium hydride. Substances which are preferably used are triethylamine, pyridine and potassium carbonate.

Examples of suitable solvents are chlorinated hydrocarbons such as methylene chloride, 1,2-dichloroethane, aromatic hydrocarbons, eg. toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide or esters such as ethyl acetate, or mixtures of these.

As a rule, the reaction temperature is in the range of from 0° C. to the boiling point of the reaction mixture.

Work-up can be effected in a manner known per se to give the product.

The pyrazoles of the formula II (where $R^{12}$=H), which are used as starting materials, which have not already been disclosed can be prepared by methods known per se (for example EP-A 240 001, J. Prakt. Chem. 315 (1973), 383).

The benzoic acid derivatives of the formula III are novel,

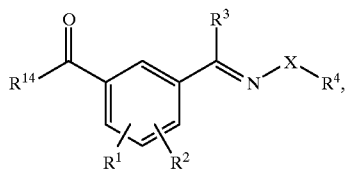

III the variables having the following meanings:

$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;

$R^3$ is hydrogen, cyano, $C_1$–$C_6$-alkyl, $C_1$–$C_6$-haloalkyl, —$OR^7$, —$SR^7$ or —$NR^7R^{10}$;

$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, it being possible for the eight last-mentioned radicals, in turn, to be unsubstituted or substituted;

X is oxygen or $NR^8$;

n is 0, 1 or 2;

$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^6$ is $C_1$–$C_6$-alkyl or $C_1$–$C_6$-haloalkyl;

$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^8$ is hydrogen or $C_1$–$C_6$-alkyl;

$R^9$ is $C_1$–$C_6$-alkyl, $C_3$–$C_6$-alkenyl, $C_3$–$C_6$-alkynyl, phenyl or benzyl;

$R^{10}$ is $C_1$–$C_6$-alkyl, $C_1$–$C_6$-haloalkyl, $C_3$–$C_6$-alkenyl or $C_3$–$C_6$-alkynyl;

$R^{14}$ is hydroxyl or a radical which can be removed by hydrolysis.

Examples of radicals which can be removed by hydrolysis are alkoxy, phenoxy, alkylthio and phenylthio radicals which can be substituted, halides, hetaryl radicals which are bonded via nitrogen, amino and imino radicals which can be substituted, and the like.

Preferred are benzoic acid halides IIIα where L=halogen (=III where $R^{14}$=halogen),

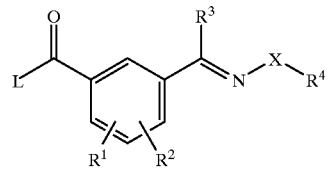

IIIα where the variables $R^1$ to $R^4$ and X have the meanings given under formula III and L is halogen, in particular chlorine or bromine.

Equally preferred are benzoic acids of the formula IIIβ (=III where $R^{14}$=hydroxyl),

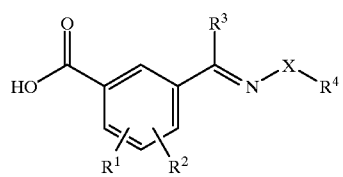

IIIβ where the variables $R^1$ to $R^4$ and X have the meanings given under formula III.

Equally preferred are benzoic esters of the formula IIIγ (=III where $R^{14}$=$C_1$–$C_6$-alkoxy),

IIIγ

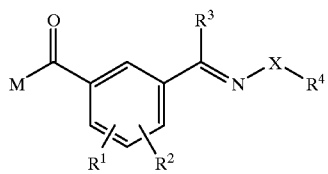

where the variables $R^1$ to $R^4$ and X have the meanings mentioned under formula III and M is $C_1$–$C_6$-alkoxy.

With regard to the preferred compounds of the formula III, the statements made under the compounds of the formula I apply to the radicals $R^1$ to $R^4$ and X.

The compounds of the formula IIIα (where $L^1$=halogen) can be synthesized by a method similar to those known from the literature (cf. L. G. Fieser, M. Fieser "Reagents for Organic Synthesis" (1967), Vol. I, pp. 767–769) by reacting benzoic acids of the formula IIIβ with halogenating agents such as thionyl chloride, thionyl bromide, phosgene, diphosgene, triphosgene, oxalyl chloride and oxalyl bromide.

The benzoic acids of the formula IIIβ can be obtained, inter alia, by hydrolyzing the benzoic esters of the formula IIIγ (where M=$C_1$–$C_6$-alkoxy).

The benzoic esters of the formula IIIγ can be obtained by various routes, for example by one of the following processes:

A)

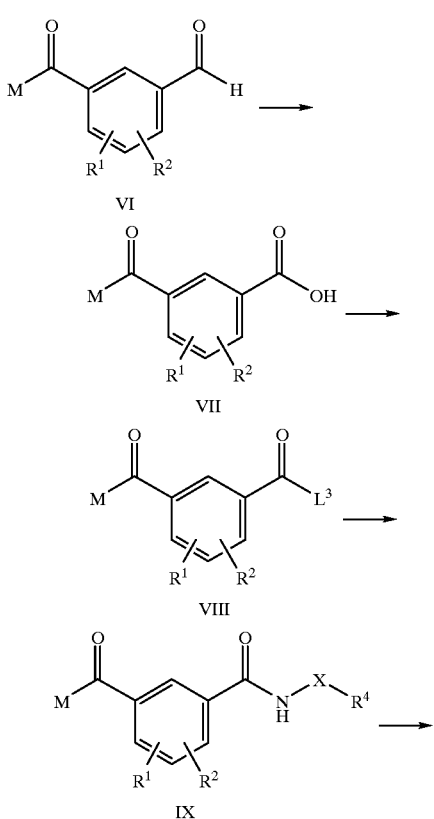

-continued

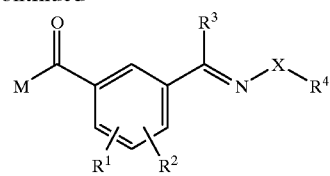

IIIγ   (where $R^3$ = $OR^7$)

Isophthalic acid derivatives of the formula VII can be obtained by oxidizing aldehydes of the formula VI in a manner known per se (J. March, "Advanced Organic Chemistry", 1985, 3rd Edition, p. 629 et seq., Wiley-Interscience Publication).

The compounds of the formula VII can first be converted into the corresponding activated carboxylic acids VIII in which $L^3$ is a nucleophilically displaceable leaving group such as halogen, eg. bromine, chlorine, hetaroyl, eg. imidazolyl, pyridyl, carboxylate, eg. acetate, trifluoroacetate and the like, by methods similar to those known from the literature, and the products can subsequently be converted into the corresponding hydroxamic acid or carbohydrazide derivatives of the formula IX (Australian J. Chem. (1969), 22, 1731–1735; ibid (1969), 22, 161–173; J. Org. Chem. (1974), 27, 1341–1349).

Alkylation of compounds of the formula IX leads to compounds of the formula IIIγ (where $R^3$=$OR^7$) in a manner known per se (EP-A 463 989; Synthesis (1983), 220–222; U.S. Pat. No. 4,931,088; J. Org. Chem. (1971), 31, 284–294; J. Chem. Soc. Perk. II (1977), 1080–1084).

B)

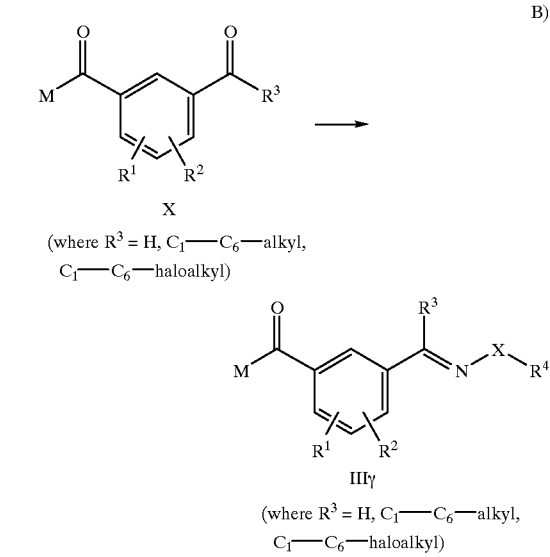

Compounds of the formula IIIγ are obtained in a manner known per se by reacting aldehydes/ketones of the formula X with "alkoxamines or alkylhydrazines". By processes similar to those known from the literature, it is possible to react aldehydes/ketones of the formula X with hydroxylamine, or hydrazine, respectively, and subsequently to alkylate the product (J. March, "Advanced Organic Chemistry", 1985, 3rd Edition, p. 359, pp. 805–806, Wiley-Interscience Publication).

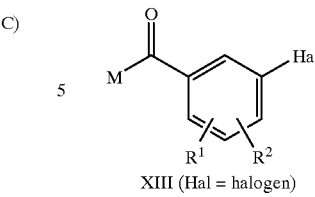

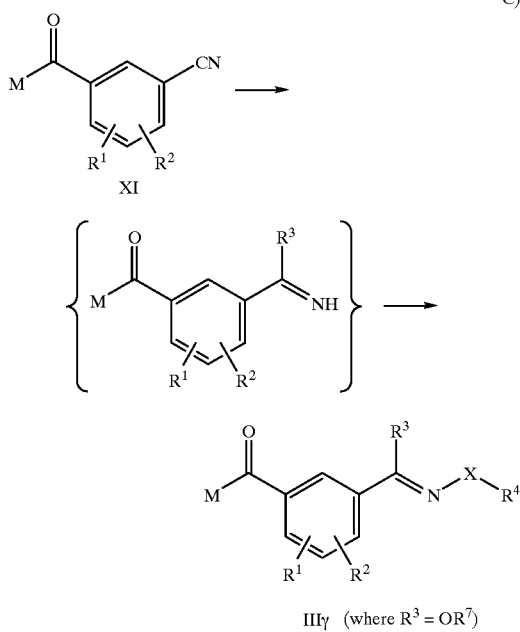

IIIγ (where R³ = OR⁷)

Nitriles of the formula XI can be converted into imino esters by alcoholysis (R⁷OH) in a manner known per se, and these imino esters can be converted in a further step with hydroxylamines or hydrazines to give compounds of the formula IIIγ (J. March, "Advanced Organic Chemistry", 1985, 3rd Edition, pp. 792–793, Wiley-Interscience Publication; U.S. Pat. No. 4,965,390).

The nitriles of the formula XI can be synthesized by methods similar to those known from the literature starting from the corresponding aldehydes VI (J. March, "Advanced Organic Chemistry", 1985, 3rd Edition, pp. 806–807, Wiley-Interscience Publication). Equally, it is possible to obtain nitriles of the formula XI from anilines of the formula XII by means of Sandmeyer reaction or from aryl halides of the formula XIII by Rosemund/von Braun reaction with metal cyanides, in particular CuCN (J. March, "Advanced Organic Chemistry", 1985, 3rd Edition, p. 594, p. 648, Wiley-Interscience Publication).

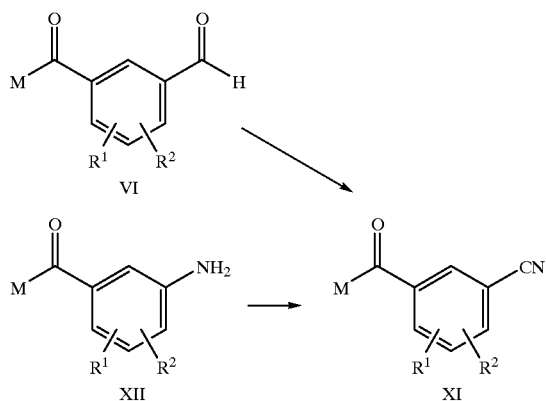

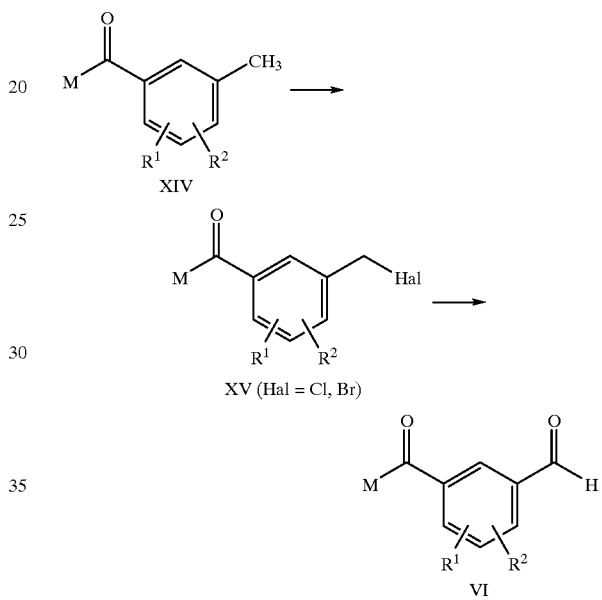

The aldehydes of the formula VI can be synthesized from corresponding toluenes of the formula XIV by processes similar to those known from the literature, by converting them into the ω-halotoluene XV and subsequently oxidizing the product (cf. Synth. Commun. 22 (1992), 1967–1971).

PREPARATION EXAMPLES 4-(2,4-Dichloro-3-ethoxyiminomethylbenzoyl)-2-ethyl-3-hyroxy-pyrazole [sic] (Compound 2.03)

A solution of 1.50 g (0.006 mol) of 2,4-dichloro-3-ethoxyimino-methylbenzoic acid, 0.61 g (0.006 mol) of 2-ethyl-3-hydroxypyrazole and 1.13 g (0.006 mol) of dicyclohexylcarbodiimide in 50 ml of dry acetonitrile was stirred for 12 hours at room temperature. The precipitate was subsequently filtered off with suction and the filtrate was taken up in water. This aqueous solution was extracted with ethyl acetate. The combined organic phases were dried and concentrated in vacuo. The residue was taken up in 50 ml of dry acetonitrile, treated with 1.20 g (0.0087 mol) of finely pulverulent calcium carbonate and refluxed for 3.5 hours. After cooling, the solvent was removed in vacuo and the residue was taken up in water. The aqueous phase was brought to pH 1–2 using 10% strength hydrochloric acid solution and extracted with ethyl acetate. The combined organic phases were subsequently washed to neutrality with water and dried, and the solvent was distilled off in vacuo. This gave 0.70 g of 4-(2,4-dichloro-3-ethoxyimino-methylbenzoyl)-2-ethyl-3-hydroxypyrazole, which was purified by precipitating with n-hexane from ethyl acetate. (M.p.: 97–98° C.)

Table 2 below lists not only the above-described benzoyl derivatives of the formula I but also others which were, or can be, prepared in a similar manner.

TABLE 2

Ia (where $R^{13}$ = H)

| No. | X | $R^1$ | $R^2$ | $R^3$ | $R^4$ | $R^{11}$ | $R^{12}$ | Physical data M.p. [° C.]; $^1$H NMR [δ in ppm] |
|---|---|---|---|---|---|---|---|---|
| 2.01 | O | $SO_2CH_3$ | Cl | H | $C_2H_5$ | $C_2H_5$ | H | 161–163 |
| 2.02 | O | Cl | Cl | H | $CH_2C\equiv CH$ | $C_2H_5$ | H | 1.45(t, 3H); 2.53 (s, 1H); 4.05(q, 2H); 4.86(s, 2H); 7.39 (s, 1H); 7.42(d, 1H); 7.52(d, 1H); 8.32 (s, 1H); 8.59(brs, 1H) |
| 2.03 | O | Cl | Cl | H | $C_2H_5$ | $C_2H_5$ | H | 97–98 |
| 2.04 | O | Cl | Cl | H | $CH_3$ | $C_2H_5$ | H | 108–109 |
| 2.05 | O | Cl | Cl | H | $CH_3$ | n-$C_3H_7$ | H | 168–170 |
| 2.06 | O | Cl | Cl | H | $CH_3$ | n-$C_4H_9$ | H | 171–176 |
| 2.07 | O | $SO_2CH_3$ | Cl | H | $CH_3$ | $CH_3$ | H | 190–195 |
| 2.08 | O | $SO_2CH_3$ | Cl | H | $C_2H_5$ | $CH_3$ | H | 140–145 |
| 2.09 | O | $SO_2CH_3$ | Cl | H | $CH_2C_6H_5$ | $CH_3$ | H | 130–135 |
| 2.10 | O | $SO_2CH_3$ | Cl | H | $CH_2C_6H_5$ | $C_2H_5$ | H | 50–55 |
| 2.11 | O | $SO_2CH_3$ | Cl | H | $CH_2$-3-thienyl | $C_2H_5$ | H | 75–80 |
| 2.12 | O | $SO_2CH_3$ | Cl | H | $CH_2$-3-thienyl | $CH_3$ | H | 140–145 |
| 2.13 | O | $SO_2CH_3$ | Cl | $CH_3$ | $CH_3$ | $CH_3$ | H | |
| 2.14 | O | $SO_2CH_3$ | Cl | $CH_3$ | $CH_3$ | $C_2H_5$ | H | |
| 2.15 | O | $SO_2CH_3$ | $CH_3$ | $CH_3$ | $CH_3$ | $CH_3$ | H | |
| 2.16 | O | $SO_2CH_3$ | $CH_3$ | $CH_3$ | $CH_3$ | $C_2H_5$ | H | Oil |

The syntheses of some starting materials are given hereinbelow:

2-Chloro-3-ethoxyiminomethyl-4-methylsulfonylbenzoic acid (Compound 3.04)

Step a) 2-Chloro-3-methyl-4-methylthioacetophenone

A solution of 157 g (2 mol) of acetyl chloride in 420 ml of 1,2-dichloroethane was added dropwise to a suspension of 286 g (2.14 mol) of aluminum trichloride in 420 ml of 1,2-dichloroethane at 15–20° C. A solution of 346 g (2 mol) of 2-chloro-6-methylthiotoluene in 1 l of 1,2-dichloroethane was subsequently added dropwise. After the reaction mixture had been stirred for 12 hours, it was poured into a mixture of 3 l of ice and 1 l of concentrated HCl. It was extracted with methylene chloride, and the organic phase was washed with water, dried with sodium sulfate and concentrated. The residue was distilled in vacuo. This gave 256 g (60% of theory) of 2-chloro-3-methyl-4-methylthioacetophenone.

(M.p.: 46° C.)

Step b) 2-Chloro-3-methyl-4-methylsulfonylacetophenone 163.0 g (0.76 mol) of 2-chloro-3-methyl-4-methylthioacetophenone were dissolved in 1.5 l of glacial acetic acid, 18.6 g of sodium tungstate were added, and 173.3 g of 30% strength hydrogen peroxide solution were added dropwise with cooling. Stirring was continued for 2 days and the mixture was subsequently diluted with water. The solid which had precipitated was filtered off with suction, washed with water and dried. This gave 164.0 g (88% of theory) of 2-chloro-3-methyl-4-methylsulfonylacetophenone.

(M.p.: 110–111° C.)

Step c) 2-Chloro-3-methyl-4-methylsulfonylbenzoic acid 82 g (0.33 mol) of 2-chloro-3-methyl-4-methylsulfonylacetophenone were dissolved in 700 ml of dioxane, and 1 l of a 12.5% strength sodium hypochlorite solution was added at room temperature. Stirring was subsequently continued for 1 hour at 80° C. After cooling, two phases formed, of which the bottom phase was diluted with water and slightly acidified. The solid which had precipitated was washed with water and dried. This gave 60 g (73% of theory) of 2-chloro-3-methyl-4-methylsulfonylbenzoic acid.

(M.p.: 230–231° C.)

Step d) Methyl 2-chloro-3-methyl-4-methylsulfonylbenzoate 100 g (0.4 mol) of 2-chloro-3-methyl-4-methylsulfonylbenzoic acid were dissolved in 1 l of methanol, and gaseous hydrogen chloride was passed in for 5 hours at reflux temperature. The mixture was subsequently concentrated. This gave 88.5 g (84% of theory) of methyl 2-chloro-3-methyl-4-methylsulfonylbenzoate.

(M.p.: 107–108° C.)

Step e) Methyl 3-bromomethyl-2-chloro-4-methylsulfonylbenzoate 82 g (0.31 mol) of methyl 2-chloro-3-methyl-4-methylsulfonylbenzoate are [sic] dissolved in 2 l of tetrachloromethane, and 56 g (0.31 mol) of N-bromosuccinimide were added, a little at a time, with exposure to light. The reaction mixture was filtered, the filtrate was concentrated, and the residue was taken up in 200 ml of methyl tert-butyl ether. The solution was treated with petroleum ether, and the solid which had precipitated was filtered off with suction and dried. This gave 74.5 g (70% of theory) of methyl 3-bromomethyl-2-chloro-4-methylsulfonylbenzoate.

(M.p.: 74–75° C.)

Step f) Methyl 2-chloro-3-formyl-4-methylsulfonylbenzoate

A solution of 41.0 g (0.12 mol) of methyl 3-bromomethyl-2-chloro-4-methylsulfonylbenzoate in 250 ml of acetonitrile was treated with 42.1 g (0.36 mol) of N-methylmorpholine N-oxide. The batch was stirred for 12 hours at room temperature and subsequently concentrated, and the residue was taken up in ethyl acetate. The solution was extracted with water, dried with sodium sulfate and concentrated. This gave 31.2 g (94% of theory) of methyl 2-chloro-3-formyl-4-methylsulfonylbenzoate (M.p.: 98–105° C.)

Step g) 2-Chloro-3-formyl-4-methylsulfonylbenzoic acid

A solution of 5.00 g of methyl 2-chloro-3-formyl-4-methylsulfonylbenzoate was slowly added dropwise to a solution of 9.60 g (0.072 mol) of lithium iodide and 70 ml of dry pyridine at reflux temperature. After the reaction mixture had been stirred for 2 hours under reflux it was cooled, and the solvent was removed in vacuo. The residue was subsequently taken up in water and brought to pH 1–2 using dilute hydrochloric acid. After the aqueous phase had been extracted with ethyl acetate, the combined organic phases were washed to neutrality with water, dried and concentrated. This gave 4.00 g of 2-chloro-3-formyl-4-methylsulfonylbenzoic acid (85% yield).

($^1$H NMR (d$^6$-DMSO, δ in ppm): 3.41 (s, 3H); 8.05 (d, 1H); 8.11 (d, 1H); 10.49 (s, 1H); 14.21 (s, br., 1H).)

Step h) 2-Chloro-3-ethoxyiminomethyl-4-methylsulfonylbenzoic acid 1.63 g (0.017 mol) of ethoxyamine hydrochloride and 1.15 g (0.0085 mol) of finely pulverulent potassium carbonate were stirred for 1 hour in 60 ml of dry methanol. 4.00 g (0.015 mol) of 2-chloro-3-formyl-4-methylsulfonylbenzoic acid in 40 ml of methanol were subsequently added. After the mixture was stirred for 12 hours at room temperature, the solvent was removed, the residue was taken up in ethyl acetate, and the organic phase was washed four times with water. After the mixture had been dried and the solvent distilled off, 3.60 g of 2-chloro-3-ethoxyiminomethyl-4-methylsulfonylbenzoic acid were obtained (78% yield).

(M.p.: 155–160° C.)

Alternative

Step g') Methyl 2-chloro-3-ethoxyiminomethyl-4-methylsulfonylbenzoate (Compound 3.01)

1.90 g (0.0195 mol) of ethoxyamine hydrochloride and 1.35 g (0.0097 mol) of finely pulverulent potassium carbonate were stirred for 1 hour at room temperature in 60 ml of dry methanol, and 4.90 g (0.0177 mol) of methyl 2-chloro-3-formyl-4-methylsulfonylbenzoate were subsequently added. After the mixture had been stirred for 8 hours at room temperature, the solvent was removed, the residue was taken up in ethyl acetate, and the organic phase was washed to neutrality with water, dried and concentrated in vacuo. This gave 5.00 g of methyl 2-chloro-3-ethoxyiminomethyl-4-methylsulfonylbenzoate. (Yield 88%).

($^1$H NMR (CDC$_3$, δ in ppm): 1.34 (t, 3H); 3.29 (s, 3H); 3.98 (s, 3H); 4.26 (q, 2H); 7.91 (d, 1H); 8.10 (d, 1H); 8.38 (s, 1H).)

Step h') 2-Chloro-3-ethoxyiminomethyl-4-methylsulfonylbenzoic acid

A solution of 4.37 g (0.0137 mol) of methyl 2-chloro-3-ethoxyiminomethyl-4-methylsulfonylbenzoate was slowly added dropwise to 7.29 g (0.055 mol) of lithium iodide in 50 ml of dry pyridine. After the mixture had been stirred for 2 hours under reflux, it was cooled, and the solvent was removed in vacuo. The residue was taken up in water and the mixture was brought to pH 1–2 with dilute hydrochloric acid. After the aqueous phase had been extracted with ethyl acetate, the combined organic phases were washed with water, dried and concentrated in vacuo. This gave 3.70 g of 2-chloro-3-ethoxyiminomethyl-4-methylsulfonylbenzoic acid. (Yield 89%).

(M.p.: 155–160° C.)

Methyl 2-chloro-3-chlorocarbonyl-4-methylsulfonylbenzoate

Step a) Methyl 2-chloro-3-hydroxycarbonyl-4-methylsulfonylbenzoate 13.8 g (0.11 mol) of sodium hydrogen phosphate monohydrate in 170 ml of water, 49.3 g (0.43 mol) of 30% strength hydrogen peroxide solution and 66.2 g (0.59 mol) of 80% strength aqueous sodium chlorite solution were added in succession at 5° C. to a solution of 115.3 g (0.42 mol) of methyl 2-chloro-3-formyl-4-methylsulfonylbenzoate and 2000 ml of acetonitrile. The reaction solution was subsequently stirred for 1 hour at 5° C. and for 12 hours at room temperature. The pH was then brought to 1 using 10% strength hydrochloric acid, and 1500 ml of aqueous 40% strength sodium hydrogen sulfite solution were added. After the mixture had been stirred for 1 hour at room temperature, the aqueous phase was extracted three times with ethyl acetate. The combined organic phases were washed with sodium hydrogen sulfite solution and dried. After the solvent had been distilled off, 102.0 g of methyl 2-chloro-3-hydroxycarbonyl-4-methylsulfonylbenzoate were obtained.

($^1$H NMR (d$^6$-DMSO, δ in ppm): 3.34 (s, 3H); 3.93 (s, 3H); 8.08 (s, 2H); 14.50 (s, br., 1H).)

Step b) Methyl 2-chloro-3-chlorocarbonyl-4-methylsulfonylbenzoate

Two drops of dimethylformamide and 11.9 g (0.1 mol) of thionyl chloride were added to a solution of 6.0 g (0.021 mol) of methyl 2-chloro-3-hydroxycarbonyl-4-methylsulfonylbenzoate and 50 ml of dry toluene. The solution was refluxed for 4 hours. After the solvent had been removed in vacuo, 6.2 g of methyl 2-chloro-3-chlorocarbonyl-4-methylsulfonylbenzoate were obtained.

(¹H NMR (CDCl₃; δ in ppm): 3.21 (s, 3H); 4.02 (s, 3H); 8.02 (d, 1H); 8.07 (d, 1H).)

2,4-Dichloro-3-(1'-methoxyimino-1'-(methoxy)methyl)benzoyl chloride (Compound 3.14)

Step a) 2,4-Dichloro-3-methylacetophenone 235.0 g (3.0 mol) of acetyl chloride were added dropwise with stirring at 100° C. in the course of 2 hours to a solution of 502.0 g (3.12 mol) of 2,6-dichlorotoluene and 408.0 g (3.06 mol) of aluminum trichloride. After the mixture had been stirred for 2 hours at 100–105° C. it was cooled, and the reaction mixture was poured onto 3 l of ice and 1 l of water. The solid which had precipitated during this process was filtered off with suction and washed to neutrality with 800 ml of water. After drying at 40° C., 500.0 g of 2,4-dichloro-3-methylacetophenone were obtained as crude product, which were subsequently distilled under a high vacuum.

(Boiling point: 121–128° C. (4 mbar))

Step b) 2,4-Dichloro-3-methyl-benzoic acid

First, 655.2 g (4.1 mol) of bromine and subsequently 203.0 g (1.0 mol) of 2,4-dichloro-3-methylacetophenone in 1300 ml of 1,4-dioxane were added dropwise to a solution of 520.0 g (13 mol) of sodium hydroxide in 2600 ml of water at 0–10° C. After the mixture had been stirred for 12 hours, the organic phase was separated off, the aqueous phase was treated with a 30% strength solution prepared with sodium pyrosulfite and water, and the mixture was brought to a pH of 1 with hydrochloric acid. The precipitate which had separated out was filtered off with suction, washed with water and dried at 60° C. in vacuo. This gave 197.0 g of 2,4-dichloro-3-methylbenzoic acid.

(M.p.: 173–175° C.)

Step c) Methyl 2,4-dichloro-3-methylbenzoate 60 ml of concentrated sulfuric acid were added dropwise to a solution of 424.0 g (2 mol) of 2,4-dichloro-3-methylbenzoic acid and 1500 ml of methanol. After the reaction mixture had been refluxed for 5 hours, it was cooled and concentrated in vacuo, and the residue was subsequently taken up in 1000 ml of methylene chloride. The organic phase was washed with water, subsequently with 5% strength sodium hydrogen carbonate solution and then again with water, dried and concentrated in vacuo. This gave 401.0 g of methyl 2,4-dichloro-3-methylbenzoate.

(Boiling point: 103–107° C. (1–1.5 mbar))

Step d) Methyl 3-bromomethyl-2,4-dichlorobenzoate 1.0 g of azobisisobutyronitrile was added to a solution of 84.0 g (0.38 mol) of methyl 2,4-dichloro-3-methylbenzoate and 67.6 g (0.38 mol) of N-bromosuccinimide in 380 ml of carbon tetrachloride. After the reaction mixture had been refluxed for 3.5 hours, it was cooled, and the precipitate which had formed was filtered off with suction. The filtrate was concentrated in vacuo and the resulting residue was extracted by stirring with methyl tert-butyl ether. This gave 108.0 g of methyl 3-bromomethyl-2,4-dichlorobenzoate.

(M.p.: 51–54° C.)

Step e) Methyl 2,4-dichloro-3-formylbenzoate 696.2 g (2.97 mol) of aqueous 50% strength N-methylmorpholine N-oxide solution were added dropwise under reflux to a solution of 312.0 g (0.99 mol) of methyl 3-bromomethyl-2,4-dichlorobenzoate in 2 l of acetonitrile. After the reaction solution had been stirred for 48 hours at room temperature, it was stirred into 6 l of water. The precipitate which had separated out was filtered off with suction, washed with water and dried in vacuo. This gave 141.3 g of methyl 2,4-dichloro-3-formylbenzoate.

(¹H NMR (CDCl₃, δ in ppm): 3.98 (s, 3H); 7.47 (d, 1H); 7.84 (d, 1H); 10.48 (s, 1H).)

Step f) Methyl 2,4-dichloro-3-hydroxycarbonylbenzoate 5.9 g (0.043 mol) of sodium dihydrogen phosphate monohydrate in 70 ml of water, 20.5 g (0.181 mol) of 30% strength hydrogen peroxide solution and 27.3 g (0.241 mol) of 80% strength sodium chlorite solution were added in succession to a solution of 40.0 g (0.172 mol) of methyl 2,4-dichloro-3-formylbenzoate and 500 ml of acetonitrile. The reaction solution was stirred for 1 hour at 5° C. and for 12 hours at room temperature. It was subsequently brought to pH 1 with 10% strength hydrochloric acid, and 500 ml of 40% strength sodium hydrogen sulfite solution were added. After the mixture had been stirred for 1 hour at room temperature, the aqueous phase was extracted three times with ethyl acetate, and the combined organic phases were washed with 1.0 l of 10% strength sodium hydrogen sulfite solution and subsequently dried. After the solvent had been distilled off, 40.0 g of methyl 2,4-dichloro-3-hydroxycarbonylbenzoate were obtained.

(¹H NMR (d⁶-DMSO, δ in ppm): 3.90 (s, 3H); 7.69 (d, 1H); 7.89 (d, 1H).)

Step g) Methyl 3-chlorocarbonyl-2,4-dichlorobenzoate

Two drops of dimethylformamide and 11.90 g (0.1 mol) of thionyl chloride were added to a solution of 5.00 g (0.02 mol) of methyl 2,4-dichloro-3-hydroxycarbonylbenzoate and 50 ml of dry toluene. The solution was refluxed for 4 hours. After the solvent had been distilled off, 5.35 g of methyl 3-chlorocarbonyl-2,4-dichlorobenzoate were obtained.

Step h) Methyl 2,4-dichloro-3-methoxyaminocarbonylbenzoate 4.60 g (0.045 mol) of triethylamine and 3.75 g (0.045 mol) of methoxyamine hydrochloride were added to a solution of 5.35 g (0.02 mol) of methyl 3-chlorocarbonyl-2,4-dichlorobenzoate and 100 ml of dichloromethane. After the reaction solution had been stirred for 12 hours at room temperature, it was washed with dilute phosphoric acid, dried and concentrated. The residue obtained was extracted by stirring with diethyl ether. This gave 4.80 g of methyl 2,4-dichloro-3-methoxyaminocarbonylbenzoate.

(M.p.: 162–164° C.)

Step i) Methyl 2,4-dichloro-3-(1'-methoxyimino-1'-(methoxy)methyl)benzoate (Compound 3.09)

A mixture of 16.0 g (0.058 mol) of methyl 2,4-dichloro-3-methoxyaminocarbonylbenzoate and 10.1 g (0.073 mol) of potassium carbonate in 300 ml of dimethylformamide was stirred for 30 minutes at room temperature. 11.0 g (0.087 mol) of dimethyl sulfate were subsequently added dropwise, the mixture was stirred for 12 hours at room temperature, and another 11.0 g of dimethyl sulfate were added. After the mixture had been heated for 6 hours at 60° C., it was cooled and stirred into 2 l of ice-water. Then, the aqueous phase was extracted with ethyl acetate, the combined organic phases were dried and the solvent was distilled off in vacuo. After chromatography of the residue on silica gel (eluant:toluene/ethyl acetate=9/1), 2.0 g of methyl 2,4-dichloro-3-(1'-methoxyimino-1'-(methoxy)methyl)benzoate were obtained.

(¹H NMR (CDCl₃, δ in ppm): 3.43 (s, 3H); 3.58 (s, 3H); 3.92 (s, 3H); 7.35 (d, 1H); 7.82 (d, 1H).)

Step j) 2,4-Dichloro-3-(1'-methoxyimino-1'-(methoxy)methyl)benzoic acid (Compound 3.10)

A solution of 2.20 g (0.008 mol) of methyl 2,4-dichloro-3-(1'-methoxyimino-1'-(methoxy)methyl)benzoate and 3.00 g (0.075 mol) of sodium hydroxide in 50 ml of water was stirred for 2 hours at 80° C. After the reaction mixture had cooled, it was stirred into 200 ml of ice-water and the pH was brought to 1 using concentrated hydrochloric acid. The aqueous phase was extracted with ethyl acetate, and the combined organic phases were dried and concentrated in vacuo. This gave 2.10 g of 2,4-dichloro-3-(1'-methoxyimino-1'-(methoxy)methyl)benzoic acid.

¹H NMR (d⁶-DMSO, δ in ppm): 3.53 (s, 3H); 3.72 (s, 3H); 7.74 (d, 1H); 7.95 (d, 1H).)

Step k) 2,4-Dichloro-3-(1'-methoxyimino-1'-(methoxy)methyl)benzoyl chloride (Compound 3.14)

A solution of 2.10 g (0.0076 mol) of 2,4-dichloro-3-(1'-(methoxy)imino-1'-methoxymethyl)benzoic acid and 20.00 g of thionyl chloride in 50 ml of dry toluene was stirred for 2 hours at 80° C. After the solvent had been removed in vacuo, 2.25 g of 2,4-dichloro-3-(1'-methoxyimino-1'-(methoxy)methyl)benzoyl chloride were obtained.

Methyl 2,4-dichloro-3-propoxyaminocarbonylbenzoate 10.7 g (0.04 mol) of methyl 3-chlorocarbonyl-2,4-dichlorobenzoate in 100 ml of methylene chloride were slowly added dropwise at 30° C. to a solution of 4.50 g ((0.04 mol) of propoxyamine hydrochloride and 4.05 g (0.04 mol) of triethylamine in 200 ml of methylene chloride. After the reaction mixture had been stirred for 2 hours at room temperature, it was washed with dilute phosphoric acid, dried and concentrated. The residue obtained was chromatographed on silica gel (eluant:toluene/ethyl acetate=9/1). This gave 11.50 g of methyl 2,4-dichloro-3-propoxyaminocarbonylbenzoate.

(M.p.: 80–81° C.)

Methyl 3-(4-chlorobenzyloxyaminocarbonyl)-2,4-dichlorobenzoate 10.70 g (0.04 mol) of methyl 3-chlorocarbonyl-2,4-dichlorobenzoate in 50 ml of methylene chloride were slowly added dropwise at approximatley 30° C. to a solution of 7.76 g (0.04 mol) of 4-chlorobenzyloxyamine hydrochloride and 4.05 g (0.04 mol) of triethylamine in 200 ml of methylene chloride. After the reaction mixture had been stirred for 12 hours at room temperature, it was washed with dilute phosphoric acid, dried and concentrated. After the residue had been extracted with stirring with diethyl ether, 19.00 g of methyl 3-(4-chlorobenzyloxyaminocarbonyl)-2,4-dichlorobenzoate acid were obtained.

(M.p.: 120–121° C.)

3-(1'-Methoxyiminoeth-1'-yl)-2-methyl-4-methylsulfonylbenzoic acid (compound 3.22)

Step a) 3-(1'-Methoxyiminoeth-1'-yl)-2-methylaniline 50.0 g (0.335 mol) of 3-amino-2-methylacetophenone, 66.3 g (0.838 mol) of pyridine and 42.0 g (0.503 mol) of O-methylhydroxylamine hydrochloride were stirred at room temperature in 400 ml of ethanol. After the solvent had been removed, the residue was taken up in methylene chloride, washed with water, dried and evaporated, giving 54.0 g (91% of theory) of 3-(1'-methoxyiminoeth-1'-yl)-2-methylaniline.

Step b) 3-(1'-Methoxyiminoeth-1'-yl)-2-methyl-4-rhodanoaniline 50.9 g (0.319 mol) of bromine were added dropwise at from −20 to −15° C. to 54.0 g (0.303 mol) of 3-(1'-methoxyiminoeth-1'-yl)-2-methylaniline, 49.3 g (0.479 mol) of sodium bromide and 77.5 g (0.956 mol) of sodium rhodanide in 300 ml of methanol. After the mixture had been stirred at this temperature for 30 minutes, the insoluble constituents were filtered off with suction, ethyl acetate was added to the filtrate, and the pH of the mixture was adjusted to 8 using aqueous sodium bicarbonate solution. The organic phase was separated off, and the aqueous phase remaining was extracted several times with ethyl acetate. The combined organic phases were then washed with water, dried and evaporated, giving 67.3 g (95% of theory) of 3-(1'-methoxyiminoeth-1'-yl)-2-methyl-4-rhodanoaniline.

Step c) 3-(1'-Methoxyiminoeth-1'-yl)-2-methyl-4-methylthioaniline 67.3 g (0.286 mol) of 3-(1'-methoxyiminoeth-1'-yl)-2-methyl-4-rhodanoaniline in 600 ml of methanol were added dropwise at from 20 to 30° C. to 40.4 g (0.315 mol) of sodium sulfide in 200 ml of water. After the mixture had been stirred at room temperature for 3 hours, 45.1 g (0.318 mol) of methyl iodide in 200 ml of methanol were added, likewise at from 20 to 30° C. The mixture was then stirred at room temperature for 12 hours, the solvent was removed, and the residue was taken up in water and extracted several times with ethyl acetate. The combined organic phases were then washed with water, dried and evaporated, and the resultant residue was digested in n-hexane/methyl tert-butyl ether, giving 43.2 g (67% of theory) of 3-(1'-methoxyiminoeth-1'-yl)-2-methyl-4-methylthioaniline.

(m.p. 83–89° C.)

Step d) 6-Bromo-2-(1'-methoxyiminoeth-1'-yl)-3-methylthiotoluene 9.23 g of 47% strength hydrobromic acid were added dropwise at room temperature to 3.00 g (13.4 mmol) of 3-(1'-methoxyiminoeth-1'-yl)-2-methyl-4-methylthioaniline in 13.40 g of glacial acetic acid. 9.23 g of water were then added, the mixture was stirred at room temperature for 10 minutes, and 0.92 g (13.4 mmol) of sodium nitrite in 1.9 ml of water was added at from −5 to 0° C. The resultant reaction mixture was then added dropwise at 0° C. to 1.92 g (13.4 mmol) of copper(I) bromide in 6 ml of 47% strength hydrobromic acid. The mixture was stirred at room temperature for 12 hours, poured into ice-water and extracted with methylene chloride. The organic phase was then washed with sodium sulfite solution and water and dried, and the solvent was removed, giving 2.50 g (65% of theory) of 6-bromo-2-(1'-methoxyiminoeth-1'-yl)-3-methylthiotoluene.

Step e) 6-Bromo-2-(1'-methoxyiminoeth-1'-yl)-3-methylsulfonyltoluene

A total of 7.0 g (34.80 mmol) of m-chloroperbenzoic acid were added in portions over the course of 96 hours to 2.5 g (8.71 mmol) of 6-bromo-2-(1'-methoxyimino-1'-yl)-3-methylthiotoluene in 50 ml of methylene chloride. The solvent was removed, the residue was taken up in an organic solvent, and the solution was washed with sodium carbonate solution, sodium sulfite solution and water, dried and evaporated. The residue was then chromatographed on silica gel (eluent:toluene/ethyl acetate), giving 0.8 g (29% of theory) of 6-bromo-2-(1'-methoxyiminoeth-1'-yl)-3-methylsulfonyltoluene.

Step f) 3-(1'-Methoxyiminoeth-1'-yl)-2-methyl-4-methylsulfonylbenzoic acid 0.77 g (2.41 mmol) of 6-bromo-2-(1'-methoxyiminoeth-1'-yl)-3-methylsulfonyltoluene, 0.03 g (0.1 mmol) of palladium acetate, 0.14 g (0.49 mmol) of tricyclohexylphosphine, 0.10 g (2.4 mmol) of lithium chloride and 0.49 g (4.81 mmol) of triethylamine were suspended in 37.5 ml of toluene and 17.5 ml of water and aerated for 36 hours at 140° C. under a pressure of 20 bar. After cooling, the insoluble constituents were then separated off, the organic phase was extracted with water (to which 1 ml of triethylamine had been added), and the resultant aqueous phase was adjusted to pH=1 using hydrochloric acid and extracted with methylene chloride. This organic phase was dried and evaporated, giving 0.62 g (90% of theory) of 3-(1'-methoxyiminoeth-1'-yl)-2-methyl-4-methylsulfonylbenzoic acid.

Other benzoic acid derivatives of the formula IIIa which were, or can be, prepared in a similar manner are listed in Table 3 below in addition to the compounds described above.

TABLE 3

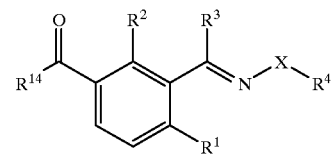

IIIa ($\triangleq$ III where $R^1$ is bonded in the 4-position and $R^2$ in the 2-position)

| No. | X | $R^1$ | $R^2$ | $R^3$ | $R^4$ | $R^{14}$ | M.p. [° C.] $^1$H NMR [ppm] |
|---|---|---|---|---|---|---|---|
| 3.01 | O | $SO_2CH_3$ | Cl | H | $C_2H_5$ | $OCH_3$ | 1.34(t, 3H); 3.29 (s, 3H); 3.98(s, 3H); 4.26(q, 2H); 7.91 (d, 1H); 8.10(d, 1H); 8.38(s, 1H) |
| 3.02 | O | Cl | Cl | H | $CH_3$ | $OCH_3$ | 55–57 |
| 3.03 | O | Cl | Cl | H | $C_2H_5$ | $OCH_3$ | 1.35(t, 3H); 3.93 (s, 3H); 4.27(q, 2H); 7.42(d, 1H); 7.69 (d, 1H); 8.24(s, 1H) |
| 3.04 | O | $SO_2CH_3$ | Cl | H | $C_2H_5$ | OH | 155–160 |
| 3.05 | O | Cl | Cl | H | $C_2H_5$ | OH | 120–123 |
| 3.06 | O | Cl | Cl | H | $CH_3$ | OH | 168–169 |
| 3.07 | O | Cl | Cl | H | $CH_2C\equiv CH$ | OH | 155–160 |
| 3.08 | O | Cl | Cl | $OC_2H_5$ | n-$C_3H_7$ | OH | 105–106 |
| 3.09 | O | Cl | Cl | $OCH_3$ | $CH_3$ | $OCH_3$ | 3.43(s, 3H); 3.58 (s, 3H); 3.92(s, 3H); 7.35(d, 1H); 7.82 (d, 1H) |
| 3.10 | O | Cl | Cl | $OCH_3$ | $CH_3$ | OH | 3.53(s, 3H); 3.72 (s, 3H); 7.74(d, 1H); 7.95(d, 1H) |
| 3.11 | O | Cl | Cl | $OCH_3$ | $CH_2$-4-Cl-$C_6H_4$ | OH | 3.55(s, 3H); 5.08 (s, 2H); 7.18–7.30 (m, 2H); 7.36(d, 1H); 8.03(d, 1H); 9.14 (s, br., 1H) |
| 3.12 | O | Cl | Cl | $OCH_3$ | n-$C_3H_7$ | $OCH_3$ | 47–48 |
| 3.13 | O | Cl | Cl | $OC_2H_5$ | n-$C_3H_7$ | $OCH_3$ | 48–50 |
| 3.14 | O | Cl | Cl | $OCH_3$ | $CH_3$ | Cl | |
| 3.15 | O | $SO_2CH_3$ | Cl | H | $CH_2C_6H_5$ | $OCH_3$ | 95–100 |
| 3.16 | O | $SO_2CH_3$ | Cl | H | $CH_2C_6H_5$ | OH | 115–120 |
| 3.17 | O | $SO_2CH_3$ | Cl | H | $CH_2$-3-thienyl | $OCH_3$ | 90–95 |
| 3.18 | O | $SO_2CH_3$ | Cl | H | $CH_3$ | $OCH_3$ | 95–100 |
| 3.19 | O | $SO_2CH_3$ | Cl | H | $CH_3$ | OH | 180–185 |
| 3.20 | O | $SO_2CH_3$ | Cl | H | $CH_2$-3-thienyl | OH | 95–100 |
| 3.21 | O | $SO_2CH_3$ | Cl | $CH_3$ | $CH_3$ | OH | |
| 3.22 | O | $SO_2CH_3$ | $CH_3$ | $CH_3$ | $CH_3$ | OH | Oil |

The 4-benzoylpyrazoles of the formula I and their agriculturally useful salts are suitable as herbicides, both in the form of stereoisomer mixtures and in the form of the pure stereoisomers. The herbicidal compositions comprising compounds of the formula I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the 4-benzoylpyrazoles of the formula I, or compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre* [sic], *Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

Moreover, the compounds of the formula I can also be used in crops which tolerate the action of herbicides due to breeding including genetic engineering methods.

The compounds of the formula I, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

The herbicidal compositions comprise a herbicidally effective amount of at least one compound of the formula I or of an agriculturally useful salt of I and auxiliaries conventionally used for the formulation of crop protection products.

Suitable inert auxiliaries are essentially: mineral oil fractions of medium to high boiling point such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, eg. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the subsrates [sic], as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants (adjuvants) are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The compounds I according to the invention can be formulated for example as follows:

I. 20 parts by weight of the compound No. 2.01 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 2.03 are dissolved in a mixture composed of parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 2.05 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2.06 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 2.01 are mixed with 97 parts by weight of finely divided kaolin. This gives a dust which comprises 3% by weight of the active ingredient.

VI. 20 parts by weight of the active ingredient No. 2.04 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 2.03 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 2.05 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The active ingredients I, or the herbicidal compositions, can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

To widen the spectrum of action and to achieve synergistic effects, the compounds of the formula I can be mixed and applied jointly with a large number of representatives of other groups of herbicidal or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, hetaryloxyalkanoic acid [sic] and its derivatives, benzoic acid and its derivatives, benzothiadiazinones, 2-aroyl-1,3-cyclohexanediones, hetaryl aryl ketones, benzylisoxazolidinones, meta-$CF_3$-phenylderivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds the formula I, alone or in combination with other herbicides, in the form of a mixture with additional other crop protection agents, for example with agents for controlling pests, phytopathogenic fungi or bacteria. Also of interest is the miscibility with mineral salt solutions which are employed for treating nutritional and trace element deficiencies. Non-phytotoxic oils and oil concentrates can also be added.

Depending on the intended purpose, the season, the target plants and the growth stage, the rates of application of active ingredient are 0.001 to 3.0, preferably 0.01 to 1.0, kg/ha active substance (a.s.)

USE EXAMPLES

The herbicidal action of the 4-benzoylpyrazoles of the formula I was demonstrated by greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover causes [sic] uniform germination of the test plants unless this was adversely affected by the active ingredients.

For the post-emergence treatment, the test plants were first grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 0.125 and 0.0625 kg/ha a.s. (active substance).

Depending on the species, the plants were kept at from 10–25° C. and 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| *Chenopodium album* | lambsquarters (goosefoot) |
| *Echinochloa crus galli* | barnyard grass |
| *Sinapis alba* | white mustard |
| *Setaria faberii* | giant foxtail |
| *Triticum aestivum* | summer wheat |

At rates of application of 0.125 and 0.0625 kg/ha (a.s.), compound 2.01 (Table 2) was very efficient post-emergence against the abovementioned mono- and dicotyledonous weeds and showed good tolerance in spring wheat.

We claim:

1. A 4-benzoylpyrazole of the formula I

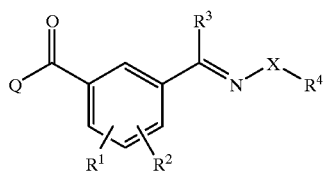

where the variables have the following meanings:

$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;

$R^3$ is hydrogen, cyano, $C_1$–$C_6$-alkyl, $C_1$–$C_6$-haloalkyl, —$OR^7$, —$SR^7$ or —$NR^7R^{10}$;

$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, it being possible for the eight last-mentioned radicals, in turn, to be substituted;

X is oxygen or $NR^8$;

n is 0, 1 or 2;

$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^6$ is $C_1$–$C_6$-alkyl or $C_1$–$C_6$-haloalkyl;

$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^8$ is hydrogen or $C_1$–$C_6$-alkyl;

$R^9$ is $C_1$–$C_6$-alkyl, $C_3$–$C_6$-alkenyl, $C_3$–$C_6$-alkynyl, phenyl or benzyl;

$R^{10}$ is $C_1$–$C_6$-alkyl, $C_1$–$C_6$-haloalkyl, $C_3$–$C_6$-alkenyl or $C_3$–$C_6$-alkynyl;

Q is a pyrazole of the formula II

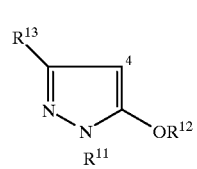

which is linked in the 4-position and where $R^{11}$ is $C_1$–$C_6$-alkyl, $C_1$–$C_6$-haloalkyl, phenyl or phenyl which is partially or fully halogenated and/or has attached to it one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{12}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl, the four last-mentioned substituents being unsubstituted or the phenyl ring being in each case partially or fully halogenated and/or having attached to it one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{13}$ is hydrogen, $C_1$–$C_6$-alkyl or $C_1$–$C_6$-haloalkyl;

or an agriculturally useful salt thereof.

2. A 4-benzoylpyrazole of the formula I as claimed in claim 1 where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

$R^2$ is hydrogen or a radical as mentioned above under $R^1$.

3. A 4-benzoylpyrazole of the formula Ia

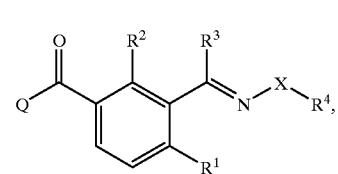

where the variables $R^1$ to $R^4$, X and Q have the meanings given under claim 1.

4. A process for the preparation of 4-benzoylpyrazoles of the formula I as claimed in claim 1, which comprises acylating a pyrazole of the formula II (where $R^{12}$=H) where the variables $R^{11}$ and $R^{13}$ have the meanings given under claim 1

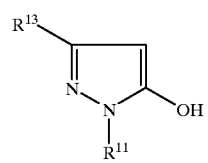

with an activated carboxylic acid IIIα or with a carboxylic acid IIIβ,

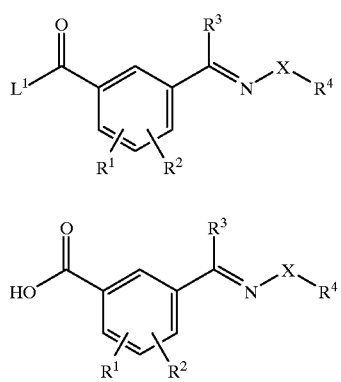

where the variables $R^1$ to $R^4$ and X have the meanings given under claim 1 and $L^1$ is a nucleophilically displaceable leaving group, subjecting the acylation product to a rearrangement reaction, if appropriate in the presence of a catalyst, to give the compounds I (where $R^{12}$=H) and, if desired, to prepare 4-benzoylpyrazoles of the formula I where $R^{12} \neq H$ reacting the product with a compound of the formula V $$L^2 R^{12} \quad\quad V$$

(where $R^{12} \neq H$)

where $R^{12}$ has the meanings given under claim 1 with the exception of hydrogen and $L^2$ is a nucleophilically displaceable leaving group.

5. A composition comprising a herbicidally active amount of at least one 4-benzoylpyrazole of the formula I or of an agriculturally useful salt of I as claimed in claim 1 and auxiliaries conventionally used for the formulation of crop protection products.

6. A process for the preparation of herbicidally active compositions as claimed in claim 5, which comprises mixing a herbicidally active amount of at least one 4-benzoylpyrazole of the formula I or of an agriculturally useful salt of I with auxiliaries conventionally used for the formulation of crop protection products.

7. A method of controlling undesirable vegetation, which comprises allowing a herbicidally active amount of at least one 4-benzoylpyrazole of the formula I or of an agriculturally useful salt of I as claimed in claim 1 to 3 to act on plants, their environment and/or on seeds.

* * * * *

UNITED STATES PATENT AND TRADEMARK OFFICE
CERTIFICATE OF CORRECTION

PATENT NO.: 6,028,035

DATED: February 22, 2000

INVENTOR(S): HILL et al.

It is certified that error appears in the above-identified patent and that said Letters Patent is hereby corrected as shown below:

Column 222, claim 1, lines 6-11, delete the formula II and substitute

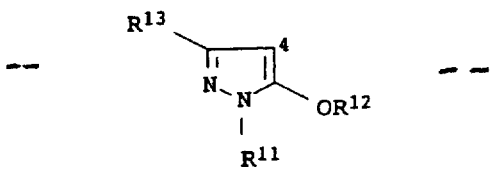

Column 224, claim 4, line 1, delete "$L^2R^{12}$" and insert -- $L^2$ —— $R^{12}$ --.

Signed and Sealed this

Sixteenth Day of January, 2001

Attest:

Q. TODD DICKINSON

Attesting Officer

Commissioner of Patents and Trademarks